US 11,744,888 B2

(12) United States Patent
Kraemer-Kuehl et al.

(10) Patent No.: US 11,744,888 B2
(45) Date of Patent: *Sep. 5, 2023

(54) METHOD OF TREATING OR PREVENTING CLINICAL SIGNS CAUSED BY INFECTIOUS BRONCHITIS VIRUS WITH 4/91 IBV VACCINE HAVING HETEROLOGOUS SPIKE PROTEIN

(71) Applicant: Boehringer Ingelheim Vetmedica GmbH, Ingelheim am Rhein (DE)

(72) Inventors: Annika Kraemer-Kuehl, Seesen (DE); Hans-Christian Philipp, Hemmingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/643,293

(22) Filed: Dec. 8, 2021

(65) Prior Publication Data
US 2022/0265815 A1 Aug. 25, 2022

Related U.S. Application Data

(63) Continuation of application No. 16/665,434, filed on Oct. 28, 2019, now Pat. No. 11,224,649.

(30) Foreign Application Priority Data

Oct. 31, 2018 (EP) ........................ 8203626

(51) Int. Cl.
*A61K 39/215* (2006.01)
*A61P 31/14* (2006.01)
*C12N 7/00* (2006.01)
*A61K 39/00* (2006.01)

(52) U.S. Cl.
CPC ............ *A61K 39/215* (2013.01); *A61P 31/14* (2018.01); *C12N 7/00* (2013.01); *A61K 2039/5256* (2013.01); *A61K 2039/552* (2013.01); *C12N 2770/20021* (2013.01); *C12N 2770/20022* (2013.01); *C12N 2770/20034* (2013.01); *C12N 2770/20071* (2013.01)

(58) Field of Classification Search
CPC .......... A61K 39/215; A61K 2039/5256; A61K 2039/552; A61K 2039/5254; A61K 2039/54; A61K 39/12; A61P 31/14; A61P 31/12; C12N 7/00; C12N 2770/20021; C12N 2770/20022; C12N 2770/20034; C12N 2770/20071; C07K 14/005
See application file for complete search history.

(56) References Cited

U.S. PATENT DOCUMENTS

| | | | | |
|---|---|---|---|---|
| 9,296,991 | B2 * | 3/2016 | Geerligs | A61P 11/10 |
| 10,772,953 | B2 * | 9/2020 | van Santen | C07K 14/165 |
| 11,065,328 | B2 * | 7/2021 | Rottier | A61K 39/215 |
| 2007/0154489 | A1 * | 7/2007 | Cavanagh | A61K 39/215 |
| | | | | 424/199.1 |
| 2012/0177675 | A1 * | 7/2012 | Britton | A61P 31/14 |
| | | | | 435/235.1 |
| 2014/0141043 | A1 * | 5/2014 | Toro Guzman | A61K 39/12 |
| | | | | 424/229.1 |
| 2016/0106828 | A1 * | 4/2016 | Toro | A61K 39/215 |
| | | | | 435/237 |

OTHER PUBLICATIONS

Franzo G, Listorti V, Naylor CJ, Lupini C, Laconi A, Felice V, Drigo M, Catelli E, Cecchinato M. Molecular investigation of a full-length genome of a Q1-like IBV strain isolated in Italy in 2013. Virus Res. Dec. 2, 2015;210:77-80. Epub Jul. 17, 2015. (Year: 2015 ).*
Franzo G, Listorti V, Naylor CJ, Catelli E, Cecchinato M. Spike protein [Infectious bronchitis virus], GenBank: AKV60429.1. Dep. Aug. 16, 2015. (Year: 2015).*
The Free Dictionary [Internet] "heterologous protein". Farlex Partner Medical Dictionary,; Farlex, 2012 [retrieved on Dec. 21, 2022].
Steven J. van Beurden et al.:"A reverse genetics system for avian coronavirus infectious bronchitis virus.." Virology Journal, vol. 14, No. 1, Dec. 12, 2017.
Casais R, et al. Reverse genetics system for the avian coronavirus infectious bronchitis virus; J Virol. Dec. 2001, 75(24), 12359-69.

* cited by examiner

*Primary Examiner* — Rachel B Gill
(74) *Attorney, Agent, or Firm* — Steffan Finnegan

(57) ABSTRACT

The present invention relates i.a. to a 4/91 IBV (infectious bronchitis virus) encoding for a heterologous S (spike) protein or fragment thereof. Further, the present invention relates to an immunogenic composition comprising said 4/91 IBV encoding for a heterologous S (spike) protein or fragment thereof. Furthermore, the present invention relates to methods for immunizing a subject comprising administering to such subject the immunogenic composition of the present invention. Moreover, the present invention relates to methods of treating or preventing clinical signs caused by IBV in a subject of need, the method comprising administering to the subject a therapeutically effective amount of an immunogenic composition according to the present invention.

10 Claims, 2 Drawing Sheets
Specification includes a Sequence Listing.

METHOD OF TREATING OR PREVENTING CLINICAL SIGNS CAUSED BY INFECTIOUS BRONCHITIS VIRUS WITH 4/91 IBV VACCINE HAVING HETEROLOGOUS SPIKE PROTEIN

CROSS-REFERENCE TO OTHER APPLICATIONS

This application is a continuation of U.S. Ser. No. 16/665,434, filed Oct. 28, 2019, which claims the benefit of EP Patent Application No. 18203626.9, filed Oct. 31, 2018, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety. The ASCII text file was created Apr. 19, 2022, contains 299,431 bytes and is named 01-3344-US-2_SL.txt.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by secondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric ortrimeric transmembrane protein, which is proteolytically cleaved into two subunits, S1 and S2. The heavily glycosylated S1 domain forms the 'head' of the spike protein and contains the receptor binding domain that interacts with 2,3-linked sialic acids on the host cell surface (Promkuntod et al. 2014. Virology. 448:26-32). The S2 domain contains the remaining part of the ectodomain (the 'stalk'), the transmembrane domain and the endodomain located in the cytoplasm.

The to date most widely used live-attenuated IBV vaccine strains were developed in the 1960s in the Netherlands, by serial passaging of a Massachusetts-like IBV strain (Bijlenga et al. 2004; Avian Pathol. 33:550-557). However, since the 1970s new IBV serotypes emerged for which the traditional Massachusetts-like vaccines did not protect sufficiently (Cook et al. 2012. Avian Pathol. 41:239-250). Therefore, there is a need for new and highly efficacious IBV vaccines against other IBV serotypes.

IBV Beaudette (Geilhausen et al. 1973. Arch Gesamte Virusforsch.: 40 (3) (1973), pp. 285-290) and H120 (G. Bijlenga et al. 2004. Avian Pathol.: 33 (6); pp. 550-557) are attenuated IBVs. However, attenuation may result in a loss of immunogenicity.

Further, recombinant IBVs have been generated. Zhou et al. 2016 (Arch Virol.; 161:3179-3187) disclose a H120 (Massachusetts genotype) IBV with Beaudette (Massachusetts genotype) spike protein. Hodgson et al. 2004 (J Virol 78: 13804-13811) disclose a Beaudette (Massachusetts genotype) IBV with M41 (Massachusetts genotype) Spike protein. Furthermore, Armesto et al. 2011 (PLoS One: 6(8):e24352) disclose IBV Beaudette (Massachusetts genotype) with a heterologous spike protein from 4/91 (4/91 genotype).

However, the recombinant IBVs disclosed in Zhou et al. 2016 and Hodgson et al. 2004 cannot be regarded as IBVs with a heterologous Spike protein as both, the IBV and the inserted spike is from the same genotype/serotype (Massachusetts). Further, all mentioned vaccines are based on a Beaudette based backbone or have a spike protein from Beaudette.

Further, no Beaudette based vaccines and no such recombinant vaccines (with heterologous spike proteins) are commercially available although Beaudette was already described many decades ago and recombinant approaches using Beaudette are known for more than one decade, respectively. Recombinant IBVs based on Beaudette are not suitable as vaccines. Wei et al 2014 (Apl Microbiol Biotechnol 98) discloses a Beaudette IBV having the S1 subunit of H120.

Ellis et al 2018 (J. Virol. 92(23)), Hodgson et al (J. Virol. 78(24)) and Armesto et al. 2011 (PLoS One: 6(8):e24352) all disclose Beaudette IBV with a M41 or 4/91 spike protein. However, Ellis et al 2018 (J. Virol. 92(23)) describe that recombinant Beaudette with chimeric spikes with heterologous S1 subunits from M41 or QX in combination with Beaudette spike S2 subunit do not confer sufficient protection against S1 homologous challenges ("*A single vaccination of specific-pathogen-free chickens with rIBV expressing S1 of virulent strains M41 or QX, BeauR-M41 (S1) and BeauR-QX(S1), gave incomplete protection against homologous challenge, based on ciliary activity and clinical signs*"; abstract). Further, Ellis et al 2018 (J. Virol. 92(23)) describe that the full length S gene (S1 and S2 from M41) only gave partial protection against challenge with an IBV of the homologous serotype (page 12), suggesting that the IBV Beaudette strain is not suitable as a backbone for recombinant IBV vaccines. Hodgson et al (J. Virol. 78(24)) further discloses that the Baudette strain "is also considered to be poorly immunogenic" and consequently, "it has never been used as a vaccinal strain" (page 13802, left column, second paragraph). Therefore, there is a need for generating novel and highly efficacious IBV vaccines and recombinant IBV vaccines, respectively. Further, there is a need for highly efficacious IBV vaccine vectors.

BRIEF DESCRIPTION OF THE DRAWINGS

FIG. 1. In ovo replication kinetics for CR88 rIBV H52 S in comparison to recombinant wild type viruses CR88 and H52. Data points represent the mean of 5 samples per time point. Error bars indicate the standard deviation.

FIG. 2. Summary of ciliostasis scoring. The sum of the 10 individual scores for the 10 rings of one animal is calculated and is represented by one dot in the graph. Maximum ciliostasis corresponds to a score of 40, while absence of ciliostasis is represented by a score of 0. Mean and significance are calculated using GraphPad Prism and an ordinary one-way ANOVA test ($p<0.0001$).

DETAILED DESCRIPTION OF THE INVENTION

Figure 3:
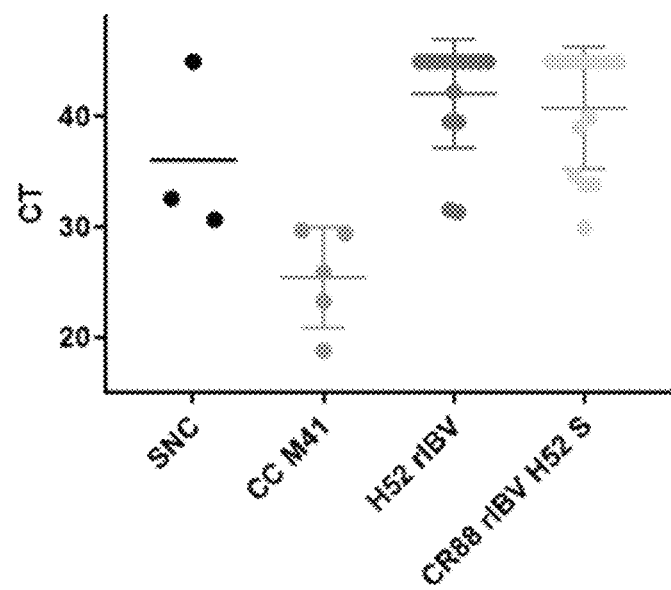
FIG. 3. Summary of RT-qPCR results of kidney tissues. Each individual bird is indicated by one data point.
Figure 4:
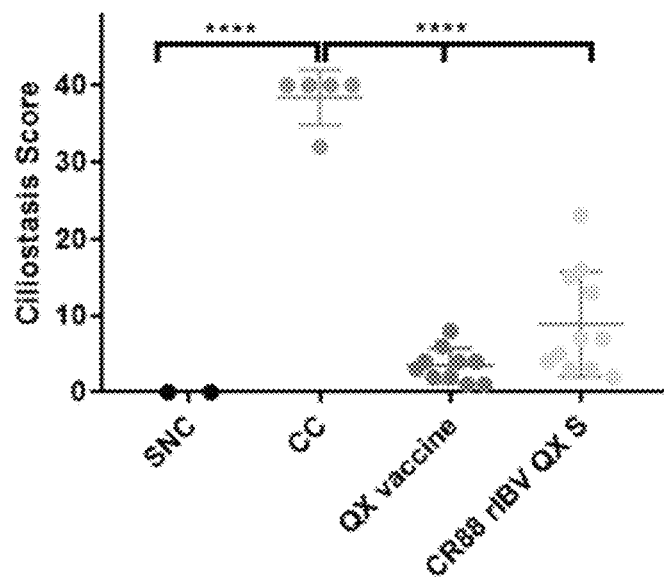
FIG. 4. Summary of ciliostasis scoring. The sum of the 10 individual scores for the 10 rings of one animal is calculated and is represented by one dot in the graph. Maximum ciliostasis corresponds to a score of 40, while absence of ciliostasis is represented by a score of 0. Mean and significance are calculated using GraphPad Prism and an ordinary one-way ANOVA test ($p<0.0001$).

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an 4/91 IBV (infectious bronchitis virus) encoding for a heterologous IBV S (spike) protein or fragment thereof.

The term "4/91 IBV" is well known to the person skilled in the art. The term "IBV" refers to an infectious bronchitis virus. The term "4/91" is interchangeably used with the term "793B" and defines the specific IBV serotype or genotype. The 4/91 serotype or genotype is well known to the person skilled in the art and comprises strains such as UK/4/91, UK/793B/91 and CR88. IBV strains are typically differentiated by the coding sequence of the 51 subunit of the spike protein (Valastro et al. 2016. Infect Genet Evol. 39:349-364) but can also be differentiated by their complete nucleotide sequence or the sequences of specific proteins such as the spike protein, nucleocapsid protein, envelope (E) protein or membrane (M) glycoprotein. Because the spike protein determines host tropism and antigenicity of IBV, the IBV genotypes are classified by the coding sequence of the subunit 1 of the spike proteins. Alternatively, IBV strains can be differentiated by their serotype. Serotype classification involves treatment of the virus with neutralizing antibodies.

It is in the general knowledge of a person skilled in the art where to obtain 4/91IBVs. 4/91 IBV strains can be commercially purchased such as exemplary NOBILIS® IB 4-91 (MSD Animal Health), CEVAC IBird® (CEVA; strain 1/96), or Gallivac IB88 (Boehringer Ingelheim; strain CR88121). Furthermore, 4/91 IBV specific vaccine strains are used for decades (Jones 2010 Rev. Bras. Cienc. Avic. vol. 12 no. 2) and, therefore, can be isolated from the field. The methods to isolate 4/91 IBV strains and to characterize the 4/91 IBV strains are well known to the person skilled in the art. Exemplary, 4/91 IBV strains can be characterized as described in SHIMAZAKI et al. 2008 (J. Vet. Med. Sci. 71(5): 583-588), Martin et al. 2014 (Avian Pathology Vol. 43, No. 3, 264-268), Zanaty et al. 2016 (World J Virol; 5(3): 125-134) or Stenzel et al. 2017 (Polish Journal of Veterinary Sciences Vol. 20, No. 3, 599-601). Further, 4/91 IBVs have been sequenced and the genomic sequences are available such as KF377577. Thus, the virus genome can be generated by synthesizing its sequence and generated upon the application of reverse genetic systems.

The term "spike" refers to a specific protein of the IBV that is well known by the person skilled in the art. The spike protein is the major inducer of antibodies and protective immune response. Further, the spike (S) protein facilitates cell entry of IBV by binding cellular receptors of the host cell and also by mediating virus-cell membrane fusion with the host cell. In addition, it determines the tissue and cell tropism of the virus strain.

The term "heterologous S (spike)" means that the spike protein or fragment thereof that has been introduced into the 4/91 IBV is from a different genotype or serotype than the 4/91 IBV. Thus, the heterologous spike is of a non-4/91 genotype or serotype.

The term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Further, the present invention also provides an immunogenic composition comprising a 4/91 IBV (infectious bronchitis virus) encoding for a heterologous S (spike) protein or fragment thereof.

Furthermore, the present invention also provides an immunogenic composition comprising an IBV (infectious bronchitis virus) as described herein. Thus, provided is an immunogenic composition comprising a 4/91 IBV (infectious bronchitis virus) encoding for a heterologous IBV S (spike) protein or fragment thereof.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

4/91—IBV—Definition by Protein encoding sequences

In another specific aspect of the IBV or the immunogenic composition according to the present invention the 4/91 IBV has a nucleotide sequence as shown for KF377577 (SEQ ID NO 53) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a nucleotide sequence as shown for SEQ ID NO 1 or sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "RNA" refers to any ribonucleic acid. The term encompasses single as well as double stranded RNA's. The RNA of the present invention encompasses isolated RNA (i.e. isolated from its natural context) and genetically modified forms. Moreover, comprised are also chemically modified RNAs including naturally occurring modified RNA such as methylated RNA or artificially modified ones such as biotinylated RNA. The terms "RNA" also specifically include RNA composed of bases other than the four biologically occurring nucleotides/bases (adenine, guanine, cytosine and uracil).

In another specific aspect of the IBV or the immunogenic composition according to the present invention the 4/91 IBV strain has a spike (S) protein having an amino acid sequence as shown for AGY56140 (SEQ ID NO 54) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV strain has a spike (51) protein having an amino acid sequence as shown for AF093793 (SEQ ID NO 60) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto. to the present invention the 4/91 IBV strain has a spike (51) protein having an amino acid sequence as shown for EU914938 (SEQ ID NO 55) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV strain has a spike (51) protein having an amino acid sequence as shown for EU914938 (SEQ ID NO 55) or a sequence having at least 90%, 91%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV strain has a spike (S1) protein having an amino acid sequence as shown for KM067900 (SEQ ID NO 56) or a sequence having at least 90%, 91%, 92%, 93%, 94% 95%, 96%, 97%, 98%, 99%, 99.2%, 99.5%, 99.6%, 99.7%, 99.8%, 99.9%, 99.95%, 99.98% or 99.99% sequence identity thereto.

It has to be understood that the spike protein sequence or nucleic acid can be used to determine whether any IBV strain is of 4/91 origin. However, because the 4/91 IBV is used as a backbone and the 4/91 spike protein or nucleic acid sequence is replaced by a heterologous spike protein or fragment thereof, the final IBV with the heterologous spike protein does not comprise any or only remaining parts of the 4/91 spike protein anymore.

In another specific aspect of the IBV or the immunogenic composition according to the present invention the 4/91 IBV strain has a spike (S) protein having an amino acid sequence as shown in SEQ ID NO:2 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a nucleocapsid (N) protein having an amino acid sequence as shown for EU780081 (SEQ ID NO 57) or a sequence having at least 95%, 96%, 97%, 98%, 99%, 99.2%, 99.5%, 99.6%, 99.7%, 99.8%, 99.9%, 99.95%, 99.98% or 99.99% sequence identity to at least one of the above mentioned sequences.

In another specific aspect of the IBV or the immunogenic composition according to the present invention the 4/91 IBV has a nucleocapsid (N) protein having an amino acid sequence as shown in SEQ ID NO:3 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has an envelope (E) protein having an amino acid sequence as shown for AGY56143 (SEQ ID NO 58) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has an envelope (E) protein having an amino acid sequence as shown in SEQ ID NO:4 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a membrane glycoprotein (M) protein having an amino acid sequence as shown for AGY56144 (SEQ ID NO 59) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the 4/91 IBV has a membrane glycoprotein (M) protein having an amino acid sequence as shown in SEQ ID NO:5 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al, Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e.,% identity=number of identical positions/total number of positions (i.e. overlapping positions)×100). Preferably, the two sequences are of the same length.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 61 so that "SEQ ID NO: X" represents any of the SEQ ID NOs mentioned herein.

In another specific aspect of the IBV or the immunogenic composition according to the present invention the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91attenuated, IB4-91 and CR88.

Heterologous S Protein

IBV Strains

IBV strains can be classified by serotype and genotype. Serotype classification involves treatment of the virus with neutralizing antibodies, whereas genotype classification generally involves examining the sequence of the S1 (spike) protein. However, the different IBV strains are well known to the person skilled in the art. Infectious bronchitis virus was first discovered in the United States in the 1930s.

The first IBV serotype identified was Massachusetts and remained the only serotype until the discovery of a different IBV serotype in 1956. Nowadays, several additional serotypes, including Arkansas and Delaware have been identified in the United States of America in addition to the originally identified Massachusetts type. Today, IBV Mass viruses can be identified in many countries of the world.

The IBV strain Beaudette is of Massachusetts type and was derived following at least 150 passages in chick embryos. The IBV strain Beaudette was originally isolated by Beaudette and Hudson (J. Am. Vet. Med. A. 90, 51-60, 1937) and passaged in chicken embryos. Other Massachusetts type IBV strains besides Beaudette are H120, H52, and M41. The H120 strain was passaged 120 times.

IBV QX is described as virulent field isolate of IBV which was originally isolated in China. However, the virus has spread towards Europe and has been identified in parts of Western Europe, predominantly in the Netherlands, but also in Germany, France, Belgium, Denmark and in the UK. In addition, the QX genotype or serotype has been described in several countries in Asia and Africa.

The strains designated "Italien-02" or "Italy-02" was isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Since 1996 a new Infectious Bronchitis virus (IBV) genotype, referred to as Q1, has circulated in China and was reported for the first time in Italy in 2011. Q1 is associated with an increase of mortality, kidney lesions and proventriculitis.

Furthermore, strains D274, B1648/D8880, D1466, V1397 and Arkansas have been identified in Europe as well.

It is in the general knowledge of a person skilled in the art where to obtain any IBV strains. IBV strains can be commercially purchased, obtained from scientific Institutes or the genomes can be synthetical synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiöse Bronchitis Virus (IBV): Molekularbiologische Untersuchungen zur Diagnostik und zum Vorkommen sowie zur Pathogenitat des Genotyps IBV QX in spezifisch pathogenfreien (SPF) Broilern, Freie Universität Berlin), Worthington et al. 2009 (Avian Pathology 37(3), 247-257), Liu et al. 2009 (Virus Genes 38: 56-65), Dolz et al. 2006 (Avian Pathology 35 (2): 77-85), Farsang et al. 2002 (Avian Pathology 31:

229-236) and Feng et al. 2014 (Virus Genes 49: 292-303) describe how to isolate and differentiate different IBV strains.

In another specific aspect of the IBV or the immunogenic composition according to the present invention the heterologous spike is of a non-4/91 genotype or serotype.

In another specific aspect of the IBV or the immunogenic composition according to the present invention the heterologous S protein or fragment thereof is from an IBV with a genotype or serotype selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Massachusetts (M41, H52, H120), Pennsylvania (such as Pennsylvania 1220/98, Pennsylvania Wolg/98), PL84084, Qu (such as Qu-mv), QX (such as GB341/96), Q1, SE 17 and Variant 2 (such as IS/1494/06, IBV/Ck/EG/CU/4/2014, gammaCoV/Ck/Poland/G052/2016).

In another specific aspect of the IBV or the immunogenic composition according to the present invention the heterologous S protein or fragment thereof is from an IBV selected from a list of genotypes or serotypes consisting of Massachusetts, QX, Q1, Italy 02, Arkansas, Connecticut, Georgia, LDT3, PL84084, Variant 2 or Brazil.

In another specific aspect of the IBV or the immunogenic composition according to the present invention the heterologous S protein or fragment thereof is from an IBV selected from a list of genotypes or serotypes consisting of Massachusetts, QX, Q1, Arkansas, Variant 2 and Brazil.

In another specific aspect of the IBV or the immunogenic composition according to the present invention the Massachusetts strain is selected from a list consisting of: H120, H52, Spain/98/308, IBMA5-1, SD/97/01, Spain/96/334, M41-M21883.

In another specific aspect of the IBV or the immunogenic composition according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV or the immunogenic composition according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV or the immunogenic composition according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV or the immunogenic composition according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10 EG, TR8 and IB VAR2-06.

In another specific aspect of the IBV or the immunogenic composition according to the present invention the Brazil strain is selected from a list consisting of: BR-1, BR-2, 23/2013 and IBV/Brasil/351/1984.

In another specific aspect of the IBV or the immunogenic composition according to the present invention the heterologous S protein or fragment thereof is from Massachusetts genotype or serotype.

In another specific aspect of the IBV or the immunogenic composition according to the present invention the heterologous S protein or fragment thereof is from genotype or serotype Massachusetts having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 6 or 7.

In another specific aspect of the IBV or the immunogenic composition according to the present invention the heterologous S protein or fragment thereof is from genotype or serotype QX having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 8 or 9.

In another specific aspect of the IBV or the immunogenic composition according to the present invention the heterologous S protein or fragment thereof is from genotype or serotype Q1 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 10 or 11.

In another specific aspect of the IBV or the immunogenic composition according to the present invention the heterologous S protein or fragment thereof is from genotype or serotype Arkansas having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 12 or 13.

In another specific aspect of the IBV or the immunogenic composition according to the present invention the heterologous S protein or fragment thereof is from genotype or serotype Variant 2 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 14 or 15.

In another specific aspect of the IBV or the immunogenic composition according to the present invention the heterologous S protein or fragment thereof is from genotype or serotype Brazil having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:16 or 17.

In another specific aspect of the IBV or the immunogenic composition according to the present invention the heterologous S protein or fragment thereof is selected from a list consisting of SEQ ID NO: 6, 7, 8, 9, 10, 11, 12, 13, 14, 15, 16 or 17.

In another specific aspect of the IBV or the immunogenic composition according to the present invention the heterologous S protein is the full length spike protein.

The present experimental data show that full length spike protein sequences can be used. However, it is well known that fragments of the spike protein sequence can be used as well such as the ectodomain of the spike protein.

In another specific aspect of the IBV or the immunogenic composition according to the present invention the fragment of the heterologous S (spike) protein has a length of at least 500, 750, 1000 or 1075 amino acids.

In another specific aspect of the IBV or the immunogenic composition according to the present invention the fragment of the heterologous S (spike) protein has a length of at least 500, 750, 1000 or 1075 amino acids from the N-Terminus.

The term "N-terminus" is well known to the person skilled in the art. The N-terminus is also termed amino-terminus, NH2-terminus, N-terminal end or amine-terminus. When the protein is translated from messenger RNA, it is created from N-terminus to C-terminus. Thus, the N-terminus is the start of an amino acid chain (protein or polypeptide) comprising said amine group (—NH2).

In another specific aspect of the IBV or the immunogenic composition according to the present invention the fragment of the heterologous S (spike) protein has a length of at least 1000 amino acids.

In another specific aspect of the IBV or the immunogenic composition according to the present invention the fragment of the heterologous S (spike) protein is the ectodomain of the spike protein.

The term "ectodomain" is well known to a person skilled in the art. The spike protein comprises different functional parts, the signal sequence, the ectodomain, the transmembrane domain and the endodomain (from N-terminus to C-terminus). Thus, after cleavage of the signal sequence, the N-terminus of the spike protein starts with the ectodomain. The IBV spike ectodomain has a length of about 1075 amino acids and differs by a few amino acids in length dependent on the IBV strain.

In another specific aspect of the IBV or the immunogenic composition according to the present invention the heterologous S (spike) protein or fragment thereof replaces the homologous S protein or fragment thereof.

In another specific aspect of the IBV or the immunogenic composition according to the present invention the heterologous S (spike) protein or fragment thereof replaces the natural occurring S protein or fragment thereof.

In another specific aspect of the IBV or the immunogenic composition according to the present invention the heterologous S (spike) protein or fragment thereof replaces the S protein or fragment thereof in 4/91 IBV.

In another specific aspect of the IBV or the immunogenic composition according to the present invention the IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated, IBV strain is one that is suitable for incorporation into an immunogenic composition comprising a modified live IBV.

In another specific aspect of the IBV or the immunogenic composition according to the present invention the IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In another specific aspect of the IBV or the immunogenic composition according to the present invention the IBV is genetically engineered.

The term "genetically engineered" refers to an IBV which has been mutated by using "reverse genetics" approaches. Preferably, the IBV according to the present invention has been genetically engineered. The reverse genetics technique involves the preparation of synthetic recombinant viral RNAs. However, "reverse genetics" techniques are well known to the person skilled in the art.

In another specific aspect of the IBV or the immunogenic composition according to the present invention the IBV is a recombinant IBV.

The term "recombinant" as used herein relates to a RNA genome (or RNA sequence, cDNA sequence or protein) having any modifications that do not naturally occur to the corresponding RNA genome (or RNA sequence, cDNA sequence or protein). For instance, a RNA genome (or RNA sequence, cDNA sequence or protein) is considered "recombinant" if it contains an insertion, deletion, inversion, relocation or a point mutation introduced artificially, e.g., by human intervention. Therefore, the RNA genomic sequence (or RNA sequence, cDNA sequence or protein) is not associated with all or a portion of the sequences (or RNA sequence, cDNA sequence or protein) with which it is associated in nature. The term "recombinant" as used with respect to a virus, means a virus produced by artificial manipulation of the viral genome. The term "recombinant virus" encompasses genetically modified viruses.

In another specific aspect of the IBV or the immunogenic composition according to the present invention the IBV is chimeric.

The term "chimeric" refers to an IBV comprising one or more nucleotide sequences from another coronavirus, preferably from another IBV strain. Exemplary, an IBV 4/91 encoding for a heterologous S (spike) protein or fragment thereof is a chimeric IBV.

In another specific aspect of the immunogenic composition according to the present invention the immunogenic composition is a vaccine. The term "vaccine" already has been described elsewhere herein. However, in case where the host displays a protective immunological response such that resistance to new infection will be enhanced and/or the clinical severity of the disease reduced, the immunogenic composition is described as a "vaccine.

In another specific aspect of the immunogenic composition according to the present invention the immunogenic composition comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol p 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from $E.$ $coli$ (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition according to the present invention the immunogenic composition is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition according to the present invention the immunogenic composition protects against a challenge with an IBV strain of the genotype or serotype of the heterologous spike protein.

In another specific aspect of the immunogenic composition according to the present invention the immunogenic composition protects against a challenge with strains of Massachusetts, QX, Q1, Arkansas, Variant 2 or Brazil genotype.

In another specific aspect of the immunogenic composition according to the present invention the immunogenic composition protects against a challenge with strains of Massachusetts genotype.

In another specific aspect of the immunogenic composition according to the present invention said immunogenic composition is formulated for a single-dose administration.

The volume for a single-dose has been defined elsewhere herein.

It has furthermore been shown that one dose of the immunogenic composition of the present invention is effective after the administration of such single dose of such immunogenic composition.

In another specific aspect of the immunogenic composition according to the present invention the immunogenic composition is administered subcutaneously, intramuscularly, oral, in ovo, via spray, via drinking water or by eye drop.

In another specific aspect of the immunogenic composition according to the present invention the immunogenic composition comprises 1 to 10 $\log_{10}$ $EID_{50}$ per dose of the IBV.

In another specific aspect of the immunogenic composition according to the present invention the immunogenic composition comprises 2 to 5 $\log_{10}$ $EID_{50}$ per dose of the IBV.

In another specific aspect of the immunogenic composition according to the present invention the immunogenic composition comprises 2 to 4 $\log_{10}$ $EID_{50}$ per dose of the IBV.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for human administration.

Thus, the present invention provides a kit comprising the IBV or the immunogenic composition as described herein.

In one specific aspect of the kit according to the present invention the kit further comprises an instruction letter for the treatment and/or prophylaxis of diseases of avians.

In one specific aspect of the kit according to the present invention the kit further comprises an instruction letter for the treatment and/or prophylaxis of diseases of poultry.

In one specific aspect of the kit according to the present invention the kit further comprises an instruction letter for the treatment and/or prophylaxis of IB (infectious bronchitis).

Method of Treatments

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular IBV infection in a flock or in the reduction in the severity of clinical signs caused by or associated with the particular IBV infection.

Further, the immunization of a subject in need with the immunogenic compositions as provided herewith, results in preventing infection of a subject by IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with a IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular IBV.

Further, the present invention provides a method of treating or preventing clinical signs caused by IBV in a subject of need, the method comprising administering to the subject a therapeutically effective amount of an immunogenic composition as described herein.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

The term "reducing" or "reduced" or "reduction" or lower" are used interchangeable in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular IBV.

Further, the present invention provides a method of reducing the ciliostasis in a subject of need, in comparison to a subject of a non-immunized control group of the same species, the method comprising administering to the subject a therapeutically effective amount of an immunogenic composition as described herein.

As shown in the Examples, the immunogenic composition as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

In one aspect of the present invention said subject is avian.

The term "avian" is well known to the person skilled in the art. The term "avian" encompasses all birds including poultry.

In one aspect of the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred to as breeders.

In one aspect of the present invention said subject is selected from the list consisting of chicken, turkey, quail, or pheasant.

In one aspect of the present invention said subject is chicken.

In one aspect of the present invention the immunogenic composition is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 μl per dose at any age. Preferably, the single-dose for eye drop vaccines has a total volume between about 5 μl and 70 μl and more preferably between about 20 μl and 50 μl with a single 20 μl, 25 μl, 30 μl, 35 μl, 40 μl, 45 μl or 50 μl dose being preferred. Most preferred, the single-dose for eye drop vaccines has a total volume between about 30 μl and 50 μl with a single 30 μl, 35 μl, 40 μl, 45 μl or 50 μl dose being preferred.

Spray vaccines may contain the dose in a volume of 25 to 1000 μl for day-old poultry. Preferably, the single-dose for spray vaccines has a total volume between about 50 μl and 5000 μl, more preferably between about 75 μl and 2000 μl, more preferably between about 100 μl and 1000 μl, even more preferably between about 200 μl and 900 μl, even more preferably between about 300 μl and 800 μl and even more preferably between about 400 μl and 700 μl with a single 400 μl, 425 μl, 450 μl, 475 μl, 500 μl, 525 μl, 550 μl, 575 μl, 600 μl, 625 μl, 650 μl, 675 μl or 700 μl dose being preferred. Most preferred the single-dose has a total volume of 400 μl, 450 μl, 500 μl, 550 μl, 600 μl, 650 μl or 700 μl.

The vaccine for in ovo vaccination may contain the dose in a volume of 50 to 100 μl, preferably 50 μl. Preferably, the single-dose for in ovo vaccines has a total volume between about 10 μl and 250 μl, more preferably between about 15 μl and 200 μl, even more preferably between about 20 μl and 150 μl, even more preferably between about 30 μl and 100 μl, even more preferably between about 30 μl and 75 μl and with a single 30 μl, 35 μl, 40 μl, 45 μl, 50 μl, 55 μl, 60 μl, 65 μl, 70 μl or 75 μl dose being preferred. Most preferred the single-dose has a total volume of 40 μl, 45 μl, 50 μl, 55 μl or 60 μl.

The vaccine for intramuscular or subcutaneous vaccination or one dose of a drinking water vaccine may contain the dose in a volume of 30 μl to 1000 μl. Preferably, the single-dose has a total volume between about 30 μl and 1000 μl, more preferably between about 50 μl and 500 μl, more preferably between about 75 μl and 250 μl and even more preferably between about 100 μl and 200 μl with a single 100 μl, 110 μl, 120 μl, 125 μl, 130 μl, 135 μl, 140 μl, 145 μl, 150 μl, 160 μl, 170 μl, 175 μl, 180 μl, 190 μl, 155 μl, or 200 μl dose being the most preferred.

In one aspect of the present invention the immunogenic composition is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the initial (first) vaccination is performed at 1-10 days of age and the second vaccination (booster) is performed with a live or inactivated vaccine at 6-12 or 16-18 weeks of age. More preferably, the initial (first) vaccination is performed at one day-of-age and the second vaccination (booster) is performed with a live or inactivated vaccine at 6-12 or 16-18 weeks of age.

In case in ovo vaccination is used, preferably the first administration is performed when embryos are between 15 to 19 days old, preferably at day 17, 18 or 19, most preferably at day 18 of age. A second administration can be performed within the first three weeks of age, preferably within the first 10 days of age.

In one aspect of the present invention said immunogenic composition is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous.

More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e.g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the administration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one aspect of the present invention said immunogenic composition is administered via eye drop.

Typically, the live vaccine for post-hatch administration comprises the attenuated IBV in a concentration of $10^2$ to $10^8$ EID$_{50}$ (50% Egg Infective Dose) per dose, preferably in a concentration of $10^2$ to $10^5$ EID$_{50}$ per dose and, more preferably, in a concentration of $10^2$ to $10^4$ EID$_{50}$ per unit dose and, even more preferably, in a concentration of $10^2$ to $10^3$ EID$_{50}$ per dose.

The live vaccine for in ovo administration typically comprises an amount of the attenuated IBV of $10^2$ to $10^7$ EID$_{50}$/embryo, preferably $10^2$ to $10^3$ EID$_{50}$/embryo in a volume of 50 to 100 preferably 50 μl.

Preferably, the immunogenic composition of the present invention comprises the IBV of the present invention in amounts of about 1 to about 10 $\log_{10}$ EID (egg infective dose)$_{50}$/ml per dose, preferably about 2 to about 8 $\log_{10}$ EID$_{50}$ per dose, preferably in an amount of about 2 to about 7 $\log_{10}$ EID$_{50}$ per dose, more preferably in an amount of about 2 to about 6 $\log_{10}$ EID$_{50}$ per dose, even more preferably in an amount of about 2 to about 5 $\log_{10}$ EID$_{50}$ per dose, even more preferably in an amount of about 2 to about 4 $\log_{10}$ EID$_{50}$ per dose, most preferably in an amount of about 2 to about 3 $\log_{10}$ EID$_{50}$ per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $\log_{10}$ $EID_{50}$ per dose.

In one aspect of the present invention the immunogenic composition comprises 1 to 10 $\log_{10}$ $EID_{50}$ per dose of the IBV.

In one aspect of the present invention the immunogenic composition comprises 2 to 5 $\log_{10}$ $EID_{50}$ per dose of the IBV.

In one aspect of the present invention the immunogenic composition comprises 2 to 4 $\log_{10}$ $EID_{50}$ per dose of the IBV.

In one aspect of the present invention the immunogenic composition is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one aspect of the present invention the immunogenic composition is administered to subjects within the first day of age. As shown in the Examples the immunogenic composition as provided herein has been proven to be safe and efficacious when administered to 1-day old poultry.

In one aspect of the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" is well known to the person skilled in that art. The term virus load is interchangeable used with the term viral titer herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialized epithelial cells, which are lined with numerous, motile, hair-like structures called cilia. The term "ciliostasis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term egg drop" encompasses a decreased egg production.

In one aspect of the present invention the treatment or prevention results in a prevention or reduction of ciliostasis as compared to subjects of a non-treated control group of the same species.

In one aspect of the present invention the treatment or prevention results in a prevention or reduction of kidney lesions as compared to subjects of a non-treated control group of the same species.

In one aspect of the present invention the treatment or prevention results in a prevention or reduction of egg drop as compared to subjects of a non-treated control group of the same species.

The present invention further provides an IBV or an immunogenic composition as described herein for therapeutic use.

The present invention further provides an IBV or an immunogenic composition as described herein for use as an immunogen or vaccine.

The present invention further provides an IBV or an immunogenic composition as described herein for use as a medicament.

The present invention further provides the use of the IBV or immunogenic composition as described herein for the manufacture of a medicament.

The present invention further provides the use of the IBV or immunogenic composition as described herein for the treatment and/or prophylaxis of IBV infections in a subject.

The present invention further provides an immunogenic composition comprising a 4/91 IBV (infectious bronchitis virus) encoding for a heterologous S (spike) protein or fragment thereof, wherein said 4/91 IBV comprises a Nucleocapsid (N) protein, Envelope (E) protein or Membrane glycoprotein (M) having an amino acid sequence as shown for SEQ ID NO:3, SEQ ID NO:4, SEQ ID NO:5, EU780081 (SEQ ID NO:57), AGY56143 (SEQ ID NO:58), AGY56144 (SEQ ID NO:59) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto, and, wherein the heterologous S protein or fragment thereof is selected from a list of genotypes or serotypes consisting of Massachusetts, QX, Q1, Arkansas, Variant 2 and Brazil or from an amino acid sequence as shown SEQ ID NOs:6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, % or 99.99% sequence identity thereto.

In another specific aspect of the immunogenic composition according to the present invention the heterologous S protein is the full length spike protein.

In another specific aspect of the immunogenic composition according to the present invention the fragment of the heterologous S (spike) protein has a length of at least 500, 750, 1000 or 1075 amino acids from the N-Terminus.

In another specific aspect of the immunogenic composition according to the present invention the fragment of the heterologous S (spike) protein is the Ectodomain of the spike protein.

In another specific aspect of the immunogenic composition according to the present invention the IBV is attenuated.

In another specific aspect of the immunogenic composition according to the present invention the 4/91 IBV is selected from a list of genotypes or serotypes consisting of CR88 and 793B.

The present invention further provides a method of preparing an immunogenic composition for the treatment and/or prophylaxis of IBV infections in a subject comprising:

a.) providing a 4/91 IBV comprising a spike (S) protein, nucleocapsid (N) protein, envelope (E) protein or membrane glycoprotein (M) having an amino acid sequence as shown for SEQ ID NO:2, SEQ ID NO:3, SEQ ID NO:4, SEQ ID NO:5, AGY6140 (SEQ ID NO:54), AF093793 (SEQ ID NO:60), EU914938 (SEQ ID NO 55), KM067900 (SEQ ID NO 56), EU780081 (SEQ ID NO 57), AGY56143 (SEQ ID NO 58), AGY56144 (SEQ ID NO 59) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or % sequence identity thereto; and b.) providing a heterologous S protein or fragment thereof selected from a list of genotypes or serotypes consisting of Massachusetts, QX, Q1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and c.) replacing the spike protein or fragment thereof of 4/91 IBV of a) with said heterologous S (spike) protein or fragment thereof of b) to have a 4/91 IBV with a heterologous S protein or fragment thereof; and d.) obtaining said 4/91 IBV with a heterologous S protein or fragment thereof; and e.) addition of a pharmaceutically acceptable carrier.

The term "obtaining" comprises the harvest, isolation, purification and/or formulation (e.g. finishing, inactivation and/or blending) of said IBV 4/91 with a heterologous S protein or fragment thereof.

The term "harvest" refers to collecting or recovering said said IBV 4/91 with a heterologous S protein or fragment thereof from the transfected or infected cell or cell line. Any conventional method known in the art can be used, e.g. any separation method. Well known methods in the art comprise centrifugation or filtration, such as using a semi-permeable membrane having a certain pore size.

The term "isolation" comprises an isolation step of said IBV 4/91 with a heterologous S protein or fragment thereof. Methods for the isolation from the transfected or infected cell or cell line are known to a person skilled in the art. Those methods comprise physical and/or chemical methods, including but are not limited to freeze thaw cycles, treatment with ultrasound and the alike.

Methods for the "purification" of said IBV 4/91 with a heterologous S protein or fragment thereof from the isolate are known to a person skilled in the art, for example by those methods described in Protein purification methods—a practical approach (E.L.V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

In another specific aspect of the method of preparing an immunogenic composition according to the present invention the fragment of the heterologous S (spike) protein is the ectodomain of the spike protein.

In another specific aspect of the immunogenic composition according to the present invention said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

In another specific aspect of the method of preparing an immunogenic composition according to the present invention the heterologous S protein is the full length spike protein.

In another specific aspect of the method of preparing an immunogenic composition according to the present invention the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/9lattenuated, IB4-91 and CR88.

The present invention further concerns a plasmid comprising a nucleic acid encoding a partial 4/91 IBV (infectious bronchitis virus) genome including a heterologous IBV S (spike) protein or fragment thereof, such as pUC57-s CR88 rIBV H52 S donor plasmid (SEQ ID NO:21).

CLAUSES

The following clauses are also described herein:
1. A 4/91 IBV (infectious bronchitis virus) encoding for a heterologous IBV S (spike) protein or fragment thereof.
2. An immunogenic composition comprising a 4/91 IBV (infectious bronchitis virus) encoding for a heterologous S (spike) protein or fragment thereof.
3. An immunogenic composition comprising an IBV (infectious bronchitis virus) of clause 1.
4/91 IBV—Definition by Protein Encoding Sequences
4. The IBV or the immunogenic composition of any one of clauses 1 to 3, wherein the 4/91 IBV has or consists of or comprises a nucleotide sequence as shown for KF377577 (SEQ ID NO 53) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
5. The IBV or the immunogenic composition of any one of clauses 1 to 4, wherein the 4/91 IBV has or consists of or comprises a nucleotide sequence as shown for SEQ ID NO 1 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
6. The IBV or the immunogenic composition of any one of clauses 1 to 5, wherein the 4/91 IBV strain has or consists of or comprises a spike (S) protein having an amino acid sequence as shown for AGY56140 (SEQ ID NO 54) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
7. The IBV or the immunogenic composition of any one of clauses 1 to 6, wherein the 4/91 IBV strain has or consists of or comprises a spike (S1) protein having an amino acid sequence as shown for AF093793 (SEQ ID NO 60) or a sequence having at least 90%, 91%, 92%, 93%, 94%, 95%, 96%, 97%, 98%, 99%, 99.2%, 99.5%, 99.6%, 99.7%, 99.8%, 99.9%, 9.95%, 99.98% or 99.99% sequence identity thereto.
8. The IBV or the immunogenic composition of any one of clauses 1 to 7, wherein the 4/91 IBV strain has or consists of or comprises a spike (S1) protein having an amino acid sequence as shown for EU914938 (SEQ ID NO 55) or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
9. The IBV or the immunogenic composition of any one of clauses 1 to 8, wherein the 4/91 IBV strain has or consists of or comprises a spike (S1) protein having an amino acid sequence as shown for KM067900 (SEQ ID NO 56) or a sequence having at least 90%, 91%, 92%, 93%, 94% 95%, 96%, 97%, 98%, 99%, 99.2%, 99.5%, 99.6%, 99.7%, 99.8%, 99.9%, 99.95%, 99.98% or 99.99% sequence identity thereto.
10. The IBV or the immunogenic composition of any one of clauses 1 to 9, wherein the 4/91 IBV strain has or consists of or comprises a spike (S) protein having an amino acid sequence as shown SEQ ID NO:2 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
11. The IBV or the immunogenic composition of any one of clauses 1 to 10, wherein the 4/91 IBV has or consists of or comprises a nucleocapsid (N) protein having an amino acid sequence as shown for EU780081 (SEQ ID NO 57) or a sequence having at least 95%, 96%, 97%, 98%, 99%, 99.2%, 99.5%, 99.6%, 99.7%, 99.8%, 99.9%, 99.95%, 99.98% or 99.99% sequence identity to at least one of the above mentioned sequences.
12. The IBV or the immunogenic composition of any one of clauses 1 to 11, wherein the 4/91 IBV has or consists of or comprises a nucleocapsid (N) protein having an amino acid sequence as shown SEQ ID NO:3 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.
13. The IBV or the immunogenic composition of any one of clauses 1 to 12, wherein the 4/91 IBV has or consists of or comprises an envelope (E) protein having an amino acid sequence as shown for AGY56143 (SEQ ID NO 58) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.
14. The IBV or the immunogenic composition of any one of clauses 1 to 13, wherein the 4/91 IBV has or consists of or comprises an envelope (E) protein having an amino acid sequence as shown in SEQ ID NO:4 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.
15. The IBV or the immunogenic composition of any one of clauses 1 to 14, wherein the 4/91 IBV has or consists of or comprises a membrane glycoprotein (M) protein having an amino acid sequence as shown for AGY56144 (SEQ ID NO 59) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

16. The IBV or the immunogenic composition of any one of clauses 1 to 15, wherein the 4/91 IBV has or consists of or comprises a membrane glycoprotein (M) protein having an amino acid sequence as shown in SEQ ID NO:5 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

17. The IBV or the immunogenic composition of any one of clauses 1 to 16, wherein the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91attenuated, IB4-91 and CR88.

Heterologous S Protein

18. The IBV or the immunogenic composition of any one of clauses 1 to 17, wherein the heterologous spike is of a non-4/91 genotype or serotype.

19. The IBV or the immunogenic composition of any one of clauses 1 to 18, wherein the heterologous S protein or fragment thereof is from an IBV with a genotype or serotype selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Massachusetts (M41, H52, H120), Pennsylvania (such as Pennsylvania 1220/98, Pennsylvania Wolg/98), PL84084, Qu (such as Qu-mv), QX (such as GB341/96), Q1, SE 17 and Variant 2 (such as IS/1494/06, IBV/Ck/EG/CU/4/2014, gamma CoV/Ck/Poland/G052/2016).

20. The IBV or the immunogenic composition of any one of clauses 1 to 19, wherein the heterologous S protein or fragment thereof is from an IBV selected from a list of genotypes or serotypes consisting of Massachusetts, QX, Q1, Italy 02, Arkansas, Connecticut, Georgia, LDT3, PL84084, Variant 2 or Brazil.

21. The IBV or the immunogenic composition of any one of clauses 1 to 20, wherein the heterologous S protein or fragment thereof is from an IBV selected from a list of genotypes or serotypes consisting of Massachusetts, QX, Q1, Arkansas, Variant 2 and Brazil.

22. The IBV or the immunogenic composition of clause 21, wherein the Massachusetts strain is selected from a list consisting of: H120, H52, Spain/98/308, IBMA5-1, SD/97/01, Spain/96/334, M41-M21883.

23. The IBV or the immunogenic composition of clause 21, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

24. The IBV or the immunogenic composition of clause 21, wherein the Q1 strain is selected from a list consisting of: CK/CH/LDL/98I, CK/CH/LSD/08-10, J2, Q1, AR08ER22, AR08BA21 and Chile-295-10.

25. The IBV or the immunogenic composition of clause 21, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

26. The IBV or the immunogenic composition of clause 21, wherein the Variant 2 strain is selected from a list consisting of: IS/1494/06, IBV/Ck/EG/CU/4/2014, gamma CoV/Ck/Poland/G052/2016, Eg/CLEVB-2/IBV/012, D1344/2/4/10 EG, TR8 and IB VAR2-06.

27. The IBV or the immunogenic composition of clause 21, wherein the Brazil strain is selected from a list consisting of: BR-1, BR-2, 23/2013 and IBV/Brasil/351/1984.

28. The IBV or the immunogenic composition of any one of clauses 1 to 27, wherein the heterologous S protein or fragment thereof is from Massachusetts genotype or serotype.

29. The IBV or the immunogenic composition of any one of clauses 1 to 28, wherein the heterologous S protein or fragment thereof is from genotype or serotype Massachusetts having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 6 or 7 or the heterologous S protein or fragment thereof consists of or comprises an amino acid sequence as shown in SEQ ID NO: 6 or 7 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

30. The IBV or the immunogenic composition of any one of clauses 1 to 29, wherein the heterologous S protein or fragment thereof is from genotype or serotype QX having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 8 or 9 or the heterologous S protein or fragment thereof consists of or comprises an amino acid sequence as shown in SEQ ID NO: 8 or 9 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

31. The IBV or the immunogenic composition of any one of clauses 1 to 30, wherein the heterologous S protein or fragment thereof is from genotype or serotype Q1 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 10 or 11 or the heterologous S protein or fragment thereof consists of or comprises an amino acid sequence as shown in SEQ ID NO: 10 or 11 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

32. The IBV or immunogenic composition of any one of clauses 1 to 31, wherein the heterologous S protein or fragment thereof is from genotype or serotype Arkansas having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 12 or 13 or the heterologous S protein or fragment thereof consists of or comprises an amino acid sequence as shown in SEQ ID NO: 12 or 13 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

33. The IBV or the immunogenic composition of any one of clauses 1 to 32, wherein the heterologous S protein or fragment thereof is from genotype or serotype Variant 2 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO: 14 or 15 or the heterologous S protein or fragment thereof consists of or comprises an amino acid sequence as shown in SEQ ID NO: 14 or 15 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

34. The IBV or the immunogenic composition of any one of clauses 1 to 33, wherein the heterologous S protein or fragment thereof is from genotype or serotype Brazil having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:16 or 17 or the heterologous S protein or fragment thereof consists of or comprises an amino acid sequence as shown in SEQ ID NO: 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

35. The IBV or the immunogenic composition of any one of clauses 1 to 34, wherein the heterologous S protein or fragment thereof is selected from a list consisting of SEQ ID NO: 6, 7, 8, 9, 10, 11, 12, 13, 14, 15, 16 or 17.

36. The IBV or the immunogenic composition of any one of clauses 1 to 35, wherein the heterologous S protein is the full length spike protein.

37. The IBV or the immunogenic composition of any one of clauses 1 to 36, wherein the fragment of the heterologous S (spike) protein has a length of at least 500, 750, 1000 or 1075 amino acids.

38. The IBV or the immunogenic composition of any one of clauses 1 to 37, wherein the fragment of the heterologous S (spike) protein has a length of at least 500, 750, 1000 or 1075 amino acids from the N-Terminus.

39. The IBV or the immunogenic composition of any one of clauses 1 to 38, wherein the fragment of the heterologous S (spike) protein has a length of at least 1000 amino acids.

40. The IBV or the immunogenic composition of any one of clauses 1 to 39, wherein the fragment of the heterologous S (spike) protein is the ectodomain of the spike protein.

41. The IBV or the immunogenic composition of any one of clauses 1 to 40, wherein the heterologous S (spike) protein or fragment thereof replaces the homologous S protein or fragment thereof.

42. The IBV or the immunogenic composition of any one of clauses 1 to 41, wherein the heterologous S (spike) protein or fragment thereof replaces the naturally occurring S protein or fragment thereof.

43. The IBV or the immunogenic composition of any one of clauses 1 to 42, wherein the heterologous S (spike) protein or fragment thereof replaces the S protein or fragment thereof in 4/91.

44. The IBV or the immunogenic composition of any one of clauses 1 to 43, wherein the IBV is attenuated.

45. The IBV or the immunogenic composition of any one of clauses 1 to 43, wherein the IBV is inactivated.

46. The IBV or the immunogenic composition of any one of clauses 1 to 45, wherein the IBV is genetically engineered.

47. The IBV or the immunogenic composition of any one of clauses 1 to 46, wherein the IBV is a recombinant IBV.

48. The immunogenic composition of any one of clauses 2 to 47, wherein the immunogenic composition is a vaccine.

49. The immunogenic composition of any one of clauses 2 to 48, wherein the immunogenic composition comprises a pharmaceutically acceptable carrier.

50. The immunogenic composition of clause 49, wherein the pharmaceutically acceptable carrier is phosphate buffered saline.

51. The immunogenic composition of any one of clauses 2 to 50, wherein the immunogenic composition is effective in the treatment and/or prophylaxis of clinical signs caused by IBV in a subject of need.

52. The immunogenic composition of any one of clauses 2 to 51, wherein the immunogenic composition protects against a challenge with an IBV strain of the genotype or serotype of the heterologous spike protein.

53. The immunogenic composition of any one of clauses 2 to 52, wherein the immunogenic composition protects against a challenge with strains of Massachusetts, QX, Q1, Arkansas Variant 2 or Brazil genotype.

54. The immunogenic composition of any one of clauses 2 to 53, wherein the immunogenic composition protects against a challenge with strains of Massachusetts genotype.

55. The immunogenic composition of any one of clauses 2 to 54, wherein said immunogenic composition is formulated for a single-dose administration.

56. The immunogenic composition of any one of clauses 2 to 55, wherein said immunogenic composition is administered subcutaneously, intramuscularly, oral, in ovo, via spray, via drinking water or by eye drop.

57. The immunogenic composition of any one of clauses 2 to 56, wherein the immunogenic composition comprises 1 to 10 $\log_{10}$ EID$_{50}$ per dose of the IBV.

58. The immunogenic composition of any one of clauses 2 to 57, wherein the immunogenic composition comprises 2 to 5 $\log_{10}$ EID$_{50}$ per dose of the IBV.

59. The immunogenic composition of any one of clauses 2 to 56, wherein the immunogenic composition comprises 2 to 4 $\log_{10}$ EID$_{50}$ per dose of the IBV.

60. A kit comprising the IBV or the immunogenic composition of any one of clauses 1 to 59.

61. The kit according to clause 60, wherein the kit further comprises an instruction letter for the treatment and/or prophylaxis of diseases of avians.

62. The kit according to clause 60, wherein the kit further comprises an instruction letter for the treatment and/or prophylaxis of diseases of poultry.

63. The kit according to clauses 60, wherein the kit further comprises an instruction letter for the treatment and/or prophylaxis of IB.

64. A method for immunizing a subject comprising administering to such subject an immunogenic composition according to any one of clauses 2 to 59.

65. A method of treating or preventing clinical signs caused by IBV in a subject of need, the method comprising administering to the subject a therapeutically effective amount of an immunogenic composition according to any one of clauses 2 to 59.

66. A method of reducing the ciliostasis in a subject of need, in comparison to a subject of a non-immunized control group of the same species, the method comprising administering to the subject a therapeutically effective amount of an immunogenic composition according to any one of clauses 2 to 59.

67. The immunogenic composition according to any one of clauses 2 to 59 for use in a method for immunizing a subject, the method comprising administering to the subject a therapeutically effective amount of said immunogenic composition.

68. The immunogenic composition according to any one of clauses 2 to 59 for use in a method of treating or preventing clinical signs caused by IBV in a subject of need, the method comprising administering to the subject a therapeutically effective amount of said immunogenic composition.

69. The immunogenic composition according to any one of clauses 2 to 59 for use in a method of reducing the ciliostasis in a subject of need, in comparison to a subject of a non-immunized control group of the same species, the method comprising administering to the subject a therapeutically effective amount of said immunogenic composition.

70. The method or use of any one of clauses 64 to 69, wherein said subject is avian.

71. The method or use of any one of clauses 64 to 70, wherein said subject is poultry.

72. The method or use of any one of clauses 64 to 71, wherein said subject is selected from the list consisting of chicken, turkey, quail, or pheasant.

73. The method or use of any one of clauses 64 to 72, wherein said subject is chicken.

74. The method or use of any one of clauses 64 to 73, wherein the immunogenic composition is administered once.

75. The method or use of any one of clauses 64 to 73, wherein the immunogenic composition is administered at two or more doses.

76. The method or use of any one of clauses 64 to 75, wherein said immunogenic composition is administered subcutaneously, intramuscularly, oral, in ovo, via spray, via drinking water or by eye drop.

77. The method or use of any one of clauses 64 to 76, wherein said immunogenic composition is administered via eye drop.

78. The method or use of any one of clauses 64 to 77, wherein the immunogenic composition comprises 1 to 10 $\log_{10}$ $EID_{50}$ per dose of the IBV.

79. The method or use of any one of clauses 64 to 78, wherein the immunogenic composition comprises 2 to 5 $\log_{10}$ $EID_{50}$ per dose of the IBV.

80. The method or use of any one of clauses 64 to 79, wherein the immunogenic composition comprises 2 to 4 $\log_{10}$ $EID_{50}$ per dose of the IBV.

81. The method or use of any one of clauses 64 to 80, wherein the immunogenic composition is administered to subjects within the first week of age, within the first three days of age, within the first two days of age, or within the first day of age.

82. The method or use of any one of clauses 64 to 81, wherein the immunogenic composition is administered to subjects within the first day of age.

83. The method or use of any one of clauses 64 to 82, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

84. The method or use of any one of clauses 64 to 83, wherein the treatment or prevention results in a prevention or reduction of ciliostasis as compared to subjects of a non-treated control group of the same species.

85. The method or use of any one of clauses 64 to 84, wherein the treatment or prevention results in a prevention or reduction of kidney lesions as compared to subjects of a non-treated control group of the same species.

86. The method or use of any one of clauses 64 to 85, wherein the treatment or prevention results in a prevention or reduction of egg drop as compared to subjects of a non-treated control group of the same species.

87. The IBV or immunogenic composition of any one of clauses 1 to 59 for therapeutic use.

88. The IBV or immunogenic composition of any one of clauses 1 to 59 for use as an immunogen or vaccine.

89. The IBV or immunogenic composition any one of clauses 1 to 59 for use as a medicament.

90. Use of the IBV or immunogenic composition of any one of clauses 1 to 59 for the manufacture of a medicament.

91. Use of the IBV or immunogenic composition of any one of clauses 1 to 59 for the treatment and/or prophylaxis of IBV infections in a subject.

92. An immunogenic composition comprising a 4/91 IBV (infectious bronchitis virus) encoding for a heterologous S (spike) protein or fragment thereof, wherein said 4/91 IBV comprises a Nucleocapsid (N) protein, Envelope (E) protein or Membrane glycoprotein (M) having or consisting of or comprising an amino acid sequence as shown for SEQ ID NO:3, SEQ ID NO:4, SEQ ID NO:5, EU780081 (SEQ ID NO 57), AGY56143 (SEQ ID NO 58), AGY56144 (SEQ ID NO 59) or a sequence having at least 85%, 88%, 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto, and, wherein the heterologous S protein or fragment thereof is selected from a list of genotypes or serotypes consisting of Massachusetts, QX, Q1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto or the heterologous S protein or fragment thereof consists of or comprises an amino acid sequence as shown in SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

93. The immunogenic composition of clause 92, wherein the heterologous S protein is the full length spike protein.

94. The immunogenic composition of clause 92 or 93, wherein the fragment of the heterologous S (spike) protein has a length of at least 500, 750, 1000 or 1075 amino acids from the N-Terminus.

95. The immunogenic composition of any one of clause 92 to 94, wherein the fragment of the heterologous S (spike) protein is the Ectodomain of the spike protein.

96. The immunogenic composition of any one of clauses 92 to 95, wherein the IBV is attenuated.

97. The immunogenic composition of any one of clauses 92 to 96, wherein the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/91attenuated, IB4-91 and CR88.

98. A method of preparing an immunogenic composition for the treatment and/or prophylaxis of IBV infections in a subject comprising:

a.) providing a 4/91 IBV comprising a spike (S) protein, Nucleocapsid (N) protein, Envelope (E) protein or Membrane glycoprotein (M) having or consisting of or comprising an amino acid sequence as shown for SEQ ID NO:2, SEQ ID NO:3, SEQ ID NO:4, SEQ ID NO:5, AGY6140 (SEQ ID NO 54), AF093793 (SEQ ID NO 60), EU914938 (SEQ ID NO 55), KM067900 (SEQ ID NO 56), EU780081 (SEQ ID NO 57), AGY56143 (SEQ ID NO 58), AGY56144

(SEQ ID NO 59) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto; and b.) providing a heterologous S protein or fragment thereof selected from a list of genotypes or serotypes consisting of Massachusetts, QX, Q 1, Arkansas, Variant 2 and Brazil or from an amino acid sequence as shown SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto or providing a heterologous S protein or fragment thereof consisting of or comprising an amino acid sequence as shown in SEQ ID NO: 6, 7, 8, 9, 10, 11, 12, 13, 14, 15, 16 or 17 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and c.) replacing the spike protein of 4/91 IBV of a) with said heterologous S (spike) protein or fragment thereof of b) to have a 4/91 IBV with a heterologous S protein or fragment thereof; and d.) obtaining said 4/91 IBV with a heterologous S protein or fragment thereof; and e.) addition of a pharmaceutically acceptable carrier.

99. The method of clause 98, wherein the fragment of the heterologous S (spike) protein is the Ectodomain of the spike protein.

100. The method of clause 98 or 99, wherein said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

101. The method of clause 98 or 100, wherein the heterologous S protein is the full length spike protein.

102. The method of any one of clauses 98 to 101, wherein the 4/91 IBV is selected from a list of strains consisting of Spain/98/328, Spain/92/35, IR-3654-VM, FR-CR88061-88, FR-85131-85, UK-1233-95, UK/3/91, Spain/00/336, UK/4/91, UK/7/91, UK/793B/91, 4/91-pathogenic, 4/9lattenuated, IB4-91 and CR88.

SEQUENCES OVERVIEW

SEQ ID NO:1 CR88 genome
SEQ ID NO:2: CR88 IBV spike (S) protein.
SEQ ID NO:3: CR88 IBV Nucleocapsid (N) protein.
SEQ ID NO:4: CR88 IBV Envelope (E) protein.
SEQ ID NO:5: CR88 IBV Membrane glycoprotein (M) protein.
SEQ ID NO:6 and 7: Heterologous S protein or fragment from genotype or serotype Massachusetts.
SEQ ID NO:8 and 9: Heterologous S protein or fragment thereof from genotype or serotype QX.
SEQ ID NO:10 and 11: Heterologous S protein or fragment thereof from genotype or serotype Q1.
SEQ ID NO:12 and 13: Heterologous S protein or fragment thereof from genotype or serotype Arkansas.
SEQ ID NO:14 and 15: Heterologous S protein or fragment thereof from genotype or serotype Variant 2.
SEQ ID NO:16 and 17: Heterologous S protein or fragment thereof from genotype or serotype Brazil.
SEQ ID NO:18: pUC57-s CR88 mIBV.
SEQ ID NO:19: IBV H52 Spike nucleic acid coding sequence
SEQ ID NO:20: IBV CR88 Spike nucleic acid coding sequence
SEQ ID NO:21 pUC57-s CR88 rIBV donor plasmid.
SEQ ID NO:22: pUC57-s CR88 rIBV H52 S donor plasmid.
SEQ ID NO:23 to SEQ ID NO:52 Primer.
SEQ ID NO:53 KF377577 (4/91 IBV nucleotide sequence)
SEQ ID NO:54 AGY56140 (4/91 IBV Spike protein amino acid sequence)
SEQ ID NO:55 EU914938 (4/91 IBV Spike protein amino acid sequence)
SEQ ID NO:56 KM067900 (4/91 IBV Spike protein amino acid sequence)
SEQ ID NO:57 EU780081 (4/91 IBV Spike protein amino acid sequence)
SEQ ID NO:58 AGY56143 (4/91 IBV E protein amino acid sequence)
SEQ ID NO:59 AGY56144 (4/91 IBV M protein amino acid sequence)
SEQ ID NO:60 AF093793 (4/91 IBV Spike protein amino acid sequence)
SEQ ID NO:61 Primer

EXAMPLES

The following examples are set forth below to illustrate specific embodiments of the present invention. These examples are merely illustrative and are understood not to limit the scope or the underlying principles of the present invention.

Example 1

Generation of Recombinant IBV CR88 in which the Coding Sequence for the CR88 Spike is Replaced by the Coding Sequence for a Heterologous Spike or Spike Ectodomain Targeted RNA Recombination and Rescue of Recombinant IBV For the generation of recombinant IBV the method of targeted RNA recombination as described by van Beurden et al. (Virol J. 2017; 14(1):109) is applied. A murinized helper virus (mIBV) is generated to enable the targeted recombination of IBV in cell culture.

Construction of an IBV CR88 Murinized Donor Plasmid

To generate the CR88 murinized (m)IBV donor plasmid the donor sequence is synthesized by a commercial supplier: 497 bases of the 5' UTR of the CR88 genome are fused to the 3' part of the lab region (752 bases) and the first 72 bases coding for the CR88 IBV spike, followed by 3753 bases of the MHV spike ectodomain, continuing with the terminal 210 bases of the CR88 IBV spike and the following sequence until the 3' end of the genome. In addition, a SacI restriction site and the sequence of the T7 promoter are added to the 5' end of the donor region, as well as a 100× polyA sequence, followed by a Not I restriction site for linearization at the 3' end. respectively. A silent A to C mutation at position 5634 of the assembled sequence is introduced to generate an XhoI restriction site. The synthesized sequence is inserted into pUC57-simple to yield the pUC57-s CR88 mIBV donor plasmid (SEQ ID NO:18).

Rescue of CR88 mIBV

CR88 mIBV is rescued in analogy to H52 mIBV (van Beurden et al. Virol J. 2017; 14(1):109) with some alterations: The virus allantoic fluid stock is concentrated via ultracentrifugation before isolation of the viral RNA for electroporation. 18 ml of viral allantoic fluid are centrifuged at 50,000×g for 2 hours through a 2 ml 20% Sucrose cushion in THE (Tris, NaCl, EDTA) buffer. The supernatant is discarded and the pellet resuspended in 150 µl TNE buffer followed by RNA isolation with QIAamp viral RNA mini kit (Qiagen). Further, chicken embryo fibroblasts (CEFs)

instead of BHK cells are used for electroporation (2 pulses 250V/300 µF, 10 sec break) and 1.25% DMSO is added to the electroporation mixture.

Construction of an IBV CR88 Donor Plasmid in which the Coding Sequence for the CR88 Spike is Replaced by the Coding Sequence for a Heterologous Spike or Spike Ectodomain Exemplary the construction for the replacement of the CR88 spike by the H52 spike is described. The IBV H52 spike nucleic acid coding sequence (SEQ ID NO:19) is used as a template to replace the IBV CR88 spike nucleic acid coding sequence (SEQ ID NO:20) in the pUC57-s CR88 rIBV donor plasmid (generated as described above for the mIBV plasmid by keeping the complete CR88 Spike sequence (SEQ ID NO:21)). Bases 1657 to 5151 of SEQ ID NO:21 are replaced with the corresponding IBV H52 spike nucleic acid coding sequence (SEQ ID NO:19). This results in the pUC57-s CR88 rIBV H52 S donor plasmid (SEQ ID NO:22) in which the IBV H52 spike is encoded by bases 1657 to 5145. For this, the H52 spike nucleic acid coding sequence and the pUC57-s CR88 backbone sequence are amplified in two separate PCR reactions with Q5® High-Fidelity DNA Polymerase (NEB; see table 1 for primers). The PCR products are purified by QIAquick gel extraction kit (QIagen) and are subsequently used for Gibson assembly with the NEBuilder® HiFi DNA Assembly Cloning Kit (NEB) according to the kit protocol to generate the pUC57-s CR88 rIBV H52 S donor plasmid (SEQ ID NO:22).

TABLE 1

Gibson assembly primers designed with the NEBuilder online tool by NEB and used to generate PCR products to assemble the pUC57-s CR88 rIBV H52 S donor plasmid (SEQ ID NO: 22).

| PCR Product | Primer |
|---|---|
| 1 CR88 backbone | tgattaaaagtcccacatcttttctaatattattaattcttctttgg (SEQ ID NO: 23) <br> ctcttaccagtaacttaccacacttaattaaattaaagactaagtc (SEQ ID NO: 24) |
| 2 H52 Spike | aagtgtggtaagttactggtaagagatgttggtaacacctcttttac (SEQ ID NO: 25) <br> agaaaagatgtgggactttaatcattaaacagacttttaggtctg (SEQ ID NO: 26) |

Targeted RNA Recombination and Rescue of Recombinant IBV

For the rescue of CR88 rIBV with heterologous spike or spike ectodomain, LR7 cells are infected with CR88 mIBV and electroporated with in vitro transcript, generated from the pUC57-s CR88 rIBV H52 S donor plasmid after NotI linearization. Subsequently, cells and supernatant are injected into 8-day old embryonated SPF chicken eggs (VALO BioMedia) which are incubated up to 9 days at 37.5° C. and 60% humidity. The allantoic fluid of eggs with dead embryos is harvested and used for an end-point dilution in 8-day old SPF eggs. Nucleic acids isolation of allantoic fluid samples of the limiting dilution is performed using the MagMAX™ Core Nucleic Acid Purification Kit (ThermoFisher) with the KingFisher™ Duo Prime Purification System (ThermoFisher). Nucleic acids are subsequently analyzed for the presence and relative quantity of rIBV via IBV specific RT-qPCR with a protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the a StepOnePlus™ Real-Time PCR System (ThermoFisher). Afterwards, the positive-tested allantoic fluid of the egg inoculated with the highest dilution is used for propagation in 8-day old embryonated SPF chicken eggs. The allantoic fluid is diluted 1:100 in 1×PBS and 100 µl are injected per egg. Allantoic fluid is harvested 48 hours post inoculation, cleared from debris and stored at −80° C. and again analyzed by RT-qPCR to confirm stock quality.

To confirm the correct insertion of the spike in the generated rIBV, viral nucleic acid is isolated with the QIAamp viral RNA mini kit followed by the SuperScript III One-Step RT-PCR using the primers listed in table 2, QIAquick PCR purification and subsequent Sanger sequencing performed by a commercial supplier.

TABLE 2

PCR and sequencing primers to confirm the correct insertion and spike sequence in CR88 rIBV H52 S.

| PCR | Name | Sequence | Region | Purpose | Amplicon [bp] |
|---|---|---|---|---|---|
| 1 | PO1565 | caggattgtgcatggtggac (SEQ ID NO: 27) | 1ab | PCR+ Sequencing | 2468 |
|   | PO764 | agaaaacctaaaggtcctgc (SEQ ID NO: 28) | S | PCR+ Sequencing |   |
|   | PO618 | taaatggtgatcttgttt (SEQ ID NO: 29) | S | Sequencing | n/a |
|   | PO1410 | tttgtatacgagagccatca (SEQ ID NO: 30) | S | Sequencing |   |
| 2 | PO1400 | ttgccttcagtatgtttgtg (SEQ ID NO: 31) | S | PCR+ Sequencing | 2531 |
|   | PO635 | ctgcgacaagacctcctg (SEQ ID NO: 32) | M | PCR+ Sequencing |   |
|   | PO619 | tgctgcttcctttaataag (SEQ ID NO: 33) | S | Sequencing | n/a |
|   | PO1183 | cgctgttgtgacactctatg (SEQ ID NO: 34) | S | Sequencing |   |

Generation and Characterization of CR88 Recombinant IBV in which the Coding Sequence for the CR88 Spike or Spike Ectodomain is Replaced by the Coding Sequence for a Spike from Another IBV Genotype The same methods as described for the generation of CR88 rIBV H52 S are applied to generate and characterize CR88 recombinant IBV in which the CR88 spike coding sequence (bases 1657 to 5151 in SEQ ID NO:21) or CR88 spike ectodomain coding sequence (bases 1711 to 4941 in SEQ ID NO:21) is replaced with the coding sequences for the IBV spike or spike ectodomain of the serotypes and genotypes listed in Table 3.

TABLE 3

Primers used for Gibson assembly of H52 rIBV donor plasmids with heterologous spikes or spike ectodomains.

| spike | PCR | product | primer |
|---|---|---|---|
| H52 S Ecto SEQ ID NO: 6 | 1 | CR88 backbone | tggccttggtatgtgtgg (SEQ ID NO: 35)<br>agcactacatagtgcatac (SEQ ID NO: 36) |
|   | 2 | H52 S Ecto | tctttggtatgcactatgtagtgctgctttgtatgactcgagttc (SEQ ID NO: 37)<br>tggcaagccacacataccaaggccacttaatataagttttgagtattgaaagttttc (SEQ ID NO: 38) |
| QX S SEQ ID NO: 7 | 1 | CR88 backbone | tgattaaaagtcccacatcttttctaatattattaattcttctttgg (SEQ ID NO: 23)<br>ctcttaccagtaacttaccacacttaattaaattaaagactaagtc (SEQ ID NO: 24) |
|   | 2 | QX S | aagtgtggtaagttactggtaagagatgttggtgaagtcactg (SEQ ID NO: 39)<br>agaaaagatgtgggacttttaatcattaaacagacttttttaggtctg (SEQ ID NO: 26) |
| QX S Ecto SEQ ID NO: 8 | 1 | CR88 backbone | tggccttggtatgtgtgg (SEQ ID NO: 35)<br>agcactacatagtgcatac (SEQ ID NO: 36) |
|   | 2 | QX S Ecto | tctttggtatgcactatgtagtgctaatttgtttgattctgataataattatg (SEQ ID NO: 40)<br>tggcaagccacacataccaaggccacttaatataagttttaattattgaaagttcttc (SEQ ID NO: 41) |
| Q1 S SEQ ID NO: 9 | 1 | CR88 backbone | tgattaaaagtcccacatcttttctaatattattaattcttctttgg (SEQ ID NO: 23)<br>ctcttaccagtaacttaccacacttaattaaattaaagactaagtc (SEQ ID NO: 24) |
|   | 2 | Q1 S | aagtgtggtaagttactggtaagagatgttggggaagtcactg (SEQ ID NO: 42)<br>agaaaagatgtgggacttttaatcattaaacagacttttttaggtctg (SEQ ID NO: 26) |
| Q1 S Ecto SEQ ID NO: 10 | 1 | CR88 backbone | tggccttggtatgtgtgg (SEQ ID NO: 35)<br>agcactacatagtgcatac (SEQ ID NO: 36) |
|   | 2 | Q1 S Ecto | tctttggtatgcactatgtagtgctgctttgtttgataataatgaaac (SEQ ID NO: 43)<br>tggcaagccacacataccaaggccatttaatataagtcttgagtattgaaag (SEQ ID NO: 44) |
| Ark S SEQ ID NO 11 | 1 | CR88 backbone | ggtaacttaacaatacagacctaaaaagtctg (SEQ ID NO: 61)<br>ctcttaccagtaacttaccacacttaattaaattaaagactaagtc (SEQ ID NO: 24) |

TABLE 3-continued

Primers used for Gibson assembly of H52 rIBV donor plasmids with heterologous spikes or spike ectodomains.

| spike | PCR | product | primer |
|---|---|---|---|
| | 2 | Ark S | aagtgtggtaagttactggtaagagatgttggtgaagtcactg (SEQ ID NO: 39)<br>gtctgtattgttaagttaccacatcgttatc (SEQ ID NO: 45) |
| Ark S Ecto<br>SEQ ID NO 12 | 1 | CR88 backbone | tggccttggtatgtgtgg (SEQ ID NO: 35)<br>agcactacatagtgcatac (SEQ ID NO: 36) |
| | 2 | Ark S Ecto | tctttggtatgcactatgtagtgctaatttatatgacaacgaatcttttg (SEQ ID NO: 46)<br>tggcaagccacacataccaaggccacttaatataagttttgagtattgaaag (SEQ ID NO: 47) |
| Variant 2 S<br>SEQ ID NO 13 | 1 | CR88 backbone | ggtaacttaacaatacagacctaaaaagtctg (SEQ ID NO: 61)<br>ctcttaccagtaacttaccacacttaattaaattaaagactaagtc (SEQ ID NO: 24) |
| | 2 | Variant 2 S | aagtgtggtaagttactggtaagagatgttggtgaagtcactg (SEQ ID NO: 39)<br>gtctgtattgttaagttaccacatcattatcaaaag (SEQ ID NO: 48) |
| Variant 2 S Ecto<br>SEQ ID NO 14 | 1 | CR88 backbone | tggccttggtatgtgtgg (SEQ ID NO: 35)<br>agcactacatagtgcatac (SEQ ID NO: 36) |
| | 2 | Variant 2 S Ecto | tctttggtatgcactatgtagtgctgctctgtttgataataatcag (SEQ ID NO: 49)<br>tggcaagccacacataccaaggccacttaatataagttttaattattgaaagttcttc (SEQ ID NO: 41) |
| Brazil S<br>SEQ ID NO 15 | 1 | CR88 backbone | tgattaaaagtcccacatcttttctaatattattaattcttctttgg (SEQ ID NO: 23)<br>ctcttaccagtaacttaccacacttaattaaattaaagactaagtc (SEQ ID NO: 24) |
| | 2 | Brazil S | aagtgtggtaagttactggtaagagatgttggttcaacctcttttac (SEQ ID NO: 50)<br>agaaaagatgtgggacttttaatcattaaacagacttttaggtctg (SEQ ID NO: 26) |
| Brazil S Ecto<br>SEQ ID NO 16 | 1 | CR88 backbone | tggccttggtatgtgtgg (SEQ ID NO: 35)<br>agcactacatagtgcatac (SEQ ID NO: 36) |
| | 2 | Brazil S Ecto | tctttggtatgcactatgtagtgcttctttgtacaataatgatagctatg (SEQ ID NO: 51)<br>tggcaagccacacataccaaggccatttaatataagtttttaaaatagaaagtgtttc (SEQ ID NO: 52) |

Primers for characterization and identification of the different spike sequences in the recombinant IBV are adapted to the respective spike sequence if necessary.

Example 2

In Ovo Replication Kinetics

Eight Eight day-old embryonated chicken eggs are inoculated with $10^2$ 50% embryo infectious dose ($EID_{50}$) of the recombinant IBV and appropriate controls. Eggs are incubated at 37.5° C., 60% humidity and candled daily after 0, 8, 24, 34, 48 and 72 hours of incubation and embryo mortality is recorded. Five preselected eggs per sample and time point are removed and transferred to 4° C. for at least 2 hours. Subsequently, the allantoic fluid is harvested and stored at −80° C. For analysis, samples are thawed and diluted 1:10 in 1×PBS without Ca and Mg and nucleic acids are extracted with the QIAamp DNA Blood Mini kit (Qiagen) with addition of carrier RNA using the Hamilton Starlet pipet robot. Extracted nucleic acids are analyzed by RT-qPCR for the relative amount of IBV RNA with a protocol adapted from Callison et al. (J Virol Methods. 2006; 138(1-2): 60-5). Briefly, the same primers and probe are used and the thermoprofile is adapted for the use of TaqMan® Fast Virus 1-Step Master Mix (ThermoFisher) and the ABI™ 7900HT Fast Real-Time PCR System (Thermo Fisher Scientific). All nucleic acid samples are analyzed in triplicates using a 10-fold dilution series of IBV H52 as reference.

Figures 1, 2:
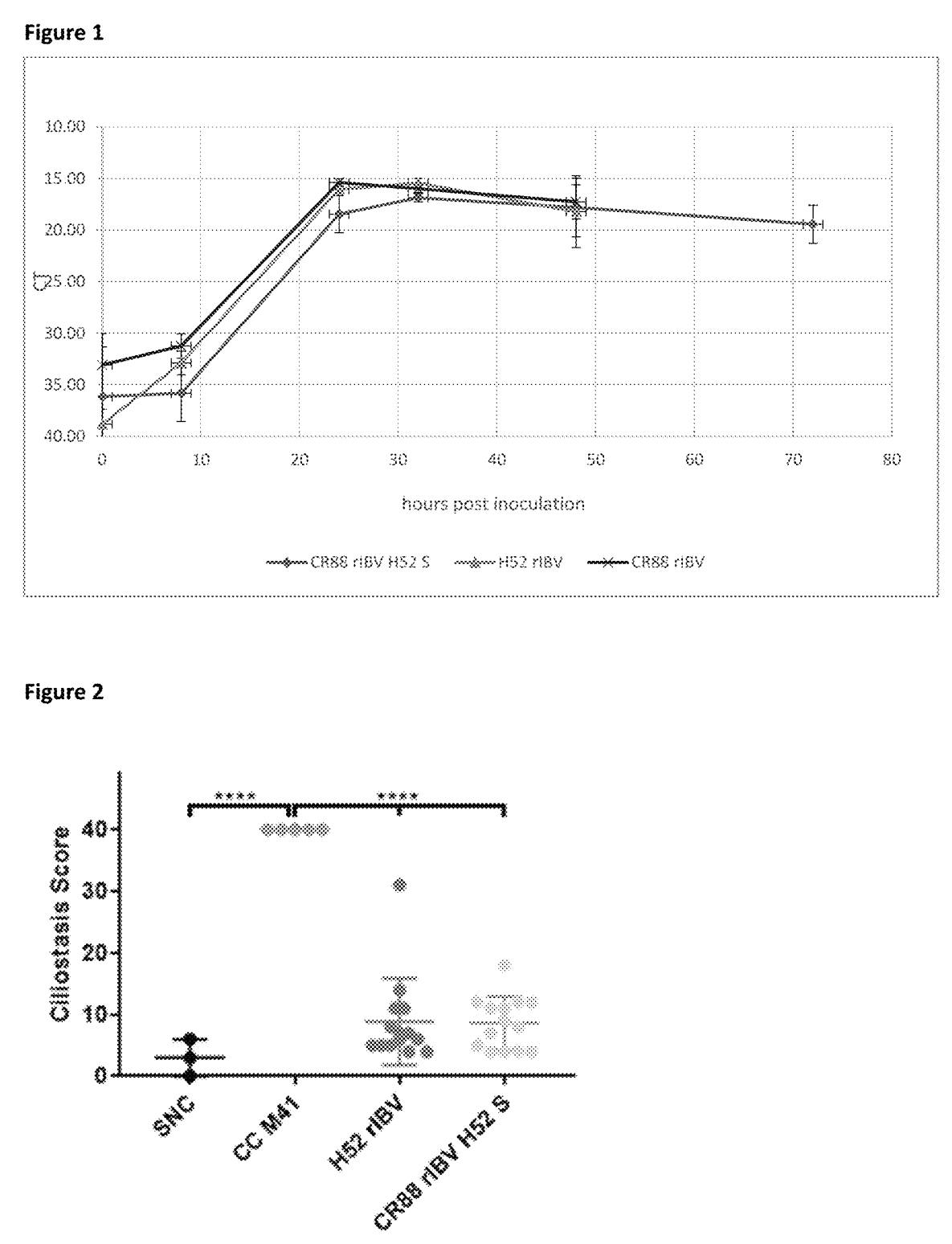

Replication of CR88 rIBV H52 S in comparison to the recombinant wild type viruses CR88 and H52 is analyzed by injecting 8 day old SPF eggs with 100 $EID_{50}$ at time point 0. Slightly different replication kinetics are observed at early time points. However, after 32 hours all viruses reach comparable ct values. All embryos are alive at 32 hours post inoculation, while at time point 48 hours post infection all remaining embryos for the wild type controls are dead. In contrast, 60 to 80% of the embryos infected with CR88 rIBV H52 S were still alive at time points 48 and 72 hours post inoculation. The replication of CR88 rIBV H52 S is considered equally efficient compared to the wild type viruses as all viruses reach a plateau after 32 hours (see FIG. 1).

Example 3

Preparation of Vaccine and Challenge Virus

To demonstrate the efficacy of the CR88 rIBV with heterologous spike or spike ectodomain in chickens, an aliquot of the virus stock is thawed and 10-fold diluted in 1×PBS to determine the 50% embryo infectious dose ($EID_{50}$) by inoculation of 100 µl into five 8-day old embryonated chicken eggs per dilution. Eggs are incubated at 37.5° C., 60% humidity until 7 days post inoculation. Eggs with dead embryos after 24 hours are excluded from the experiment. All other eggs with dead embryos at 7 days post inoculation are considered positive. All eggs with living embryos are candled from the bottom at 7 days post inoculation to identify dwarfs, which are considered positive. The $EID_{50}$/ml is calculated with the formula of Reed and Muench (Am J Epidemiol, 1938; 27(3):493-497). For vaccination the virus stock is diluted in 1×PBS to obtain a titer of $10^{4.3}$ $EID_{50}$/ml ($10^3$ $EID_{50}$ per chicken in 50 μl).

The challenge viruses M41, QX, Q1, Ark, Variant 2 and Brazil are propagated in 10-day-old embryonated SPF eggs. 24 hours post inoculation the eggs are transferred to 4° C. for at least 2 hours. The allantoic fluid is harvested, aliquoted and stored at −80° C. The virus titer is determined as described above. The titer is set to $10^{4.3}$ to $10^{5.3}$ $EID_{50}$/ml by dilution with 1×PBS ($10^3$ to $10^4$ $EID_{50}$ per chicken in 50 μl).

Example 4

Determination of Vaccine Efficacy

Fertilized SPF eggs are incubated for 18 days in an egg setter at 99.7° F. and 50% humidity with 1 turn per hour. At day 18 of incubation the eggs are candled and fertile eggs are transferred to the hatcher and incubated at 99° F. and 70% humidity until hatch. Chicks without clinical signs or deformation are randomly distributed into respective treatment groups and transferred into separate isolators. At least two chicks serve as strict negative control (SNC) group, five chicks are enrolled in the challenge control (CC) group and at least 10 in groups which are vaccinated with the recombinant IBV with heterologous spike or spike ectodomain and subsequently challenged. Animals are kept under housing conditions in compliance to local and national requirements for animal welfare recommendations. The light regime is adjusted to 16 hours light per day. Feed and water are provided ad libitum. After transfer to the isolator, chicks are vaccinated (1-day old) with $10^3 EID_{50}$ per chicken via eye drop (total volume 50 μl, 25 μl per eye) while the SNC and CC groups remain untreated. At 21 days post vaccination chickens of the CC and vaccinated groups are challenged with $10^3$ to $10^4$ $EID_{50}$ per chicken of the respective spike-homologous challenge strain (M41, QX, Q1, Ark, Variant 2 or Brazil) via eye drop (total volume 50 μl, 24 μl per eye). At 7 days post challenge all chickens are euthanized, choanal swabs are taken and kidneys are removed and stored in RNAlater Stabilization Solution (ThermoFisher) at 4° C. for IBV-specific RT-qPCR analysis. In addition, tracheas are removed and transferred into 50 ml tubes with warm cell culture medium. Afterwards, tracheas are cleaned from connective tissues and flushed with cell culture medium. The tracheas are cut into tracheal rings using the McIlwain tissue chopper set to 0.6-0.8 mm slice thickness. Per trachea three rings of the upper part, four rings of the middle part and three rings of the lower part are analyzed for ciliar beating by light microscopy and scored for ciliostasis (see table 4). A ring is recorded as normal if more than 50% of the internal ring shows vigorous ciliar movement (Score 2 and lower). A ring is recorded as positive for ciliostasis if less than 50% of the cilia are beating (Score 3 and 4).

For IBV-specific RT-qPCR analysis kidney tissue pieces are warmed up to room temperature and transferred to separate 2 ml Precellys tubes, which are filled with medium and PBS, respectively. Kidneys are homogenized with the Precellys® tissue homogenizer (Bertin Instruments) for 1×20 sec at 6800 rpm. Choanal wabs are eluted in 2 ml 1×PBS. Nucleic acids are isolated from 200 μl eluate and tissue homogenate respectively using the MagMAX™ Core Nucleic Acid Purification Kit (ThermoFisher) and the KingFisher™ Duo Prime Purification System (ThermoFisher). RT-qPCR is performed as described for the in ovo kinetics above, except for using a StepOnePlus™ Real-Time PCR System (ThermoFisher) for analysis in duplicates.

TABLE 5

Scoring of ciliostasis in tracheal rings.

| Ciliar activity [%] | Ciliostasis score |
|---|---|
| 100 | 0 |
| <100-75 | 1 |
| <75-50 | 2 |
| <50-25 | 3 |
| <25-0 | 4 |

Example 5

Efficacy of Recombinant IBV 4/91 Encoding a Heterologous Spike or Spike Ectodomain The objective of the studies is to demonstrate that vaccination with a recombinant IBV CR88 (4/91 genotype and serotype) encoding a heterologous spike or fragment thereof is able to confer protection against challenge with a spike-homologous challenge strain.

It is analyzed if the recombinant IBV CR88 (4/91 genotype) encoding the spike ectodomain of IBV H52 (Mass genotype) is able to confer protection against challenge with a virulent M41 strain (Mass genotype), considered as homologous challenge for the encoded IBV H52 spike and as heterologous challenge considering the IBV CR88 backbone. All chickens are observed daily for clinical signs. No clinical signs are recorded after vaccination or challenge. Back titrations for the vaccination with CR88 rIBV H52 S and the H52 rIBV wild type at 1-day of age determine a titer of $10^{4.38}$ $EID_{50}$/ml and $10^{4.5}$ $EID_{50}$/ml, respectively (target $10^{4.3}$ $EID_{50}$/ml) as well as $10^{4.32}$ $EID_{50}$/ml (target $10^{4.3}$ $EID_{50}$/ml) for the M41 challenge virus applied at 21 days post vaccination. Ciliostasis is scored as described above and results are depicted in and summarized in table 5.

TABLE 5

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | Not affected [%] |
|---|---|---|---|---|
| 1 | — | — | 3.0 | 100 |
| 2 | — | M41 | 40.0 | 0 |
| 3 | H52 | M41 | 8.9 | 93 |
| 4 | CR88 rIBV H52 S | M41 | 8.6 | 93 |

All animals of the strict negative control show normal ciliar movement while all animals of the challenge control group are positive for ciliostasis. In contrast, 93% of the animals vaccinated with CR88 rIBV H52 S or H52 rIBV wild type are protected. In addition, the viral load in the kidneys of animals vaccinated with CR88 rIBV H52 S is reduced compared to the animals of the challenge control (FIG. 3).

Further, it is analyzed if the recombinant IBV CR88 encoding the spike of IBV QX is able to confer protection against challenge with a virulent D388 QX strain, considered as homologous challenge for the encoded IBV QX spike and as heterologous challenge considering the IBV CR88 backbone. All chickens are observed daily for clinical signs. No clinical signs are recorded after vaccination or challenge. Back titrations for the vaccination with CR88 rIBV QX S and the QX vaccine at 1-day of age determine titers that exceeded $10^5$ $EID_{50}$/ml (target $10^{4.3}$ $EID_{50}$/ml) as well as $10^{4.83}$ $EID_{50}$/ml (target $10^{4.3}$ $EID_{50}$/ml) for the D388 QX challenge virus applied at 21 days post vaccination, respectively. Ciliostasis is scored as described above and results are depicted in and summarized in Table 6 Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0).

TABLE 6

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | Not affected [%] |
|---|---|---|---|---|
| 1 | — | — | 0 | 100 |
| 2 | — | D388 QX | 38.4 | 0 |
| 3 | QX vaccine | D388 QX | 3.5 | 100 |
| 3 | CR88 rIBV QX S | D388 QX | 8.9 | 100 |

All animals of the strict negative control show normal ciliar movement while all animals of the challenge control group are positive for ciliostasis. In contrast, 100% of the animals vaccinated with CR88 rIBV QX S or the QX vaccine are protected.

Similar results are obtained with the other CR88 rIBV with heterologous spikes or spike ectodomains.

The results highlight the suitability of IBV H52 as a potent backbone for the generation of recombinant IBV with heterologous spike and show excellent results, in particular, when compared to prior art data for the IBV Beaudette backbone.

The invention claimed is:

1. A method of reducing or eliminating subsequent Infectious Bronchitis Virus-infection (IBV-infection) clinical signs in a subject, relative to a non-vaccinated control subject of the same species, the method comprising administering to the subject an immunogenic composition comprising a genetically engineered 4/91 IBV encoding for a heterologous IBV S protein or fragment thereof in a pharmaceutically-acceptable carrier, wherein the heterologous IBV S protein or fragment thereof comprises an amino acid sequence having at least 90% sequence identity to at least one of SEQ ID NOs: 6, 7, 8, 9, 10, 11, 12, 13, 14, 15, 16, or 17.

2. The method of claim 1, wherein the administration reduces or eliminates ciliostasis risk in the subject, relative to a non-vaccinated control subject of the same species.

3. The method of claim 1, wherein the subject is a poultry.

4. The method of claim 1, wherein the administration reduces or eliminates ciliostasis, rales, egg drop, kidney lesions, watery diarrhea, weight loss, viral load, and/or viral shedding in the subject relative to a non-vaccinated control subject of the same species if the subject is subsequently infected with IBV.

5. The method of claim 1, wherein the heterologous IBV S protein or fragment thereof is from an IBV with a genotype or serotype selected from: Massachusetts, QX, Q1, Arkansas, Variant 2, and Brazil.

6. The method of claim 1, wherein the 4/91 IBV is attenuated.

7. The method of claim 1, wherein the immunogenic composition is a vaccine.

8. The method of claim 1, wherein the immunogenic composition is part of a kit.

9. The method of claim 1, wherein the immunogenic composition is administered to the subject.

10. The method of claim 1, wherein the heterologous IBV S protein or fragment thereof is not a 4/91 IBV genotype or serotype.

* * * * *

SEQUENCE LISTING

```
<160> NUMBER OF SEQ ID NOS: 61

<210> SEQ ID NO 1
<211> LENGTH: 27659
<212> TYPE: DNA
<213> ORGANISM: Unknown
<220> FEATURE:
<223> OTHER INFORMATION: Description of Unknown:
      Avian infectious bronchitis virus sequence

<400> SEQUENCE: 1
acttaagtgt gatataaata tatatcatac atactagcct tgtgctagat ttccaactta     60
acaaaacgga cttaaatacc tacagttggt ccctataggt gttccattgc agtgcacttt    120
agtgccctgg atggcacctg gccacctgtc aggttttgt tattaaaata atattgttgc    180
tggtatcact gcttgttttg ccgtgtctca ctttatacat ccgttgcttg ggctacctag    240
tatccagcgt cctactggcg ttgtggtcgg ttcgagtgcg aagaacctct ggttcatcta    300
gcggtacgcg ggtgtgtgga agtagcgctt cagacgtacc ggttctgttg cgtgaaatac    360
ggggtcacct cccccacat acctctaagg gcttttgagc ctagcgttgg gctacgttct    420
cgcacaaggt cggctatacg gcgtttgtag ggggtagtgc caaacaaccc ctgaggtgac    480
aggttctggt ggtgtttagt gagcagacat acaatagaca gtgacaacat ggcttcaagc    540
ctaaaacagg gagtatctcc caaaccaagg gatgtcattc ttgttgccaa agacattccc    600
gaacaactcc gtgacgcttt gttttctat acgtcacata aacccaagga ttacgctgaa    660
```

```
gcctttgccc ttaggcagaa gtttgaccgt aatctgcaga ctgggaagca gtttaaattt      720
gaaactgtgt gtggtctctt cctcttgaag ggagttgaca aaataacacc tggtgtccca      780
gcaaaagttt taaaagccag ttctaagttg gcagatttag aaggcatttt tggtgtctct      840 cctttgcac ggaagtaccg tgatctgttg aaaacagcat gccagtggtc tcttacagta      900
gatacactgg atgctcgtgc acaaactctt gatgaaattt ttaaccccac tgaaatactt      960
tggcttcagg tggctgcaaa aattcaagtt tcagctatgg caatgcgcag gcttgttgga     1020
gaagtaactg caaaagtcat ggatgctctt ggctctaatt tgagtgctct ttttcaaatt     1080
gttagagaac aaatagtcag aatctttcaa aaggcactgg ctattttga agatgtgagt      1140 gaattaccac agcgtattgc agcacttaag atggcctttg ccaagattgc taagtcaatt     1200
actgttgtgg ttgtggaaag aactctagtt gttagagagt tcgcaggaac ttgtcttgca     1260
agcatcaatg gtgctgttgc aaaattcttc gaagaacttc caaatggctt tatgggttct     1320
aaaattttca caacattggc cttctttaaa aagcagctg tgaaaattgt ggaaaatata     1380
ccaaatgcac caagaggtac tagaggtttt gaggtcgttg gcaatgccaa aggtacacaa     1440
gttattgtgc gtggcatgcg aaatgactta acgctgcttg accaaaaagc tgacattcct     1500
gttgagaaag aaggttggtc tgcaatttt gaaggacatc tttgctatgt ctttaagagc      1560
ggtgaccgtt tttatgcggc acctcttct ggaaattttg cattgcatga tgtacattgt      1620
tgtgagcgtg ttgtctgtct gtctgatggt gtaacaccgg agataaatga tggactcatt     1680
ctagcagcaa tttattcatc tgttagtgtt tcagaactcg tggcagcact taaaaagggc     1740
gaaccattta agttcttggg gcataaattt tgtgtacgcga aggacgcagc agtgtcgttt    1800
actttagcga aggctgccac tattgcagat gtactgaagc tgtttcaatc agctcgtgtg     1860
caagcggaag atgtgtggtc tgcatttact gaaaagtctt ttaatttctg gaaactcgca     1920
tatggaaaag tgcgtaatct tgaagaagtt gtgaagactc atttttgtaa agctcaaatg     1980
tcacttatcg ttctagtagc agtgcttgga aaggtgttt ggcatattgc ttctcaggtc      2040
atctacaaat taggtggtct ttttactaaa gttgttgact tttgtgaaaa acactggaaa     2100 ggttttgtg tacagttgaa gaaggctaag ctcattgtga ctgaaaatct ttgtgttctt      2160
aagggagtgg cacagcattg ttttcaacta ttgctggatg caatacattc tttgtatatg     2220
agttttaaga agtgtgcact tggtagaatt catggagact tactcttctg gaaaggggt      2280 gtacacaaaa ttgttcaaga tggcgatgaa gtttggtttg acgccattga tagtattgat     2340
gttgaagatc tgggtgttgt caaagaaaaa cctatagatt ttgaggtttg tgatgacgta     2400
acacttccag aaaatcaacc cggtcatatg gttcaaatcg aggatgacgg aaagaactat     2460
atgttcttcc gcttcaaaaa ggatgagaat atttattata caccaatgtc tcaacttggt     2520
gcaattaatg tagtttgcaa agcaggcggc aaaaccgtta cctttggaga cattacagtg     2580
aaagaaatac cgccacctga tgtcgtgcct attaaggtta gcatagagtg ttgtggtgag     2640
ccatggaata caatcttcaa gaaagcttat aaagagccca ttgaagttga cagacctc       2700 acagttgaac aattgctctc tgtgatttat gagaaaatgt gtgacgacct caaactgttt     2760
ccagaggcac ctgagcctcc accatttgag aatgttgccc ttgttgataa gaacggtaaa     2820
gatttggatt gcataaaatc atgccacctt atctaccgtg attgtgagag cgatgatgac     2880
atcgaggaag aagatgctga agagtgtgac accgattcag ctgatgctga agcatgtgac     2940
acagcctcag agtgtgaaga gaggacgag gatactaaaa tgttggctct tatacaagac     3000
ccagcaagta ataaatacc cttccacttt gatgatgatt atagcgtcta taatggatgt     3060
```

-continued

```
attgttcata gagacgctct tgatgtagtg aatctaccat ctggcgaaga aacttttgtt      3120
gttaataact gttttgaggg agctattaaa ccactcccac agaaagttat tgatgttcta      3180
ggtgactggg gcgaggctgt tgatgcacaa gaacaattgt gtcaacagga atctacccaa      3240
gtcacacttg agaaaccagt tgagggtcct actggtattt gtcacgtaat ggctgaacaa      3300
gctgttgttg atgaacagga ggtagtttct gtatttgaag aaaagtctga ggttattgtt      3360
tacacacctg cagatctgga agttgttaaa gaaacagcag gagaacttga tgagttcatt      3420
ctcatctttg atgtccctaa agaagaagtt gtgtctcaag agaaagataa gccacaggtt      3480
gagcaagagc ctactcaagt tgttaaacca acgtgaga agaaggctaa aaagttcaga        3540
gttaaaccat ctacatgtga aaagcccaaa ttttttggagt acaaaacatg tgtgggtgat     3600
ctgactgttg taattgctaa ggcattggat gagtttaaag agttctgcat tgtaaacgct      3660
gcaaatgaac atatgtctca tggtggtggc gttgcgaaag caattgcaga cttctgtgga      3720
cctgattttg tggaatattg tgaggcctat gttaagaaac atgggccaca acagagactt      3780
gttacacctt cgtttgtcaa gggcattcaa tgtgtgaaca atgttgtggg acctcgtcat      3840
ggagacagca acttgcgtga gaaactcgtt gttgcttaca agaatgttct tgtggatggc      3900
gtcttcaact atgtagtgcc agttctctct tcagggattt ttggtgtgga ttttaaaatg      3960
tcaatagacg caatgcgtga agcctttgat ggttgcgaca tacgcatcct tttgttttct      4020
ctgagtcaag aacacatcga ctattttgat gtaacttgca agcagaagac aatttatctt      4080
acggaggatg tgttaaaata ccgctccgtt gttgtaaaac ctggcgactc attgagtcaa      4140
tttggacagg tttttgctaa aaataaggca gtctttacag ctgatgatgt tgaggataaa      4200
gaaatcctct tcgttcctac tactgacaag actgttcttg attattatca tttagatgcg      4260
caaaagtatg tgatatattt acaagctctt gcgcagaaat gggatgttca atatagggac      4320
aattttattg cattagagtg gcgtgatgga aattgctggg ttagttcagc aatagtgctc      4380
cttcaggctg ctaaggtaaa gtttagaggt tttcttgcag aagcatgggc taagtttttg      4440
ggtggtgatc ccactgattt tgtggcctgg tgttatgcaa gttgcaatgc taaagttggt      4500
gagttttcag atgctaattg gctcttggct aatctggcag aacattttga tgcagattac      4560
acgaatgcac ttcttaagaa gcgcgtatca tgtaactgcg gtgttaagag ttatgagctt      4620
aggggtcttg aagcttgcat tcaaccagta agggcaccta accttctaca ttttaagaca      4680
caatattcaa attgcccaac ctgtggcgca aatagtacgg atgaagtaat agaagcttca      4740
ttaccttact tattgctctt tgctaccgat ggtcctgcta cagttgattg tgatgaaaat      4800
gctgtaggga ctgttgtttt cattgggtct actaatagtg gacactgtta tacacaagcc      4860
atgggtaagg cttttgataa tcttgctaaa gatagaaaat ttggaaagaa gtcgccttac      4920
attacagcaa tgtacacacg cttctcccctt aagagtgaaa acccttttgcc tgtcaagcag     4980 agccagggta aaactaaagt agtaaaagaa gatgtttcta atctagcaac aagttcaaaa     5040
gtcagttttg atgatcttac tgactttgag cagtggtatg atagcaacat ctatgaaagt      5100
cttaaagtgc aggaaacgcc tgataattct gatgggtatg tgtcatttac aacaaaagaa      5160
gattctaagt tgccactgac acttaaagtt agaggtatta atcagttgt tgattttagg      5220 tcgaaggatg gtttcactta caaattaata cctgatattg atgaaaattc aaaagcacca      5280
atttactatc cagtcttgga ctctattagt cttaaggcaa tatgggtgga aggtggtgct      5340
aattttgttg ttgggcatcc aaattattat agtaaatctc tccgcattcc tacttttttgg     5400
```

```
gaaagtgcag agagttttgt taaaatgggt gataaagttg atggtgtaac tatgggcctt   5460
tggcgtgcag agcatcttaa caaacctaat cttgagaaaa ttttcaacat tgctaagaaa   5520
gctattgttg gatctagtgt tgttactacg caatgtggta aagtaattag taaggcggct   5580
acattcattg ctgataaaat aggtgggggt gtagttcgca acattataga tagaattaag   5640
ggtctttgtg ggtttacacg tgggcatttt gaaagaaaat tgtctccaca attcataaaa   5700
acacttatat tcttcttctt ctactttata aaggctagtg ctaagggttt agttgctagc   5760
tataagaatg tgttatgtaa ggtggtattc gctactttat ttatagtgtg gtttatatat   5820
acaagtaatc cagtagtgtt tactggaaca cgtatgttag acttcctatt tgagggttct   5880
ttgtgtggtc cttataatga ctacggtaaa gattcttttg atgtgttacg ctattgtgga   5940
gatgatttta cttgtcgtgt gtgtttacat gacagagact ctctacattt gtataaacat   6000
gcttatagca tagaacagat ttataaagct gcaagttctg gcattgtttt taattggaat   6060
tggctttatt tggtctttct aattttattt gttaagccag tggcaggttt tgttattatt   6120
tgctattgtg ttaagttttt agtgttgagt tcaactgtgc tccaaactgg tgtaggtttt   6180
ctagactggt ttattcaaac agttttact cactttaatt ttatgggtgc aggtttctat   6240
ttctggctct tttataaatt gtacatacag gttcatcata tactgtattg taaggatata   6300
acatgtgaag tgtgtaagag agttgcacgc agtaacaggc atggggttag tgttgttgtt   6360
ggtggacgca agcaaattgt gcatgtgtac actaactctg gttacaactt ttgtaagaga   6420
cataattggt attgtaggaa ttgtgatgta tatggtcacc aaaacacatt tatgtctcct   6480
gaagttgctg gtgagctgtc tgaaaagctt aaacgccatg ttaaacctac agcacatgct   6540
taccacgttg tggatgaggc ttgcgtagtt gatgattttg ttaacttaaa atacaaagct   6600
gcaactcctg gtaaggatgg tgcacctcct gcagttaaat gtttcagtgt tacagatttc   6660
ttgaagaaag ctgttttct taaggatgcg ctgaaatgtg aacaaatatc taatgatggt   6720
tttatagtgt gtaatacgca gagtgcgcat gctttagagg aagcaaagaa tgcagccatc   6780
tattatgcgc aatacctgtg taaacctata cttatactcg accaggcact ctaccagaat   6840
ttaatagtgg aacctgtatc gaagagcgtt gtcaacaaag tgtgtgacat tttgtctagg   6900 ataaatttctg tagatactgc atctttggat tataaagcag gtacagttcg tgatgccttg   6960
ctgtctgtta ctaaagatga agaagctgta gatatggcta tcttctgtca taatcatgaa   7020
gttgaatata caggtgatgg ttttactaat gttataccgt catatggtat agaccctgat   7080
aaattaacac ctcgtgatag agggttttg ataaatgcag atgcttctgt tgctaactta   7140
agagttaaaa atgctccgcc ggtagtatgg aagttttctg atcttattaa gttgtctgac   7200
agttgtctta atatttaat ctcagcaact gtcaagtcag ggtctcgttt ctttataaca   7260
agatctggtg ctaaacaaat ttttcctgt agtactcaga aattgttggt agagaaaaag   7320
gctggtggtg tcattagtgg tacctttaat tggtttaaga gttgttgtaa atggctcttg   7380
atcttctatg tgctttttac attgtgttgt ttgggttgtt atcatatgga gacgaataaa   7440
agttttgttc atcctatgta tgatgttaac tctacaatgc atgttgaagg ctttaaggtt   7500
atagataaag gtgttattag agacattgta ccagaggatg cttgtttctc taataagttt   7560
gctaactttg atgcattttg gggtaaacca tatgtgaata gtagagactg tccaattgtt   7620
acagcagtca tagatggcgc tggaacaata gcagctggtg ttcctggttt tgtagactgg   7680
gttcttgatg gtgttatgtt tgtacacatg acacaaacag aaagaaaacc ctggtacatt   7740
cccacgtggt ttaacagaga aattgttggt tacactcagg attcaattat tactgaaggt   7800
```

```
agtttttata catctatagc gttgttttct gctaggtgtt tatacttaac agccagtaat   7860
acaccgcaat tgtattgttt taatggtgat aatgatgctc ctggagcctt accatttggt   7920
agtattgttc ctcataaggt ctacttccaa ccaaatggtg ttaggcttgt agttccacaa   7980
caaatactac acacacccta catagtgaag tttgtttcag acagctattg tagaggtagt   8040
gtatgtgagt atactaaacc aggttactgt gtgtcattga actcacagtg ggttttgttt   8100
aatgatgaat acacaagcaa acctggcgtt ttctgtggtt ctactgttag agaacttatg   8160
tttaatatgg ttaatacatt ctttactggt gtcaatccta atatttatat gcaactagca   8220
actatgtttt tgatactagt tgttgttgtt ttaattttg caatggttat aaagtttcaa   8280
ggtgttttta aagcttatgc gaccattgtt tttacaataa tgttagtttg ggttgttaat   8340
gcatttgttt tgtgtgtaca tagttataac agtgttttag ctgttatatt attggtaatc   8400
tattgttatg catcattggt tacaagtcgt aatactgcta taataatgca ttgttggctt   8460
gtgtttacct ttggtttaat tgtacccata tggttggcgt gttgctacct ggcatttgtt   8520
ttatatatgt acacaccatt gttttttctgg tgttacggta ctactaaaaa tactcgtaaa   8580
ttgtatgatg gcaacgagtt tgttggtagt tatgatcttg ctgcgaagag cacttttgtt   8640
attcgcggtc ctgaatttgt taagcttacg aacgagatag gtgataagtt tgaacactat   8700
ctctcagcgt atgctagact taaatactac tcaggcactg gcagtgaaca agattacttg   8760
caagcctgtc gtgcatggtt agcttatgct ttggaccagt atagaaatag tggtgtggaa   8820
attgtgtata ctccaccacg ttactctatt ggtgttagta gattacaggc tggttttaag   8880
aaactagttt ctcctagtag tgctgttgaa aggtgcattg ttagtgtctc ttatagaggt   8940
aataagctta atggactgtg gctaggtgat actatctact gtccgcgaca tgttctaggc   9000
aagttttcag gcgatcaatg gagtgatgta cttaatcttg ctaataatca tgagtttgag   9060
gttgtaactc aaaatggtgt tactttgaat gttgttagta gacggttgag aggcgcagtt   9120
ttaattttac aaactgctgt cgccaatgct gacactccta agtataagtt tgttaaagct   9180
aattgtggag atagtttcac aattgcttgt tcttatggtg gtacagttgt gggactctac   9240
cctgttacta tgcgttctaa tggtactatt agagcgtctt tccttgcagg agcttgtggc   9300
tcagttggtt ttaatataga aaagggtgta gttaatttct tttatatgca ccatcttgag   9360
ttacctaatg cattacacac cggaactgac ctagcgggtg acttctatgg tggttatgtg   9420
gatgaagagg ttgcacaaag ggtgccacca gataatttag ttactaacaa tattgtagca   9480
tggctttatg cagcaattat tagtgttaaa gagagtagct tctcactgcc taatggttg    9540 gagagtacta ctgccagtgt tgaagattat aataagtggg ctggtgataa tggttttaca   9600
ccatttctca ctagtactgc tattactaaa ttaagtgcta taacgggagt tgatgtttgt   9660
aaactccttc gcactattat ggtaaaaagt agtcaatggg gtagtgatcc catttagga    9720 caatacaatt ttgaagatga attgacacct gagtctgtct ttaatcaggt tggcggtgtt   9780
agattacagt cttctattgt aagaagagcc acatcttggt tttggagtag atgtgtgtta   9840
gcttgcttct tgtttgtgtt gtgtgctgta gttttgttta cggcagtacc acttagatat   9900
tatttacatg cagctgttat tttgttagtg gctgtacttt ttatttcttt tactgttaaa   9960
catgttatgg catatatgga acttttttcta ttgccgacat tggttacagt tattattgga  10020
gtttgtgctg aagttccttt catatacaat actctaatta gtcaagttat tatttttctta  10080 agtcaatggt atgatcctgt agtttttgat actatagtac catggatgtt gttgccatta  10140
```

-continued

```
gtgttgtaca ctgcttttaa gtgtgtacaa ggttgctata tgaattcgtt caatacttcg   10200
ttgttaatgc tgtaccagtt tatgaagtta ggttttgtta tttatacctc ttctaacact   10260
cttactgcat atacagaagg taattgggag ttattctttg agttggttca cactactgtg   10320
ttggctaatg ttagtagtaa ttccttaatt ggtttaattg tctttaagtg tgctaagtgg   10380
atgttgtatt attgtaatgc aacatacttt aacaattatg ttttaatggc agttatggtt   10440
aatggcatag gctggctttg cacttgttac tttggattgt attggtggat taataaggtt   10500
tttggtttaa ccttaggtaa atacaatttt aaagtttcag tagaccaata taggtatatg   10560
tgtctgcata agatagaccc ccctaaaact gtgtgggaag tcttttcgac aaatatactt   10620
atacaaggga ttggtggtga ccgtgtgttg cctattgcta cagttcaatc taaattgagt   10680
gatgtaaagt gtacaactgt tgtgttaatg caacttttga ctaagcttaa tgttgaagca   10740
aattcaaaaa tgcatgctta tcttgttgag ttacacaata aaatcctcgc atctgatgat   10800
gttggagagt gcatggataa tttattgggt atgcttatta cactattttg tatagattct   10860
actattgatt taggtgagta ttgtgatgat atacttaaga ggtcaactgt attacaatca   10920
gttactcaag agttttcaca catacccctct tatgctgaat atgaaagagc taagaatctt   10980
tatgaaaagg ttttagctga ttctaaaaat ggtggtgtaa cacagcaaga gcttgctgca   11040
tatcgtaaag ctgccaatat tgcaaagtca gttttttgata gagatttggc tgttcaaaag   11100
aagttagaca gcatggcaga acgtgctatg acaacaatgt ataaagaggc gcgtgtaact   11160
gatagacgag caaaattagt ctcatcacta catgcgttac tttttttcaat gcttaagaaa   11220 atagattctg aaaagcttaa tgtcttattt gatcaggcta gtagtggtgt tgtacctcta   11280
gctactgttc caattgtttg tagtaataag cttacccttg tagtaccaga tccagaaact   11340
tgggtcaagt gtgtggaagg tatgcatgtt acatattcaa cagttgtttg gaatatagat   11400
actgttattg atgctgatgg tacagaggta catccaactt ctacaggtag tggattgaca   11460
tactgtataa gtggtgccaa tatagcatgg ccttttaaagg ttaacttgac taggaatggg   11520
cataataagg ttgatgttgc tttgcagaat aatgagctta tgcctcatgg tgtaaaaaca   11580
aaggcttgcg tagcaggtgt ggatcaagca cattgtagcg tagagtctaa atgttattat   11640
acaaatatta gtggcaattc agttgtagct gccattactt cttcaaatcc aaatctgaaa   11700
gtagcttcat ttttgaacga ggcaggcaat cagatttatg tagacttaga cccaccatgc   11760
aaatttggca tgaaggtggg tgacaaggtt gaggttgttt acttgtatttt tataaagaat   11820 acaaggtcga ttgttagggg tatggtactt ggtgctatat ctaatgttgt tgtcttacag   11880
tctaaagggc atgaaacaga ggaagtggat gctgttggca ttctttcact tgttctttt   11940 gcagtagatc ctgcagacac gtattgtaaa tatgtggcag caggtaatca acctctaggt   12000
aactgtgtta aaatgttgac agttcataat ggtagtggct ttgctataac atcgaagcca   12060
agtccaactc ctgatcagga ttcctacgga ggagcttctg tgtgtctcta ttgtagggca   12120
cacatagcac atcctggtgg tgcaggaaat ttagatgggc gttgtcaatt taaaggttcc   12180
tttgtgcaaa taccaactat ggagaaagac cctgttggat tctgtctacg taataaggtt   12240
tgcactgtct gtcaatgttg gattggttat ggatgtcagt gcgatgcact tagacaacca   12300
aaaccttctg ttcaatcagc tgccaatgta gctgatttcg ataagaatta tttaaacggg   12360 tacgggggtag cagtgaggct cggctgatac cccttgctag tggatgtgat cctgatgttg   12420
tgaagcgagc ctttgatgtt tgtaataagg aatcagccgg tatgtttcgt aatttgaagc   12480
gtaactgtgc gcggttccaa gaagtacgtg atactgaaga tggaagtctt gagtattgtg   12540
```

```
attcattctt cgtggttaaa caaaccactc ctagtaatta tgaacatgag aaagcttgtt    12600
atgaagactt aaagtcagaa gtgacggctg accatgattt ctttgtgttc aataagaaca    12660
tttataatat tagtaggcaa cgtcttacta agtatactat gatggatttt tgctatgctt    12720
tgaggcattt tgacccaaag gactgcgaag ttcttaaaga aatacttgtc acttatggtt    12780
gtatagaaga ttatcaccct aagtggtttg aagagaataa ggattggtac gacccaatag    12840
aaaacccaaa atattatgcc atgttggcta aaatggggcc tattgtacga cgtgctttat    12900
tgaatgctat tgagttcgga aaccttatgg ttgagaaagg ttatgttggt gtagttacac    12960
ttgacaacca agatcttaat ggcaaatttt atgactttgg tgattttcag aaaacagcac    13020
ttggtgctgg ggttcctatt tttgatacat attattccta catgatgccc atcatagcca    13080
tgacggatgc tttagcacct gaaaggtatt ttgaatatga tgtgcataag ggttataagt    13140
cttatgatct tctcaagtat gattatactg aggagaaaca agatttgttt cagaagtact    13200
ttaagtattg ggaccaggag taccatccta actgccgtga ctgtagtgat acaggtgtt    13260 tgatacattg tgcaaacttc aacatattgt tttctacatt gataccacag acttcttttg    13320
gtaatttgtg tagaaaagtg tttgttgatg gtgtacccttt tatagctact tgtggctatc    13380
attctaaaga acttggtgtt attatgaatc aagataacac catgtcgttt tcaaaaatgg    13440
gtttaagtca actcatgcag tttgttggag accctgcctt gttagtggga acatccaata    13500
atttagtcga tcttagaacg tcttgttttta gtgtttgtgc attagcgtct ggtattactc    13560
atcaaacggt aaaaccgggt cactttaaca aggatttcta tgattttgca gagaaggccg    13620
gtatgtttaa agagggttct tctataccac ttaaacattt cttctaccca caaactggta    13680
atgctgctat aaacgattat gattactatc gttataacag gcctaccatg tttgatatac    13740
gtcaacttct attttgttta gaagtgactt ctaaatactt tgactgttat gaaggcggct    13800
gtataccagc aagccaagtt gtagttaata atttagataa gagtgcaggc tacccatttta    13860 ataaatttgg aaaagctcgc ctctattatg aaatgagtct agatgaacag gaccaactct    13920
ttgagagtac aaagaagaat gtcctgccta ctataactca aatgaattta aaatatgcca    13980
tatccgcgaa aaatagagcg cgtacagtgg caggtgtgtc tatcctttct actatgacta    14040
ataggcaatt tcatcagaag attcttaagt ctatagttaa cactagaaat gctcctgtag    14100
ttattggaac aaccaagttt tatggcggtt gggacaatat gttgaggaat ctgattcaag    14160
gtgttgaaga ccctattctt atgggttggg attatcctaa gtgtgataga gcaatgccaa    14220
atttgctgcg tatagcagca tccttggtac ttgctcgcaa acacactaat tgttgtactt    14280
ggtctgaacg catttatagg ttgtataatg aatgcgctca ggttttatct gaaactgttt    14340
tagctacagg tggtgtttat gtaaaacctg gtggtactag cagtggtgat gctactactg    14400
cttatgcaaa cagcgttttc aacataatac aagccacatc tgctaatgtt gcgcgtcttt    14460
tgagtgttat aacgcgtgat attgtttatg atgacattaa gagcctgcag tatgagttgt    14520
accagcaggt ttataggcga gttaattttg acccagcctt tgtagaaaag ttttattctt    14580
acttatgtaa gaatttctct ttgatgatct tgtctgacga tggtgttgtt tgttacaaca    14640
acacattggc caaacagggt cttgttgcgg acatttctgg ctttagagaa attctctact    14700
accaaaataa tgtttatatg gctgattcta agtgttgggt tgaaccagac ttagaaaaag    14760
gcccacatga atttttgttca cagcacacaa tgctagtgga ggtggatggt gagcctaagt    14820
atttgccata tccagatccc tcacgcattt tgggtgcatg tgtctttgta gatgaagtgg    14880
```

```
ataagacaga acctgtggct gttatggagc gttatatagc tcttgccata gacgcttacc    14940
cactagtaca tcacgaaaat gaggagtaca ggaaggtttt ctttgtgctt ctttcatata    15000
tcagaaaact ctatcaagag ctttctcaga atatgcttat ggactactct tttgtgatgg    15060
atatagacaa gggtagtaaa ttttgggaac aggagttcta tgagaatatg tatagagccc    15120
ctacaacttt acagtcttgt ggtgtttgtg tagtgtgcaa tagtcaaact atactacgct    15180
gtggtaattg tattcgaaaa ccattttgt gttgtaaatg ttgttatgac catgtcatgc     15240
acacagacca taaaaatgtt ttgtctataa acccatacat ctgttcgcaa cccggttgcg    15300
gtgaagcaga tgttactaaa ttataccttg gaggtatgtc atacttctgt ggtaatcata    15360
aaccaaaatt gtcaataccg ttagtatcta atggtactgt ctttggtatt tacagggcta    15420
attgtgctgg tagtgaaaat gttgatgatt taatcaact agctactact aattgggcta     15480
ctgtagaacc ttatatttta gcaaatcgtt gtagtgactc attgagacgc tttgctgctg    15540
aaacagtaaa agccacagag gaattacata acagcaatt tgctagtgct gaggtgagag     15600
aagtactctc agatcgtgaa ttgatcctat catgggagcc aggtaaaacc aggccaccat    15660
tgaatagaaa ttatgttttc acaggctatc actttacaag aactagtaag gtgcagcttg    15720
gtgattttac ctttgaaaaa ggtgaaggta agatgttgt ctattataga gcaacgtcta     15780
ctgctaaatt gtctgttgga gacattttg ttttaacctc acacaatgtt gtttctcttg     15840
tagcgccaac gttgtgtccg cagcaaacct tttctaggtt tgtgaattta agacctaatg    15900
taatggtacc ggaatgtttt gtaaataaca ttccacttta ccatttagta ggtaagcaga    15960
agcgtactac agtacaaggt cctcctggca gtggtaagtc acactttgct ataggccttg    16020
ctgcttactt tagtaacgcg cgtgttgtct ttactgcttg ttctcatgca gctgttgatg    16080
ctttatgtga aaaagctttt aagtttctta agtcgatga ttgcactcgg atagtacctc     16140
aaaggactac tgtcgagtgc ttttctaagt ttaaagctaa cgacacaggc aaaaagtaca    16200
tttttagtac tataaatgcc ttgccagaag ttagttgtga cattcttttg gttgatgagg    16260
ttagtatgtt gaccaattac gaattgtctt ttattaatgg taagataaat taccaatatg    16320
ttgtgtatgt aggtgaccca gctcaattac cggcacctcg taccttactt aatggctcac    16380
tttcaccaaa ggattataat gttgtcacaa accttatggt ttgtgttaaa cctgatatat    16440
tccttgcgaa gtgttaccgt tgtcctaagg aaattgtaga cactgtgtct actctagtat    16500
atgatggaaa gtttattgca aataacccag aatcacgtca gtgtttcaag gttatagtta    16560
ataatggtaa ttctgatgta ggacatgaaa gtggttcagc ctacaacaca actcaattag    16620
aatttgtgaa agatttgtt tgtcgcaata aggaatggcg ggaagcaaca ttcatttcac     16680
cttacaatgc tatgaaccag agagcctacc gtatgcttgg acttaatgtt cagacagtag    16740
actcatctca aggttcggag tatgattatg ttatttctg tgtaactgca gattcgcagc     16800
atgcactgaa tattaacaga tttaatgtgg cgcttacaag agctaagcgt ggtatactag    16860
ttgtcatgcg tcagcgtgat gaattgtact ctgctcttaa gtttacagag ctaaatagtg    16920
aagcaagtct gcaaggtaca ggtttgttta aaatttgcaa caagaatttt agtggtgttc    16980
atcctgctta tgcagtcaca actaaggctc ttgctgcaac ttacaaagtt aatgatgaac    17040
ttgctgcact tgttaatgtg gaagccggtt cagaaataac atataaacat cttatttctc    17100
ttctaggatt taggatgagt gttaatgttg aaggttgcca taacatgttt ataacacgtg    17160
acgaggcaat tcgcaacgta agagggtggg taggattcga tgtagaagcc acacatgctt    17220
gtggtactaa cattggcact aacttacctt ttcaagtagg tttctcgact ggtgcagact    17280
```

```
ttgtagttac acctgaggga cttgtagata cttcgatagg caataatttt gagcctgtga  17340
attccaaagc acctccaggt gagcaattta atcacttgag agctttattt aagagtgcta  17400
aaccttggca cgttataaga ccaaggatag tgcaaatgtt agcagataat ctatgcaatg  17460
tctctgattg tgtagtgttt gttacttggt gtcatggcct agaactaact acgttgcgct  17520
attttgttaa aataggcaaa gaacaattgt gttcgtgtgg ttctagagct acgactttta  17580
attcacatac tcaagcttat gcttgttgga ggcattgttt gggttttgat tttgtctata  17640
acccactttt agtggatatt caacaatggg gttactcagg taatctacaa tttaaccatg  17700
gtttgcattg taatgtgcat ggacatgccc atgtggcttc tgcggacgcc attatgacgc  17760
gttgccttgc aattaacaat gcattttgtc aagatgtcaa ctgggatttg acatatcctc  17820
atattgcaaa tgaggatgaa gtcaactcta gttgtcggta tttacagcgc atgtatctta  17880
atgcatgtgt tgatgctctt aaagttaatg ttgtctatga tataggcaac cctaaaggta  17940
taaagtgtgt tagacgtgtg gatgtcaatt ttagattcta tgataagaat ccaattgtac  18000
ccaacgtcaa acagtttgag tatgactata atcagcacaa ggataagttt gctgatggtc  18060
tttgtatgtt ttggaattgc aatgtggatt gttatcctga caattcacta gtctgtagat  18120
acgacacacg aaatttgagt gtgtttaatc taccaggttg taatggtggt agtctgtatg  18180
tgaacaaaca tgcatttcac acacctaaat ttgaccgcat tagctttcgc aatttgaaag  18240
ctatgccatt tttcttctat gattcatcgc cttgtgaaac cattcaagtt gatggagttt  18300
cacaagacct tgtgtcatta gctactaagg attgtatcac aaaatgcaac attggggtg  18360
ctgtttgtaa aaagcacgct cagatgtatg cagagtttgt gacttcttat aatgcagctg  18420
ttacagctgg ttttactttt tgggttacta ataattttaa cccttataat ttgtggaaaa  18480
gttttttcagc tctccagtct attgacaata ttgcttataa tatgtataag ggtggtcatt  18540
atgatgctat cgcaggagaa atgcccacag tcataactgg agataaagtt tttgttatag  18600
atcaaggtgt agaaaaggca gtttttgtta atcaaacaac actgcctacg tctgtggcgt  18660
ttgaattgta tgcgaagaga aatattcgca cactgccaaa caaccgtatt ttgaagggtc  18720
ttggtgtaga tgtaaccaat ggttttgtaa tttgggatta tgctaaccag acaccactat  18780
atcgtaatac tgtcaaggta tgtgcataca cagacattga gccaaatggc ctaatagttc  18840
tgtatgatga tagatatggt gattaccagt cttttcttgc tgctgacaat gctgttttaa  18900
tttctacaca gtgttataag cggtattcat atgtagaaat accatcagat ttgcttgttc  18960
agaatggtat gccactaaaa gatggagcga acctatatgt ttataagcgc gttaatggtg  19020
tgtttgttac actacccaac actttaaaca cacagggccg caattatgaa acttttgaac  19080
ctcgtagtga cgttgagcgt gattttctcg acatgtcaga ggaagatttt gtagaaaagt  19140
atggtaaaga cttaggtcta caacacatac tgtatggtga agttggtaaa ccacaattgg  19200
gtggtttaca cactgttata ggtatgtaca gactttacg tgcgaataag ttgaatgcaa  19260
agtctgtcac taattcggat tctgatgtca tgcaaaatta ttttgtgttg cagacaatg  19320
gttcttacaa gcaagtgtgc actgttgtgg attactgct tgatgatttc ttagaacttc  19380
ttaggaacat actgaatgag tatggtacta ataagtcaaa agttgtaaca gtgtcaattg  19440
attaccatag cataaatttt atgacttggt ttgaagatgg cagtattaaa acatgttatc  19500
cacagcttca atcagcgtgg acatgtggtt ataatatgcc tgaacttat aaagtccaga  19560
attgcgttat ggaaccttgc aacattccta actatggtgt tggaataacg ttgccaagtg  19620
```

```
gtattatgat gaatgtagca aagtatacac aactttgtca atatctttcg aaaacaacaa    19680
tgtgtgtgcc gcataatatg cgagtaatgc attttggagc aggaagtgac aaaggagtgg    19740
ccccaggtag cgctgttctt aggcagtggc ttcccgaagg tacactcctt gtcgataatg    19800
atattgtaga ttatgtatct gatgcacatg tctctgtgct ttcagattgc aataaatgta    19860
aaacagagca caagtttgat cttgtgatat ctgatatgta tacagataat gattcaaaga    19920
gaaagcatga aggcgttgta gccaataacg gcaatgatga cgtcttcata tacctttcaa    19980
actttcttcg taacaattta gctctgggag gcagttttgc cgtaaaagta acagagacaa    20040
gttggcatga gagtttatat gacattgcac aggattgtgc atggtggaca atgttttgta    20100
cagcagtgaa tgcttcttcg tcagaagcat tcttgattgg tgttaattat ttgggtgcaa    20160
gtgaaaaggt tagagttagt ggtaaaaccc tgcacgcaaa ttatatattt tggaggaatt    20220
gtaattattt acaaacttca gcctatagta tatttgacgt tgctaagttt gatttgaaat    20280
taaaagcaac gccagttgtg aatttgaaaa ctgaacaaaa gacagactta gtctttaatt    20340
taattaagtg tggtaagtta ctggtaagag atgttggaca aaccgctttt actagtgact    20400
ctttggtatg cactatgtag tgctttgctc tatgataata atacttacgt ttactactac    20460
caaagtgcct ttaggcctgg tccaggttgg cacctatatg ggggtgctta tgcagtagat    20520 agggtttta atgaaaccaa caatgcaggc agtgcatctg attgcactgc tggtactttt    20580
tatgaaagcc ataatatttc tgcttcttct gtagccatga cagtaccaca taatggtatg    20640
tcttggtcag cttcacaatt ttgtacagct cattgtaact tctcagactt tacagtgttc    20700
gttacgcatt gttttaaaaa tcaactcggt agttgtccct tgacaggtat gattcctcag    20760
aatcatattc gtatttctgc tatgagagat ggagttttgt tttataactt aacagttagc    20820
gtatctaaat accctagatt taaatcgctt caatgtgtta gcaattctac atctgtctat    20880
gtaaatggtg accttgtttt cacttctaat gaaacttctt acgttacggg tgcaggcgtt    20940
tattttaaaa gtggtgggcc tgtaacttat aaagttatga agaagttaa agccctagcc    21000 tactttatta atggtaccgc acaagaggtt attttatgtg ataactcacc tagaggtttg    21060
cttgcatgtc agtataacac tggtaatttt tcagatggat tctacccttt tactaatcat    21120
tctttagtta aggataggtt tattgtatat cgagaaagta gcactaacac tacttaaag    21180 ttaactaatt tcagttttac taatgtaagt aatgcttctc ctaattcagg tggcgttgat    21240
actttccaat tatatcaaac aagtactgct caggatggtt attataattt taatttatca    21300
tttctgagta gttttgtgta taaaccatct gattttatgt atgggtcata ccacccacat    21360
tgtaagttta gaccagagaa tattaataat ggcttatggt ttaattcatt atctgtgtca    21420
cttacttacg gacccattca aggtggttgt aagcaatctg tttttagtaa tagagcaact    21480
tgttgctatg cttattctta tcaagggcct agtagatgta agggtgttta tagaggggag    21540
ctaacgcaat actttgaatg tggacttcta gtttacgtaa ctaagagtga tggctctcgt    21600
atacaaacta gaagtgaacc actggtgtta actcaatata attataacaa cattactttta    21660 aataagtgtg ttgagtataa tatatatggt agggttggtc aaggttttat tactaatgta    21720
actgaagcaa ctgctaatta tagttatcta gcagatggtg gtttagctat tttagatacc    21780
tcaggagcca tagacatatt tgttgttcaa ggtgcatatg gtcttaatta ttataaggtt    21840
aatccctgtg aagatgttaa ccaacagttt gtagtgtctg gtggcaactt agttggcatt    21900
cttacatctc ataatgaaac aggttctgaa tctattgaga accagtttta catcaaactc    21960
actaacggaa cacgtcgctc tagacgttct gttactggga atgttacaaa ttgcccttat    22020
```

```
gttagttatg gcaagttttg tataaaacca gatggttctt tatctataat agtaccacaa   22080
gaattagaac agtttgtggc gcctttattc aatgttactg agcatgtgct catacctgat   22140
agttttaatt taactgtcac agatgagtac atacaaactc gtatggataa ggttcaaatt   22200
atttgccttc agtatgtttg tggtaattct attgaatgca gaaagttgtt tcagcagtat   22260
ggacctgttt gtgataatat attgtctgtt gtaaatggtg taggtcaaag agaggatatg   22320
gaacttttaa gtttctattc ttctactaaa cctagtggtt acaatacacc aatttttaat   22380
aatgttagca ctggtgactt taatatttcg ctcctactaa caccacctaa tagtcctact   22440
gggcgctctt ttattgaaga tcttctcttt acaagtgtag aatctgttgg attaccaact   22500
gatgaagagt ataaaaagtg tacagcagga cctttaggtt ttgttaaaga ccttgtttgt   22560
gctagagagt ataatggttt gctcgttctg cctcctatta ttactgcgga aatgcaaacc   22620
atgtatacta gttctttagt agcctctatg gctttaggtg gcattactgc agctggtgct   22680 atacctttg ctacacaact gcaggccaga attaaccatt gggtattac taattctctt   22740 ttgttgaaaa accaagaaaa aattgctgct tcctttaata aggccatcgg tcatatgcag   22800
gaagggttta aaagtacttc tctagcatta caacagattc aagatgttgt taataaacag   22860
agttctattc ttacagagac tatgcaatca cttaataaaa attttggtgc tatttcctct   22920
gtaattcaag acatttacca gcaactagat gctattcagg cagatgctca ggttgatcgt   22980
cttattacag gtagactctc ttcactatct gttttagctt ctgctaaaca ggcagagtat   23040
catagagtgt cacaacagcg tgagttggcc actcagaaaa ttaatgagtg tgttaagtct   23100
cagtctaata ggtattcatt ttgtggtaat ggtagacatg ttctaaccat accacagaat   23160
gcacccaatg gcatagtgtt tatacacttt acatacactc cagagagttt tgttaatgtt   23220
acggcaatag tagggttttg cgtaaaccca gctaatgcta gtcattatgc aatagtgcct   23280
gttaatggca ggggtgtttt tatagaagtt aatggtagtt actatatcac tgctcgtgat   23340
atgtatatgc caagagatat tactgcagga gacatagtca ctttgacttc ttgtcaagca   23400
aactatgtta atgtaaataa aaccgtcatt aacacttttg tggaagatga cgatttttgat   23460 ttttatgatg aattgtcaaa atggtggaat gatactaagc atgagctacc agattttgat   23520
gaattcaatt ataccgttcc agttttaaat attagtaatg aaattgacag aattcaacag   23580
gttattcagg gattaaatga ttccctaata gaccttgaaa cactctcaat tctcaaaact   23640
tatattaaat ggccttggta tgtgtggctt gccattgcat tccttaccat tatttttatt   23700
ctggtacttt gttggatatt tttcatgacc ggttgttgcg gttgttgttg tggatgcttt   23760
ggtatcatac cgttaatgag taagtgtggt aagaaatctt cttactacac gacttttgat   23820
aatgatgtgg taacttaaca atacagacct aaaaagtctg tttaatgatt aaaagtccca   23880 catctttct aatattatta attcttcttt ggtgtaaact tgcattaagt tgttttaaag   23940
agtgtgttat aacactccag caactagtac aaatttact ccaaattatt aatagtaact   24000
tacaatctag acttctgctt tggcacagtc tagactaatg ttagattttg aagcaattat   24060
tgaaactggt cagcaaataa ctcaacaaat tagtttctat ttacagcata tttcaagggt   24120
gctaagtact gaattatttg accccttga agtttgtgtt tacagaggag gtaattgttg   24180
ggagttagag tcagctgacg agttttcagg tgatgacgaa tatattgagt agatcgctag   24240
aggagaacgg aagtttccta acagcggttt acgtgttttt aggattttta gcactttatc   24300
tactaggtag agcgcttcaa gcttttgtac aagcggctga cgcttgttgt ctttttggt    24360
```

```
atacatgggt agtagttcct ggagccaagg gcacagcctt tgtttataat catacatatg   24420
gtaaaaaact taacaaaccg gagttagaaa cggttattgt taacgaattt ccaaaaaacg   24480
gttggaaata tggataatac catcaattgt actcttggta ctgaacaagc agttcagctt   24540
tttaaggaat ataatctgtt tgtaactgca ttcctgttgt ttttaaccat actacttcag   24600
tatggatacg caactaggag caaggttatt tacatactga aaatgatagt gttatggtgc   24660
ttttggcccc ttaacattgc agtaggtgta atctcatgta tatacccacc aaacacagga   24720
ggtcttgtcg cagcgataat tcttacagtg tttgcgtgtc tttcttttat aggttattgg   24780
atccagagta ttagactttt taagcggtgc aggtcatggg ggtcatttaa ccccgaatct   24840
aatgccgtag gttcaatact cctaactaat ggtcaacaat gtaattttgc tatagagagt   24900
gtgccgatgg tgcttttctcc tattataaag aatggtgctc tttattgcga gggtcagtgg   24960
cttgctaaat gtgaaccaga ccacttgcct agagatatat tgtatgcac accggataga   25020
cgtaatatct atcgtatggt gcaaaaatat actggtgacc aaagcggaag taagaaaagg   25080
tttgccacat ttgtctatgc aaagcagtca gtagatactg gcgagctaga aagtgtgtca   25140
gcagtaggag gtagtcttta cacataaatg tgtgtgtgta gagagtattt aaaattattc   25200
tttgacagtg cctccgtttt aagagcgcgg aagagtatta ttttgagga tattaatata   25260
aatcctcttt gtttcatact ctcctttcag gagttattat ttaaaaaaca gttttttccac   25320
tcttttgtgc caaaaacaat tgttgttaat ggtgtaacct ttcaggtaga caatggaaaa   25380
gtctactacg aaggaagacc aattttccaa aaaggttgtt gtagtttgtg gtccaattat   25440
aagaaagatt agaataatta aaccacctac aacacttatt tttacaaatg gcgttttagg   25500
ttacaaacgc ttaacaaata cggatgatga aatggctgac tagttttgga agagcttca   25560
tctcctgtta taaatcccta ttactaactc aattaagagt attagatagg ttaattttag   25620
atcacggacc caagcgcaca ttaacgtgtg ctaggcgagt gcttttagtt caattagatt   25680
tagtttatag gttggcttat acgcccaccc aatcgctggt atgaataata gtaaagataa   25740
tccttttcgc ggagcaatag caagaaaagc gcgaatttat ctgagaggag gattagattg   25800
tgtttactt cttaacaaag caggacaagc agagccttgt cccgcgtgta cctcccctagt   25860
attccaaggg aaaacttgtg aggaacacta ttataataac aatcttttgt catggcaagc   25920
ggtaaggcaa ctggaaagac agacgcccca gcgccagtca tcaaactagg aggaccaaag   25980
ccacctaaag ttggttcttc tggaaatgca tcatggtttc aaccgataaa ggccaagaag   26040
ctaaattcac ctgtgcctaa atttgacggt agtggtgttc ctgaaaatga aaatctcaag   26100
tcaagccagc aacatggata ctggagacgc caacacaggt ttaagcctgg caaaggtgga   26160
agaaaaccag tccctgatgc ttggtacttt tactacactg gaacaggacc ggccgccgac   26220
ctgaattggg gtgaaactca agatggtata gtgtgggttg ctgcaaggg tgctgatact   26280
aaatctagat caaaccaggg tacaagggat cctgataagt ttgaccaata cccactacga   26340
ttctcagatg gaggaccgga tggtaatttc cgttgggact tcataccaat aaatcgtggt   26400
aggagtggga gatcaacagc agcttcatca gcagcatcta gtagagcacc atctcgtgag   26460
gggtcacgtg gacgtagaag cggagttgaa gatgatctta gctcgcgc agcaaagatt   26520
atacaggacc agcaaagaa gggtgcgcgc attaccaagg ctaaggctga tgaaatggct   26580
catcgccgct attgcaagcg cactatccca cctggtttta aggttgagca gtatttggt   26640
ccccgtacta aaggtaagga aggaaatttt ggtgatgaca gatgaatga ggaaggtgtt   26700
aaggatgggc gtgttacggc aatgctcaac ctagtcccta gcagtcatgc ttgtcttttt   26760
```

```
ggaagtaggg tgacgcccaa actgcagcca gatggtcttc acctgagatt tgaatttact  26820
actgtggtgt cacgtgatga tccgcagttt gataattatg tgaaaatttg tgatcagtgt  26880
gtcgatggtg tagggacgcg tccaaaggac gatgaatcga gaccaaagtc acgcccaaat  26940
tcaagacctg caactagagg aaattctcca gcgccgagac aacagcgccc aaagaaggag  27000
aaaaagccca agaagcagga tgatgaagta gataaggcat tgacctcaga tgaggagagg  27060
aacaatgcac agctggaatt tgatgatgaa cccaaggtga ttaactgggg ggactctgca  27120
ctaggtgaaa atgaactttg attaacataa tggacttgct gcatttgctg tcacatttg   27180 ttaaatatta tttttgtgtt ttactatcaa ttattacagg tattgattgt gattatgttc  27240
aatacttaag cttcttctgg ttgcttttg cttgttgtat tgttgctgtg cttttatta   27300 ttgtgattct cattagtttg ctttatcgta gaaattcaat agtaagagtt aaggaagata  27360
ggcatgtagc ttagcaccta catgtctatc gccagggaaa tgtctaatct gtctacttag  27420
tagcctggaa acgaacggta gacccttaga ttttaattta gtttaatttt tagtttagtt  27480
taagttagtt tagagtaggt ataaagatgc cagtgccggg gccacgcgta gtacgaccga  27540
gggtacagca ctaggacgcc cactagggga agagctaaat tttagtttaa gttaagttta  27600
attggctaaa tatagttaaa atttataggc tagtatagag ttagagcaaa aaaaaaaaa   27659
```

<210> SEQ ID NO 2
<211> LENGTH: 1155
<212> TYPE: PRT
<213> ORGANISM: Unknown
<220> FEATURE:
<223> OTHER INFORMATION: Description of Unknown:
    Avian infectious bronchitis virus sequence

<400> SEQUENCE: 2

Met Leu Asp Lys Pro Leu Leu Val Thr Leu Trp Tyr Ala Leu Cys
1               5                   10                  15

Ser Ala Leu Leu Tyr Asp Asn Asn Thr Tyr Val Tyr Tyr Gln Ser
            20                  25                  30

Ala Phe Arg Pro Gly Pro Gly Trp His Leu Tyr Gly Gly Ala Tyr Ala
            35                  40                  45

Val Asp Arg Val Phe Asn Glu Thr Asn Asn Ala Gly Ser Ala Ser Asp
        50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
            100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
    130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
            180                 185                 190

Lys Ser Gly Gly Pro Val Thr Tyr Lys Val Met Lys Glu Val Lys Ala

```
            195                 200                 205
Leu Ala Tyr Phe Ile Asn Gly Thr Ala Gln Glu Val Ile Leu Cys Asp
210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
                260                 265                 270

Asn Phe Ser Phe Thr Asn Val Ser Asn Ala Ser Pro Asn Ser Gly Gly
            275                 280                 285

Val Asp Thr Phe Gln Leu Tyr Gln Thr Ser Thr Ala Gln Asp Gly Tyr
            290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
                340                 345                 350

Tyr Gly Pro Ile Gln Gly Gly Cys Lys Gln Ser Val Phe Ser Asn Arg
            355                 360                 365

Ala Thr Cys Cys Tyr Ala Tyr Ser Tyr Gln Gly Pro Ser Arg Cys Lys
370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
                420                 425                 430

Cys Val Glu Tyr Asn Ile Tyr Gly Arg Val Gly Gln Gly Phe Ile Thr
            435                 440                 445

Asn Val Thr Glu Ala Thr Ala Asn Tyr Ser Tyr Leu Ala Asp Gly Gly
450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
                500                 505                 510

Ser His Asn Glu Thr Gly Ser Glu Ser Ile Glu Asn Gln Phe Tyr Ile
            515                 520                 525

Lys Leu Thr Asn Gly Thr Arg Arg Ser Arg Arg Ser Val Thr Gly Asn
530                 535                 540

Val Thr Asn Cys Pro Tyr Val Ser Tyr Gly Lys Phe Cys Ile Lys Pro
545                 550                 555                 560

Asp Gly Ser Leu Ser Ile Ile Val Pro Gln Glu Leu Glu Gln Phe Val
                565                 570                 575

Ala Pro Leu Phe Asn Val Thr Glu His Val Leu Ile Pro Asp Ser Phe
                580                 585                 590

Asn Leu Thr Val Thr Asp Glu Tyr Ile Gln Thr Arg Met Asp Lys Val
            595                 600                 605

Gln Ile Ile Cys Leu Gln Tyr Val Cys Gly Asn Ser Ile Glu Cys Arg
610                 615                 620
```

-continued

```
Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
            645                 650                 655

Ser Ser Thr Lys Pro Ser Gly Tyr Asn Thr Pro Ile Phe Asn Asn Val
        660                 665                 670

Ser Thr Gly Asp Phe Asn Ile Ser Leu Leu Thr Pro Pro Asn Ser
    675                 680                 685

Pro Thr Gly Arg Ser Phe Ile Glu Asp Leu Leu Phe Thr Ser Val Glu
690                 695                 700

Ser Val Gly Leu Pro Thr Asp Glu Glu Tyr Lys Lys Cys Thr Ala Gly
705                 710                 715                 720

Pro Leu Gly Phe Val Lys Asp Leu Val Cys Ala Arg Glu Tyr Asn Gly
            725                 730                 735

Leu Leu Val Leu Pro Pro Ile Ile Thr Ala Glu Met Gln Thr Met Tyr
            740                 745                 750

Thr Ser Ser Leu Val Ala Ser Met Ala Leu Gly Gly Ile Thr Ala Ala
        755                 760                 765

Gly Ala Ile Pro Phe Ala Thr Gln Leu Gln Ala Arg Ile Asn His Leu
770                 775                 780

Gly Ile Thr Asn Ser Leu Leu Leu Lys Asn Gln Glu Lys Ile Ala Ala
785                 790                 795                 800

Ser Phe Asn Lys Ala Ile Gly His Met Gln Glu Gly Phe Lys Ser Thr
            805                 810                 815

Ser Leu Ala Leu Gln Gln Ile Gln Asp Val Val Asn Lys Gln Ser Ser
        820                 825                 830

Ile Leu Thr Glu Thr Met Gln Ser Leu Asn Lys Asn Phe Gly Ala Ile
    835                 840                 845

Ser Ser Val Ile Gln Asp Ile Tyr Gln Gln Leu Asp Ala Ile Gln Ala
850                 855                 860

Asp Ala Gln Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
            885                 890                 895

Arg Glu Leu Ala Thr Gln Lys Ile Asn Glu Cys Val Lys Ser Gln Ser
        900                 905                 910

Asn Arg Tyr Ser Phe Cys Gly Asn Gly Arg His Val Leu Thr Ile Pro
    915                 920                 925

Gln Asn Ala Pro Asn Gly Ile Val Phe Ile His Phe Thr Tyr Thr Pro
930                 935                 940

Glu Ser Phe Val Asn Val Thr Ala Ile Val Gly Phe Cys Val Asn Pro
945                 950                 955                 960

Ala Asn Ala Ser His Tyr Ala Ile Val Pro Val Asn Gly Arg Gly Val
            965                 970                 975

Phe Ile Glu Val Asn Gly Ser Tyr Tyr Ile Thr Ala Arg Asp Met Tyr
        980                 985                 990

Met Pro Arg Asp Ile Thr Ala Gly Asp Ile Val Thr Leu Thr Ser Cys
    995                 1000                1005

Gln Ala Asn Tyr Val Asn Val Asn Lys Thr Val Ile Asn Thr Phe
    1010                1015                1020

Val Glu Asp Asp Asp Phe Asp Phe Tyr Asp Glu Leu Ser Lys Trp
    1025                1030                1035
```

```
Trp Asn Asp Thr Lys His Glu Leu Pro Asp Phe Asp Glu Phe Asn
    1040                1045                1050

Tyr Thr Val Pro Val Leu Asn Ile Ser Asn Glu Ile Asp Arg Ile
    1055                1060                1065

Gln Gln Val Ile Gln Gly Leu Asn Asp Ser Leu Ile Asp Leu Glu
    1070                1075                1080

Thr Leu Ser Ile Leu Lys Thr Tyr Ile Lys Trp Pro Trp Tyr Val
    1085                1090                1095

Trp Leu Ala Ile Ala Phe Leu Thr Ile Ile Phe Ile Leu Val Leu
    1100                1105                1110

Cys Trp Ile Phe Phe Met Thr Gly Cys Cys Gly Cys Cys Cys Gly
    1115                1120                1125

Cys Phe Gly Ile Ile Pro Leu Met Ser Lys Cys Gly Lys Lys Ser
    1130                1135                1140

Ser Tyr Tyr Thr Thr Phe Asp Asn Asp Val Val Thr
    1145                1150                1155

<210> SEQ ID NO 3
<211> LENGTH: 409
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 3

Met Ala Ser Gly Lys Ala Thr Gly Lys Thr Asp Ala Pro Ala Pro Val
1               5                   10                  15

Ile Lys Leu Gly Gly Pro Lys Pro Pro Lys Val Gly Ser Ser Gly Asn
                20                  25                  30

Ala Ser Trp Phe Gln Pro Ile Lys Ala Lys Lys Leu Asn Ser Pro Val
        35                  40                  45

Pro Lys Phe Asp Gly Ser Gly Val Pro Glu Asn Glu Asn Leu Lys Ser
    50                  55                  60

Ser Gln Gln His Gly Tyr Trp Arg Arg Gln His Arg Phe Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Glu Thr Gln Asp Gly
            100                 105                 110

Ile Val Trp Val Ala Ala Lys Gly Ala Asp Thr Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Ile
145                 150                 155                 160

Asn Arg Gly Arg Ser Gly Arg Ser Thr Ala Ala Ser Ser Ala Ala Ser
                165                 170                 175

Ser Arg Ala Pro Ser Arg Glu Gly Ser Arg Gly Arg Arg Ser Gly Val
            180                 185                 190

Glu Asp Asp Leu Ile Ala Arg Ala Ala Lys Ile Ile Gln Asp Gln Gln
        195                 200                 205

Lys Lys Gly Ala Arg Ile Thr Lys Ala Lys Ala Asp Glu Met Ala His
    210                 215                 220

Arg Arg Tyr Cys Lys Arg Thr Ile Pro Pro Gly Tyr Lys Val Glu Gln
225                 230                 235                 240
```

Val Phe Gly Pro Arg Thr Lys Gly Lys Glu Gly Asn Phe Gly Asp Asp
            245                 250                 255

Lys Met Asn Glu Glu Gly Val Lys Asp Gly Arg Val Thr Ala Met Leu
        260                 265                 270

Asn Leu Val Pro Ser Ser His Ala Cys Leu Phe Gly Ser Arg Val Thr
        275                 280                 285

Pro Lys Leu Gln Pro Asp Gly Leu His Leu Arg Phe Glu Phe Thr Thr
        290                 295                 300

Val Val Ser Arg Asp Asp Pro Gln Phe Asp Asn Tyr Val Lys Ile Cys
305                 310                 315                 320

Asp Gln Cys Val Asp Gly Val Gly Thr Arg Pro Lys Asp Asp Glu Ser
                325                 330                 335

Arg Pro Lys Ser Arg Pro Asn Ser Arg Pro Ala Thr Arg Gly Asn Ser
            340                 345                 350

Pro Ala Pro Arg Gln Gln Arg Pro Lys Lys Glu Lys Lys Pro Lys Lys
        355                 360                 365

Gln Asp Asp Glu Val Asp Lys Ala Leu Thr Ser Asp Glu Glu Arg Asn
        370                 375                 380

Asn Ala Gln Leu Glu Phe Asp Asp Glu Pro Lys Val Ile Asn Trp Gly
385                 390                 395                 400

Asp Ser Ala Leu Gly Glu Asn Glu Leu
                405

<210> SEQ ID NO 4
<211> LENGTH: 94
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 4

Met Thr Asn Ile Leu Ser Arg Ser Leu Glu Glu Asn Gly Ser Phe Leu
1               5                   10                  15

Thr Ala Val Tyr Val Phe Leu Gly Phe Leu Ala Leu Tyr Leu Leu Gly
            20                  25                  30

Arg Ala Leu Gln Ala Phe Val Gln Ala Ala Asp Ala Cys Cys Leu Phe
        35                  40                  45

Trp Tyr Thr Trp Val Val Pro Gly Ala Lys Gly Thr Ala Phe Val
    50                  55                  60

Tyr Asn His Thr Tyr Gly Lys Lys Leu Asn Lys Pro Glu Leu Glu Thr
65                  70                  75                  80

Val Ile Val Asn Glu Phe Pro Lys Asn Gly Trp Lys Tyr Gly
                85                  90

<210> SEQ ID NO 5
<211> LENGTH: 224
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 5

Met Asp Asn Thr Ile Asn Cys Thr Leu Gly Thr Glu Gln Ala Val Gln
1               5                   10                  15

Leu Phe Lys Glu Tyr Asn Leu Phe Val Thr Ala Phe Leu Leu Phe Leu
            20                  25                  30

Thr Ile Leu Leu Gln Tyr Gly Tyr Ala Thr Arg Ser Lys Val Ile Tyr
            35                  40                  45

Ile Leu Lys Met Ile Val Leu Trp Cys Phe Trp Pro Leu Asn Ile Ala
     50                  55                  60

Val Gly Val Ile Ser Cys Ile Tyr Pro Pro Asn Thr Gly Gly Leu Val
 65                  70                  75                  80

Ala Ala Ile Ile Leu Thr Val Phe Ala Cys Leu Ser Phe Ile Gly Tyr
                 85                  90                  95

Trp Ile Gln Ser Ile Arg Leu Phe Lys Arg Cys Arg Ser Trp Trp Ser
                100                 105                 110

Phe Asn Pro Glu Ser Asn Ala Val Gly Ser Ile Leu Leu Thr Asn Gly
            115                 120                 125

Gln Gln Cys Asn Phe Ala Ile Glu Ser Val Pro Met Val Leu Ser Pro
130                 135                 140

Ile Ile Lys Asn Gly Ala Leu Tyr Cys Glu Gly Gln Trp Leu Ala Lys
145                 150                 155                 160

Cys Glu Pro Asp His Leu Pro Arg Asp Ile Phe Val Cys Thr Pro Asp
                165                 170                 175

Arg Arg Asn Ile Tyr Arg Met Val Gln Lys Tyr Thr Gly Asp Gln Ser
            180                 185                 190

Gly Ser Lys Lys Arg Phe Ala Thr Phe Val Tyr Ala Lys Gln Ser Val
            195                 200                 205

Asp Thr Gly Glu Leu Glu Ser Val Ser Ala Val Gly Gly Ser Leu Tyr
210                 215                 220

<210> SEQ ID NO 6
<211> LENGTH: 1162
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 6

Met Leu Val Thr Pro Leu Leu Leu Val Thr Leu Leu Cys Ala Leu Cys
 1               5                  10                  15

Ser Ala Ala Leu Tyr Asp Ser Ser Ser Tyr Val Tyr Tyr Tyr Gln Ser
                 20                  25                  30

Ala Phe Arg Pro Pro Asp Gly Trp His Leu His Gly Gly Ala Tyr Ala
             35                  40                  45

Val Val Asn Ile Ser Ser Glu Ser Asn Asn Ala Gly Ser Ser Ser Gly
 50                  55                  60

Cys Thr Val Gly Ile Ile His Gly Gly Arg Val Val Asn Ala Ser Ser
 65                  70                  75                  80

Ile Ala Met Thr Ala Pro Ser Ser Gly Met Ala Trp Ser Ser Ser Gln
                 85                  90                  95

Phe Cys Thr Ala Tyr Cys Asn Phe Ser Asp Thr Thr Val Phe Val Thr
                100                 105                 110

His Cys Tyr Lys His Gly Gly Cys Pro Ile Thr Gly Met Leu Gln Gln
            115                 120                 125

His Ser Ile Arg Val Ser Ala Met Lys Asn Gly Gln Leu Phe Tyr Asn
            130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr

```
                    165                 170                 175
Ser Asn Glu Thr Thr Asp Val Thr Ser Ala Gly Val Tyr Phe Lys Ala
                180                 185                 190
Gly Gly Pro Ile Thr Tyr Lys Val Met Arg Glu Val Arg Ala Leu Ala
                195                 200                 205
Tyr Phe Val Asn Gly Thr Ala Gln Asp Val Ile Leu Cys Asp Gly Ser
            210                 215                 220
Pro Arg Gly Leu Leu Ala Cys Gln Tyr Asn Thr Gly Asn Phe Ser Asp
225                 230                 235                 240
Gly Phe Tyr Pro Phe Thr Asn Ser Ser Leu Val Lys Gln Lys Phe Ile
                245                 250                 255
Val Tyr Arg Glu Asn Ser Val Asn Thr Thr Phe Thr Leu His Asn Phe
                260                 265                 270
Thr Phe His Asn Glu Thr Gly Ala Asn Pro Asn Pro Ser Gly Val Gln
            275                 280                 285
Asn Ile Gln Thr Tyr Gln Thr Gln Thr Ala Gln Ser Gly Tyr Tyr Asn
            290                 295                 300
Phe Asn Phe Ser Phe Leu Ser Ser Phe Val Tyr Lys Glu Ser Asn Phe
305                 310                 315                 320
Met Tyr Gly Ser Tyr His Pro Ser Cys Asn Phe Arg Leu Glu Thr Ile
                325                 330                 335
Asn Asn Gly Leu Trp Phe Asn Ser Leu Ser Val Ser Ile Ala Tyr Gly
                340                 345                 350
Pro Leu Gln Gly Gly Cys Lys Gln Ser Val Phe Ser Gly Arg Ala Thr
                355                 360                 365
Cys Cys Tyr Ala Tyr Ser Tyr Gly Gly Pro Leu Leu Cys Lys Gly Val
            370                 375                 380
Tyr Ser Gly Glu Leu Asp His Asn Phe Glu Cys Gly Leu Leu Val Tyr
385                 390                 395                 400
Val Thr Lys Ser Gly Gly Ser Arg Ile Gln Thr Ala Thr Glu Pro Pro
                405                 410                 415
Val Ile Thr Gln His Asn Tyr Asn Asn Ile Thr Leu Asn Thr Cys Val
                420                 425                 430
Asp Tyr Asn Ile Tyr Gly Arg Thr Gly Gln Gly Phe Ile Thr Asn Val
            435                 440                 445
Thr Asp Ser Ala Val Ser Tyr Asn Tyr Leu Ala Asp Ala Gly Leu Ala
            450                 455                 460
Ile Leu Asp Thr Ser Gly Ser Ile Asp Ile Phe Val Val Gln Ser Glu
465                 470                 475                 480
Tyr Gly Leu Asn Tyr Tyr Lys Val Asn Pro Cys Glu Asp Val Asn Gln
                485                 490                 495
Gln Phe Val Val Ser Gly Gly Lys Leu Val Gly Ile Leu Thr Ser Arg
                500                 505                 510
Asn Glu Thr Gly Ser Gln Leu Leu Glu Asn Gln Phe Tyr Ile Lys Ile
            515                 520                 525
Thr Asn Gly Thr Arg Arg Phe Arg Arg Ser Ile Thr Glu Ser Val Glu
            530                 535                 540
Asn Cys Pro Tyr Val Ser Tyr Gly Lys Phe Cys Ile Lys Pro Asp Gly
545                 550                 555                 560
Ser Ile Ala Thr Ile Val Pro Lys Gln Leu Glu Gln Phe Val Ala Pro
                565                 570                 575
Leu Leu Asn Val Thr Glu Asn Val Leu Ile Pro Asn Ser Phe Asn Leu
                580                 585                 590
```

-continued

Thr Val Thr Asp Glu Tyr Ile Gln Thr Arg Met Asp Lys Val Gln Ile
            595                 600                 605

Asn Cys Leu Gln Tyr Ile Cys Gly Asn Ser Leu Glu Cys Arg Asn Leu
            610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
            645                 650                 655

Thr Lys Pro Ala Gly Phe Asn Thr Pro Val Leu Ser Asn Val Ser Thr
            660                 665                 670

Gly Glu Phe Asn Ile Thr Leu Phe Leu Thr Thr Pro Ser Ser Pro Arg
            675                 680                 685

Arg Arg Ser Phe Ile Glu Asp Leu Leu Phe Thr Ser Val Glu Ser Val
            690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
            725                 730                 735

Val Leu Pro Pro Ile Ile Thr Ala Glu Met Gln Thr Leu Tyr Thr Ser
            740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
            770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
            805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
            835                 840                 845

Val Ile Gln Glu Ile Tyr Gln Gln Leu Asp Ala Ile Gln Ala Asn Ala
            850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
            885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
            930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
            965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile Val Thr Leu Thr Ser Cys Gln Ala
            995                 1000                1005

```
Asn Tyr Val Ser Val Asn Lys Thr Val Ile Thr Thr Phe Val Asp
    1010                1015                1020

Asn Asp Asp Phe Asp Phe Asn Asp Glu Leu Ser Lys Trp Trp Asn
1025                1030                1035

Asp Thr Lys His Glu Leu Pro Asp Phe Asp Lys Phe Asn Tyr Thr
    1040                1045                1050

Val Pro Ile Leu Asp Ile Asp Ser Glu Ile Asp Arg Ile Gln Gly
    1055                1060                1065

Val Ile Gln Gly Leu Asn Asp Ser Leu Ile Asp Leu Glu Lys Leu
    1070                1075                1080

Ser Ile Leu Lys Thr Tyr Ile Lys Trp Pro Trp Tyr Val Trp Leu
    1085                1090                1095

Ala Ile Ala Phe Ala Thr Ile Ile Phe Ile Leu Ile Leu Gly Trp
    1100                1105                1110

Val Phe Phe Met Thr Gly Cys Cys Gly Cys Cys Cys Gly Cys Phe
    1115                1120                1125

Gly Ile Met Pro Leu Met Ser Lys Cys Gly Lys Lys Ser Ser Tyr
    1130                1135                1140

Tyr Thr Thr Phe Asp Asn Asp Val Val Thr Glu Gln Tyr Arg Pro
    1145                1150                1155

Lys Lys Ser Val
    1160

<210> SEQ ID NO 7
<211> LENGTH: 1075
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 7

Ala Leu Tyr Asp Ser Ser Ser Tyr Val Tyr Tyr Tyr Gln Ser Ala Phe
1               5                   10                  15

Arg Pro Pro Asp Gly Trp His Leu His Gly Gly Ala Tyr Ala Val Val
            20                  25                  30

Asn Ile Ser Ser Glu Ser Asn Asn Ala Gly Ser Ser Ser Gly Cys Thr
        35                  40                  45

Val Gly Ile Ile His Gly Gly Arg Val Val Asn Ala Ser Ser Ile Ala
    50                  55                  60

Met Thr Ala Pro Ser Ser Gly Met Ala Trp Ser Ser Ser Gln Phe Cys
65                  70                  75                  80

Thr Ala Tyr Cys Asn Phe Ser Asp Thr Thr Val Phe Val Thr His Cys
                85                  90                  95

Tyr Lys His Gly Gly Cys Pro Ile Thr Gly Met Leu Gln Gln His Ser
            100                 105                 110

Ile Arg Val Ser Ala Met Lys Asn Gly Gln Leu Phe Tyr Asn Leu Thr
        115                 120                 125

Val Ser Val Ala Lys Tyr Pro Thr Phe Lys Ser Phe Gln Cys Val Asn
    130                 135                 140

Asn Leu Thr Ser Val Tyr Leu Asn Gly Asp Leu Val Tyr Thr Ser Asn
145                 150                 155                 160

Glu Thr Thr Asp Val Thr Ser Ala Gly Val Tyr Phe Lys Ala Gly Gly
                165                 170                 175

Pro Ile Thr Tyr Lys Val Met Arg Glu Val Arg Ala Leu Ala Tyr Phe
            180                 185                 190
```

Val Asn Gly Thr Ala Gln Asp Val Ile Leu Cys Asp Gly Ser Pro Arg
195                 200                 205

Gly Leu Leu Ala Cys Gln Tyr Asn Thr Gly Asn Phe Ser Asp Gly Phe
    210                 215                 220

Tyr Pro Phe Thr Asn Ser Ser Leu Val Lys Gln Lys Phe Ile Val Tyr
225                 230                 235                 240

Arg Glu Asn Ser Val Asn Thr Thr Phe Thr Leu His Asn Phe Thr Phe
            245                 250                 255

His Asn Glu Thr Gly Ala Asn Pro Asn Pro Ser Gly Val Gln Asn Ile
        260                 265                 270

Gln Thr Tyr Gln Thr Gln Thr Ala Gln Ser Gly Tyr Tyr Asn Phe Asn
    275                 280                 285

Phe Ser Phe Leu Ser Ser Phe Val Tyr Lys Glu Ser Asn Phe Met Tyr
    290                 295                 300

Gly Ser Tyr His Pro Ser Cys Asn Phe Arg Leu Glu Thr Ile Asn Asn
305                 310                 315                 320

Gly Leu Trp Phe Asn Ser Leu Ser Val Ser Ile Ala Tyr Gly Pro Leu
            325                 330                 335

Gln Gly Gly Cys Lys Gln Ser Val Phe Ser Gly Arg Ala Thr Cys Cys
        340                 345                 350

Tyr Ala Tyr Ser Tyr Gly Gly Pro Leu Leu Cys Lys Gly Val Tyr Ser
    355                 360                 365

Gly Glu Leu Asp His Asn Phe Glu Cys Gly Leu Leu Val Tyr Val Thr
    370                 375                 380

Lys Ser Gly Gly Ser Arg Ile Gln Thr Ala Thr Glu Pro Pro Val Ile
385                 390                 395                 400

Thr Gln His Asn Tyr Asn Asn Ile Thr Leu Asn Thr Cys Val Asp Tyr
            405                 410                 415

Asn Ile Tyr Gly Arg Thr Gly Gln Gly Phe Ile Thr Asn Val Thr Asp
        420                 425                 430

Ser Ala Val Ser Tyr Asn Tyr Leu Ala Asp Ala Gly Leu Ala Ile Leu
    435                 440                 445

Asp Thr Ser Gly Ser Ile Asp Ile Phe Val Val Gln Ser Glu Tyr Gly
    450                 455                 460

Leu Asn Tyr Tyr Lys Val Asn Pro Cys Glu Asp Val Asn Gln Gln Phe
465                 470                 475                 480

Val Val Ser Gly Gly Lys Leu Val Gly Ile Leu Thr Ser Arg Asn Glu
            485                 490                 495

Thr Gly Ser Gln Leu Leu Glu Asn Gln Phe Tyr Ile Lys Ile Thr Asn
        500                 505                 510

Gly Thr Arg Arg Phe Arg Arg Ser Ile Thr Glu Ser Val Glu Asn Cys
    515                 520                 525

Pro Tyr Val Ser Tyr Gly Lys Phe Cys Ile Lys Pro Asp Gly Ser Ile
    530                 535                 540

Ala Thr Ile Val Pro Lys Gln Leu Glu Gln Phe Val Ala Pro Leu Leu
545                 550                 555                 560

Asn Val Thr Glu Asn Val Leu Ile Pro Asn Ser Phe Asn Leu Thr Val
            565                 570                 575

Thr Asp Glu Tyr Ile Gln Thr Arg Met Asp Lys Val Gln Ile Asn Cys
        580                 585                 590

Leu Gln Tyr Ile Cys Gly Asn Ser Leu Glu Cys Arg Asn Leu Phe Gln
    595                 600                 605

```
Gln Tyr Gly Pro Val Cys Asp Asn Ile Leu Ser Val Val Asn Ser Val
        610             615                 620

Gly Gln Lys Glu Asp Met Glu Leu Leu Asn Phe Tyr Ser Ser Thr Lys
625             630                 635                 640

Pro Ala Gly Phe Asn Thr Pro Val Leu Ser Asn Val Ser Thr Gly Glu
                645                 650                 655

Phe Asn Ile Thr Leu Phe Leu Thr Thr Pro Ser Ser Pro Arg Arg Arg
            660                 665                 670

Ser Phe Ile Glu Asp Leu Leu Phe Thr Ser Val Glu Ser Val Gly Leu
        675                 680                 685

Pro Thr Asp Asp Ala Tyr Lys Asn Cys Thr Ala Gly Pro Leu Gly Phe
690                 695                 700

Leu Lys Asp Leu Ala Cys Ala Arg Glu Tyr Asn Gly Leu Leu Val Leu
705                 710                 715                 720

Pro Pro Ile Ile Thr Ala Glu Met Gln Thr Leu Tyr Thr Ser Ser Leu
                725                 730                 735

Val Ala Ser Met Ala Phe Gly Gly Ile Thr Ala Ala Gly Ala Ile Pro
            740                 745                 750

Phe Ala Thr Gln Leu Gln Ala Arg Ile Asn His Leu Gly Ile Thr Gln
        755                 760                 765

Ser Leu Leu Leu Lys Asn Gln Glu Lys Ile Ala Ala Ser Phe Asn Lys
770                 775                 780

Ala Ile Gly His Met Gln Glu Gly Phe Arg Ser Thr Ser Leu Ala Leu
785                 790                 795                 800

Gln Gln Ile Gln Asp Val Val Asn Lys Gln Ser Ala Ile Leu Thr Glu
                805                 810                 815

Thr Met Ala Ser Leu Asn Lys Asn Phe Gly Ala Ile Ser Ser Val Ile
            820                 825                 830

Gln Glu Ile Tyr Gln Gln Leu Asp Ala Ile Gln Ala Asn Ala Gln Val
        835                 840                 845

Asp Arg Leu Ile Thr Gly Arg Leu Ser Ser Leu Ser Val Leu Ala Ser
850                 855                 860

Ala Lys Gln Ala Glu Tyr Ile Arg Val Ser Gln Gln Arg Glu Leu Ala
865                 870                 875                 880

Thr Gln Lys Ile Asn Glu Cys Val Lys Ser Gln Ser Ile Arg Tyr Ser
                885                 890                 895

Phe Cys Gly Asn Gly Arg His Val Leu Thr Ile Pro Gln Asn Ala Pro
            900                 905                 910

Asn Gly Ile Val Phe Ile His Phe Ser Tyr Thr Pro Asp Ser Phe Val
        915                 920                 925

Asn Val Thr Ala Ile Val Gly Phe Cys Val Lys Pro Ala Asn Ala Ser
930                 935                 940

Gln Tyr Ala Ile Val Pro Ala Asn Gly Arg Gly Ile Phe Ile Gln Val
945                 950                 955                 960

Asn Gly Ser Tyr Tyr Ile Thr Ala Arg Asp Met Tyr Met Pro Arg Ala
                965                 970                 975

Ile Thr Ala Gly Asp Ile Val Thr Leu Thr Ser Cys Gln Ala Asn Tyr
            980                 985                 990

Val Ser Val Asn Lys Thr Val Ile  Thr Thr Phe Val Asp  Asn Asp Asp
        995                 1000                1005

Phe Asp  Phe Asn Asp Glu Leu  Ser Lys Trp Trp Asn  Asp Thr Lys
    1010                 1015                1020

His Glu  Leu Pro Asp Phe Asp  Lys Phe Asn Tyr Thr  Val Pro Ile
```

```
                    1025                1030                1035

Leu Asp  Ile Asp Ser Glu  Ile Asp Arg Ile Gln  Gly Val Ile Gln
    1040             1045                1050

Gly Leu  Asn Asp Ser Leu  Ile Asp Leu Glu Lys  Leu Ser Ile Leu
    1055             1060                1065

Lys Thr  Tyr Ile Lys Trp  Pro
    1070             1075

<210> SEQ ID NO 8
<211> LENGTH: 1156
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 8

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Ser Ser Thr Asn Tyr Thr Asn Asn Ala Gly Ser Ala His
    50                  55                  60

Gly Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
        115                 120                 125

Ile Pro Arg Asp His Ile Arg Ile Ser Ala Met Lys Asn Gly Ser Leu
    130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Val Leu Cys
    210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Ser Asn Val Ser Asn Ala Gln Pro Asn Ser Gly
        275                 280                 285

Gly Val Asn Thr Phe His Leu Tyr Gln Thr Gln Thr Ala Gln Ser Gly
    290                 295                 300
```

-continued

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
            325                 330                 335

Glu Thr Ile Asn Ser Gly Leu Trp Phe Asn Ser Leu Ser Val Ser Leu
                340                 345                 350

Thr Tyr Gly Pro Leu Gln Gly Gly Cys Lys Gln Ser Val Phe Ser Gly
            355                 360                 365

Lys Ala Thr Cys Cys Tyr Ala Tyr Ser Tyr Arg Gly Pro Met Ala Cys
370                 375                 380

Lys Gly Val Tyr Ser Gly Glu Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
            420                 425                 430

Lys Cys Val Ala Tyr Asn Ile Tyr Gly Arg Val Gly Gln Gly Phe Ile
                435                 440                 445

Thr Asn Val Thr Asp Ser Ala Ala Asn Phe Ser Tyr Leu Ala Asp Gly
450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
            515                 520                 525

Val Lys Leu Thr Asn Ser Ser His Arg Arg Lys Arg Ser Ile Gly Gln
530                 535                 540

Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Glu Leu Lys Gln Phe
            565                 570                 575

Val Ala Pro Leu Leu Asn Ile Thr Glu Ser Val Leu Ile Pro Asn Ser
            580                 585                 590

Phe Asn Leu Thr Val Thr Asp Glu Tyr Ile Gln Thr Arg Met Asp Lys
            595                 600                 605

Val Gln Ile Asn Cys Leu Gln Tyr Val Cys Gly Asn Ser Leu Glu Cys
610                 615                 620

Arg Lys Leu Phe Gln Gln Tyr Gly Pro Val Cys Asp Asn Ile Leu Ser
625                 630                 635                 640

Val Val Asn Ser Val Ser Gln Lys Glu Asp Met Glu Leu Leu Ser Phe
            645                 650                 655

Tyr Ser Thr Lys Pro Lys Gly Tyr Asp Thr Pro Val Leu Ser Asn
            660                 665                 670

Val Ser Thr Gly Glu Phe Asn Ile Ser Leu Leu Leu Lys Pro Pro Ser
            675                 680                 685

Ser Pro Ser Gly Arg Ser Phe Ile Glu Glu Leu Leu Phe Thr Ser Val
            690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn

```
                725             730             735
Gly Leu Leu Val Leu Pro Pro Ile Ile Thr Ala Asp Met Gln Thr Met
            740             745             750

Tyr Thr Ala Ser Leu Val Gly Ala Met Ala Phe Gly Gly Ile Thr Ser
            755             760             765

Ala Ala Ala Ile Pro Phe Ala Thr Gln Ile Gln Ala Arg Ile Asn His
            770             775             780

Leu Gly Ile Thr Gln Ser Leu Leu Met Lys Asn Gln Glu Lys Ile Ala
785             790             795             800

Ala Ser Phe Asn Lys Ala Ile Gly His Met Gln Glu Gly Phe Arg Ser
            805             810             815

Thr Ser Leu Ala Leu Gln Gln Ile Gln Asp Val Val Asn Lys Gln Ser
            820             825             830

Ala Ile Leu Thr Glu Thr Met Asn Ser Leu Asn Lys Asn Phe Gly Ala
            835             840             845

Ile Thr Ser Val Ile Gln Asp Ile Tyr Ala Gln Leu Asp Ala Ile Gln
            850             855             860

Ala Asp Ala Gln Val Asp Arg Leu Ile Thr Gly Arg Leu Ser Ser Leu
865             870             875             880

Ser Val Leu Ala Ser Ala Lys Gln Ser Glu Tyr Ile Arg Val Ser Gln
            885             890             895

Gln Arg Glu Leu Ala Thr Gln Lys Ile Asn Glu Cys Val Lys Ser Gln
            900             905             910

Ser Asn Arg Tyr Gly Phe Cys Gly Ser Gly Arg His Val Leu Ser Ile
            915             920             925

Pro Gln Asn Ala Pro Asn Gly Ile Val Phe Ile His Phe Thr Tyr Thr
            930             935             940

Pro Glu Ser Phe Val Asn Val Thr Ala Ile Val Gly Phe Cys Val Asn
945             950             955             960

Pro Ala Asn Ala Ser Gln Tyr Ala Ile Val Pro Ala Asn Gly Arg Gly
            965             970             975

Ile Phe Ile Gln Val Asn Gly Thr Tyr Tyr Ile Thr Ala Arg Asp Met
            980             985             990

Tyr Met Pro Arg Asp Ile Thr Ala Gly Asp Ile Val Thr Leu Thr Ser
            995             1000            1005

Cys Gln Ala Asn Tyr Val Asn Val Asn Lys Thr Val Ile Thr Thr
            1010            1015            1020

Phe Val Glu Asp Asp Asp Phe Asp Phe Asp Asp Glu Leu Ser Lys
            1025            1030            1035

Trp Trp Asn Asp Thr Lys His Gln Leu Pro Asp Phe Asp Asp Phe
            1040            1045            1050

Asn Tyr Thr Val Pro Ile Leu Asn Ile Ser Gly Glu Ile Asp Tyr
            1055            1060            1065

Ile Gln Gly Val Ile Gln Gly Leu Asn Asp Ser Leu Ile Asp Leu
            1070            1075            1080

Glu Glu Leu Ser Ile Ile Lys Thr Tyr Ile Lys Trp Pro Trp Tyr
            1085            1090            1095

Val Trp Leu Ala Ile Phe Phe Ala Ile Ile Ile Phe Ile Leu Ile
            1100            1105            1110

Leu Gly Trp Val Phe Phe Met Thr Gly Cys Cys Gly Cys Cys Cys
            1115            1120            1125

Gly Cys Phe Gly Ile Ile Pro Leu Met Ser Lys Cys Gly Lys Lys
            1130            1135            1140
```

Ser Ser Tyr Tyr Thr Thr Phe Asp Asn Asp Val Val Thr
1145                1150                1155

<210> SEQ ID NO 9
<211> LENGTH: 1078
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 9

Asn Leu Phe Asp Ser Asp Asn Asn Tyr Val Tyr Tyr Gln Ser Ala
1               5                   10                  15

Phe Arg Pro Pro Asn Gly Trp His Leu Gln Gly Gly Ala Tyr Ala Val
                20                  25                  30

Val Ser Ser Thr Asn Tyr Thr Asn Asn Ala Gly Ser Ala His Gly Cys
            35                  40                  45

Thr Val Gly Val Ile Lys Asp Val Tyr Asn Gln Ser Val Ala Ser Ile
50                  55                  60

Ala Met Thr Ala Pro Leu Gln Gly Met Ala Trp Ser Lys Ser Gln Phe
65                  70                  75                  80

Cys Ser Ala His Cys Asn Phe Ser Glu Ile Thr Val Phe Val Thr His
                85                  90                  95

Cys Tyr Ser Ser Gly Ser Gly Ser Cys Pro Ile Thr Gly Met Ile Pro
                100                 105                 110

Arg Asp His Ile Arg Ile Ser Ala Met Lys Asn Gly Ser Leu Phe Tyr
                115                 120                 125

Asn Leu Thr Val Ser Val Ser Lys Tyr Pro Asn Phe Lys Ser Phe Gln
130                 135                 140

Cys Val Asn Asn Phe Thr Ser Val Tyr Leu Asn Gly Asp Leu Val Phe
145                 150                 155                 160

Thr Ser Asn Lys Thr Thr Asp Val Thr Ser Ala Gly Val Tyr Phe Lys
                165                 170                 175

Ala Gly Gly Pro Val Asn Tyr Ser Ile Met Lys Glu Phe Lys Val Leu
                180                 185                 190

Ala Tyr Phe Val Asn Gly Thr Ala Gln Asp Val Val Leu Cys Asp Asn
                195                 200                 205

Ser Pro Lys Gly Leu Leu Ala Cys Gln Tyr Asn Thr Gly Asn Phe Ser
                210                 215                 220

Asp Gly Phe Tyr Pro Phe Thr Asn Ser Thr Leu Val Arg Glu Lys Phe
225                 230                 235                 240

Ile Val Tyr Arg Glu Ser Ser Val Asn Thr Thr Leu Ala Leu Thr Asn
                245                 250                 255

Phe Thr Phe Ser Asn Val Ser Asn Ala Gln Pro Asn Ser Gly Gly Val
                260                 265                 270

Asn Thr Phe His Leu Tyr Gln Thr Gln Thr Ala Gln Ser Gly Tyr Tyr
                275                 280                 285

Asn Phe Asn Leu Ser Phe Leu Ser Gln Phe Val Tyr Lys Ala Ser Asp
                290                 295                 300

Phe Met Tyr Gly Ser Tyr His Pro Ser Cys Ser Phe Arg Pro Glu Thr
305                 310                 315                 320

Ile Asn Ser Gly Leu Trp Phe Asn Ser Leu Ser Val Ser Leu Thr Tyr
                325                 330                 335

Gly Pro Leu Gln Gly Gly Cys Lys Gln Ser Val Phe Ser Gly Lys Ala

```
                   340             345             350
Thr Cys Cys Tyr Ala Tyr Ser Tyr Arg Gly Pro Met Ala Cys Lys Gly
            355             360             365

Val Tyr Ser Gly Glu Leu Ser Thr Asn Phe Glu Cys Gly Leu Leu Val
    370             375             380

Tyr Val Thr Lys Ser Asp Gly Ser Arg Ile Gln Thr Arg Thr Glu Pro
385             390             395             400

Leu Val Leu Thr Gln Tyr Asn Tyr Asn Ile Thr Leu Asp Lys Cys
            405             410             415

Val Ala Tyr Asn Ile Tyr Gly Arg Val Gly Gln Gly Phe Ile Thr Asn
            420             425             430

Val Thr Asp Ser Ala Ala Asn Phe Ser Tyr Leu Ala Asp Gly Gly Leu
            435             440             445

Ala Ile Leu Asp Thr Ser Gly Ala Ile Asp Val Phe Val Val Gln Gly
            450             455             460

Ile Tyr Gly Leu Asn Tyr Tyr Lys Val Asn Pro Cys Glu Asp Val Asn
465             470             475             480

Gln Gln Phe Val Val Ser Gly Gly Asn Ile Val Gly Ile Leu Thr Ser
                485             490             495

Arg Asn Glu Thr Gly Ser Glu Gln Val Glu Asn Gln Phe Tyr Val Lys
            500             505             510

Leu Thr Asn Ser Ser His Arg Arg Lys Arg Ser Ile Gly Gln Asn Val
            515             520             525

Thr Ser Cys Pro Tyr Val Ser Tyr Gly Arg Phe Cys Ile Glu Pro Asp
            530             535             540

Gly Ser Leu Lys Met Ile Val Pro Glu Glu Leu Lys Gln Phe Val Ala
545             550             555             560

Pro Leu Leu Asn Ile Thr Glu Ser Val Leu Ile Pro Asn Ser Phe Asn
                565             570             575

Leu Thr Val Thr Asp Glu Tyr Ile Gln Thr Arg Met Asp Lys Val Gln
            580             585             590

Ile Asn Cys Leu Gln Tyr Val Cys Gly Asn Ser Leu Glu Cys Arg Lys
            595             600             605

Leu Phe Gln Gln Tyr Gly Pro Val Cys Asp Asn Ile Leu Ser Val Val
            610             615             620

Asn Ser Val Ser Gln Lys Glu Asp Met Glu Leu Leu Ser Phe Tyr Ser
625             630             635             640

Ser Thr Lys Pro Lys Gly Tyr Asp Thr Pro Val Leu Ser Asn Val Ser
                645             650             655

Thr Gly Glu Phe Asn Ile Ser Leu Leu Leu Lys Pro Pro Ser Ser Pro
            660             665             670

Ser Gly Arg Ser Phe Ile Glu Glu Leu Leu Phe Thr Ser Val Glu Thr
            675             680             685

Val Gly Leu Pro Thr Asp Ala Glu Tyr Lys Lys Cys Thr Ala Gly Pro
            690             695             700

Leu Gly Thr Leu Lys Asp Leu Ile Cys Ala Arg Glu Tyr Asn Gly Leu
705             710             715             720

Leu Val Leu Pro Pro Ile Ile Thr Ala Asp Met Gln Thr Met Tyr Thr
                725             730             735

Ala Ser Leu Val Gly Ala Met Ala Phe Gly Gly Ile Thr Ser Ala Ala
            740             745             750

Ala Ile Pro Phe Ala Thr Gln Ile Gln Ala Arg Ile Asn His Leu Gly
            755             760             765
```

Ile Thr Gln Ser Leu Leu Met Lys Asn Gln Glu Lys Ile Ala Ala Ser
        770                 775                 780

Phe Asn Lys Ala Ile Gly His Met Gln Glu Gly Phe Arg Ser Thr Ser
785                 790                 795                 800

Leu Ala Leu Gln Gln Ile Gln Asp Val Val Asn Lys Gln Ser Ala Ile
                805                 810                 815

Leu Thr Glu Thr Met Asn Ser Leu Asn Lys Asn Phe Gly Ala Ile Thr
            820                 825                 830

Ser Val Ile Gln Asp Ile Tyr Ala Gln Leu Asp Ala Ile Gln Ala Asp
        835                 840                 845

Ala Gln Val Asp Arg Leu Ile Thr Gly Arg Leu Ser Ser Leu Ser Val
    850                 855                 860

Leu Ala Ser Ala Lys Gln Ser Glu Tyr Ile Arg Val Ser Gln Gln Arg
865                 870                 875                 880

Glu Leu Ala Thr Gln Lys Ile Asn Glu Cys Val Lys Ser Gln Ser Asn
                885                 890                 895

Arg Tyr Gly Phe Cys Gly Ser Gly Arg His Val Leu Ser Ile Pro Gln
            900                 905                 910

Asn Ala Pro Asn Gly Ile Val Phe Ile His Phe Thr Tyr Thr Pro Glu
        915                 920                 925

Ser Phe Val Asn Val Thr Ala Ile Val Gly Phe Cys Val Asn Pro Ala
    930                 935                 940

Asn Ala Ser Gln Tyr Ala Ile Val Pro Ala Asn Gly Arg Gly Ile Phe
945                 950                 955                 960

Ile Gln Val Asn Gly Thr Tyr Tyr Ile Thr Ala Arg Asp Met Tyr Met
                965                 970                 975

Pro Arg Asp Ile Thr Ala Gly Asp Ile Val Thr Leu Thr Ser Cys Gln
            980                 985                 990

Ala Asn Tyr Val Asn Val Asn Lys Thr Val Ile Thr Thr Phe Val Glu
        995                 1000                1005

Asp Asp Asp Phe Asp Phe Asp Asp Glu Leu Ser Lys Trp Trp Asn
        1010                1015                1020

Asp Thr Lys His Gln Leu Pro Asp Phe Asp Asp Phe Asn Tyr Thr
        1025                1030                1035

Val Pro Ile Leu Asn Ile Ser Gly Glu Ile Asp Tyr Ile Gln Gly
        1040                1045                1050

Val Ile Gln Gly Leu Asn Asp Ser Leu Ile Asp Leu Glu Glu Leu
        1055                1060                1065

Ser Ile Ile Lys Thr Tyr Ile Lys Trp Pro
        1070                1075

<210> SEQ ID NO 10
<211> LENGTH: 1166
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 10

Met Leu Gly Lys Ser Leu Phe Ile Val Thr Leu Leu Phe Ala Leu Cys
1               5                   10                  15

Ser Ala Ala Leu Phe Asp Asn Asn Glu Thr Val Tyr Tyr Tyr Gln Ser
            20                  25                  30

Ala Phe Arg Pro Ala Asp Gly Trp His Leu His Gly Gly Ala Tyr Ala

```
            35                  40                  45
Val Val Asn Val Ser Leu Glu Thr Asn Asn Ala Gly Thr Ala Ser Gln
 50                  55                  60

Cys Ile Ala Gly Ala Ile Ser Trp Ser Lys Asn Phe Ser Ala Ser Ala
 65                  70                  75                  80

Val Ala Met Thr Ala Pro Glu Leu Gly Met Thr Trp Ser Thr Gly Gln
                     85                  90                  95

Phe Cys Thr Ala His Cys Asn Phe Ser Asp Phe Thr Val Phe Val Thr
                    100                 105                 110

His Cys Phe Lys His Gly Asn Gly Leu Cys Pro Leu Thr Gly Leu Ile
                    115                 120                 125

Pro Ser Gly Phe Ile Arg Val Ser Ala Met Arg Lys Gly Ser Asn Ser
130                 135                 140

Leu Phe Tyr Asn Leu Thr Val Ser Val Thr Lys Tyr Pro Arg Phe Lys
145                 150                 155                 160

Ser Leu Gln Cys Val Asn Asn Tyr Thr Ser Val Tyr Leu Asn Gly Asp
                    165                 170                 175

Leu Val Phe Thr Ser Asn Glu Thr Lys Pro Val Ser Ala Ala Gly Val
                    180                 185                 190

Ser Phe Lys Ala Gly Gly Pro Ile Thr Tyr Lys Thr Met Ser Glu Val
                    195                 200                 205

Lys Val Leu Ala Tyr Phe Val Asn Gly Thr Ala Gln Thr Val Ile Pro
210                 215                 220

Cys Asp Gly Ser Pro Arg Gly Leu Leu Ala Cys Gln Tyr Asn Thr Gly
225                 230                 235                 240

Asn Phe Ser Asp Gly Phe Tyr Pro Tyr Thr Asn Ser Ser Leu Val Lys
                    245                 250                 255

Glu Arg Phe Ile Val Tyr Arg Glu Ser Ser Val Asn Thr Thr Leu Val
                    260                 265                 270

Leu Thr Asn Phe Thr Phe Ser Asn Val Ser Asn Ala Pro Pro Asn Thr
                    275                 280                 285

Gly Gly Val His Ser Ile Val Leu His Gln Thr Gln Thr Ala Gln Ser
290                 295                 300

Gly Tyr Tyr Asn Phe Asn Phe Ser Phe Leu Ser Ser Phe Arg Tyr Val
305                 310                 315                 320

Glu Ser Asp Phe Met Tyr Gly Ser Tyr His Pro Lys Cys Ser Phe Arg
                    325                 330                 335

Leu Glu Thr Ile Asn Asn Gly Leu Trp Phe Asn Ser Leu Ser Val Ser
                    340                 345                 350

Leu Gly Tyr Gly Pro Leu Gln Gly Gly Cys Lys Gln Ser Val Phe Asn
                    355                 360                 365

Asn Met Ala Thr Cys Cys Tyr Ala Tyr Ser Tyr Ser Gly Pro Thr Leu
                    370                 375                 380

Cys Lys Gly Val Tyr Ser Gly Gln Leu Gln Lys Thr Phe Glu Cys Gly
385                 390                 395                 400

Leu Leu Val Phe Val Thr Lys Ser Asp Gly Ser Arg Ile Gln Thr Arg
                    405                 410                 415

Asn Glu Pro Leu Val Leu Thr Gln His Asn Tyr Asn Asn Ile Thr Leu
                    420                 425                 430

Asn Lys Cys Val Glu Tyr Asn Ile Tyr Gly Arg Val Gly Gln Gly Leu
                    435                 440                 445

Ile Thr Asn Ile Thr Asp Ser Ala Ala Asn His Gly Tyr Leu Ala Asp
450                 455                 460
```

```
Gly Gly Leu Ala Val Leu Asp Thr Ser Gly Ala Ile Asp Val Phe Val
465                 470                 475                 480

Val Gln Gly Val Tyr Gly Leu Thr Tyr Tyr Lys Val Asn Pro Cys Glu
            485                 490                 495

Asp Val Asn Gln Gln Phe Val Ser Gly Gln Leu Val Gly Ile
        500                 505                 510

Leu Thr Ser Arg Asn Glu Thr Gly Ser Gln Pro Ile Glu Asn Arg Phe
        515                 520                 525

Tyr Val Lys Phe Pro Asn Ser Arg Arg Thr Gly Arg Ser Thr Ile
        530                 535                 540

Ala Asn Val Thr Asn Cys Pro Tyr Val Ser Tyr Gly Lys Phe Cys Ile
545                 550                 555                 560

Lys Pro Asp Gly Ser Val Ser Glu Ile Val Pro Gln Glu Ile Glu His
                565                 570                 575

Phe Val Ala Pro Leu Leu Asn Val Thr Glu His Val Leu Ile Pro Asn
            580                 585                 590

Ser Phe Asn Leu Thr Val Thr Asp Glu Tyr Ile Gln Thr Arg Met Asp
        595                 600                 605

Lys Ile Gln Ile Asn Cys Arg Gln Tyr Val Cys Gly Asn Ser Ile Glu
610                 615                 620

Cys Arg Lys Leu Phe Gln Gln Tyr Gly Pro Val Cys Asp Asn Ile Leu
625                 630                 635                 640

Ser Val Val Asn Thr Val Gly Gln Arg Glu Asp Met Glu Leu Leu Ser
                645                 650                 655

Phe Tyr Ser Ser Thr Lys Pro Lys Asp Tyr Asn Ile Pro Ile Phe Ser
            660                 665                 670

Asn Val Ser Thr Gly Asp Phe Asn Ile Ser Leu Leu Leu Thr Pro Pro
            675                 680                 685

Asn Ser Pro Thr Gly Arg Ser Phe Ile Glu Asp Ile Leu Phe Thr Ser
        690                 695                 700

Val Glu Ser Val Gly Leu Pro Thr Asp Glu Glu Tyr Lys Lys Cys Thr
705                 710                 715                 720

Ala Gly Pro Leu Gly Phe Val Lys Asp Leu Val Cys Ala Arg Glu Tyr
            725                 730                 735

Asn Gly Leu Leu Val Leu Pro Pro Ile Ile Thr Ala Asp Met Gln Thr
            740                 745                 750

Met Tyr Thr Ser Thr Leu Val Ala Ser Met Ala Leu Gly Gly Ile Thr
        755                 760                 765

Ala Ala Gly Ala Ile Pro Phe Ala Thr Gln Leu Gln Ala Arg Ile Asn
        770                 775                 780

His Leu Gly Ile Thr Gln Ser Leu Leu Leu Lys Asn Gln Glu Lys Ile
785                 790                 795                 800

Ala Ala Ser Phe Asn Lys Ala Ile Gly His Met Gln Glu Gly Phe Arg
            805                 810                 815

Ser Thr Ser Leu Ala Leu Gln Gln Ile Gln Asp Val Val Asn Lys Gln
        820                 825                 830

Ser Ser Ile Leu Thr Glu Thr Met Ala Ser Leu Asn Lys Asn Phe Gly
        835                 840                 845

Ala Ile Ser Ser Val Leu Gln Asp Ile Tyr Gln Gln Leu Asp Ala Ile
        850                 855                 860

Gln Ala Asp Ala Gln Val Asp Arg Ile Ile Thr Gly Arg Leu Ser Ser
865                 870                 875                 880
```

```
Leu Ser Val Leu Ala Ser Ala Lys Gln Ser Glu Tyr Tyr Arg Val Ser
            885                 890                 895

Gln Gln Arg Glu Leu Ala Thr Gln Lys Ile Asn Glu Cys Val Lys Ser
        900                 905                 910

Gln Ser Thr Arg Tyr Ser Phe Cys Gly Asn Gly Arg His Val Leu Thr
        915                 920                 925

Ile Pro Gln Asn Ala Pro Asn Gly Ile Val Phe Ile His Phe Thr Tyr
        930                 935                 940

Thr Pro Glu Ser Phe Val Asn Val Thr Ala Ile Val Gly Phe Cys Val
945                 950                 955                 960

Asn Pro Pro Asn Ala Ser Gln Tyr Ala Leu Val Pro Ala Asn Gly Arg
            965                 970                 975

Gly Ile Phe Ile Gln Val Asn Gly Ser Tyr Tyr Ile Thr Ala Arg Asp
            980                 985                 990

Met Tyr Met Pro Arg Asp Ile Thr Ala Gly Asp Ile Val Thr Leu Thr
            995                 1000                1005

Ser Cys Gln Ala Asn Tyr Val Ser Val Asn Arg Thr Val Ile Thr
        1010                1015                1020

Thr Phe Val Asp Asn Asp Asp Phe Asp Phe Asp Asp Glu Leu Ser
        1025                1030                1035

Lys Trp Trp Asn Asp Thr Lys His Glu Leu Pro Asp Phe Asp Glu
        1040                1045                1050

Phe Asn Tyr Thr Ile Pro Val Leu Asn Ile Ser Asn Glu Ile Asp
        1055                1060                1065

Arg Ile Gln Glu Val Ile Gln Gly Leu Asn Asp Ser Leu Ile Asp
        1070                1075                1080

Leu Glu Ala Leu Ser Ile Leu Lys Thr Tyr Ile Lys Trp Pro Trp
        1085                1090                1095

Tyr Val Trp Leu Ala Ile Ala Phe Leu Thr Ile Ile Phe Ile Leu
        1100                1105                1110

Val Leu Cys Trp Ile Phe Phe Met Thr Gly Cys Cys Gly Cys Cys
        1115                1120                1125

Cys Gly Cys Phe Gly Ile Met Pro Leu Met Ser Lys Cys Gly Lys
        1130                1135                1140

Lys Ser Ser Tyr Tyr Thr Thr Phe Asp Asn Asp Val Val Thr Glu
        1145                1150                1155

Gln Tyr Arg Pro Lys Lys Ser Val
        1160                1165

<210> SEQ ID NO 11
<211> LENGTH: 1079
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 11

Ala Leu Phe Asp Asn Asn Glu Thr Val Tyr Tyr Tyr Gln Ser Ala Phe
1               5                   10                  15

Arg Pro Ala Asp Gly Trp His Leu His Gly Gly Ala Tyr Ala Val Val
            20                  25                  30

Asn Val Ser Leu Glu Thr Asn Asn Ala Gly Thr Ala Ser Gln Cys Ile
        35                  40                  45

Ala Gly Ala Ile Ser Trp Ser Lys Asn Phe Ser Ala Ser Ala Val Ala
    50                  55                  60
```

-continued

```
Met Thr Ala Pro Glu Leu Gly Met Thr Trp Ser Thr Gly Gln Phe Cys
 65                  70                  75                  80

Thr Ala His Cys Asn Phe Ser Asp Phe Thr Val Phe Val Thr His Cys
                 85                  90                  95

Phe Lys His Gly Asn Gly Leu Cys Pro Leu Thr Gly Leu Ile Pro Ser
            100                 105                 110

Gly Phe Ile Arg Val Ser Ala Met Arg Lys Gly Ser Asn Ser Leu Phe
            115                 120                 125

Tyr Asn Leu Thr Val Ser Val Thr Lys Tyr Pro Arg Phe Lys Ser Leu
130                 135                 140

Gln Cys Val Asn Asn Tyr Thr Ser Val Tyr Leu Asn Gly Asp Leu Val
145                 150                 155                 160

Phe Thr Ser Asn Glu Thr Lys Pro Val Ser Ala Ala Gly Val Ser Phe
                165                 170                 175

Lys Ala Gly Gly Pro Ile Thr Tyr Lys Thr Met Ser Glu Val Lys Val
            180                 185                 190

Leu Ala Tyr Phe Val Asn Gly Thr Ala Gln Thr Val Ile Pro Cys Asp
            195                 200                 205

Gly Ser Pro Arg Gly Leu Leu Ala Cys Gln Tyr Asn Thr Gly Asn Phe
210                 215                 220

Ser Asp Gly Phe Tyr Pro Tyr Thr Asn Ser Ser Leu Val Lys Glu Arg
225                 230                 235                 240

Phe Ile Val Tyr Arg Glu Ser Ser Val Asn Thr Thr Leu Val Leu Thr
                245                 250                 255

Asn Phe Thr Phe Ser Asn Val Ser Asn Ala Pro Pro Asn Thr Gly Gly
            260                 265                 270

Val His Ser Ile Val Leu His Gln Thr Gln Thr Ala Gln Ser Gly Tyr
            275                 280                 285

Tyr Asn Phe Asn Phe Ser Phe Leu Ser Ser Phe Arg Tyr Val Glu Ser
290                 295                 300

Asp Phe Met Tyr Gly Ser Tyr His Pro Lys Cys Ser Phe Arg Leu Glu
305                 310                 315                 320

Thr Ile Asn Asn Gly Leu Trp Phe Asn Ser Leu Ser Val Ser Leu Gly
                325                 330                 335

Tyr Gly Pro Leu Gln Gly Gly Cys Lys Gln Ser Val Phe Asn Asn Met
            340                 345                 350

Ala Thr Cys Cys Tyr Ala Tyr Ser Tyr Ser Gly Pro Thr Leu Cys Lys
            355                 360                 365

Gly Val Tyr Ser Gly Gln Leu Gln Lys Thr Phe Glu Cys Gly Leu Leu
            370                 375                 380

Val Phe Val Thr Lys Ser Asp Gly Ser Arg Ile Gln Thr Arg Asn Glu
385                 390                 395                 400

Pro Leu Val Leu Thr Gln His Asn Tyr Asn Asn Ile Thr Leu Asn Lys
                405                 410                 415

Cys Val Glu Tyr Asn Ile Tyr Gly Arg Val Gly Gln Gly Leu Ile Thr
            420                 425                 430

Asn Ile Thr Asp Ser Ala Ala Asn His Gly Tyr Leu Ala Asp Gly Gly
            435                 440                 445

Leu Ala Val Leu Asp Thr Ser Gly Ala Ile Asp Val Phe Val Val Gln
            450                 455                 460

Gly Val Tyr Gly Leu Thr Tyr Tyr Lys Val Asn Pro Cys Glu Asp Val
465                 470                 475                 480
```

-continued

```
Asn Gln Gln Phe Val Val Ser Gly Gly Gln Leu Val Gly Ile Leu Thr
                485                 490                 495
Ser Arg Asn Glu Thr Gly Ser Gln Pro Ile Glu Asn Arg Phe Tyr Val
            500                 505                 510
Lys Phe Pro Asn Ser Arg Arg Thr Gly Arg Ser Thr Ile Ala Asn
        515                 520                 525
Val Thr Asn Cys Pro Tyr Val Ser Tyr Gly Lys Phe Cys Ile Lys Pro
    530                 535                 540
Asp Gly Ser Val Ser Glu Ile Val Pro Gln Ile Glu His Phe Val
545                 550                 555                 560
Ala Pro Leu Leu Asn Val Thr Glu His Val Leu Ile Pro Asn Ser Phe
                565                 570                 575
Asn Leu Thr Val Thr Asp Glu Tyr Ile Gln Thr Arg Met Asp Lys Ile
            580                 585                 590
Gln Ile Asn Cys Arg Gln Tyr Val Cys Gly Asn Ser Ile Glu Cys Arg
        595                 600                 605
Lys Leu Phe Gln Gln Tyr Gly Pro Val Cys Asp Asn Ile Leu Ser Val
    610                 615                 620
Val Asn Thr Val Gly Gln Arg Glu Asp Met Glu Leu Leu Ser Phe Tyr
625                 630                 635                 640
Ser Ser Thr Lys Pro Lys Asp Tyr Asn Ile Pro Ile Phe Ser Asn Val
                645                 650                 655
Ser Thr Gly Asp Phe Asn Ile Ser Leu Leu Thr Pro Pro Asn Ser
            660                 665                 670
Pro Thr Gly Arg Ser Phe Ile Glu Asp Ile Leu Phe Thr Ser Val Glu
        675                 680                 685
Ser Val Gly Leu Pro Thr Asp Glu Glu Tyr Lys Lys Cys Thr Ala Gly
    690                 695                 700
Pro Leu Gly Phe Val Lys Asp Leu Val Cys Ala Arg Glu Tyr Asn Gly
705                 710                 715                 720
Leu Leu Val Leu Pro Pro Ile Ile Thr Ala Asp Met Gln Thr Met Tyr
                725                 730                 735
Thr Ser Thr Leu Val Ala Ser Met Ala Leu Gly Gly Ile Thr Ala Ala
            740                 745                 750
Gly Ala Ile Pro Phe Ala Thr Gln Leu Gln Ala Arg Ile Asn His Leu
        755                 760                 765
Gly Ile Thr Gln Ser Leu Leu Leu Lys Asn Gln Glu Lys Ile Ala Ala
    770                 775                 780
Ser Phe Asn Lys Ala Ile Gly His Met Gln Glu Gly Phe Arg Ser Thr
785                 790                 795                 800
Ser Leu Ala Leu Gln Gln Ile Gln Asp Val Val Asn Lys Gln Ser Ser
                805                 810                 815
Ile Leu Thr Glu Thr Met Ala Ser Leu Asn Lys Asn Phe Gly Ala Ile
            820                 825                 830
Ser Ser Val Leu Gln Asp Ile Tyr Gln Gln Leu Asp Ala Ile Gln Ala
        835                 840                 845
Asp Ala Gln Val Asp Arg Ile Ile Thr Gly Arg Leu Ser Ser Leu Ser
    850                 855                 860
Val Leu Ala Ser Ala Lys Gln Ser Glu Tyr Tyr Arg Val Ser Gln Gln
865                 870                 875                 880
Arg Glu Leu Ala Thr Gln Lys Ile Asn Glu Cys Val Lys Ser Gln Ser
                885                 890                 895
Thr Arg Tyr Ser Phe Cys Gly Asn Gly Arg His Val Leu Thr Ile Pro
```

900                 905                 910
Gln Asn Ala Pro Asn Gly Ile Val Phe Ile His Phe Thr Tyr Thr Pro
            915                 920                 925
Glu Ser Phe Val Asn Val Thr Ala Ile Val Gly Phe Cys Val Asn Pro
        930                 935                 940
Pro Asn Ala Ser Gln Tyr Ala Leu Val Pro Ala Asn Gly Arg Gly Ile
945                 950                 955                 960
Phe Ile Gln Val Asn Gly Ser Tyr Tyr Ile Thr Ala Arg Asp Met Tyr
                965                 970                 975
Met Pro Arg Asp Ile Thr Ala Gly Asp Ile Val Thr Leu Thr Ser Cys
            980                 985                 990
Gln Ala Asn Tyr Val Ser Val Asn Arg Thr Val Ile Thr Thr Phe Val
        995                 1000                1005
Asp Asn Asp Asp Phe Asp Phe Asp Asp Glu Leu Ser Lys Trp Trp
    1010                1015                1020
Asn Asp Thr Lys His Glu Leu Pro Asp Phe Asp Glu Phe Asn Tyr
        1025                1030                1035
Thr Ile Pro Val Leu Asn Ile Ser Asn Glu Ile Asp Arg Ile Gln
    1040                1045                1050
Glu Val Ile Gln Gly Leu Asn Asp Ser Leu Ile Asp Leu Glu Ala
        1055                1060                1065
Leu Ser Ile Leu Lys Thr Tyr Ile Lys Trp Pro
    1070                1075

<210> SEQ ID NO 12
<211> LENGTH: 1159
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 12

Met Leu Val Lys Ser Leu Phe Leu Val Thr Ile Leu Phe Ala Leu Cys
1               5                   10                  15
Ser Ala Asn Leu Tyr Asp Asn Glu Ser Phe Val Tyr Tyr Tyr Gln Ser
            20                  25                  30
Ala Phe Arg Pro Gly His Gly Trp His Leu His Gly Gly Ala Tyr Ala
        35                  40                  45
Val Val Asn Val Ser Ser Glu Asn Asn Asn Ala Gly Thr Ala Pro Ser
    50                  55                  60
Cys Thr Ala Gly Ala Ile Gly Tyr Ser Lys Asn Phe Ser Ala Ala Ser
65                  70                  75                  80
Val Ala Met Thr Ala Pro Leu Ser Gly Met Ser Trp Ser Ala Ser Ser
                85                  90                  95
Phe Cys Thr Ala His Cys Asn Phe Thr Ser Tyr Ile Val Phe Val Thr
            100                 105                 110
His Cys Phe Lys Ser Gly Ser Asn Ser Cys Pro Leu Thr Gly Leu Ile
        115                 120                 125
Pro Ser Gly Tyr Ile Arg Ile Ala Ala Met Lys His Gly Ser Arg Thr
    130                 135                 140
Pro Gly His Leu Phe Tyr Asn Leu Thr Val Ser Val Thr Lys Tyr Pro
145                 150                 155                 160
Lys Phe Arg Ser Leu Gln Cys Val Asn Asn His Thr Ser Val Tyr Leu
                165                 170                 175

```
Asn Gly Asp Leu Val Phe Thr Ser Gly Tyr Thr Glu Asp Val Val Ala
            180                 185                 190

Ala Gly Val His Phe Lys Ser Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
                260                 265                 270

Thr Leu Thr Leu Thr Asn Phe Thr Phe Ser Asn Glu Ser Gly Ala Pro
            275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
            340                 345                 350

Val Ser Leu Thr Tyr Gly Pro Ile Gln Gly Gly Cys Lys Gln Ser Val
            355                 360                 365

Phe Asn Gly Lys Ala Thr Cys Cys Tyr Ala Tyr Ser Tyr Gly Gly Pro
370                 375                 380

Arg Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
            405                 410                 415

Thr Ala Thr Gln Pro Pro Val Leu Thr Gln Asn Phe Tyr Asn Asn Ile
            420                 425                 430

Thr Leu Gly Lys Cys Val Asp Tyr Asn Val Tyr Gly Arg Thr Gly Gln
            435                 440                 445

Gly Phe Ile Thr Asn Val Thr Asp Leu Ala Thr Ser His Asn Tyr Leu
450                 455                 460

Ala Asp Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
                485                 490                 495

Cys Glu Asp Val Asn Gln Gln Phe Val Val Ser Gly Gly Lys Leu Val
                500                 505                 510

Gly Ile Leu Thr Ser Arg Asn Glu Thr Gly Ser Gln Pro Leu Glu Asn
            515                 520                 525

Gln Phe Tyr Ile Lys Ile Thr Asn Gly Thr His Arg Ser Arg Arg Ser
            530                 535                 540

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
                565                 570                 575

Glu Gln Phe Val Ala Pro Leu Leu Asn Val Thr Glu Asn Val Leu Ile
            580                 585                 590

Pro Asn Ser Phe Asn Leu Thr Val Thr Asp Glu Tyr Ile Gln Thr His
```

-continued

```
            595                 600                 605
Met Asp Lys Ile Gln Ile Asn Cys Leu Gln Tyr Val Cys Gly Asn Ser
610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                    645                 650                 655

Leu Ser Phe Tyr Ser Ser Thr Lys Pro Ser Gly Phe Asn Thr Pro Val
                660                 665                 670

Phe Ser Asn Leu Ser Thr Gly Glu Phe Asn Ile Ser Leu Leu Leu Thr
            675                 680                 685

Thr Pro Ser Ser Pro Arg Gly Arg Ser Phe Ile Glu Asp Leu Leu Phe
690                 695                 700

Thr Ser Val Glu Ser Val Gly Leu Pro Thr Asp Glu Ala Tyr Lys Lys
705                 710                 715                 720

Cys Thr Ala Gly Pro Leu Gly Phe Leu Lys Asp Leu Ala Cys Ala Arg
                    725                 730                 735

Glu Tyr Asn Gly Leu Leu Val Leu Pro Pro Ile Ile Thr Ala Glu Met
                740                 745                 750

Gln Thr Leu Tyr Thr Ser Ser Leu Val Val Ser Met Ala Phe Gly Gly
            755                 760                 765

Ile Thr Ser Ala Gly Ala Ile Pro Phe Ala Thr Gln Leu Gln Ala Arg
770                 775                 780

Ile Asn His Leu Gly Ile Thr Gln Ser Leu Leu Leu Lys Asn Gln Glu
785                 790                 795                 800

Lys Ile Ala Ala Ser Phe Asn Lys Ala Ile Gly His Met Gln Glu Gly
                    805                 810                 815

Phe Arg Ser Thr Ser Leu Ala Leu Gln Gln Ile Gln Asp Val Val Asn
                820                 825                 830

Lys Gln Ser Ala Ile Leu Thr Glu Thr Met Ala Ser Leu Asn Lys Asn
            835                 840                 845

Phe Gly Ala Ile Ser Ser Val Ile Gln Glu Ile Tyr Gln Gln Leu Asp
850                 855                 860

Ala Ile Gln Ala Asn Ala Gln Val Asp Arg Leu Ile Thr Gly Arg Leu
865                 870                 875                 880

Ser Ser Leu Ser Val Leu Ala Ser Ala Lys Gln Ala Glu Tyr Ile Arg
                    885                 890                 895

Val Ser Gln Gln Arg Glu Leu Ala Thr Gln Lys Ile Asn Glu Cys Val
                900                 905                 910

Lys Ser Gln Ser Ile Arg Tyr Ser Phe Cys Gly Asn Gly Arg His Val
            915                 920                 925

Leu Thr Ile Pro Gln Asn Ala Pro Asn Gly Ile Val Phe Ile His Phe
930                 935                 940

Ser Tyr Thr Pro Asp Ser Phe Val Asn Val Thr Ala Ile Val Gly Phe
945                 950                 955                 960

Cys Val Lys Pro Ala Asn Ala Ser Gln Tyr Ala Ile Val Pro Ala Asn
                    965                 970                 975

Gly Arg Gly Ile Phe Ile Gln Val Asn Gly Ser Tyr Tyr Ile Thr Ala
                980                 985                 990

Arg Asp Met Tyr Met Pro Arg Ala  Ile Thr Ala Gly Asp  Ile Val Thr
            995                 1000                1005

Leu Thr  Ser Cys Gln Ala Asn  Tyr Val Ser Val Asn  Lys Thr Val
       1010                1015                1020
```

Ile Thr Thr Phe Val Asp Asn Asp Asp Phe Asp Phe Asn Asp Glu
1025                1030                1035

Leu Ser Lys Trp Trp Asn Asp Thr Lys His Glu Leu Pro Asp Phe
1040                1045                1050

Asp Lys Phe Asn Tyr Thr Val Pro Ile Leu Asp Ile Asp Ser Glu
1055                1060                1065

Ile Asp Arg Ile Gln Gly Val Ile Gln Gly Leu Asn Asp Ser Leu
1070                1075                1080

Ile Asp Leu Glu Lys Leu Ser Ile Leu Lys Thr Tyr Ile Lys Trp
1085                1090                1095

Pro Trp Tyr Val Trp Leu Ala Ile Ala Phe Ala Thr Ile Ile Phe
1100                1105                1110

Ile Leu Ile Leu Gly Trp Val Phe Phe Met Thr Gly Cys Cys Gly
1115                1120                1125

Cys Cys Cys Gly Cys Phe Gly Ile Met Pro Leu Met Ser Lys Cys
1130                1135                1140

Gly Lys Lys Ser Ser Tyr Tyr Thr Thr Phe Asp Asn Asp Val Val
1145                1150                1155

Thr

<210> SEQ ID NO 13
<211> LENGTH: 1081
<212> TYPE: PRT
<213> ORGANISM: Unknown
<220> FEATURE:
<223> OTHER INFORMATION: Description of Unknown:
    Avian infectious bronchitis virus sequence

<400> SEQUENCE: 13

Asn Leu Tyr Asp Asn Glu Ser Phe Val Tyr Tyr Gln Ser Ala Phe
1               5                   10                  15

Arg Pro Gly His Gly Trp His Leu His Gly Gly Ala Tyr Ala Val Val
                20                  25                  30

Asn Val Ser Ser Glu Asn Asn Asn Ala Gly Thr Ala Pro Ser Cys Thr
                35                  40                  45

Ala Gly Ala Ile Gly Tyr Ser Lys Asn Phe Ser Ala Ala Ser Val Ala
50                  55                  60

Met Thr Ala Pro Leu Ser Gly Met Ser Trp Ser Ala Ser Ser Phe Cys
65                  70                  75                  80

Thr Ala His Cys Asn Phe Thr Ser Tyr Ile Val Phe Val Thr His Cys
                    85                  90                  95

Phe Lys Ser Gly Ser Asn Ser Cys Pro Leu Thr Gly Leu Ile Pro Ser
                100                 105                 110

Gly Tyr Ile Arg Ile Ala Ala Met Lys His Gly Ser Arg Thr Pro Gly
            115                 120                 125

His Leu Phe Tyr Asn Leu Thr Val Ser Val Thr Lys Tyr Pro Lys Phe
        130                 135                 140

Arg Ser Leu Gln Cys Val Asn Asn His Thr Ser Val Tyr Leu Asn Gly
145                 150                 155                 160

Asp Leu Val Phe Thr Ser Gly Tyr Thr Glu Asp Val Val Ala Ala Gly
                165                 170                 175

Val His Phe Lys Ser Gly Gly Pro Ile Thr Tyr Lys Val Met Arg Glu
                180                 185                 190

Val Lys Ala Leu Ala Tyr Phe Val Asn Gly Thr Ala His Asp Val Ile
            195                 200                 205

-continued

```
Leu Cys Asp Asp Thr Pro Arg Gly Leu Leu Ala Cys Gln Tyr Asn Thr
    210                 215                 220
Gly Asn Phe Ser Asp Gly Phe Tyr Pro Phe Thr Asn Thr Ser Ile Val
225                 230                 235                 240
Lys Asp Lys Phe Ile Val Tyr Arg Glu Ser Ser Val Asn Thr Thr Leu
                245                 250                 255
Thr Leu Thr Asn Phe Thr Phe Ser Asn Glu Ser Gly Ala Pro Pro Asn
                260                 265                 270
Thr Gly Gly Val Asp Ser Phe Ile Leu Tyr Gln Thr Gln Thr Ala Gln
            275                 280                 285
Ser Gly Tyr Tyr Asn Phe Asn Phe Ser Phe Leu Ser Ser Phe Val Tyr
        290                 295                 300
Arg Glu Ser Asn Tyr Met Tyr Gly Ser Tyr His Pro Arg Cys Ser Phe
305                 310                 315                 320
Arg Pro Glu Thr Leu Asn Gly Leu Trp Phe Asn Ser Leu Ser Val Ser
                325                 330                 335
Leu Thr Tyr Gly Pro Ile Gln Gly Gly Cys Lys Gln Ser Val Phe Asn
                340                 345                 350
Gly Lys Ala Thr Cys Cys Tyr Ala Tyr Ser Tyr Gly Gly Pro Arg Ala
            355                 360                 365
Cys Lys Gly Val Tyr Arg Gly Glu Leu Thr Gln His Phe Glu Cys Gly
        370                 375                 380
Leu Leu Val Tyr Val Thr Lys Ser Asp Gly Ser Arg Ile Gln Thr Ala
385                 390                 395                 400
Thr Gln Pro Pro Val Leu Thr Gln Asn Phe Tyr Asn Asn Ile Thr Leu
                405                 410                 415
Gly Lys Cys Val Asp Tyr Asn Val Tyr Gly Arg Thr Gly Gln Gly Phe
                420                 425                 430
Ile Thr Asn Val Thr Asp Leu Ala Thr Ser His Asn Tyr Leu Ala Asp
            435                 440                 445
Gly Gly Leu Ala Ile Leu Asp Thr Ser Gly Ala Ile Asp Ile Phe Val
        450                 455                 460
Val Gln Gly Glu Tyr Gly Pro Asn Tyr Tyr Lys Val Asn Leu Cys Glu
465                 470                 475                 480
Asp Val Asn Gln Gln Phe Val Val Ser Gly Gly Lys Leu Val Gly Ile
                485                 490                 495
Leu Thr Ser Arg Asn Glu Thr Gly Ser Gln Pro Leu Glu Asn Gln Phe
                500                 505                 510
Tyr Ile Lys Ile Thr Asn Gly Thr His Arg Ser Arg Arg Ser Val Asn
            515                 520                 525
Glu Asn Val Thr Asn Cys Pro Tyr Val Ser Tyr Gly Lys Phe Cys Ile
        530                 535                 540
Lys Pro Asp Gly Ser Val Ser Pro Ile Val Pro Lys Glu Leu Glu Gln
545                 550                 555                 560
Phe Val Ala Pro Leu Leu Asn Val Thr Glu Asn Val Leu Ile Pro Asn
                565                 570                 575
Ser Phe Asn Leu Thr Val Thr Asp Glu Tyr Ile Gln Thr His Met Asp
                580                 585                 590
Lys Ile Gln Ile Asn Cys Leu Gln Tyr Val Cys Gly Asn Ser Leu Ala
            595                 600                 605
Cys Arg Lys Leu Phe Gln Gln Tyr Gly Pro Val Cys Asp Asn Ile Leu
        610                 615                 620
```

```
Ser Val Val Asn Ser Val Gly Gln Lys Glu Asp Met Glu Leu Leu Ser
625                 630                 635                 640

Phe Tyr Ser Ser Thr Lys Pro Ser Gly Phe Asn Thr Pro Val Phe Ser
            645                 650                 655

Asn Leu Ser Thr Gly Glu Phe Asn Ile Ser Leu Leu Leu Thr Thr Pro
        660                 665                 670

Ser Ser Pro Arg Gly Arg Ser Phe Ile Glu Asp Leu Leu Phe Thr Ser
    675                 680                 685

Val Glu Ser Val Gly Leu Pro Thr Asp Glu Ala Tyr Lys Lys Cys Thr
690                 695                 700

Ala Gly Pro Leu Gly Phe Leu Lys Asp Leu Ala Cys Ala Arg Glu Tyr
705                 710                 715                 720

Asn Gly Leu Leu Val Leu Pro Pro Ile Ile Thr Ala Glu Met Gln Thr
                725                 730                 735

Leu Tyr Thr Ser Ser Leu Val Val Ser Met Ala Phe Gly Gly Ile Thr
            740                 745                 750

Ser Ala Gly Ala Ile Pro Phe Ala Thr Gln Leu Gln Ala Arg Ile Asn
        755                 760                 765

His Leu Gly Ile Thr Gln Ser Leu Leu Leu Lys Asn Gln Glu Lys Ile
770                 775                 780

Ala Ala Ser Phe Asn Lys Ala Ile Gly His Met Gln Glu Gly Phe Arg
785                 790                 795                 800

Ser Thr Ser Leu Ala Leu Gln Gln Ile Gln Asp Val Val Asn Lys Gln
                805                 810                 815

Ser Ala Ile Leu Thr Glu Thr Met Ala Ser Leu Asn Lys Asn Phe Gly
            820                 825                 830

Ala Ile Ser Ser Val Ile Gln Glu Ile Tyr Gln Gln Leu Asp Ala Ile
        835                 840                 845

Gln Ala Asn Ala Gln Val Asp Arg Leu Ile Thr Gly Arg Leu Ser Ser
850                 855                 860

Leu Ser Val Leu Ala Ser Ala Lys Gln Ala Glu Tyr Ile Arg Val Ser
865                 870                 875                 880

Gln Gln Arg Glu Leu Ala Thr Gln Lys Ile Asn Glu Cys Val Lys Ser
                885                 890                 895

Gln Ser Ile Arg Tyr Ser Phe Cys Gly Asn Gly Arg His Val Leu Thr
            900                 905                 910

Ile Pro Gln Asn Ala Pro Asn Gly Ile Val Phe Ile His Phe Ser Tyr
        915                 920                 925

Thr Pro Asp Ser Phe Val Asn Val Thr Ala Ile Val Gly Phe Cys Val
930                 935                 940

Lys Pro Ala Asn Ala Ser Gln Tyr Ala Ile Val Pro Ala Asn Gly Arg
945                 950                 955                 960

Gly Ile Phe Ile Gln Val Asn Gly Ser Tyr Tyr Ile Thr Ala Arg Asp
                965                 970                 975

Met Tyr Met Pro Arg Ala Ile Thr Ala Gly Asp Ile Val Thr Leu Thr
            980                 985                 990

Ser Cys Gln Ala Asn Tyr Val Ser Val Asn Lys Thr Val Ile Thr Thr
        995                1000                1005

Phe Val Asp Asn Asp Asp Phe Asp Phe Asn Asp Glu Leu Ser Lys
            1010                1015                1020

Trp Trp Asn Asp Thr Lys His Glu Leu Pro Asp Phe Asp Lys Phe
            1025                1030                1035

Asn Tyr Thr Val Pro Ile Leu Asp Ile Asp Ser Glu Ile Asp Arg
```

```
                      1040               1045                  1050

Ile Gln Gly Val Ile Gln Gly Leu Asn Asp Ser Leu Ile Asp Leu
            1055                1060                1065

Glu Lys Leu Ser Ile Leu Lys Thr Tyr Ile Lys Trp Pro
        1070                1075                1080
```

<210> SEQ ID NO 14
<211> LENGTH: 1156
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 14

```
Met Leu Val Lys Ser Leu Phe Ile Val Thr Leu Leu Phe Ala Leu Cys
1               5                   10                  15

Ser Ala Ala Leu Phe Asp Asn Asn Gln Ala Val Tyr Tyr Tyr Gln Ser
                20                  25                  30

Ala Phe Arg Pro Ser Ser Gly Trp His Lys His Gly Gly Ala Tyr Ala
            35                  40                  45

Val Ala Asn Val Ser Leu Glu Tyr Ala Asn Ala Gly Ser Ser Thr His
50                  55                  60

Cys Thr Ala Gly Ala Ile Tyr Trp Ser Lys Asn Phe Thr Ala Ser Ser
65                  70                  75                  80

Val Ala Met Thr Ala Pro Gly Thr Gly Met Ser Trp Ser Thr Ala Gln
                85                  90                  95

Phe Cys Thr Ala His Cys Asn Phe Ser Asp Phe Thr Val Phe Val Thr
            100                 105                 110

His Cys Tyr Lys Ser Gly Asp Val Cys Pro Leu Thr Gly Leu Ile Pro
        115                 120                 125

Ser Gly Tyr Ile Arg Ile Ser Ala Met Thr Lys Gly Thr Thr Ser Leu
130                 135                 140

Phe Tyr Asn Leu Thr Val Pro Val Thr Lys Tyr Pro Lys Phe Lys Ser
145                 150                 155                 160

Leu Gln Cys Val Asp Asn Phe Thr Ser Val Tyr Leu Asn Gly Asp Leu
                165                 170                 175

Val Phe Thr Ser Asn Glu Thr Lys Asp Val Ser Ala Ala Gly Val His
            180                 185                 190

Phe Lys Ala Gly Gly Pro Ile Thr Tyr Lys Val Met Glu Lys Val Asp
        195                 200                 205

Val Leu Ala Tyr Phe Val Asn Gly Thr Ala Gln Asp Val Ile Leu Cys
210                 215                 220

Asp Asn Ser Pro Arg Gly Leu Leu Ala Cys Gln Tyr Asn Thr Gly Asn
225                 230                 235                 240

Phe Ser Asp Gly Phe Tyr Pro Phe Thr Asn Ile Ser Leu Val Lys Glu
                245                 250                 255

Lys Phe Ile Val Tyr Arg Glu Thr Ser Val Asn Thr Thr Leu Val Leu
            260                 265                 270

Thr Asn Phe Thr Phe Thr Asn Val Ser Asn Ala Leu Pro Asn Thr Gly
        275                 280                 285

Gly Val Asn Thr Ile Asn Ile Tyr Gln Thr Gln Thr Ala Gln Ser Gly
290                 295                 300

Cys Tyr Asn Phe Asn Phe Ser Phe Leu Ser Ser Phe Val Tyr Lys Gln
305                 310                 315                 320
```

```
Ser Asp Phe Met Tyr Gly Ser Tyr His Pro Lys Cys Asp Phe Arg Pro
            325                 330                 335

Glu Thr Ile Asn Asn Gly Leu Trp Phe Asn Ser Leu Ser Val Ser Leu
            340                 345                 350

Ala Tyr Gly Pro Leu Gln Gly Gly Cys Lys Gln Ser Val Phe Ser Asn
            355                 360                 365

Arg Ala Thr Cys Cys Tyr Ala Tyr Ser Tyr Asn Gly Pro Arg Leu Cys
        370                 375                 380

Lys Gly Val Tyr Ile Gly Glu Leu Gln Gln Tyr Phe Glu Cys Gly Leu
385                 390                 395                 400

Leu Val Tyr Val Thr Lys Ser Asp Gly Ser Arg Ile Gln Thr Arg Asn
                405                 410                 415

Glu Pro Leu Val Leu Thr His His Asn Tyr Asn Asn Ile Thr Leu Asp
            420                 425                 430

Arg Cys Val Glu Tyr Asn Ile Tyr Gly Arg Ser Gly Gln Gly Phe Ile
            435                 440                 445

Thr Asn Val Thr Ala Ala Ala Asn Tyr Asn Tyr Leu Ala Asp Gly
        450                 455                 460

Gly Leu Ala Ile Leu Asp Thr Ser Gly Ala Ile Asp Ile Phe Val Val
465                 470                 475                 480

Gln Gly Glu Tyr Gly Pro Asn Tyr Tyr Lys Val Asn Pro Cys Glu Asp
                485                 490                 495

Val Asn Gln Gln Phe Val Val Ser Gly Gly Ile Val Gly Val Leu
            500                 505                 510

Thr Ser His Asn Glu Thr Gly Ser Gln Gln Leu Glu Asn Leu Phe Tyr
            515                 520                 525

Val Lys Leu Thr Asn Ser Thr Arg Arg Thr Arg Arg Ser Thr Ile Ala
        530                 535                 540

Asn Val Thr Thr Cys Pro Tyr Val Ser Tyr Gly Arg Phe Cys Ile Lys
545                 550                 555                 560

Pro Asp Gly Leu Val Ser Glu Ile Val Pro Gln Glu Leu Asp Tyr Phe
                565                 570                 575

Val Ala Pro Leu Leu Asn Val Thr Glu His Val Leu Ile Pro Asn Ser
            580                 585                 590

Phe Asn Leu Thr Val Thr Asp Glu Tyr Ile Gln Thr Arg Met Glu Lys
            595                 600                 605

Val Gln Ile Asn Cys Leu Gln Tyr Val Cys Gly Asn Ser Ile Glu Cys
        610                 615                 620

Arg Asn Leu Phe Gln Gln Tyr Gly Pro Val Cys Asp Asn Ile Leu Ser
625                 630                 635                 640

Ile Val Asn Ser Val Gly Gln Arg Glu Asp Met Glu Ser Leu Thr Phe
                645                 650                 655

Tyr Ser Ser Thr Lys Pro Lys Gly Tyr Asn Thr Pro Ile Phe Ser Asn
            660                 665                 670

Ile Ser Thr Gly Asp Phe Asn Ile Ser Leu Met Leu Thr Pro Pro Ser
            675                 680                 685

Ser Pro Ser Gly Arg Ser Phe Ile Glu Asp Leu Leu Phe Thr Ser Val
        690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
                725                 730                 735

Gly Leu Leu Val Leu Pro Pro Ile Ile Thr Ala Asp Met Gln Thr Met
```

```
                740             745             750
Tyr Thr Ala Ser Leu Val Gly Ala Met Ala Phe Gly Gly Ile Thr Ser
            755             760             765
Ala Ala Ala Ile Pro Phe Ala Thr Gln Ile Gln Ala Arg Ile Asn His
            770             775             780
Leu Gly Ile Thr Gln Ser Leu Leu Met Lys Asn Gln Glu Lys Ile Ala
785             790             795             800
Ala Ser Phe Asn Lys Ala Ile Gly His Met Gln Glu Gly Phe Arg Ser
            805             810             815
Thr Ser Leu Ala Leu Gln Gln Ile Gln Asp Val Val Asn Lys Gln Ser
            820             825             830
Ala Ile Leu Thr Glu Thr Met Asn Ser Leu Asn Lys Asn Phe Gly Ala
            835             840             845
Ile Thr Ser Val Ile Gln Asp Ile Tyr Ala Gln Leu Asp Ala Ile Gln
            850             855             860
Ala Asp Ala Gln Val Asp Arg Leu Ile Thr Gly Arg Leu Ser Ser Leu
865             870             875             880
Ser Val Leu Ala Ser Ala Lys Gln Ser Glu Tyr Ile Arg Val Ser Gln
            885             890             895
Gln Arg Glu Leu Ala Thr Gln Lys Ile Asn Glu Cys Val Lys Ser Gln
            900             905             910
Ser Asn Arg Tyr Gly Phe Cys Gly Ser Gly Arg His Val Leu Ser Ile
            915             920             925
Pro Gln Asn Ala Pro Asn Gly Ile Val Phe Ile His Phe Thr Tyr Thr
            930             935             940
Pro Glu Ser Phe Val Asn Val Thr Ala Ile Val Gly Phe Cys Val Ser
945             950             955             960
Pro Ala Asn Ala Ser Gln Tyr Ala Ile Val Pro Ala Asn Gly Arg Gly
            965             970             975
Ile Phe Ile Gln Val Asn Gly Thr Tyr Tyr Ile Thr Ala Arg Asp Met
            980             985             990
Tyr Met Pro Arg Asp Ile Thr Ala  Gly Asp Ile Val Thr  Leu Thr Ser
            995             1000            1005
Cys Gln  Ala Asn Tyr Val Asn  Val Asn Lys Thr Val  Ile Thr Thr
    1010            1015            1020
Phe Val  Glu Asp Asp Phe  Asp Phe Asp Asp Glu  Leu Ser Lys
    1025            1030            1035
Trp Trp  Asn Glu Thr Lys His  Glu Ile Pro Asp Phe  Asp Glu Phe
    1040            1045            1050
Asn Tyr  Thr Val Pro Ile Leu  Asn Ile Ser Ser Glu  Ile Asp Arg
    1055            1060            1065
Ile Gln  Gly Val Ile Gln Gly  Leu Asn Asp Ser Leu  Ile Asn Leu
    1070            1075            1080
Glu Glu  Leu Ser Ile Ile Lys  Thr Tyr Ile Lys Trp  Pro Trp Tyr
    1085            1090            1095
Val Trp  Leu Ala Ile Gly Phe  Ala Ile Ile Ile Phe  Ile Leu Ile
    1100            1105            1110
Leu Gly  Trp Val Phe Phe Met  Thr Gly Cys Cys Gly  Cys Cys Cys
    1115            1120            1125
Gly Cys  Phe Gly Ile Ile Pro  Leu Met Ser Lys Cys  Gly Lys Lys
    1130            1135            1140
Ser Ser  Tyr Tyr Thr Thr Phe  Asp Asn Asp Val Val  Thr
    1145            1150            1155
```

<210> SEQ ID NO 15
<211> LENGTH: 1078
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 15

```
Ala Leu Phe Asp Asn Asn Gln Ala Val Tyr Tyr Gln Ser Ala Phe
1               5                   10                  15

Arg Pro Ser Ser Gly Trp His Lys His Gly Ala Tyr Ala Val Ala
            20                  25                  30

Asn Val Ser Leu Glu Tyr Ala Asn Ala Gly Ser Ser Thr His Cys Thr
            35                  40                  45

Ala Gly Ala Ile Tyr Trp Ser Lys Asn Phe Thr Ala Ser Ser Val Ala
        50                  55                  60

Met Thr Ala Pro Gly Thr Gly Met Ser Trp Ser Thr Ala Gln Phe Cys
65                  70                  75                  80

Thr Ala His Cys Asn Phe Ser Asp Phe Thr Val Phe Val Thr His Cys
                85                  90                  95

Tyr Lys Ser Gly Asp Val Cys Pro Leu Thr Gly Leu Ile Pro Ser Gly
            100                 105                 110

Tyr Ile Arg Ile Ser Ala Met Thr Lys Gly Thr Thr Ser Leu Phe Tyr
        115                 120                 125

Asn Leu Thr Val Pro Val Thr Lys Tyr Pro Lys Phe Lys Ser Leu Gln
    130                 135                 140

Cys Val Asp Asn Phe Thr Ser Val Tyr Leu Asn Gly Asp Leu Val Phe
145                 150                 155                 160

Thr Ser Asn Glu Thr Lys Asp Val Ser Ala Ala Gly Val His Phe Lys
                165                 170                 175

Ala Gly Gly Pro Ile Thr Tyr Lys Val Met Glu Lys Val Asp Val Leu
            180                 185                 190

Ala Tyr Phe Val Asn Gly Thr Ala Gln Asp Val Ile Leu Cys Asp Asn
        195                 200                 205

Ser Pro Arg Gly Leu Leu Ala Cys Gln Tyr Asn Thr Gly Asn Phe Ser
    210                 215                 220

Asp Gly Phe Tyr Pro Phe Thr Asn Ile Ser Leu Val Lys Glu Lys Phe
225                 230                 235                 240

Ile Val Tyr Arg Glu Thr Ser Val Asn Thr Thr Leu Val Leu Thr Asn
                245                 250                 255

Phe Thr Phe Thr Asn Val Ser Asn Ala Leu Pro Asn Thr Gly Gly Val
            260                 265                 270

Asn Thr Ile Asn Ile Tyr Gln Thr Gln Thr Ala Gln Ser Gly Cys Tyr
        275                 280                 285

Asn Phe Asn Phe Ser Phe Leu Ser Ser Phe Val Tyr Lys Gln Ser Asp
    290                 295                 300

Phe Met Tyr Gly Ser Tyr His Pro Lys Cys Asp Phe Arg Pro Glu Thr
305                 310                 315                 320

Ile Asn Asn Gly Leu Trp Phe Asn Ser Leu Ser Val Ser Leu Ala Tyr
                325                 330                 335

Gly Pro Leu Gln Gly Gly Cys Lys Gln Ser Val Phe Ser Asn Arg Ala
            340                 345                 350

Thr Cys Cys Tyr Ala Tyr Ser Tyr Asn Gly Pro Arg Leu Cys Lys Gly
```

```
               355                 360                 365
Val Tyr Ile Gly Glu Leu Gln Gln Tyr Phe Glu Cys Gly Leu Leu Val
            370                 375                 380
Tyr Val Thr Lys Ser Asp Gly Ser Arg Ile Gln Thr Arg Asn Glu Pro
385                 390                 395                 400
Leu Val Leu Thr His His Asn Tyr Asn Asn Ile Thr Leu Asp Arg Cys
                405                 410                 415
Val Glu Tyr Asn Ile Tyr Gly Arg Ser Gly Gln Gly Phe Ile Thr Asn
            420                 425                 430
Val Thr Ala Ala Ala Asn Tyr Asn Tyr Leu Ala Asp Gly Gly Leu
            435                 440                 445
Ala Ile Leu Asp Thr Ser Gly Ala Ile Asp Ile Phe Val Val Gln Gly
            450                 455                 460
Glu Tyr Gly Pro Asn Tyr Tyr Lys Val Asn Pro Cys Glu Asp Val Asn
465                 470                 475                 480
Gln Gln Phe Val Val Ser Gly Gly Ile Val Gly Val Leu Thr Ser
                485                 490                 495
His Asn Glu Thr Gly Ser Gln Gln Leu Glu Asn Leu Phe Tyr Val Lys
                500                 505                 510
Leu Thr Asn Ser Thr Arg Arg Thr Arg Arg Ser Thr Ile Ala Asn Val
                515                 520                 525
Thr Thr Cys Pro Tyr Val Ser Tyr Gly Arg Phe Cys Ile Lys Pro Asp
            530                 535                 540
Gly Leu Val Ser Glu Ile Val Pro Gln Glu Leu Asp Tyr Phe Val Ala
545                 550                 555                 560
Pro Leu Leu Asn Val Thr Glu His Val Leu Ile Pro Asn Ser Phe Asn
                565                 570                 575
Leu Thr Val Thr Asp Glu Tyr Ile Gln Thr Arg Met Glu Lys Val Gln
                580                 585                 590
Ile Asn Cys Leu Gln Tyr Val Cys Gly Asn Ser Ile Glu Cys Arg Asn
            595                 600                 605
Leu Phe Gln Gln Tyr Gly Pro Val Cys Asp Asn Ile Leu Ser Ile Val
            610                 615                 620
Asn Ser Val Gly Gln Arg Glu Asp Met Glu Ser Leu Thr Phe Tyr Ser
625                 630                 635                 640
Ser Thr Lys Pro Lys Gly Tyr Asn Thr Pro Ile Phe Ser Asn Ile Ser
                645                 650                 655
Thr Gly Asp Phe Asn Ile Ser Leu Met Leu Thr Pro Pro Ser Ser Pro
                660                 665                 670
Ser Gly Arg Ser Phe Ile Glu Asp Leu Leu Phe Thr Ser Val Glu Thr
            675                 680                 685
Val Gly Leu Pro Thr Asp Ala Glu Tyr Lys Lys Cys Thr Ala Gly Pro
            690                 695                 700
Leu Gly Thr Leu Lys Asp Leu Ile Cys Ala Arg Glu Tyr Asn Gly Leu
705                 710                 715                 720
Leu Val Leu Pro Pro Ile Ile Thr Ala Asp Met Gln Thr Met Tyr Thr
                725                 730                 735
Ala Ser Leu Val Gly Ala Met Ala Phe Gly Gly Ile Thr Ser Ala Ala
                740                 745                 750
Ala Ile Pro Phe Ala Thr Gln Ile Gln Ala Arg Ile Asn His Leu Gly
            755                 760                 765
Ile Thr Gln Ser Leu Leu Met Lys Asn Gln Glu Lys Ile Ala Ala Ser
            770                 775                 780
```

Phe Asn Lys Ala Ile Gly His Met Gln Glu Gly Phe Arg Ser Thr Ser
785                 790                 795                 800

Leu Ala Leu Gln Gln Ile Gln Asp Val Val Asn Lys Gln Ser Ala Ile
                805                 810                 815

Leu Thr Glu Thr Met Asn Ser Leu Asn Lys Asn Phe Gly Ala Ile Thr
                820                 825                 830

Ser Val Ile Gln Asp Ile Tyr Ala Gln Leu Asp Ala Ile Gln Ala Asp
                835                 840                 845

Ala Gln Val Asp Arg Leu Ile Thr Gly Arg Leu Ser Ser Leu Ser Val
850                 855                 860

Leu Ala Ser Ala Lys Gln Ser Glu Tyr Ile Arg Val Ser Gln Gln Arg
865                 870                 875                 880

Glu Leu Ala Thr Gln Lys Ile Asn Glu Cys Val Lys Ser Gln Ser Asn
                885                 890                 895

Arg Tyr Gly Phe Cys Gly Ser Gly Arg His Val Leu Ser Ile Pro Gln
                900                 905                 910

Asn Ala Pro Asn Gly Ile Val Phe Ile His Phe Thr Tyr Thr Pro Glu
                915                 920                 925

Ser Phe Val Asn Val Thr Ala Ile Val Gly Phe Cys Val Ser Pro Ala
930                 935                 940

Asn Ala Ser Gln Tyr Ala Ile Val Pro Ala Asn Gly Arg Gly Ile Phe
945                 950                 955                 960

Ile Gln Val Asn Gly Thr Tyr Tyr Ile Thr Ala Arg Asp Met Tyr Met
                965                 970                 975

Pro Arg Asp Ile Thr Ala Gly Asp Ile Val Thr Leu Thr Ser Cys Gln
                980                 985                 990

Ala Asn Tyr Val Asn Val Asn Lys Thr Val Ile Thr Thr Phe Val Glu
                995                 1000                1005

Asp Asp Asp Phe Asp Phe Asp Asp Glu Leu Ser Lys Trp Trp Asn
1010                1015                1020

Glu Thr Lys His Glu Ile Pro Asp Phe Asp Glu Phe Asn Tyr Thr
1025                1030                1035

Val Pro Ile Leu Asn Ile Ser Ser Glu Ile Asp Arg Ile Gln Gly
1040                1045                1050

Val Ile Gln Gly Leu Asn Asp Ser Leu Ile Asn Leu Glu Glu Leu
1055                1060                1065

Ser Ile Ile Lys Thr Tyr Ile Lys Trp Pro
1070                1075

<210> SEQ ID NO 16
<211> LENGTH: 1169
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 16

Met Leu Val Gln Pro Leu Leu Leu Val Thr Leu Leu Cys Ala Leu Cys
1               5                   10                  15

Ser Ala Ser Leu Tyr Asn Asn Asp Ser Tyr Val Tyr Tyr Gln Ser
                20                  25                  30

Ala Phe Arg Pro Phe Asn Gly Trp His Leu His Gly Gly Ala Tyr Ala
                35                  40                  45

Val Val Asn Val Ser Gln Glu Thr Ala Asn Ala Gly Ser Ser Pro Ser

-continued

```
           50                  55                  60
Cys Thr Ala Gly Ala Ile Tyr Trp Ser Lys Asn Phe Thr Ala Ser Ser
 65                  70                  75                  80

Val Ala Met Thr Ala Pro Leu Gln Gly Met Gln Trp Ser Thr Ile Gln
                 85                  90                  95

Phe Cys Thr Ala His Cys Asn Phe Thr Asn Ile Val Val Phe Val Thr
                100                 105                 110

His Cys Tyr Lys Ser Gly Ser Thr Val Cys Pro Leu Thr Gly Leu Ile
                115                 120                 125

Pro Gln Asn His Ile Arg Ile Ser Ala Met Lys Gln Gly Asn Asn Gly
            130                 135                 140

Pro Ser Gly Leu Phe Tyr Asn Leu Thr Val Pro Val Thr Lys Tyr Ser
145                 150                 155                 160

Lys Phe Lys Ser Leu Gln Cys Val Asn Asn Gln Thr Ser Val Tyr Leu
                165                 170                 175

Asn Gly Asp Leu Val Phe Thr Ser Asn Glu Thr Lys Asp Val Ser Gly
                180                 185                 190

Ala Gly Val Tyr Phe Lys Ala Gly Gly Pro Ile Thr Tyr Lys Val Met
            195                 200                 205

Arg Glu Val Lys Ala Leu Ala Tyr Phe Val Asn Gly Thr Ala His Asp
210                 215                 220

Val Ile Leu Cys Asp Gly Ser Pro Arg Gly Leu Leu Ala Cys Gln Tyr
225                 230                 235                 240

Asn Thr Gly Lys Phe Ser Asp Gly Phe Tyr Pro Phe Thr Asn Asp Thr
                245                 250                 255

Leu Val Lys Glu Lys Phe Ile Val Tyr Arg Glu Asn Ser Val Asn Thr
                260                 265                 270

Thr Leu Thr Leu Thr Asn Phe Thr Phe Tyr Asn Glu Ser Asn Ala Leu
            275                 280                 285

Pro Asn Asn Gly Gly Val Asp Thr Ile Gln Leu Tyr Gln Thr His Thr
290                 295                 300

Ala Gln Ser Gly Tyr Tyr Asn Phe Asn Phe Ser Phe Leu Ser Ser Phe
305                 310                 315                 320

Gln Tyr Val Glu Ser Asn Phe Met Tyr Gly Ser Tyr His Pro Lys Cys
                325                 330                 335

Gly Phe Arg Pro Glu Ser Ile Asn Asn Gly Leu Trp Phe Asn Ser Leu
                340                 345                 350

Ser Val Ser Leu Ala Tyr Gly Pro Leu Gln Gly Gly Cys Lys Gln Ser
            355                 360                 365

Val Phe His Gly Arg Ala Thr Cys Cys Tyr Ala Tyr Ser Tyr Asn Gly
370                 375                 380

Pro Thr Leu Cys Lys Gly Val Tyr Ser Gly Glu Leu Thr Arg Ser Tyr
385                 390                 395                 400

Gln Cys Gly Leu Leu Val Phe Val Thr Lys Ser Asp Gly Ser Arg Ile
                405                 410                 415

Gln Thr Ser Thr Lys Pro Ile Val Leu Thr Gln His Asn Tyr Asn Asn
            420                 425                 430

Ile Thr Leu Asp Arg Cys Val Glu Tyr Asn Ile Tyr Gly Arg Val Gly
            435                 440                 445

Gln Gly Phe Ile Thr Asn Val Thr Glu Ser Ala Ala Phe Asn Tyr
            450                 455                 460

Leu Glu Asp Gly Gly Leu Ala Ile Leu Asp Thr Ser Gly Ala Ile Asp
465                 470                 475                 480
```

```
Ile Phe Val Val Gln Gly Glu Tyr Gly Phe Asn Tyr Lys Val Asn
            485                 490                 495

Pro Cys Glu Asp Val Asn Gln Gln Phe Val Val Ser Gly Asn Leu
            500                 505                 510

Val Gly Ile Leu Thr Ser Ile Asn Gln Thr Gly Ser Gln Ser Ile Glu
            515                 520                 525

Asn Gln Phe Tyr Val Lys Leu Thr Asn Gly Ser Arg Arg Ser Arg Arg
            530                 535                 540

Ser Val Ser Glu Asn Val Thr Ser Cys Pro Tyr Val Ser Tyr Gly Lys
545                 550                 555                 560

Phe Cys Ile Lys Pro Asp Gly Ser Leu Ser Thr Ile Val Pro Lys Glu
            565                 570                 575

Leu Glu Gln Phe Val Ala Pro Leu Leu Asn Val Thr Glu His Val Leu
            580                 585                 590

Ile Pro Asp Ser Phe Asn Leu Thr Val Thr Asp Glu Tyr Ile Gln Thr
            595                 600                 605

Arg Met Asp Lys Val Gln Ile Asn Cys Leu Gln Tyr Val Cys Gly Asn
            610                 615                 620

Ser Phe Glu Cys Arg Lys Leu Phe Gln Gln Tyr Gly Pro Val Cys Asp
625                 630                 635                 640

Asn Ile Leu Ser Val Val Asn Ser Val Gly Gln Lys Glu Asp Met Glu
            645                 650                 655

Leu Leu Ser Phe Tyr Ser Ser Thr Lys Pro Ser Gly Ile Ser Gln Pro
            660                 665                 670

Leu Phe Asn Asn Phe Ser Thr Gly Asp Phe Asn Ile Ser Leu Leu Leu
            675                 680                 685

Thr Ser Pro Ser Ser Pro Ser Gly Arg Ser Phe Ile Glu Asp Leu Leu
            690                 695                 700

Phe Thr Ser Val Glu Ser Val Gly Leu Pro Thr Asp Glu Ala Tyr Lys
705                 710                 715                 720

Lys Cys Thr Ser Gly Pro Leu Gly Phe Val Lys Asp Leu Val Cys Ala
            725                 730                 735

Arg Glu Tyr Asn Gly Leu Leu Val Leu Pro Pro Ile Ile Thr Ala Glu
            740                 745                 750

Met Gln Thr Met Tyr Thr Ser Ser Leu Val Ala Ser Met Ala Leu Gly
            755                 760                 765

Gly Ile Thr Ala Ala Gly Ala Ile Pro Phe Ala Thr Gln Leu Gln Ala
            770                 775                 780

Arg Ile Asn His Leu Gly Ile Thr Gln Ser Leu Leu Met Lys Asn Gln
785                 790                 795                 800

Glu Lys Ile Ala Ala Ser Phe Asn Arg Ala Ile Gly His Met Gln Glu
            805                 810                 815

Gly Phe Lys Ser Thr Ser Leu Ala Leu Gln Gln Ile Gln Asp Val Val
            820                 825                 830

Asn Lys Gln Ser Ala Ile Leu Thr Glu Thr Met Ala Ser Leu Asn Lys
            835                 840                 845

Asn Phe Gly Ala Ile Ser Ser Val Leu Gln Asp Ile Tyr Gln Gln Leu
            850                 855                 860

Asp Val Ile Gln Ala Asp Ala Gln Val Asp Arg Ile Ile Thr Gly Arg
865                 870                 875                 880

Leu Ser Ser Leu Ser Val Leu Ala Ser Ala Lys Gln Ser Glu Tyr Ile
            885                 890                 895
```

```
Ala Val Ser Gln Gln Arg Ala Leu Ala Thr Gln Lys Ile Asn Glu Cys
                900                 905                 910

Val Lys Ser Gln Ser Thr Arg Tyr Ser Phe Cys Gly Asn Gly Arg His
            915                 920                 925

Val Leu Thr Ile Pro Gln Asn Ala Pro Asn Gly Ile Val Phe Ile His
        930                 935                 940

Phe Thr Tyr Thr Pro Glu Ser Phe Val Asn Val Thr Ala Ile Val Gly
945                 950                 955                 960

Phe Cys Val Lys Pro Pro Asn Ala Ser His Tyr Ala Ile Val Pro Val
                965                 970                 975

Asn Gly Arg Gly Ile Phe Ile Gln Val Asn Gly Thr Tyr Tyr Ile Thr
            980                 985                 990

Ser Arg Asp Met Tyr Met Pro Arg Asn Ile Thr Ala Gly Asp Ile Val
        995                 1000                1005

Thr Leu Thr Ser Cys Gln Ala Asn Tyr Val Ser Val Asn Lys Thr
    1010                1015                1020

Val Ile Ser Thr Phe Val Glu Asp Asp Asp Phe Asp Phe Asp Asp
    1025                1030                1035

Glu Leu Ser Lys Trp Trp Asn Asp Thr Lys His Glu Leu Pro Asp
    1040                1045                1050

Phe Asp Glu Phe Asn Tyr Thr Ile Pro Val Leu Asn Ile Ser Asn
    1055                1060                1065

Glu Ile Asp Arg Ile Gln Gly Val Ile Gln Gly Leu Asn Asp Ser
    1070                1075                1080

Leu Ile Asp Leu Glu Thr Leu Ser Ile Leu Lys Thr Tyr Ile Lys
    1085                1090                1095

Trp Pro Trp Tyr Val Trp Leu Ala Ile Phe Phe Ala Ile Val Ile
    1100                1105                1110

Phe Ile Leu Ile Ile Gly Trp Val Phe Phe Met Thr Gly Cys Cys
    1115                1120                1125

Gly Cys Cys Cys Gly Cys Phe Gly Ile Ile Pro Leu Met Asn Lys
    1130                1135                1140

Cys Gly Lys Lys Ser Ser Tyr Tyr Thr Thr Phe Asp Asn Asp Val
    1145                1150                1155

Val Thr Glu Gln Tyr Arg Pro Lys Lys Ser Val
    1160                1165

<210> SEQ ID NO 17
<211> LENGTH: 1082
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 17

Ser Leu Tyr Asn Asn Asp Ser Tyr Val Tyr Tyr Gln Ser Ala Phe
1               5                   10                  15

Arg Pro Phe Asn Gly Trp His Leu His Gly Gly Ala Tyr Ala Val Val
                20                  25                  30

Asn Val Ser Gln Glu Thr Ala Asn Ala Gly Ser Ser Pro Ser Cys Thr
            35                  40                  45

Ala Gly Ala Ile Tyr Trp Ser Lys Asn Phe Thr Ala Ser Ser Val Ala
        50                  55                  60

Met Thr Ala Pro Leu Gln Gly Met Gln Trp Ser Thr Ile Gln Phe Cys
65                  70                  75                  80
```

```
Thr Ala His Cys Asn Phe Thr Asn Ile Val Phe Val Thr His Cys
                 85                  90                  95
Tyr Lys Ser Gly Ser Thr Val Cys Pro Leu Thr Gly Leu Ile Pro Gln
            100                 105                 110
Asn His Ile Arg Ile Ser Ala Met Lys Gln Gly Asn Asn Gly Pro Ser
        115                 120                 125
Gly Leu Phe Tyr Asn Leu Thr Val Pro Val Thr Lys Tyr Ser Lys Phe
130                 135                 140
Lys Ser Leu Gln Cys Val Asn Asn Gln Thr Ser Val Tyr Leu Asn Gly
145                 150                 155                 160
Asp Leu Val Phe Thr Ser Asn Glu Thr Lys Asp Val Ser Gly Ala Gly
                165                 170                 175
Val Tyr Phe Lys Ala Gly Gly Pro Ile Thr Tyr Lys Val Met Arg Glu
            180                 185                 190
Val Lys Ala Leu Ala Tyr Phe Val Asn Gly Thr Ala His Asp Val Ile
        195                 200                 205
Leu Cys Asp Gly Ser Pro Arg Gly Leu Leu Ala Cys Gln Tyr Asn Thr
210                 215                 220
Gly Lys Phe Ser Asp Gly Phe Tyr Pro Phe Thr Asn Asp Thr Leu Val
225                 230                 235                 240
Lys Glu Lys Phe Ile Val Tyr Arg Glu Asn Ser Val Asn Thr Thr Leu
                245                 250                 255
Thr Leu Thr Asn Phe Thr Phe Tyr Asn Glu Ser Asn Ala Leu Pro Asn
            260                 265                 270
Asn Gly Gly Val Asp Thr Ile Gln Leu Tyr Gln Thr His Thr Ala Gln
        275                 280                 285
Ser Gly Tyr Tyr Asn Phe Asn Phe Ser Phe Leu Ser Ser Phe Gln Tyr
290                 295                 300
Val Glu Ser Asn Phe Met Tyr Gly Ser Tyr His Pro Lys Cys Gly Phe
305                 310                 315                 320
Arg Pro Glu Ser Ile Asn Asn Gly Leu Trp Phe Asn Ser Leu Ser Val
                325                 330                 335
Ser Leu Ala Tyr Gly Pro Leu Gln Gly Gly Cys Lys Gln Ser Val Phe
            340                 345                 350
His Gly Arg Ala Thr Cys Cys Tyr Ala Tyr Ser Tyr Asn Gly Pro Thr
        355                 360                 365
Leu Cys Lys Gly Val Tyr Ser Gly Glu Leu Thr Arg Ser Tyr Gln Cys
370                 375                 380
Gly Leu Leu Val Phe Val Thr Lys Ser Asp Gly Ser Arg Ile Gln Thr
385                 390                 395                 400
Ser Thr Lys Pro Ile Val Leu Thr Gln His Asn Tyr Asn Asn Ile Thr
                405                 410                 415
Leu Asp Arg Cys Val Glu Tyr Asn Ile Tyr Gly Arg Val Gly Gln Gly
            420                 425                 430
Phe Ile Thr Asn Val Thr Glu Ser Ala Ala Ala Phe Asn Tyr Leu Glu
        435                 440                 445
Asp Gly Gly Leu Ala Ile Leu Asp Thr Ser Gly Ala Ile Asp Ile Phe
        450                 455                 460
Val Val Gln Gly Glu Tyr Gly Phe Asn Tyr Tyr Lys Val Asn Pro Cys
465                 470                 475                 480
Glu Asp Val Asn Gln Gln Phe Val Val Ser Gly Gly Asn Leu Val Gly
                485                 490                 495
```

```
Ile Leu Thr Ser Ile Asn Gln Thr Gly Ser Gln Ser Ile Glu Asn Gln
                500                 505                 510

Phe Tyr Val Lys Leu Thr Asn Gly Ser Arg Arg Ser Arg Arg Ser Val
            515                 520                 525

Ser Glu Asn Val Thr Ser Cys Pro Tyr Val Ser Tyr Gly Lys Phe Cys
        530                 535                 540

Ile Lys Pro Asp Gly Ser Leu Ser Thr Ile Val Pro Lys Glu Leu Glu
545                 550                 555                 560

Gln Phe Val Ala Pro Leu Leu Asn Val Thr Glu His Val Leu Ile Pro
                565                 570                 575

Asp Ser Phe Asn Leu Thr Val Thr Asp Glu Tyr Ile Gln Thr Arg Met
            580                 585                 590

Asp Lys Val Gln Ile Asn Cys Leu Gln Tyr Val Cys Gly Asn Ser Phe
        595                 600                 605

Glu Cys Arg Lys Leu Phe Gln Gln Tyr Gly Pro Val Cys Asp Asn Ile
    610                 615                 620

Leu Ser Val Val Asn Ser Val Gly Gln Lys Glu Asp Met Glu Leu Leu
625                 630                 635                 640

Ser Phe Tyr Ser Ser Thr Lys Pro Ser Gly Ile Ser Gln Pro Leu Phe
                645                 650                 655

Asn Asn Phe Ser Thr Gly Asp Phe Asn Ile Ser Leu Leu Leu Thr Ser
            660                 665                 670

Pro Ser Ser Pro Ser Gly Arg Ser Phe Ile Glu Asp Leu Leu Phe Thr
        675                 680                 685

Ser Val Glu Ser Val Gly Leu Pro Thr Asp Glu Ala Tyr Lys Lys Cys
    690                 695                 700

Thr Ser Gly Pro Leu Gly Phe Val Lys Asp Leu Val Cys Ala Arg Glu
705                 710                 715                 720

Tyr Asn Gly Leu Leu Val Leu Pro Pro Ile Ile Thr Ala Glu Met Gln
                725                 730                 735

Thr Met Tyr Thr Ser Ser Leu Val Ala Ser Met Ala Leu Gly Gly Ile
            740                 745                 750

Thr Ala Ala Gly Ala Ile Pro Phe Ala Thr Gln Leu Gln Ala Arg Ile
        755                 760                 765

Asn His Leu Gly Ile Thr Gln Ser Leu Leu Met Lys Asn Gln Glu Lys
    770                 775                 780

Ile Ala Ala Ser Phe Asn Arg Ala Ile Gly His Met Gln Glu Gly Phe
785                 790                 795                 800

Lys Ser Thr Ser Leu Ala Leu Gln Gln Ile Gln Asp Val Val Asn Lys
                805                 810                 815

Gln Ser Ala Ile Leu Thr Glu Thr Met Ala Ser Leu Asn Lys Asn Phe
            820                 825                 830

Gly Ala Ile Ser Ser Val Leu Gln Asp Ile Tyr Gln Gln Leu Asp Val
        835                 840                 845

Ile Gln Ala Asp Ala Gln Val Asp Arg Ile Ile Thr Gly Arg Leu Ser
    850                 855                 860

Ser Leu Ser Val Leu Ala Ser Ala Lys Gln Ser Glu Tyr Ile Ala Val
865                 870                 875                 880

Ser Gln Gln Arg Ala Leu Ala Thr Gln Lys Ile Asn Glu Cys Val Lys
                885                 890                 895

Ser Gln Ser Thr Arg Tyr Ser Phe Cys Gly Asn Gly Arg His Val Leu
            900                 905                 910

Thr Ile Pro Gln Asn Ala Pro Asn Gly Ile Val Phe Ile His Phe Thr
```

```
        915                 920                 925

Tyr Thr Pro Glu Ser Phe Val Asn Val Thr Ala Ile Val Gly Phe Cys
    930                 935                 940

Val Lys Pro Pro Asn Ala Ser His Tyr Ala Ile Val Pro Val Asn Gly
945                 950                 955                 960

Arg Gly Ile Phe Ile Gln Val Asn Gly Thr Tyr Tyr Ile Thr Ser Arg
                965                 970                 975

Asp Met Tyr Met Pro Arg Asn Ile Thr Ala Gly Asp Ile Val Thr Leu
            980                 985                 990

Thr Ser Cys Gln Ala Asn Tyr Val  Ser Val Asn Lys Thr  Val Ile Ser
        995                 1000                1005

Thr Phe  Val Glu Asp Asp Asp  Phe Asp Phe Asp Asp  Glu Leu Ser
    1010                1015                1020

Lys Trp  Trp Asn Asp Thr Lys  His Glu Leu Pro Asp  Phe Asp Glu
    1025                1030                1035

Phe Asn  Tyr Thr Ile Pro Val  Leu Asn Ile Ser Asn  Glu Ile Asp
    1040                1045                1050

Arg Ile  Gln Gly Val Ile Gln  Gly Leu Asn Asp Ser  Leu Ile Asp
    1055                1060                1065

Leu Glu  Thr Leu Ser Ile Leu  Lys Thr Tyr Ile Lys  Trp Pro
    1070                1075                1080
```

<210> SEQ ID NO 18
<211> LENGTH: 11860
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Plasmit with IBV

<400> SEQUENCE: 18

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tgagctctaa tacgactcac tatagggact taagtgtgat ataaatatat    480
atcatacata ctagccttgt gctagatttc caacttaaca aaacggactt aaatacctac    540
agttggtccc tataggtgtt ccattgcagt gcactttagt gccctggatg gcacctggcc    600
acctgtcagg tttttgttat taaaataata ttgttgctgg tatcactgct tgttttgccg    660
tgtctcactt tatacatccg ttgcttgggc tacctagtat ccagcgtcct actggcgttg    720
tggtcggttc gagtgcgaag aacctctggt tcatctagcg gtacgcgggt gtgtggaagt    780
agcgcttcag acgtaccggt tctgttgcgt gaaatacggg gtcacctccc cccacatacc    840
tctaagggct tttgagccta gcgttgggct acgttctcgc acaaggtcgg ctatacggcg    900
tttgtagggg gtagtgccaa acaacccctg aggtgacagg ttctggtggt gtttcgaaaa    960
caacaatgtg tgtgccgcat aatatgcgag taatgcattt tggagcagga agtgacaaag   1020
```

```
gagtggcccc aggtagcgct gttcttaggc agtggcttcc cgaaggtaca ctccttgtcg    1080
ataatgatat tgtagattat gtatctgatg cacatgtctc tgtgctttca gattgcaata    1140
aatgtaaaac agagcacaag tttgatcttg tgatatctga tatgtataca gataatgatt    1200
caaagagaaa gcatgaaggc gttgtagcca ataacggcaa tgatgacgtc ttcatatacc    1260
tttcaaactt tcttcgtaac aatttagctc tgggaggcag ttttgccgta aaagtaacag    1320
agacaagttg gcatgagagt ttatatgaca ttgcacagga ttgtgcatgg tggacaatgt    1380
tttgtacagc agtgaatgct tcttcgtcag aagcattctt gattggtgtt aattatttgg    1440
gtgcaagtga aaaggttaga gttagtggta aaaccctgca cgcaaattat atattttgga    1500
ggaattgtaa ttatttacaa acttcagcct atagtatatt tgacgttgct aagtttgatt    1560
tgaaattaaa agcaacgcca gttgtgaatt tgaaaactga acaaaagaca gacttagtct    1620
ttaatttaat taagtgtggt aagttactgg taagagatgt tggacaaacc gcttttacta    1680
gtgactcttt ggtatgcact atgtagtgct ttgctctatg ataataatta tattggtgat    1740
tttagatgta tccagcttgt gaactcaaac ggtgctaatg ttagtgctcc aagcattagc    1800
actgagaccg ttgaagtttc acaaggcctg gggacatatt atgtgttaga tcgagtttat    1860
ttaaatgcca cattattgct tactggttac tacccggtcg atggttctaa gtttagaaac    1920
ctcgctctta cgggaactaa ctcagttagc ttgtcgtggt ttcaaccacc ctatttaagt    1980
cagtttaatg atggcatatt tgcgaaggtg cagaacctta agacaagtac gccatcaggt    2040
gcaactgcat attttcctac tatagttata ggtagtttgt ttggctatac ttcctatacc    2100
gttgtaatag agccatataa tggtgttata atggcctcag tgtgccagta taccatttgt    2160
cagttaccct acactgattg taagcctaac actaatggta ataagcttat agggttttgg    2220
cacacggatg taaacccccc aatttgtgtg ttaaagcgaa atttcacgct taatgttaat    2280
gctgatgcat tttattttca ttttttaccaa catggtggta cttttttatgc gtactatgcg    2340 gataaaccct ccgctactac gttttttgttt agtgtatata ttggcgatat tttaacacag    2400
tattatgtgt taccttttcat ctgcaaccca acagctggta gcacttttgc tccgcgctat    2460
tgggttacac ctttggttaa gcgccaatat ttgtttaatt tcaaccagaa gggtgtcatt    2520
actagtgctg ttgattgtgc tagtagttat accagtgaaa taaaatgtaa gacccagagc    2580
atgttaccta gcactggtgt ctatgagtta tccggttata cggtccaacc agttggagtt    2640
gtataccggc gtgttgctaa cctcccagct tgtaatatag aggagtggct tactgctagg    2700
tcagtcccct cccctctcaa ctgggagcgt aagacttttc agaattgtaa ttttaattta    2760
agcagcctgt tacgttatgt tcaggctgag agtttgtttt gtaataatat cgatgcttcc    2820
aaagtgtatg gcaggtgctt tggtagtatt tcagttgata agtttgctgt accccgaagt    2880
aggcaagttg atttacagct tggtaactct ggatttctgc agactgctaa ttataagatt    2940
gatacagctg ccacttcgtg tcagctgcat tacaccttgc ctaagaataa tgtcaccata    3000
aacaaccata acccctcgtc ttggaatagg aggtatggct ttaatgatgc tggcgtcttt    3060
ggcaaaaacc aacatgacgt tgtttacgct cagcaatgtt ttactgtaag atctagttat    3120
tgcccgtgtg ctcaaccgga catagttagc ccttgcacta ctcagactaa gcctaagtct    3180
gcttttgtta atgtgggtga ccattgtgaa ggcttaggtg ttttagaaga taattgtggc    3240
aatgctgatc cacataaggg ttgtatctgt gccaacaatt catttattgg atggtcacat    3300
gatacctgcc ttgttaatga tcgctgccaa attttttgcta atatattgtt aaatggcatt    3360
aatagtggta ccacatgttc cacagatttg cagttgccta atactgaagt ggttactggc    3420
```

```
atttgtgtca aatatgacct ctacggtatt actggacaag gtgtttttaa agaggttaag    3480
gctgactatt ataatagctg gcaaacccctt ctgtatgatg ttaatggtaa tttgaatggt    3540
tttcgtgatc ttaccactaa caagacttat acgataagga gctgttatag tggccgtgtt    3600
tctgctgcat tcataaaga tgcacccgaa ccggctctgc tctatcgtaa tataaattgt    3660
agctatgttt ttagcaataa tatttcccgt gaggagaacc cacttaatta ctttgatagt    3720
tatttgggtt gtgttgttaa tgctgataac cgcacggatg aggcgcttcc taattgtgat    3780
ctccgtatgg gtgctggctt atgcgttgat tattcaaaat cacgcagggc tcaccgatca    3840
gtttctactg gctatcggtt aactacattt gagccataca ctccgatgtt agttaatgat    3900
agtgtccaat ccgttgatgg attatatgag atgcaaatac caaccaattt tactattggg    3960
caccatgagg agttcattca aactagatct ccaaaggtga ctatagattg tgctgcattt    4020
gtctgtggtg ataacactgc atgcaggcag cagttggttg agtatggctc tttctgtgtt    4080
aatgttaatg ccattcttaa tgaggttaat aacctcttgg ataatatgca actacaagtt    4140
gctagtgcat taatgcaggg tgttactata agttcgagac tgccagacgg catctcaggc    4200
cctatagatg acattaattt tagtcctcta cttggatgca taggttcaac atgtgctgaa    4260
gacggcaatg gacctagtgc aatccgaggg cgttctgcta tagaggattt gttatttgac    4320
aaggtcaaat tatctgatgt tggctttgtc gaggcttata ataattgcac cggtggtcaa    4380
gaagttcgtg acctcctttg tgtacaatct tttaatggca tcaaagtatt acctcctgtg    4440
ttgtcagaga gtcagatctc tggctacaca accggtgcta ctgcggcagc tatgttccca    4500
ccgtggtcag cagctgccgg tgtgccattt agtttaagtg ttcaatatag aattaatggt    4560
ttaggtgtca ctatgaatgt gcttagtgag aaccaaaaga tgattgctag tgcttttaac    4620
aatgcgctgg gtgctatcca ggatgggttt gatgcaacca attctgcttt aggtaagatc    4680
cagtccgttg ttaatgcaaa tgctgaagca ctcaataact tactaaatca actttctaac    4740
aggtttggtg ctattagtgc ttctttacaa gaaattctaa ctcggcttga ggctgtagaa    4800
gcaaaagccc agatagatcg tcttattaat ggcaggttaa ctgcacttaa tgcgtatata    4860
tccaagcaac ttagtgatag tacgcttatt aaagttagtg ctgctcaggc catagaaaag    4920
gtcaatgagt gcgttaagag ccaaaccacg cgtattaatt tctgtggcaa tggtaatcat    4980
atattatctc ttgtccagaa tgcgcctat ggcttatatt ttatacactt cagctatgtg    5040
ccaatatcct ttacaaccgc aaatgtgagt cctggacttt gcatttctgg tgatagagga    5100
ttagcaccta agctggata tttttgttcaa gatgatggaa atggaagtt cacaggcagt    5160
tcatattact accctgaacc cattacagat aaaaacagtg tcattatgag tagttgcgca    5220
gtaaactaca caaaggcacc tgaagttttc ttgaacactt caatacctaa tccacccgac    5280
tttaaggagg agttagataa atggtttaag aatcagacgt ctattgcgcc tgatttatct    5340
ctcgatttcg agaagttaaa tgttactttg ctggacctga cgtatgagat gaacaggatt    5400
caggatgcaa ttaagaagtt aaatgagagc tacatcaacc tcaaggaagt tggcacatat    5460
gaaatgtatg tgaaatggcc ttggtatgtg tggcttgcca ttgcattcct taccattatt    5520
tttattctgg tactttgttg gatatttttc atgaccggtt gttgcggttg ttgttgtgga    5580
tgctttggta tcataccgtt aatgagtaag tgtggtaaga aatcttctta ctacacgact    5640
tttgataatg atgtggtaac ttaacaatac agacctaaaa agtctgtttta atgattaaaa    5700
gtcccacatc tttttctaata ttattaattc ttctttggtg taaacttgca ttaagttgtt    5760
```

```
ttaaagagtg tgttataaca ctccagcaac tagtacaaat tttactccaa attattaata      5820
gtaacttaca atctagactt ctgctttggc acagtctaga ctaatgttag attttgaagc      5880
aattattgaa actggtcagc aaataactca acaaattagt ttctatttac agcatatttc      5940
aagggtgcta agtactgaat tatttgaccc ctttgaagtt tgtgtttaca gaggaggtaa      6000
ttgttgggag ttagagtcag ctgacgagtt ttcaggtgat gacgaatata ttgagtagat      6060
cgctcgagga gaacggaagt tttctaacag cggtttacgt gttttttagga ttttttagcac    6120 tttatctact aggtagagcg cttcaagctt ttgtacaagc ggctgacgct tgttgtcttt      6180
tttggtatac atgggtagta gttcctggag ccaagggcac agcctttgtt tataatcata      6240
catatggtaa aaaacttaac aaaccggagt tagaaacggt tattgttaac gaatttccaa      6300
aaaacggttg gaaatatgga taataccatc aattgtactc ttggtactga caagcagtt       6360 cagctttta aggaatataa tctgtttgta actgcattcc tgttgttttt aaccatacta       6420
cttcagtatg gatacgcaac taggagcaag gttatttaca tactgaaaat gatagtgtta     6480
tggtgctttt ggccccttaa cattgcagta ggtgtaatct catgtatata cccaccaaac     6540
acaggaggtc ttgtcgcagc gataattctt acagtgtttg cgtgtctttc ttttataggt     6600
tattggatcc agagtattag actttttaag cggtgcaggt catggtggtc atttaaccc       6660 gaatctaatg ccgtaggttc aatactccta actaatggtc aacaatgtaa ttttgctata    6720
gagagtgtgc cgatggtgct ttctcctatt ataaagaatg gtgctcttta ttgcgagggt    6780
cagtggcttg ctaaatgtga accagaccac ttgcctagag atatatttgt atgcacaccg    6840
gatagacgta atatctatcg tatggtgcaa aaatatactg gtgaccaaag cggaagtaag    6900
aaaaggtttg ccacatttgt ctatgcaaag cagtcagtag atactggcga gctagaaagt    6960
gtgtcagcag taggaggtag tctttacaca taaatgtgtg tgtgtagaga gtatttaaaa     7020
ttattctttg acagtgcctc cgttttaaga gcgcggaaga gtattatttt tgaggatatt     7080
aatataaatc ctctttgttt catactctcc tttcaggagt tattatttaa aaaacagttt     7140
ttccactctt ttgtgccaaa acaattgtt gttaatggtg taacctttca ggtagacaat       7200
ggaaaagtct actacgaagg aagaccaatt ttccaaaaag gttgttgtag tttgtggtcc      7260
aattataaga aagattagaa taattaaacc acctacaaca cttatttta caaatggcgt       7320 tttaggttac aaacgcttaa caaatacgga tgatgaaatg gctgactagt tttgaagag      7380 ctttcatctc ctgttataaa tccctattac taactcaatt aagagtatta gataggttaa     7440
ttttagatca cggacccaag cgcacattaa cgtgtgctag gcgagtgctt ttagttcaat     7500
tagatttagt ttataggttg gcttatacgc ccacccaatc gctggtatga ataatagtaa      7560
agataatcct tttcgcggag caatagcaag aaaagcgcga atttatctga gaggaggatt     7620
agattgtgtt tactttctta acaaagcagg acaagcagag ccttgtcccg cgtgtacctc      7680
cctagtattc aagggaaaa cttgtgagga acactattat aataacaatc ttttgtcatg       7740
gcaagcggta aggcaactgg aaagacagac gccccagcgc cagtcatcaa actaggagga     7800
ccaaagccac ctaaagttgg ttcttctgga aatgcatcat ggtttcaacc gataaaggcc     7860
aagaagctaa attcacctgt gcctaaattt gacggtagtg gtgttcctga aaatgaaaat    7920
ctcaagtcaa gccagcaaca tggatactgg agacgccaac acaggtttaa gcctggcaaa    7980
ggtggaagaa aaccagtccc tgatgcttgg tactttact acactggaac aggaccggcc      8040
gccgacctga attggggtga aactcaagat ggtatagtgt gggttgctgc aaagggtgct    8100 gataactaaat ctagatcaaa ccagggtaca agggatcctg ataagtttga ccaatacca    8160
```

```
ctacgattct cagatggagg accggatggt aatttccgtt gggacttcat accaataaat    8220
cgtggtagga gtgggagatc aacagcagct tcatcagcag catctagtag agcaccatct    8280 cgtgagggt cacgtggacg tagaagcgga gttgaagatg atcttatagc tcgcgcagca    8340
aagattatac aggaccagca aaagaagggt gcgcgcatta ccaaggctaa ggctgatgaa    8400
atggctcatc gccgctattg caagcgcact atcccacctg gttataaggt tgagcaagta    8460
tttggtcccc gtactaaagg taaggaagga aattttggtg atgacaagat gaatgaggaa    8520
ggtgttaagg atgggcgtgt tacggcaatg ctcaacctag tccctagcag tcatgcttgt    8580 cttttttggaa gtagggtgac gcccaaactg cagccagatg gtcttcacct gagatttgaa    8640
tttactactg tggtgtcacg tgatgatccg cagtttgata attatgtgaa aatttgtgat    8700
cagtgtgtcg atggtgtagg gacgcgtcca aaggacgatg aatcgagacc aaagtcacgc    8760
ccaaattcaa gacctgcaac tagaggaaat tctccagcgc cgagacaaca gcgcccaaag    8820
aaggagaaaa agcccaagaa gcaggatgat gaagtagata aggcattgac ctcagatgag    8880
gagaggaaca atgcacagct ggaatttgat gatgaaccca aggtgattaa ctgggggggac    8940 tctgcactag gtgaaaatga actttgatta acataatgga cttgctgcat ttgctgtcac    9000
attttgttaa atattatttt tgtgttttac tatcaattat tacaggtatt gattgtgatt    9060
atgttcaata cttaagcttc ttctggttgc ttttgcttg ttgtattgtt gctgtgcttt    9120
ttattattgt gattctcatt agtttgcttt atcgtagaaa ttcaatagta agagttaagg    9180
aagataggca tgtagcttag cacctacatg tctatcgcca gggaaatgtc taatctgtct    9240
acttagtagc ctggaaacga acggtagacc cttagatttt aatttagttt aattttagt    9300 ttagtttaag ttagtttaga gtaggtataa agatgccagt gccggggcca cgcgtagtac    9360
gaccgagggt acagcactag gacgcccact aggggaagag ctaaatttta gtttaagtta    9420
agtttaattg gctaaatata gttaaaattt ataggctagt atagagttag agcaaaaaaa    9480
aaaaaaaaaa aaaaaaaaaa aaaaaaaaaa aaaaaaaaaa aaaaaaaaaa aaaaaaaaaa    9540
aaaaaaaaaa aaaaaaaaaa aaaaaaaaaa aaagcggccg catcggatgc cgggaccgac    9600
gagtgcagag gcgtgcaagc gagcttggcg taatcatggt catagctgtt tcctgtgtga    9660
aattgttatc cgctcacaat tccacacaac atacgagccg gaagcataaa gtgtaaagcc    9720
tggggtgcct aatgagtgag ctaactcaca ttaattgcgt tgcgctcact gcccgctttc    9780
cagtcgggaa acctgtcgtg ccagctgcat taatgaatcg gccaacgcgc ggggagaggc    9840
ggtttgcgta ttgggcgctc ttccgcttcc tcgctcactg actcgctgcg ctcggtcgtt    9900
cggctgcggc gagcggtatc agctcactca aaggcggtaa tacggttatc cacagaatca    9960
ggggataacg caggaaagaa catgtgagca aaaggccagc aaaaggccag gaaccgtaaa    10020
aaggccgcgt tgctggcgtt tttccatagg ctccgccccc ctgacgagca tcacaaaaat    10080
cgacgctcaa gtcagaggtg gcgaaacccg acaggactat aaagatacca ggcgtttccc    10140
cctggaagct ccctcgtgcg ctctcctgtt ccgaccctgc cgcttaccgg atacctgtcc    10200
gcctttctcc cttcgggaag cgtggcgctt tctcatagct cacgctgtag gtatctcagt    10260
tcggtgtagg tcgttcgctc caagctgggc tgtgtgcacg aacccccgt tcagcccgac    10320 cgctgcgcct tatccggtaa ctatcgtctt gagtccaacc cggtaagaca cgacttatcg    10380
ccactggcag cagccactgg taacaggatt agcagagcga ggtatgtagg cggtgctaca    10440
gagttcttga agtggtggcc taactacggc tacactagaa gaacagtatt tggtatctgc    10500
```

```
gctctgctga agccagttac cttcggaaaa agagttggta gctcttgatc cggcaaacaa    10560
accaccgctg gtagcggtgg ttttttttgtt tgcaagcagc agattacgcg cagaaaaaaa    10620
ggatctcaag aagatccttt gatcttttct acggggtctg acgctcagtg aacgaaaac     10680
tcacgttaag ggattttggt catgagatta tcaaaaagga tcttcaccta gatcctttta    10740
aattaaaaat gaagttttaa atcaatctaa agtatatatg agtaaacttg gtctgacagt    10800
taccaatgct taatcagtga ggcacctatc tcagcgatct gtctatttcg ttcatccata    10860
gttgcctgac tccccgtcgt gtagataact acgatacggg agggcttacc atctggcccc    10920
agtgctgcaa tgataccgcg agacccacgc tcaccggctc cagatttatc agcaataaac    10980
cagccagccg gaagggccga gcgcagaagt ggtcctgcaa ctttatccgc ctccatccag    11040
tctattaatt gttgccggga agctagagta agtagttcgc cagttaatag tttgcgcaac    11100
gttgttgcca ttgctacagg catcgtggtg tcacgctcgt cgtttggtat ggcttcattc    11160
agctccggtt cccaacgatc aaggcgagtt acatgatccc ccatgttgtg caaaaaagcg    11220
gttagctcct tcggtcctcc gatcgttgtc agaagtaagt tggccgcagt gttatcactc    11280
atggttatgg cagcactgca taattctctt actgtcatgc catccgtaag atgcttttct    11340
gtgactggtg agtactcaac caagtcattc tgagaatagt gtatgcggcg accgagttgc    11400
tcttgcccgg cgtcaatacg ggataatacc gcgccacata gcagaacttt aaaagtgctc    11460
atcattggaa aacgttcttc ggggcgaaaa ctctcaagga tcttaccgct gttgagatcc    11520
agttcgatgt aacccactcg tgcacccaac tgatcttcag catctttac tttcaccagc    11580
gtttctgggt gagcaaaaac aggaaggcaa aatgccgcaa aaaagggaat aagggcgaca    11640
cggaaatgtt gaatactcat actcttcctt tttcaatatt attgaagcat ttatcagggt    11700
tattgtctca tgagcggata catatttgaa tgtatttaga aaaataaaca ataggggtt    11760
ccgcgcacat ttccccgaaa agtgccacct gacgtctaag aaaccattat tatcatgaca    11820
ttaacctata aaaataggcg tatcacgagg cccttcgtc                          11860
```

<210> SEQ ID NO 19
<211> LENGTH: 3489
<212> TYPE: DNA
<213> ORGANISM: Unknown
<220> FEATURE:
<223> OTHER INFORMATION: Description of Unknown:
      Avian infectious bronchitis virus sequence

<400> SEQUENCE: 19

```
atgttggtaa cacctctttt actagtgact cttttgtgtg cactatgtag tgctgctttg      60
tatgactcga gttcttacgt gtactactac caaagtgcct tcagaccacc tgatggttgg    120
catttacatg ggggtgcgta tgcggttgtt aatatttcta gtgaatctaa taatgcaggc    180
tcttcatctg ggtgtactgt tggtattatt catggtggtc gtgttgttaa tgcttcttct    240
atagctatga cggcaccgtc atcaggtatg gcttggtcta gcagtcagtt ttgtactgca    300
tactgtaact tttcagatac tacagtgttt gttacacatt gttataaaca tggtgggtgt    360
cctataactg gcatgcttca acagcattct atacgtgttt ctgctatgaa aaatggccag    420
cttttctata taaattacagt tagtgtagct aagtacccta cttttaaatc atttcagtgt    480
gttaataatt taacatccgt atatttaaat ggtgatcttg tttacacctc taatgagacc    540
acagatgtta catctgcagg tgtttatttt aaagctggtg gacctataac ttataaagtt    600
atgagagaag ttagagccct ggcttatttt gttaatggta ctgcacaaga tgttattttg    660
```

```
tgtgatgggt cacctagagg cttgttagca tgccagtata atactggcaa ttttttcagat    720 ggcttttatc cttttactaa tagtagttta gttaagcaga agtttattgt ctatcgtgaa    780
aatagtgtta atactacttt tacgttacac aatttcactt ttcataatga gactggcgcc    840
aacccaaatc ctagtggtgt ccagaatatt caaacttacc aaacacaaac agctcagagt    900
ggttattata attttaattt ttcctttctg agtagttttg tttataagga gtctaatttt    960
atgtatggat cttatcaccc aagttgtaat tttagactag aaactattaa taatggtttg   1020
tggtttaatt cactttcagt tagtattgct tacggtcctc ttcaaggtgg ttgcaagcaa   1080
tctgtcttta gtggtagagc aacctgttgt tatgcttact catatggagg tcctttgctg   1140
tgtaaaggtg tttattcagg tgagttagat cataattttg aatgtggact gttagtttat   1200
gttactaaga gcggtggctc tcgtatacaa acagccactg aaccgccagt tataactcaa   1260
cacaattata ataatattac tttaaatact tgtgttgatt ataatatata tggcagaact   1320
ggccagggtt ttattactaa tgtaaccgac tcagctgtta gttataatta tctagcagac   1380
gcaggtttgg ctattttaga tacatctggt tccatagaca tctttgtcgt acaaagtgaa   1440
tatggtctta attattataa ggttaaccct tgcgaagatg tcaaccagca gtttgtagtt   1500
tctggtggta aattagtagg tattcttact tcacgtaatg agactggttc ccagcttctt   1560
gagaatcagt tttacatcaa aatcactaat ggaacacgtc gttttagacg ttctattact   1620
gaaagtgttg aaaattgccc ttatgttagt tatggtaagt tttgtataaa acctgatggc   1680
agtattgcca caatagtacc aaaacagtta gaacagtttg tggcaccttt acttaatgtt   1740
actgaaaatg tgctcatacc taacagtttt aatttaactg ttacagatga gtacatacaa   1800
actcggatgg ataaggtcca aattaattgc ctgcagtata tttgtggcaa ttctctggag   1860
tgcagaaatt tgtttcaaca atatggtcct gtttgcgaca acatattgtc tgtagtaaat   1920
agtgttggtc aaaaagaaga tatggaactt ttgaatttct attcttctac taagccggct   1980
ggttttaata caccagttct tagtaatgtt agcactggtg agtttaatat tactctttttt  2040 ttaacaacgc ctagtagtcc tagaaggcgt tcttttattg aagaccttct atttacaagt   2100
gttgaatctg ttggattacc aacagatgac gcatacaaaa attgcactgc aggtccttta   2160
ggctttctga agaccttgc atgtgctcgt gaatataatg gtttgcttgt gttgcctcct   2220
attataacag cagaaatgca aactttgtat acaagctctc tagtagcttc tatggctttt   2280
ggtggtatta ctgcagctgg tgctatacct tttgccacac aactgcaggc tagaattaat   2340
cacttgggta ttacccagtc acttcttttg aagaatcaag aaaaaattgc tgcttccttt   2400
aataaggcca tcggtcatat gcaggaaggt tttagaagta catctttagc attacaacaa   2460
attcaagatg ttgttaataa gcagagtgct attcttactg agactatggc atcacttaat   2520
aaaaattttg gtgccatttc ttctgtgatt caagaaatct accagcaact tgacgccata   2580
caagcaaatg ctcaagtgga tcgtcttata actggtagat tgtcatcact ttctgtttta   2640
gcatctgcta agcaggcgga gtatattaga gtgtcacaac agcgtgagtt agctactcag   2700
aagattaatg agtgtgttaa gtcacagtcc attaggtact ccttttgtgg taatggacga   2760
catgttttaa ccataccgca aaatgcacct aatggtatag tgtttataca ctttcttac    2820 actccagata gttttgttaa tgttactgca atagtgggtt tttgtgtaaa gccagctaat   2880
gctagtcagt atgcaatagt acccgctaat ggtaggggta ttttataca gttaatggt    2940 agttactaca tcactgcacg agatatgtat atgccaagag ctattactgc aggagatata   3000
gttacgctta cttcttgtca agcaaattat gtaagtgtaa ataagaccgt cattactaca   3060
```

| | |
|---|---|
| ttcgtagaca atgatgattt tgattttaat gacgaattgt caaaatggtg gaatgatact | 3120 |
| aagcatgagc taccagactt tgacaaattc aattacacag tacctatact tgacattgat | 3180 |
| agtgaaattg atcgtattca aggcgttata cagggtctta atgactctct aatagacctt | 3240 |
| gaaaaacttt caatactcaa aacttatatt aagtggcctt ggtatgtgtg ctagccata | 3300 |
| gcttttgcca ctattatctt catcttaata ttaggatggg ttttcttcat gactgggtgt | 3360 |
| tgtggttgtt gttgtggatg ctttggcatt atgcctctaa tgagtaagtg tggtaagaaa | 3420 |
| tcttcttatt acacgacttt tgataacgat gtggtaactg aacaatacag acctaaaaag | 3480 |
| tctgtttaa | 3489 |

```
<210> SEQ ID NO 20
<211> LENGTH: 3495
<212> TYPE: DNA
<213> ORGANISM: Unknown
<220> FEATURE:
<223> OTHER INFORMATION: Description of Unknown:
      Avian infectious bronchitis virus sequence

<400> SEQUENCE: 20
```

| | |
|---|---|
| atgttggaca aaccgctttt actagtgact ctttggtatg cactatgtag tgctttgctc | 60 |
| tatgataata atacttacgt ttactactac caaagtgcct ttaggcctgg tccaggttgg | 120 |
| cacctatatg ggggtgctta tgcagtagat agggtttta atgaaaccaa caatgcaggc | 180 |
| agtgcatctg attgcactgc tggtactttt tatgaaagcc ataatatttc tgcttcttct | 240 |
| gtagccatga cagtaccaca taatggtatg tcttggtcag cttcacaatt ttgtacagct | 300 |
| cattgtaact tctcagactt tacagtgttc gttacgcatt gttttaaaaa tcaactcggt | 360 |
| agttgtccct tgacaggtat gattcctcag aatcatattc gtatttctgc tatgagagat | 420 |
| ggagttttgt tttataactt aacagttagc gtatctaaat ccctagatt taaatcgctt | 480 |
| caatgtgtta gcaattctac atctgtctat gtaaatggtg accttgtttt cacttctaat | 540 |
| gaaacttctt acgttacggg tgcaggcgtt tattttaaaa gtggtgggcc tgtaacttat | 600 |
| aaagttatga aagaagttaa agcccctagcc tactttatta atggtaccgc acaagaggtt | 660 |
| atttatgtg ataactcacc tagaggttg cttgcatgtc agtataacac tggtaatttt | 720 |
| tcagatggat tctaccccttt tactaatcat tcttagttta aggataggtt tattgtatat | 780 |
| cgagaaagta gcactaacac tactttaaag ttaactaatt tcagttttac taatgtaagt | 840 |
| aatgcttctc ctaattcagg tggcgttgat actttccaat tatatcaaac aagtactgct | 900 |
| caggatggtt attataattt taatttatca tttctgagta gttttgtgta taaaccatct | 960 |
| gattttatgt atgggtcata ccacccacat tgtaagtta gaccagagaa tattaataat | 1020 |
| ggcttatggt taattcatt atctgtgtca cttacttacg gacccattca aggtggttgt | 1080 |
| aagcaatctg ttttagtaa tagagcaact tgttgctatg cttattctta tcaagggcct | 1140 |
| agtagatgta agggtgttta tagagggag ctaacgcaat actttgaatg tggacttcta | 1200 |
| gtttacgtaa ctaagagtga tggctctcgt atacaaacta gaagtgaacc actggtgtta | 1260 |
| actcaatata attataacaa cattacttta aataagtgtg ttgagtataa tatatatggt | 1320 |
| agggttggtc aaggttttat tactaatgta actgaagcaa ctgctaatta gttatcta | 1380 |
| gcagatggtg gttagctat tttagatacc tcaggagcca tagacatatt tgttgttcaa | 1440 |
| ggtgcatatg gtcttaatta ttataaggtt aatccctgtg aagatgttaa ccaacagttt | 1500 |
| gtagtgtctg gtggcaactt agttggcatt cttacatctc ataatgaaac aggttctgaa | 1560 |

```
tctattgaga accagtttta catcaaactc actaacggaa cacgtcgctc tagacgttct    1620
gttactggga atgttacaaa ttgcccttat gttagttatg gcaagttttg tataaaacca    1680
gatggttctt tatctataat agtaccacaa gaattagaac agtttgtggc gcctttattc    1740
aatgttactg agcatgtgct cataccgtga gttttaatt taactgtcac agatgagtac    1800
atacaaactc gtatggataa ggttcaaatt atttgccttc agtatgtttg tggtaattct    1860
attgaatgca gaaagttgtt tcagcagtat ggacctgttt gtgataatat attgtctgtt    1920
gtaaatggtg taggtcaaag agaggatatg gaacttttaa gtttctattc ttctactaaa    1980
cctagtggtt acaatacacc aattttttaat aatgttagca ctggtgactt taatatttcg    2040
ctcctactaa caccacctaa tagtcctact gggcgctctt ttattgaaga tcttctcttt    2100
acaagtgtag aatctgttgg attaccaact gatgaagagt ataaaaagtg tacagcagga    2160
cctttaggtt ttgttaaaga ccttgtttgt gctagagagt ataatggttt gctcgttctg    2220
cctcctatta ttactgcgga aatgcaaacc atgtatacta gttctttagt agcctctatg    2280
gctttaggtg gcattactgc agctggtgct ataccttttg ctacacaact gcaggccaga    2340
attaaccatt tgggtattac taattctctt ttgttgaaaa accaagaaaa aattgctgct    2400
tcctttaata aggccatcgg tcatatgcag gaagggttta aaagtacttc tctagcatta    2460
caacagattc aagatgttgt taataaacag agttctattc ttacagagac tatgcaatca    2520
cttaataaaa attttggtgc tatttcctct gtaattcaag acatttacca gcaactagat    2580
gctattcagg cagatgctca ggttgatcgt cttattacag gtagactctc ttcactatct    2640
gttttagctt ctgctaaaca ggcagagtat catagagtgt cacaacagcg tgagttggcc    2700
actcagaaaa ttaatgagtg tgttaagtct cagtctaata ggtattcatt tgtgggtaat    2760
ggtagacatg ttctaaccat accacagaat gcacccaatg gcatagtgtt tatacacttt    2820
acatacactc cagagagttt tgttaatgtt acggcaatag tagggttttg cgtaaaccca    2880
gctaatgcta gtcattatgc aatagtgcct gttaatggca ggggtgtttt tatagaagtt    2940
aatggtagtt actatatcac tgctcgtgat atgtatatgc caagagatat tactgcagga    3000
gacatagtca ctttgacttc ttgtcaagca aactatgtta atgtaaataa aaccgtcatt    3060
aacacttttg tggaagatga cgattttgat ttttatgatg aattgtcaaa atggtggaat    3120
gatactaagc atgagctacc agattttgat gaattcaatt ataccgttcc agttttaaat    3180
attagtaatg aaattgacag aattcaacag gttattcagg gattaaatga ttccctaata    3240 gacctttgaaa cactctcaat tctcaaaact tatattaaat ggccttggta tgtgtggctt    3300
gccattgcat tccttaccat tatttttatt ctggtacttt gttggatatt tttcatgacc    3360
ggttgttgcg gttgttgttg tggatgcttt ggtatcatac cgttaatgag taagtgtggt    3420
aagaaatctt cttactacac gacttttgat aatgatgtgg taacttaaca atacagacct    3480
aaaaagtctg tttaa                                                    3495

<210> SEQ ID NO 21
<211> LENGTH: 11320
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Plasmid with IBV

<400> SEQUENCE: 21
```

-continued

```
tcgcgcgttt cggtgatgac ggtgaaaacc tctgacacat gcagctcccg gagacggtca        60
cagcttgtct gtaagcggat gccgggagca gacaagcccg tcagggcgcg tcagcgggtg       120
ttggcgggtg tcggggctgg cttaactatg cggcatcaga gcagattgta ctgagagtgc       180
accatatgcg gtgtgaaata ccgcacagat gcgtaaggag aaaataccgc atcaggcgcc       240
attcgccatt caggctgcgc aactgttggg aagggcgatc ggtgcgggcc tcttcgctat       300
tacgccagct ggcgaaaggg ggatgtgctg caaggcgatt aagttgggta acgccagggt       360
tttcccagtc acgacgttgt aaaacgacgg ccagtgaatt ggagatcggt acttcgcgaa       420
tgcgtcgaga tgagctctaa tacgactcac tatagggact taagtgtgat ataaatatat       480
atcatacata ctagccttgt gctagatttc aacttaaca aaacggactt aaatacctac        540
agttggtccc tataggtgtt ccattgcagt gcactttagt gccctggatg cacctggcc        600 acctgtcagg ttttgttat taaaataata ttgttgctgg tatcactgct tgttttgccg        660
tgtctcactt tatacatccg ttgcttgggc tacctagtat ccagcgtcct actggcgttg       720
tggtcggttc gagtgcgaag aacctctggt tcatctagcg gtacgcgggt gtgtggaagt       780
agcgcttcag acgtaccggt tctgttgcgt gaaatacggg gtcacctccc cccacatacc       840
tctaagggct tttgagccta gcgttgggct acgttctcgc acaaggtcgg ctatacggcg       900
tttgtagggg gtagtgccaa acaacccctg aggtgacagg ttctggtggt gtttcgaaaa       960
caacaatgtg tgtgccgcat aatatgcgag taatgcattt tggagcagga agtgacaaag      1020
gagtggcccc aggtagcgct gttcttaggc agtggcttcc cgaaggtaca ctccttgtcg      1080
ataatgatat tgtagattat gtatctgatg cacatgtctc tgtgctttca gattgcaata      1140
aatgtaaaac agagcacaag tttgatcttg tgatatctga tatgtataca gataatgatt      1200
caaagagaaa gcatgaaggc gttgtagcca ataacggcaa tgatgacgtc ttcatatacc      1260
tttcaaactt tcttcgtaac aatttagctc tgggaggcag ttttgccgta aaagtaacag      1320
agacaagttg gcatgagagt ttatatgaca ttgcacagga ttgtgcatgg tggacaatgt      1380
tttgtacagc agtgaatgct tcttcgtcag aagcattctt gattggtgtt aattatttgg      1440
gtgcaagtga aaaggttaga gttagtggta aaaccctgca cgcaaattat atattttgga      1500
ggaattgtaa ttatttacaa acttcagcct atagtatatt tgacgttgct aagtttgatt      1560
tgaaattaaa agcaacgcca gttgtgaatt tgaaaactga acaaaagaca gacttagtct      1620
ttaatttaat taagtgtggt aagttactgg taagagatgt tggacaaacc gcttttacta      1680
gtgactcttt ggtatgcact atgtagtgct ttgctctatg ataataatac ttacgtttac      1740
tactaccaaa gtgcctttag gcctggtcca ggttggcacc tatatggggg tgcttatgca      1800
gtagataggg tttttaatga aaccaacaat gcaggcagtg catctgattg cactgctggt      1860 acttttatg aaagccataa tatttctgct tcttctgtag ccatgacagt accacataat      1920
ggtatgtctt ggtcagcttc acaattttgt acagctcatt gtaacttctc agactttaca      1980
gtgttcgtta cgcattgttt taaaaatcaa ctcggtagtt gtcccttgac aggtatgatt      2040
cctcagaatc atattcgtat ttctgctatg agagatggag ttttgtttta aacttaaca      2100 gttagcgtat ctaaataccc tagatttaaa tcgcttcaat gtgttagcaa ttctacatct      2160
gtctatgtaa atggtgacct tgttttcact tctaatgaaa cttcttacgt tacgggtgca      2220
ggcgtttatt ttaaaagtgg tgggcctgta acttataaag ttatgaaaga agttaaagcc      2280
ctagcctact ttattaatgg taccgcacaa gaggttattt tatgtgataa ctcacctaga      2340
```

-continued

```
ggtttgcttg catgtcagta taacactggt aattttttcag atggattcta ccctttttact   2400
aatcattctt tagttaagga taggtttatt gtatatcgag aaagtagcac taacactact   2460
ttaaagttaa ctaatttcag ttttactaat gtaagtaatg cttctcctaa ttcaggtggc   2520
gttgatactt tccaattata tcaaacaagt actgctcagg atggttatta aattttttaat   2580
ttatcatttc tgagtagttt tgtgtataaa ccatctgatt ttatgtatgg gtcataccac   2640
ccacattgta agtttagacc agagaatatt aataatggct tatggtttaa ttcattatct   2700
gtgtcactta cttacggacc cattcaaggt ggttgtaagc aatctgtttt tagtaataga   2760
gcaacttgtt gctatgctta ttcttatcaa gggcctagta gatgtaaggg tgttttataga   2820
ggggagctaa cgcaatactt tgaatgtgga cttctagttt acgtaactaa gagtgatggc   2880
tctcgtatac aaactagaag tgaaccactg gtgttaactc aatataatta taacaacatt   2940
actttaaata gtgtgttga gtataatata tatggtaggg ttggtcaagg ttttattact   3000
aatgtaactg aagcaactgc taattatagt tatctagcag atggtggttt agctatttta   3060
gatacctcag gagccataga catatttgtt gttcaaggtg catatggtct taattattat   3120
aaggttaatc cctgtgaaga tgttaaccaa cagtttgtag tgtctggtgg caacttagtt   3180
ggcattctta catctcataa tgaaacaggt tctgaatcta ttgagaacca gttttacatc   3240
aaactcacta acggaacacg tcgctctaga cgttctgtta ctgggaatgt tacaaattgc   3300
ccttatgtta gttatggcaa gttttgtata aaaccagatg gttctttatc tataatagta   3360
ccacaagaat tagaacagtt tgtggcgcct ttattcaatg ttactgagca tgtgctcata   3420
cctgatagtt ttaatttaac tgtcacagat gagtacatac aaaactcgtat ggataaggtt   3480
caaattattt gccttcagta tgtttgtggt aattctattg aatgcagaaa gttgtttcag   3540
cagtatggac ctgtttgtga taatatattg tctgttgtaa atggtgtagg tcaaagagag   3600
gatatggaac ttttaagttt ctattcttct actaaaccta gtggttacaa tacaccaatt   3660
tttaataatg ttagcactgg tgactttaat atttcgctcc tactaacacc acctaatagt   3720
cctactgggc gctcttttat tgaagatctt ctctttacaa gtgtagaatc tgttggatta   3780
ccaactgatg aagagtataa aaagtgtaca gcaggacctt taggttttgt taaagacctt   3840
gtttgtgcta gagagtataa tggtttgctc gttctgcctc ctattattac tgcggaaatg   3900
caaaccatgt atactagttc tttagtagcc tctatggctt taggtggcat tactgcagct   3960
ggtgctatac ctttttgctac acaactgcag gccagaatta accatttggg tattactaat   4020
tctctttttgt tgaaaaacca agaaaaaatt gctgcttcct ttaataaggc catcggtcat   4080
atgcaggaag ggtttaaaag tacttctcta gcattacaac agattcaaga tgttgttaat   4140
aaacagagtt ctattcttac agagactatg caatcactta ataaaaattt tggtgctatt   4200
tcctctgtaa ttcaagacat ttaccagcaa ctagatgcta ttcaggcaga tgctcaggtt   4260
gatcgtctta ttcaggtag actctcttca ctatctgttt tagcttctgc taaacaggca   4320
gagtatcata gagtgtcaca acagcgtgag ttggccactc agaaaattaa tgagtgtgtt   4380
aagtctcagt ctaataggta ttcatttttgt ggtaatggta gacatgttct aaccatacca   4440
cagaatgcac ccaatggcat agtgtttata cactttacat acactccaga gagttttgtt   4500
aatgttacgg caatagtagg gttttgcgta aacccagcta atgctagtca ttatgcaata   4560
gtgcctgtta atggcagggg tgttttttata gaagttaatg gtagttacta tatcactgct   4620
cgtgatatgt atatgccaag agatattact gcaggagaca tagtcacttt gacttcttgt   4680
caagcaaact atgttaatgt aaataaaacc gtcattaaca cttttgtgga agatgacgat   4740
```

```
tttgatttt  atgatgaatt  gtcaaaatgg  tggaatgata  ctaagcatga  gctaccagat  4800
tttgatgaat  tcaattatac  cgttccagtt  ttaaatatta  gtaatgaaat  tgacagaatt  4860
caacaggtta  ttcagggatt  aaatgattcc  ctaatagacc  ttgaaacact  ctcaattctc  4920
aaaacttata  ttaaatggcc  ttggtatgtg  tggcttgcca  ttgcattcct  taccattatt  4980
tttattctgg  tactttgttg  gatattttc  atgaccggtt  gttgcggttg  ttgttgtgga  5040
tgctttggta  tcataccgtt  aatgagtaag  tgtggtaaga  aatcttctta  ctacacgact  5100
tttgataatg  atgtggtaac  ttaacaatac  agacctaaaa  agtctgttta  atgattaaaa  5160
gtcccacatc  ttttctaata  ttattaattc  ttctttggtg  taaacttgca  ttaagttgtt  5220
ttaaagagtg  tgttataaca  ctccagcaac  tagtacaaat  tttactccaa  attattaata  5280
gtaacttaca  atctagactt  ctgctttggc  acagtctaga  ctaatgttag  attttgaagc  5340
aattattgaa  actggtcagc  aaataactca  acaaattagt  ttctatttac  agcatatttc  5400
aagggtgcta  agtactgaat  tatttgaccc  ctttgaagtt  tgtgtttaca  gaggaggtaa  5460
ttgttgggag  ttagagtcag  ctgacgagtt  tcaggtgat  gacgaatata  ttgagtagat  5520
cgctcgagga  gaacggaagt  tttctaacag  cggtttacgt  gttttagga  ttttagcac  5580 tttatctact  aggtagagcg  cttcaagctt  ttgtacaagc  ggctgacgct  tgttgtcttt  5640
tttggtatac  atgggtagta  gttcctggag  ccaagggcac  agcctttgtt  tataatcata  5700
catatggtaa  aaaacttaac  aaaccggagt  tagaaacggt  tattgttaac  gaatttccaa  5760
aaaacggttg  gaaatatgga  taataccatc  aattgtactc  ttggtactga  acaagcagtt  5820
cagcttttta  aggaatataa  tctgtttgta  actgcattcc  tgttgttttt  aaccatacta  5880
cttcagtatg  gatacgcaac  taggagcaag  gttatttaca  tactgaaaat  gatagtgtta  5940
tggtgctttt  ggcccttaa  cattgcagta  ggtgtaatct  catgtatata  cccaccaaac  6000
acaggaggtc  ttgtcgcagc  gataattctt  acagtgtttg  cgtgtctttc  ttttataggt  6060
tattggatcc  agagtattag  acttttaag  cggtgcaggt  catggtggtc  atttaacccc  6120
gaatctaatg  ccgtaggttc  aatactccta  actaatggtc  aacaatgtaa  ttttgctata  6180
gagagtgtgc  cgatggtgct  ttctcctatt  ataaagaatg  gtgctcttta  ttgcgagggt  6240
cagtggcttg  ctaaatgtga  accagaccac  ttgcctagag  atatatttgt  atgcacaccg  6300
gatagacgta  atatctatcg  tatggtgcaa  aaatatactg  gtgaccaaag  cggaagtaag  6360
aaaaggtttg  ccacatttgt  ctatgcaaag  cagtcagtag  atactggcga  gctagaaagt  6420
gtgtcagcag  taggaggtag  tctttacaca  taaatgtgtg  tgtgtagaga  gtatttaaaa  6480
ttattctttg  acagtgcctc  cgttttaaga  gcgcggaaga  gtattatttt  tgaggatatt  6540
aatataaatc  ctctttgttt  catactctcc  tttcaggagt  tattatttaa  aaaacagttt  6600
ttccactctt  ttgtgccaaa  aacaattgtt  gttaatggtg  taacctttca  ggtagacaat  6660
ggaaaagtct  actacgaagg  aagaccaatt  ttccaaaaag  gttgttgtag  tttgtggtcc  6720
aattataaga  aagattagaa  taattaaacc  acctacaaca  cttatttta  caaatggcgt  6780 tttaggttac  aaacgcttaa  caaatacgga  tgatgaaatg  gctgactagt  tttggaagag  6840 cttcatctc  ctgttataaa  tccctattac  taactcaatt  aagagtatta  gataggttaa  6900
ttttagatca  cggacccaag  cgcacattaa  cgtgtgctag  gcgagtgctt  ttagttcaat  6960
tagatttagt  ttataggttg  gcttatacgc  ccacccaatc  gctggtatga  ataatagtaa  7020
agataatcct  tttcgcggag  caatagcaag  aaaagcgcga  atttatctga  gaggaggatt  7080
```

```
agattgtgtt tactttctta acaaagcagg acaagcagag ccttgtcccg cgtgtacctc    7140
cctagtattc caagggaaaa cttgtgagga acactattat aataacaatc ttttgtcatg    7200
gcaagcggta aggcaactgg aaagacagac gccccagcgc cagtcatcaa actaggagga    7260
ccaaagccac ctaaagttgg ttcttctgga aatgcatcat ggtttcaacc gataaaggcc    7320
aagaagctaa attcacctgt gcctaaattt gacggtagtg gtgttcctga aaatgaaaat    7380
ctcaagtcaa gccagcaaca tggatactgg agacgccaac acaggtttaa gcctggcaaa    7440
ggtggaagaa aaccagtccc tgatgcttgg tacttttact acactggaac aggaccggcc    7500
gccgacctga attggggtga aactcaagat ggtatagtgt gggttgctgc aaagggtgct    7560
gatactaaat ctagatcaaa ccagggtaca agggatcctg ataagtttga ccaataccca    7620
ctacgattct cagatggagg accgatggt aatttccgtt gggacttcat accaataaat    7680
cgtggtagga gtgggagatc aacagcagct tcatcagcag catctagtag agcaccatct    7740
cgtgaggggt cacgtggacg tagaagcgga gttgaagatg atcttatagc tcgcgcagca    7800
aagattatac aggaccagca aaagaagggt gcgcgcatta ccaaggctaa ggctgatgaa    7860
atggctcatc gccgctattg caagcgcact atcccacctg gttataaggt tgagcaagta    7920
tttggtcccc gtactaaagg taaggaagga aattttggtg atgacaagat gaatgaggaa    7980
ggtgttaagg atgggcgtgt tacggcaatg ctcaacctag tccctagcag tcatgcttgt    8040 cttttttggaa gtagggtgac gcccaaactg cagccagatg tcttcacct gagatttgaa    8100 tttactactg tggtgtcacg tgatgatccg cagtttgata attatgtgaa aatttgtgat    8160
cagtgtgtcg atggtgtagg gacgcgtcca aaggacgatg aatcgagacc aaagtcacgc    8220
ccaaattcaa gacctgcaac tagaggaaat ctccagcgc cgagacaaca gcgcccaaag    8280
aaggagaaaa agcccaagaa gcaggatgat gaagtagata aggcattgac ctcagatgag    8340
gagaggaaca atgcacagct ggaatttgat gatgaaccca aggtgattaa ctgggggggac    8400 tctgcactag gtgaaaatga actttgatta acataatgga cttgctgcat tgctgtcac    8460 attttgttaa atattatttt tgtgttttac tatcaattat tacaggtatt gattgtgatt    8520
atgttcaata cttaagcttc ttctggttgc ttttttgcttg ttgtattgtt gctgtgcttt    8580
ttattattgt gattctcatt agtttgcttt atcgtagaaa ttcaatagta agagttaagg    8640
aagataggca tgtagcttag cacctacatg tctatcgcca gggaaatgtc taatctgtct    8700
acttagtagc ctggaaacga acggtagacc cttagatttt aatttagttt aattttttagt    8760 ttagtttaag ttagtttaga gtaggtataa agatgccagt gccggggcca cgcgtagtac    8820
gaccgagggt acagcactag gacgcccact aggggaagag ctaaattta gtttaagtta    8880 agtttaattg gctaaatata gttaaaattt ataggctagt atagagttag agcaaaaaaa    8940
aaaaaaaaaa aaaaaaaaaa aaaaaaaaa aaaaaaaaa aaaaaaaaa aaaaaaaaa      9000 aaaaaaaaa aaaaaaaaaa aaaaaaaaa aaagcggccg catcggatgc cgggaccgac    9060
gagtgcagag gcgtgcaagc gagcttggcg taatcatggt catagctgtt tcctgtgtga    9120
aattgttatc cgctcacaat tccacacaac atacgagccg aagcataaa gtgtaaagcc    9180 tggggtgcct aatgagtgag ctaactcaca ttaattgcgt tgcgctcact gcccgctttc    9240
cagtcgggaa acctgtcgtg ccagctgcat taatgaatcg gccaacgcgc ggggagaggc    9300
ggtttgcgta ttgggcgctc ttccgcttcc tcgctcactg actcgctgcg ctcggtcgtt    9360
cggctgcggc gagcggtatc agctcactca aaggcggtaa tacggttatc cacagaatca    9420
ggggataacg caggaaagaa catgtgagca aaaggccagc aaaaggccag gaaccgtaaa    9480
```

-continued

```
aaggccgcgt tgctggcgtt tttccatagg ctccgccccc ctgacgagca tcacaaaaat   9540
cgacgctcaa gtcagaggtg gcgaaacccg acaggactat aaagatacca ggcgtttccc   9600
cctggaagct ccctcgtgcg ctctcctgtt ccgaccctgc cgcttaccgg atacctgtcc   9660
gcctttctcc cttcgggaag cgtggcgctt tctcatagct cacgctgtag gtatctcagt   9720
tcggtgtagg tcgttcgctc caagctgggc tgtgtgcacg aaccccccgt tcagcccgac   9780
cgctgcgcct tatccggtaa ctatcgtctt gagtccaacc cggtaagaca cgacttatcg   9840
ccactggcag cagccactgg taacaggatt agcagagcga ggtatgtagg cggtgctaca   9900
gagttcttga agtggtggcc taactacggc tacactagaa gaacagtatt tggtatctgc   9960
gctctgctga agccagttac cttcggaaaa agagttggta gctcttgatc cggcaaacaa  10020
accaccgctg gtagcggtgg tttttttgtt tgcaagcagc agattacgcg cagaaaaaaa  10080
ggatctcaag aagatccttt gatcttttct acggggtctg acgctcagtg gaacgaaaac  10140
tcacgttaag ggattttggt catgagatta tcaaaaagga tcttcaccta gatcctttta  10200
aattaaaaat gaagttttaa atcaatctaa agtatatatg agtaaacttg gtctgacagt  10260
taccaatgct taatcagtga ggcacctatc tcagcgatct gtctatttcg ttcatccata  10320
gttgcctgac tccccgtcgt gtagataact acgatacggg agggcttacc atctggcccc  10380
agtgctgcaa tgataccgcg agacccacgc tcaccggctc cagatttatc agcaataaac  10440
cagccagccg gaagggccga gcgcagaagt ggtcctgcaa ctttatccgc ctccatccag  10500
tctattaatt gttgccggga agctagagta agtagttcgc cagttaatag tttgcgcaac  10560
gttgttgcca ttgctacagg catcgtggtg tcacgctcgt cgtttggtat ggcttcattc  10620
agctccggtt cccaacgatc aaggcgagtt acatgatccc ccatgttgtg caaaaaagcg  10680
gttagctcct tcggtcctcc gatcgttgtc agaagtaagt tggccgcagt gttatcactc  10740
atggttatgg cagcactgca taattctctt actgtcatgc catccgtaag atgcttttct  10800
gtgactggtg agtactcaac caagtcattc tgagaatagt gtatgcggcg accgagttgc  10860
tcttgcccgg cgtcaatacg ggataatacc gcgccacata gcagaacttt aaaagtgctc  10920
atcattggaa aacgttcttc ggggcgaaaa ctctcaagga tcttaccgct gttgagatcc  10980
agttcgatgt aacccactcg tgcacccaac tgatcttcag catcttttac tttcaccagc  11040
gtttctgggt gagcaaaaac aggaaggcaa aatgccgcaa aaaagggaat aagggcgaca  11100
cggaaatgtt gaatactcat actcttcctt tttcaatatt attgaagcat ttatcagggt  11160
tattgtctca tgagcggata catatttgaa tgtatttaga aaaataaaca aataggggtt  11220
ccgcgcacat ttccccgaaa agtgccacct gacgtctaag aaaccattat tatcatgaca  11280
ttaacctata aaaataggcg tatcacgagg ccctttcgtc                        11320
```

<210> SEQ ID NO 22
<211> LENGTH: 11314
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Plasmid with IBV

<400> SEQUENCE: 22

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
```

-continued

```
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt ggagatcggt acttcgcgaa      420
tgcgtcgaga tgagctctaa tacgactcac tatagggact taagtgtgat ataaatatat      480
atcatacata ctagccttgt gctagatttc aacttaaca aaacggactt aaatacctac       540
agttggtccc tataggtgtt ccattgcagt gcactttagt gccctggatg cacctggcc       600 acctgtcagg tttttgttat taaaataata ttgttgctgg tatcactgct tgttttgccg      660
tgtctcactt tatacatccg ttgcttgggc tacctagtat ccagcgtcct actggcgttg      720
tggtcggttc gagtgcgaag aacctctggt tcatctagcg gtacgcgggt gtgtggaagt      780
agcgcttcag acgtaccggt tctgttgcgt gaaatacggg gtcacctccc cccacatacc      840
tctaagggct tttgagccta gcgttgggct acgttctcgc acaaggtcgg ctatacggcg      900
tttgtagggg gtagtgccaa acaacccctg aggtgacagg ttctggtggt gtttcgaaaa      960
caacaatgtg tgtgccgcat aatatgcgag taatgcattt tggagcagga agtgacaaag     1020
gagtggcccc aggtagcgct gttcttaggc agtggcttcc cgaaggtaca ctccttgtcg     1080
ataatgatat tgtagattat gtatctgatg cacatgtctc tgtgctttca gattgcaata     1140
aatgtaaaac agagcacaag tttgatcttg tgatatctga tatgtataca gataatgatt     1200
caaagagaaa gcatgaaggc gttgtagcca ataacggcaa tgatgacgtc ttcatatacc     1260
tttcaaactt tcttcgtaac aatttagctc tgggaggcag ttttgccgta aaagtaacag     1320
agacaagttg gcatgagagt ttatatgaca ttgcacagga ttgtgcatgg tggacaatgt     1380
tttgtacagc agtgaatgct tcttcgtcag aagcattctt gattggtgtt aattatttgg     1440
gtgcaagtga aaaggttaga gttagtggta aaaccctgca cgcaaattat atattttgga     1500
ggaattgtaa ttatttacaa acttcagcct atagtatatt tgacgttgct aagtttgatt     1560
tgaaattaaa agcaacgcca gttgtgaatt tgaaaactga acaaaagaca gacttagtct     1620
ttaatttaat taagtgtggt aagttactgg taagagatgt tggtaacacc tcttttacta     1680
gtgactcttt tgtgtgcact atgtagtgct gctttgtatg actcgagttc ttacgtgtac     1740
tactaccaaa gtgccttcag accacctgat ggttggcatt tacatggggg tgcgtatgcg     1800
gttgttaata tttctagtga atctaataat gcaggctctt catctgggtg tactgttggt     1860
attattcatg gtggtcgtgt tgttaatgct tcttctatag ctatgacggc accgtcatca     1920
ggtatggctt ggtctagcag tcagttttgt actgcatact gtaactttc agatactaca     1980 gtgtttgtta cacattgtta taaacatggt gggtgtccta taactggcat gcttcaacag     2040
cattctatac gtgtttctgc tatgaaaaat ggccagcttt tctataattt aacagttagt     2100
gtagctaagt accctacttt taaatcattt cagtgtgtta ataatttaac atccgtatat     2160
ttaaatggtg atcttgttta cacctctaat gagaccacag atgttacatc tgcaggtgtt     2220
tattttaaag ctggtggacc tataactat aaagttatga gagaagttag agccctggct     2280
tattttgtta atggtactgc acaagatgtt attttgtgtg atgggtcacc tagaggcttg     2340
ttagcatgcc agtataatac tggcaatttt tcagatggct tttatccttt tactaatagt     2400
agtttagtta agcagaagtt tattgtctat cgtgaaaata tgttaatac tactttacg     2460
```

```
ttacacaatt tcacttttca taatgagact ggcgccaacc caaatcctag tggtgtccag    2520
aatattcaaa cttaccaaac acaaacagct cagagtggtt attataattt taattttcc     2580 tttctgagta gttttgttta taaggagtct aattttatgt atggatctta tcacccaagt    2640 tgtaattta  gactagaaac tattaataat ggtttgtggt ttaattcact ttcagttagt    2700
attgcttacg gtcctcttca aggtggttgc aagcaatctg tctttagtgg tagagcaacc    2760
tgttgttatg cttactcata tggaggtcct ttgctgtgta aaggtgttta ttcaggtgag    2820
ttagatcata attttgaatg tggactgtta gtttatgtta ctaagagcgg tggctctcgt    2880
atacaaacag ccactgaacc gccagttata actcaacaca attataataa tattacttta    2940
aatacttgtg ttgattataa tatatatggc agaactggcc agggttttat tactaatgta    3000
accgactcag ctgttagtta taattatcta gcagacgcag gtttggctat tttagataca    3060
tctggttcca tagacatctt tgtcgtacaa agtgaatatg gtcttaatta ttataaggtt    3120
aacccttgcg aagatgtcaa ccagcagttt gtagtttctg gtggtaaatt agtaggtatt    3180
cttacttcac gtaatgagac tggttcccag cttcttgaga atcagttta  catcaaaatc    3240 actaatggaa cacgtcgttt tagacgttct attactgaaa gtgttgaaaa ttgcccttat    3300
gttagttatg gtaagttttg tataaaacct gatggcagta ttgccacaat agtaccaaaa    3360
cagttagaac agtttgtggc accttactt  aatgttactg aaaatgtgct catacctaac    3420
agttttaatt taactgttac agatgagtac atacaaactc ggatggataa ggtccaaatt    3480
aattgcctgc agtatatttg tggcaattct ctggagtgca gaaatttgtt tcaacaatat    3540
ggtcctgttt gcgacaacat attgtctgta gtaaatagtg ttggtcaaaa agaagatatg    3600
gaacttttga atttctattc ttctactaag ccggctggtt ttaatacacc agttcttagt    3660
aatgttagca ctggtgagtt taatattact cttttttta  caacgcctag tagtcctaga    3720
aggcgttctt ttattgaaga ccttctattt acaagtgttg aatctgttgg attaccaaca    3780
gatgacgcat acaaaaattg cactgcaggt cctttaggct ttctgaaaga ccttgcatgt    3840
gctcgtgaat ataatggttt gcttgtgttg cctcctatta taacagcaga aatgcaaact    3900
ttgtatacaa gctctctagt agcttctatg gcttttggtg gtattactgc agctggtgct    3960
ataccttttg ccacacaact gcaggctaga attaatcact gggtattac  ccagtcactt    4020 ctttttgaaga atcaagaaaa aattgctgct tcctttaata aggccatcgg tcatatgcag    4080
gaaggtttta gaagtacatc tttagcatta acaaaattc  aagatgttgt taataagcag    4140
agtgctattc ttactgagac tatggcatca cttaataaaa attttggtgc catttcttct    4200
gtgattcaag aaatctacca gcaacttgac gccatacaag caaatgctca agtggatcgt    4260
cttataactg gtagattgtc atcacttcct gttttagcat ctgctaagca ggcggagtat    4320
attagagtgt cacaacagcg tgagttagct actcagaaga ttaatgagtg tgttaagtca    4380
cagtccatta ggtactcctt tgtggtaat  ggacgacatg ttttaaccat accgcaaaat    4440
gcacctaatg gtatagtgtt tatacacttt tcttacactc cagatagttt tgttaatgtt    4500
actgcaatag tgggttttg  tgtaaagcca gctaatgcta gtcagtatgc aatagtaccc    4560
gctaatggta gggtatttt  tatacaagtt aatggtagtt actacatcac tgcacgagat    4620
atgtatatgc caagagctat tactgcagga gatatagtta cgcttacttc ttgtcaagca    4680
aattatgtaa gtgtaaataa gaccgtcatt actacattcg tagacaatga tgattttgat    4740
tttaatgacg aattgtcaaa atggtggaat gatactaagc atgagctacc agactttgac    4800
aaattcaatt acacagtacc tatacttgac attgatagtg aaattgatcg tattcaaggc    4860
```

```
gttatacagg gtcttaatga ctctctaata gaccttgaaa aactttcaat actcaaaact   4920
tatattaagt ggccttggta tgtgtggcta gccatagctt ttgccactat tatcttcatc   4980
ttaatattag gatgggtttt cttcatgact gggtgttgtg gttgttgttg tggatgcttt   5040
ggcattatgc ctctaatgag taagtgtggt aagaaatctt cttattacac gacttttgat   5100
aacgatgtgg taactgaaca atacagacct aaaaagtctg tttaatgatt aaaagtccca   5160
catcttttct aatattatta attcttcttt ggtgtaaact tgcattaagt tgttttaaag   5220
agtgtgttat aacactccag caactagtac aaattttact ccaaattatt aatagtaact   5280
tacaatctag acttctgctt tggcacagtc tagactaatg ttagattttg aagcaattat   5340
tgaaactggt cagcaaataa ctcaacaaat tagtttctat ttacagcata tttcaagggt   5400
gctaagtact gaattatttg acccctttga agtttgtgtt tacagaggag gtaattgttg   5460
ggagttagag tcagctgacg agttttcagg tgatgacgaa tatattgagt agatcgctcg   5520
aggagaacgg aagttttcta acagcggttt acgtgttttt aggatttttta gcactttatc   5580 tactaggtag agcgcttcaa gcttttgtac aagcggctga cgcttgttgt cttttttggt   5640
atacatgggt agtagttcct ggagccaagg gcacagcctt tgtttataat catacatatg   5700
gtaaaaaact taacaaaccg gagttagaaa cggttattgt taacgaattt ccaaaaaacg   5760
gttgaaaata tggataatac catcaattgt actcttggta ctgaacaagc agttcagctt   5820
tttaaggaat ataatctgtt tgtaactgca ttcctgttgt ttttaaccat actacttcag   5880
tatggatacg caactaggag caaggttatt tacatactga aaatgatagt gttatggtgc   5940
ttttggcccc ttaacattgc agtaggtgta atctcatgta tatacccacc aaacacagga   6000
ggtcttgtcg cagcgataat tcttacagtg tttgcgtgtc tttctttttat aggttattgg   6060 atccagagta ttagactttt taagcggtgc aggtcatggt ggtcatttaa ccccgaatct   6120
aatgccgtag gttcaatact cctaactaat ggtcaacaat gtaattttgc tatagagagt   6180
gtgccgatgg tgctttctcc tattataaag aatggtgctc tttattgcga gggtcagtgg   6240
cttgctaaat gtgaaccaga ccacttgcct agagatatat ttgtatgcac accggataga   6300
cgtaatatct atcgtatggt gcaaaaatat actggtgacc aaagcggaag taagaaaagg   6360
tttgccacat ttgtctatgc aaagcagtca gtagatactg gcgagctaga aagtgtgtca   6420
gcagtaggag gtagtcttta cacataaatg tgtgtgtgta gagagtattt aaaattattc   6480
tttgacagtg cctccgtttt aagagcgcgg aagagtatta tttttgagga tattaatata   6540
aatcctcttt gtttcatact ctcctttcag gagttattat ttaaaaaaca gtttttccac   6600
tcttttgtgc caaaaacaat tgttgttaat ggtgtaacct tcaggtaga caatggaaaa   6660 gtctactacg aaggaagacc aattttccaa aaaggttgtt gtagtttgtg gtccaattat   6720
aagaaagatt agaataatta aaccacctac aacacttatt tttacaaatg gcgttttagg   6780
ttacaaacgc ttaacaaata cggatgatga aatggctgac tagttttgga agagctttca   6840
tctcctgtta taaatcccta ttactaactc aattaagagt attagatagg ttaattttag   6900
atcacggacc caagcgcaca ttaacgtgtg ctaggcgagt gcttttagtt caattagatt   6960
tagtttatag gttggcttat acgcccaccc aatcgctggt atgaataata gtaaagataa   7020
tccttttcgc ggagcaatag caagaaaagc gcgaatttat ctgagaggag gattagattg   7080
tgtttacttt cttaacaaag caggacaagc agagccttgt cccgcgtgta cctcccctagt   7140 attccaaggg aaaacttgtg aggaacacta ttataataac aatctttgt catggcaagc   7200
```

```
ggtaaggcaa ctggaaagac agacgcccca gcgccagtca tcaaactagg aggaccaaag    7260
ccacctaaag ttggttcttc tggaaatgca tcatggtttc aaccgataaa ggccaagaag    7320
ctaaattcac ctgtgcctaa atttgacggt agtggtgttc ctgaaaatga aaatctcaag    7380
tcaagccagc aacatggata ctggagacgc aacacaggt ttaagcctgg caaaggtgga    7440
agaaaaccag tccctgatgc ttggtacttt tactacactg gaacaggacc ggccgccgac    7500
ctgaattggg gtgaaactca agatggtata gtgtgggttg ctgcaaaggg tgctgatact    7560
aaatctagat caaaccaggg tacaagggat cctgataagt ttgaccaata cccactacga    7620
ttctcagatg gaggaccgga tggtaatttc cgttgggact tcataccaat aaatcgtggt    7680
aggagtggga gatcaacagc agcttcatca gcagcatcta gtagagcacc atctcgtgag    7740
gggtcacgtg gacgtagaag cggagttgaa gatgatctta tagctcgcgc agcaaagatt    7800
atacaggacc agcaaaagaa gggtgcgcgc attaccaagg ctaaggctga tgaaatggct    7860
catcgccgct attgcaagcg cactatccca cctggttata aggttgagca agtatttggt    7920
ccccgtacta aaggtaagga aggaaatttt ggtgatgaca agatgaatga ggaaggtgtt    7980
aaggatgggc gtgttacggc aatgctcaac ctagtcccta gcagtcatgc ttgtcttttt    8040
ggaagtaggg tgacgcccaa actgcagcca gatggtcttc acctgagatt tgaatttact    8100
actgtggtgt cacgtgatga tccgcagttt gataattatg tgaaaatttg tgatcagtgt    8160
gtcgatggtg tagggacgcg tccaaaggac gatgaatcga gaccaaagtc acgcccaaat    8220
tcaagacctg caactagagg aaattctcca gcgccgagac aacagcgccc aaagaaggag    8280
aaaaagccca gaagcagga tgatgaagta gataaggcat gacctcaga tgaggagagg    8340 aacaatgcac agctggaatt tgatgatgaa cccaaggtga ttaactgggg ggactctgca    8400
ctaggtgaaa atgaactttg attaacataa tggacttgct gcatttgctg tcacattttg    8460
ttaaatatta ttttttgtgtt ttactatcaa ttattacagg tattgattgt gattatgttc    8520
aatacttaag cttcttctgg ttgcttttg cttgttgtat tgttgctgtg cttttattta    8580
ttgtgattct cattagtttg ctttatcgta gaaattcaat agtaagagtt aaggaagata    8640
ggcatgtagc ttagcaccta catgtctatc gccagggaaa tgtctaatct gtctacttag    8700
tagcctggaa acgaacggta gacccttaga tttaatttta gtttaatttt tagtttagtt    8760
taagttagtt tagagtaggt ataaagatgc cagtgccggg gccacgcgta gtacgaccga    8820
gggtacagca ctaggacgcc cactagggga agagctaaat tttagtttaa gttaagttta    8880
attggctaaa tatagttaaa atttataggc tagtatagag ttagagcaaa aaaaaaaaaa    8940
aaaaaaaaaa aaaaaaaaaa aaaaaaaaa aaaaaaaaa aaaaaaaaa aaaaaaaaaa    9000 aaaaaaaaaa aaaaaaaaaa aaaaaagcg gccgcatcgg atgccgggac cgacgagtgc    9060
agaggcgtgc aagcgagctt ggcgtaatca tggtcatagc tgtttcctgt gtgaaattgt    9120
tatccgctca caattccaca caacatacga gccggaagca taagtgtaa agcctggggt    9180 gcctaatgag tgagctaact cacattaatt gcgttgcgct cactgcccgc tttccagtcg    9240
ggaaacctgt cgtgccagct gcattaatga atcggccaac gcgcgggag aggcggtttg    9300 cgtattgggc gctcttccgc ttcctcgctc actgactcgc tgcgctcggt cgttcggctg    9360
cggcgagcgg tatcagctca ctcaaaggcg gtaatacggt tatccacaga atcaggggat    9420
aacgcaggaa agaacatgtg agcaaaaggc cagcaaaagg ccaggaaccg taaaaaggcc    9480
gcgttgctgg cgttttccca taggctccgc cccctgacg agcatcacaa aaatcgacgc    9540
tcaagtcaga ggtggcgaaa cccgacagga ctataaagat accaggcgtt tccccctgga    9600
```

```
agctccctcg tgcgctctcc tgttccgacc ctgccgctta ccggatacct gtccgccttt   9660
ctcccttcgg gaagcgtggc gctttctcat agctcacgct gtaggtatct cagttcggtg   9720
taggtcgttc gctccaagct gggctgtgtg cacgaacccc ccgttcagcc cgaccgctgc   9780
gccttatccg gtaactatcg tcttgagtcc aacccggtaa gacacgactt atcgccactg   9840
gcagcagcca ctggtaacag gattagcaga gcgaggtatg taggcggtgc tacagagttc   9900
ttgaagtggt ggcctaacta cggctacact agaagaacag tatttggtat ctgcgctctg   9960
ctgaagccag ttaccttcgg aaaaagagtt ggtagctctt gatccggcaa acaaaccacc  10020
gctggtagcg gtggtttttt tgtttgcaag cagcagatta cgcgcagaaa aaaggatct   10080 caagaagatc ctttgatctt ttctacgggg tctgacgctc agtggaacga aaactcacgt  10140
taagggattt tggtcatgag attatcaaaa aggatcttca cctagatcct tttaaattaa  10200
aaatgaagtt ttaaatcaat ctaaagtata tatgagtaaa cttggtctga cagttaccaa  10260
tgcttaatca gtgaggcacc tatctcagcg atctgtctat ttcgttcatc catagttgcc  10320
tgactccccg tcgtgtagat aactacgata cgggagggct taccatctgg ccccagtgct  10380
gcaatgatac cgcgagaccc acgctcaccg gctccagatt tatcagcaat aaaccagcca  10440
gccggaaggg ccgagcgcag aagtggtcct gcaactttat ccgcctccat ccagtctatt  10500
aattgttgcc gggaagctag agtaagtagt tcgccagtta atagtttgcg caacgttgtt  10560
gccattgcta caggcatcgt ggtgtcacgc tcgtcgtttg gtatggcttc attcagctcc  10620
ggttcccaac gatcaaggcg agttacatga tcccccatgt tgtgcaaaaa agcggttagc  10680
tccttcggtc ctccgatcgt tgtcagaagt aagttggccg cagtgttatc actcatggtt  10740
atggcagcac tgcataattc tcttactgtc atgccatccg taagatgctt ttctgtgact  10800
ggtgagtact caaccaagtc attctgagaa tagtgtatgc ggcgaccgag ttgctcttgc  10860
ccggcgtcaa tacgggataa taccgcgcca catagcagaa ctttaaaagt gctcatcatt  10920
ggaaaacgtt cttcggggcg aaaactctca aggatcttac cgctgttgag atccagttcg  10980
atgtaaccca ctcgtgcacc caactgatct tcagcatctt ttactttcac cagcgtttct  11040
gggtgagcaa aaacaggaag gcaaaatgcc gcaaaaaagg gaataagggc gacacggaaa  11100
tgttgaatac tcatactctt ccttttcaa tattattgaa gcatttatca gggttattgt  11160
ctcatgagcg gatacatatt tgaatgtatt tagaaaaata aacaaatagg ggttccgcgc  11220
acatttcccc gaaaagtgcc acctgacgtc taagaaacca ttattatcat gacattaacc  11280
tataaaaata ggcgtatcac gaggccctt cgtc                                11314
```

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 23

```
tgattaaaag tcccacatct tttctaatat tattaattct tctttgg              47
```

<210> SEQ ID NO 24
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ctcttaccag taacttacca cacttaatta aattaaagac taagtc                   46

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
aagtgtggta agttactggt aagagatgtt ggtaacacct cttttac                  47

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agaaaagatg tgggactttt aatcattaaa cagacttttt aggtctg                  47

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
caggattgtg catggtggac                                                20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
agaaaaccta aaggtcctgc                                                20

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
taaatggtga tcttgttt                                                  18

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 30
tttgtatacg agagccatca                                        20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ttgccttcag tatgtttgtg                                        20

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctgcgacaag acctcctg                                          18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgctgcttcc tttaataag                                         19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgctgttgtg acactctatg                                        20

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tggccttggt atgtgtgg                                          18

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 36
agcactacat agtgcatac                                              19

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tctttggtat gcactatgta gtgctgcttt gtatgactcg agttc                 45

<210> SEQ ID NO 38
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggcaagcca cataccaa ggccacttaa tataagtttt gagtattgaa agtttttc     58

<210> SEQ ID NO 39
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aagtgtggta agttactggt aagagatgtt ggtgaagtca ctg                   43

<210> SEQ ID NO 40
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tctttggtat gcactatgta gtgctaattt gtttgattct gataataatt atg        53

<210> SEQ ID NO 41
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggcaagcca cataccaa ggccacttaa tataagtttt aattattgaa agttcttc     58

<210> SEQ ID NO 42
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
```
aagtgtggta agttactggt aagagatgtt ggggaagtca ctg                     43

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tctttggtat gcactatgta gtgctgcttt gtttgataat aatgaaac                48

<210> SEQ ID NO 44
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tggcaagcca cataccaa ggccatttaa tataagtctt gagtattgaa ag            52

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtctgtattg ttaagttacc acatcgttat c                                  31

<210> SEQ ID NO 46
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tctttggtat gcactatgta gtgctaattt atatgacaac gaatcttttg              50

<210> SEQ ID NO 47
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tggcaagcca cataccaa ggccacttaa tataagtttt gagtattgaa ag            52

<210> SEQ ID NO 48
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

-continued gtctgtattg ttaagttacc acatcattat caaaag                            36

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tctttggtat gcactatgta gtgctgctct gtttgataat aatcag                 46

<210> SEQ ID NO 50
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aagtgtggta agttactggt aagagatgtt ggttcaacct cttttac                47

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tctttggtat gcactatgta gtgcttcttt gtacaataat gatagctatg             50

<210> SEQ ID NO 52
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tggcaagcca cacataccaa ggccatttaa tataagtttt taaatagaa agtgtttc     58

<210> SEQ ID NO 53
<211> LENGTH: 27618
<212> TYPE: DNA
<213> ORGANISM: Unknown
<220> FEATURE:
<223> OTHER INFORMATION: Description of Unknown:
      Avian infectious bronchitis virus sequence

<400> SEQUENCE: 53
acttaagtgt gatataaata tatatcatac atactagcct tgcgctagat ttccaactta 60
acaaaacgga cttaaatacc tacagctggt ccccataggt gttccattgc agtgcacttt 120
agtgccctgg atggcacctg gccacctgtc aggtttttgt tgttaaaata tcattgttgc 180
tggtatcact gcttgttttg ccgtgtctca ctttatacat ccgttgcttg ggctacctag 240
tgtccagcgt cctacgggcg ccgtggctgg tccgagtgcg aagaacctct ggttcatcta 300
gcggtacgcg ggtgtgtgga agtagcgctt cagacgtatc ggttctgttg cgtgaaatac 360
ggggtcacct ccccccacat acctctaagg gcttttgagc ctagcgttgg gctacgttct 420

```
cgcacaaggt cggttatacg acgtttgtag ggggtagtgc cgaacaaccc ctgaggtgac    480
aggttctggt ggtgtttagt gagcagacat acaatagaca gtgacaacat ggcttcaagc    540
ctaaaacagg gagtatctcc caaaccaagg gatgtcattc ttgttgccaa agacattccc    600
gaacaattat gtgacgcttt gttttttctat acgtcacatg accccaagga ttacgctgat    660
gcttttgcca ttaggcagaa gtttgaccgt aaccttcaga ctgggaagca gtttaaactt    720
gaaactgtgt gtggtctctt cctcttgaag ggagttgaca aaataacacc tggtgtccca    780
gcaaaagtct taaaagccac ctctaagctg gctgatttgg aagacatctt tggtgtctct    840
cctcttgcac gtaaatatcg tgatttgttg aagacagcat gccagtggtc tctcactgtg    900
gaaacactgg atgctcgtgc gcaaactctt gatgaaatct ttgacccaac tgaaatactt    960
tggcttcagg tagcttcaaa gatccaggtt tcagctatgg caatgcgcag acttgttgga   1020
gaagtaactg caagagtcat ggaatctcta ggttcaaatt tgagcgttct ttttcaagtt   1080
gttaaagaac aaatagtcag aatctttgaa aaggcactgg ctattttgta gagtgtgaat   1140
gatttaccac agcgtattgc agcactaaaa atggcttttg ccaagtgtgc gaaatcaatt   1200
acagttgtgg ttgttggaaa gactcttctt gttaaagagt ttgctggaac ttgtcttgca   1260
agcattaatg gtgctattgc aaaggttttt gaagaactgc caactggctt tatgggtgcc   1320
aaaattttca acacttgc cttctttaaa gaagcagctg tgaaaattgt ggaaaatata   1380
ccaaatgcac caagaggtac tagaggtttt gaagtcgttg gtaacgccaa gggaacgcaa   1440
gttgttgtgc gtggcatgcg aaatgattta actctgctcg accaaaaagc tgacattcct   1500
gttgagaaag aaggttggtc tgcaattctt gaaggacatc tgtgttatgt ctttaagagt   1560
ggtgatcgtt tttatgcggc acctctttct gggaattttg cattgcatga tgtgcattgt   1620
tgtgagcgtg ttgtctgtct gtctgatggt gtaacaccag agataaatga tggactcatt   1680
ctagcagcaa tctattcatc ttttagtgtc tcagaactcg tggcagcact taaaaagggt   1740
gaaccattca gttcttggg tcataaattt gtgtatgcga aggatgcagc agtctctttc   1800
actcttgcaa aagcagccac tattgcagat gtactgaagc tgtttcaatc agctcgtgtg   1860
caaatagaag atgtgtggtc tgcatttact gaaaagtctt ttaatttctg gaaattcgca   1920
tatggaaaag tgcgtaatct tgaagaagtt gtgaagactc attttttgtaa agctcaaatg   1980
tcaattatta ttctagcagc agtgcttggc gaaggcattt ggcatcttgt ttcacaggtc   2040
atctataaag taggtggtct ttttactaga gtcgttgact tttgtgaaaa acactggaag   2100
ggttctgtg cacaacttaa aaaggctaag ctcgttgtca cagaaacttt ttgtgttctt   2160
aagggagtgg cacagcattg ttttcaacta ttgctggatg caatacattc tttgtatatg   2220
agttttaaga agtgtgcact tggtagaatt catggagact tactcttctg gaaaggggt   2280
gtacacaaaa ttgttcaaga tggcgatgaa gtttggtttg acgccattga tagtattgat   2340
gttgaagatc tgggtgttgt ccaagaaaaa cccatagatt ttgaggtttg tgaagacgta   2400
acacttccag aaaatcaacc tggtcatatg gttcaaatcg aggatgacgg aaagaactat   2460
atgttcttcc gcttcaaaag ggatgagaac atctactata caccaatgtc tcaacttggt   2520
gcaattaatg tagtttgcaa agcaggcggt aaaaccgtta cctttggaga caccattgtg   2580
aaagaaatac cgccacctga tgttgtgcct attaaggtta gcatagagtg ttgtggtgaa   2640
ccatggaata caatcttcaa gaaagctat aaagagccca ttgaagttga aactgacctc   2700
acagtagaac aattgctctc tgtgatctat gagaaaatgt gcgacgacct caattgtttt   2760
ccagaggcac cagagccacc gccatttgag aatgtcgcac ttgttgataa aaacggtaaa   2820
```

```
gacttggatt gcataaaatc atgccatctt atctaccgtg attatgagag tgatgatgac    2880
atcgaggaag aagatgctga ggagtgtgat actgatttag aatgtgaaga agaggatgag    2940
gatactaaag tgttggctct tatacaagac cctgcaagta ataaatacccc tcttcctctt   3000 gatgatgatt atagcgtctt taatggatgt attgtacata aggacgctct tgacgtcgta    3060
aatctaccat ctggtgaaga aacctttgtt gtcaacaact gctttgaggg agctgtaaaa    3120
ccactgcctc agaaagttgt tgatgttcta ggtgactggg gtgaggctgt tgatgcgcaa    3180
gagcaaattg cacaaactac ttcagaggaa accccctatca gtagtttgga ggcaactatt    3240
gagcaagttg ttgttgagga acagaaaata atttctgttg ttgaagaaga acagcaggtg    3300
gcggtctaca cacctgcaga cctacaagtt gttgaagaaa cactagatga gtttattctt    3360
attgctgatg tttccacaga agaaattgtg cctcatgaag agaaggagtc acagattgaa    3420
caggagccta ttcaagttgt taaatcacaa cgtgaaaaga aggctaaaaa gttcaaggtt    3480
aaatctacta catgtgagaa acccaaattt ttggagtaca caacatgtgt gggtggccta    3540
acggtagtga ttgccaaagc attggatgag tttaaagagt tctgcattgt aaatgctgct    3600
aatgagcata tgtctcacgg tggcggcgtt gctaaggcaa ttgcggactt ttgtggacct    3660
gattttgtgg agtattgtga ggactatgtt aagaaacatg ggcctcaaca aagacttgtc    3720
acaccttcat ttgtcaaagg cattcaatgt gtgaacaatg ttgtaggacc tcgccatgga    3780
gacagtaact tgcatgataa gcttgttgct gcttacaaga atgttcttgt agatggtgtt    3840
gtcaattatg ttgtgccagt cctctcatca ggaattttg gtgttgattt taagatgtct    3900
atagacgcta tgcgcaaggc ttttgaaggt tgcgacatac gcgttcttct tttctccttg    3960
tctcaagaac acatcgatta tttcgatgtt acttgtaaac agaagacaat ttatcttaca    4020
gaggacggtg ttaaataccg ctctgctact gtgaaaccag gtgactcttt gagtcaattt    4080
ggaccggttt tgctagaaa caagacagtc tttacagcag acgatgttga ggacaaagaa    4140
attctcttca ttcctactac tgacaagact gtcctcgaat attatggttt ggatgcgcaa    4200
aagtatgtaa tatacttgca aactcttgca cagaagtgga atgtccaata tagggacaat    4260
tttgttatac ttgagtggcg tgatggaaat tgctggatta atgcagcagt agtgctcctt    4320
caagctgcta agattaggtt taaaggtttt cttgcagaag catgggcaca acttttggt    4380 ggagacccaa ctgattttgt agcctggtgc tatgcaagtt gcaatgctaa tgttggtgag    4440
ttttcagatg ctaattggct tcttgctaat ttggcagaat actttgatgc tgattacacg    4500
aatgcattcc ttaagaggcg tgtgtcatgt aactgtgggg ttaagaattg tgaagttaga    4560
ggccttgaag cttgtattca accagtaaag gcacccaatc ttcttcattt taagactcag    4620
tacacaaatt gtacagtgtg tgatgcaaat agtgtggatg aggtggtaga agcctcacta    4680
ccatatctgt tgctccttgc tactgatggt cctactacag tggattgtga tgaaaatgct    4740
gtagggaatg ttgttttcat tggctctact aacagtggcc attgttatac acaagccatt    4800
ggtaaggctt ttgacaatct tgctaaagat agaaaatttg gaaagaagtc tccttacatt    4860
actgcaatgt atacacactt ctctcttaag ggtgaaaatc ctttacctgt tgttaaacag    4920
agtaaaggaa aaactaaagt tgtaaaagag gatgtttcta tcttgccac tagttctaaa    4980 gtcagttttg ataatcttac tgattttgaa cagtggtatg atagtaacat ctacgagtgt    5040
cttagagtac aggaaatgcc tgataatttt tgatgaatatg tgtcatttac aacaaaggaa    5100
gattctaagt tgccattgac gcttaaagtt agaggtatta gatcagttgt tgattttaaa    5160
```

```
tcaaaggatg gttttactta caagttaaca cctgatactg atgaaaattc aaaggcacca    5220
gtatactacc ctgtcttaga tgctattagt cttaaggcaa tatgggttga aggtactgca    5280
aattttcttg ttggtcatcc aaactactat agtaaatctc ttcgcattcc cactttttgg    5340
gaaaatgcag agagctttgt taaaatagga gaaaaagttg atggtgtgac tactggtctt    5400
tggcgtgcag aacaccttaa taaacctaac ttggagagaa ttttcaacat tgctaagaaa    5460
gcaattgttg ggaccagtgt tgttactaca caatgtggta aattacttag taaagcagct    5520
acattcattg ctgataaact aggtgggggt gtagttcgca atattacaga tagagttaag    5580
ggtctttgtg gattcacacg tgggcatttt gaaagaaaat tgtctccaca attcataaaa    5640
acacttatat tcttcttctt ttattttgta aaggctagtg ctaagagtgt cgccactagt    5700
tataagcgtg tgttatgtaa ggtggtcttt actacgctat ttatattatg gtttatgtac    5760
acaagtaaac cagtaatttt tactggaata cgtatattag acttttatt tgaaggttct    5820
gtctgtggtc cttataatga ctatggtaaa gatactttg atgtactacg ctattgtgaa    5880
gatgatttta cttgtcgtgt gtgttacat gacagggatt cactcacttt ataaagcat    5940
gcttatagcg tagaacaatt ttataaaagt gcagtttctg gcattagttt taattggaat    6000
tggctttatt tggtctttct aattttattt gttaagccag tagcgggttt tgttattatt    6060
tgctattgtg ttaagtattt ggtactgagt tcaactgtat tacaaactgg tgtaggtttt    6120
ctagattggt ttgttcagac agttttcact cactttaatt tcatgggtgc agggttttat    6180
ttctggctct tttataagat atacatacag gttcatcata tactgtattg taaggatata    6240
acatgtgaag tgtgcaagaa ggttgtacgc agcaataggc aagaggttag cgttgtagtt    6300
ggtggacgca agcaaatagt gcatgtctac actaactcag gctataattt ttgtaagaga    6360
cataactggt attgtagaaa ttgtgatgag tatggtcatc aaaacacatt tatgtctccc    6420
gaagttgctg gcgagctctc cgataagctt aagcgtcatg ttaaacctac agcatatgct    6480
taccacgttg tggatgatgc gtgcgtagtt gatggttttg ttaatttaaa atacaaagct    6540
gcaattcctg gcaaggatag tgcatctcct gccgttaagt gttttagtgt tacagatttc    6600
ttgaagaaag ctgttttttct taaggaagca ttgaaatgtg aacaaatatc caatgatagt    6660
tttatagtgt gtaatacaca gagtgcgcat gcattagagg aagcaaaaaa tgctgccatc    6720
tattatgcgc aatgtctgtg taagccaata cttatacttg accaggcact ttatgagcaa    6780
ttagtagtgg aacctgtgtc taagtgtgtt gtagacaagg tgtgtagcat tttgtccaat    6840
ataatatctg tagatactgc agccttaaat tataaagcgg gcacacttcg tgattgtctg    6900
ctttctgtta ctaaagacga agaagctgta gatatggcta tcttctgtca taaccatgat    6960
gttgaataca ctactgatgg ttttactaat gtgataccat cttatggtgt agacactgat    7020
aggttgacac ctcgtgatag aggattttta ataaatgcgg atgcttctgt tgctaattta    7080
cgagttaaaa attctccacc agtagtatgg aagttttctg atcttattaa gttgtctgac    7140
agttgcctta atatttaat ttcagctact gtcaagtcag ggggtcgttt ctttataaca    7200
aagtctggtg ctaagcaagt ttttcttgc cacacccaga aattgttggt agagaaaaag    7260
gcaggtggtg tcactagtga tactttaaa tggttgaaaa gctgttttaa gtggctatt    7320
atcttttaca tactttttac agcatgttgt ttgagttact actatgtgga gatgaataga    7380
agtttgttc accccatgta tgatgtaaac tctacactgc atgttgaagg ttttaaagtt    7440
atagataaag gtgttattag ggaaattgtg tctgaagata catgtttctc taataaatac    7500
gttaattttg atgccttctg gggtaaacca tatgaaaata tagaaactg tccaattgtc    7560
```

```
actgctgtta tagatggtga tgggacagta gctgctggtg ttcctggttt tgtatcatgg    7620
gttttggatg gtgctatgtt tgtacatatg acacagactg agagaaaacc gtggtacatt    7680
cctacttggt ttaatagaga aattgtaggt tacactcagg attcaattat tactgagggt    7740 agttttata  catctatagc tttattttca gctagatgtt tgtacctgac agccagcaat    7800
acacctcaat tgtattgctt taatggtgat aatgatgcac ctggagcctt atcattcggt    7860
agtattattc ctcatagggt ttacttccaa ccaaatggtg ttaggcttat agttcctcaa    7920
caaatatttc acacaccata catagtaaag tttgtatcag acagctattg tagaggtagt    7980
gtatgtgaat atactaaacc aggttactgt gtatcattaa actcccaatg gttttgttt     8040 aatgatgaat acacaagtaa gccaggcgtg ttttgtggtt ctactgttag agaacttatg    8100
tttaatatgg ttagtacatt tttcacaggt gtcaaccta  atatttatat gcagctagca    8160
attatgtttt tgatactagt tgttgttgta ttaatttttg caatggtcat aaagtttcaa    8220
ggtgttttta aagcttatgc aaccgttgtg tttacaataa tgttagtttg ggttattaat    8280
gcatttgttt tgtgtgtaca tagttataat agtgttttag ctgttgtatt actagtactt    8340
tattgttatg cctcattggt aacaagccgc aatacttcta ttataatgca ttgctggctt    8400
gtcttcactt ttggtttaat agtacccacg tggctggctt gtgtttattt agggtttatt    8460
ctctatatgt atacaccact attttctgg  tgttatggta ctactaaaaa tactcgtaaa    8520
ctgtatgatg caacgagtt  tgttggtagt tatgatcttg ctgcgaagag cacttttgtt    8580
attcgtggtt ctgaatttgt taagcttacg aatgagatag gtgataaatt tgaagcttac    8640
cttgcagcgt atgctagact taaatattac tcaggcactg gcagtgagca agactacttg    8700
caagcctgtc gtgcatggtt agcttatgct ttggaccaat atagaaatag tggtgtggaa    8760
attgtgtata caccaccacg ttactctatt ggtgttagta gattacaggc tggttttaag    8820
aaactagttt ctcctagtag tgctgttgaa aggtgcattg ttagtgtctc ttatagaggt    8880
aataatctta atggactatg gctaggtgac actactattg gtcctcgcca tgtgttaggt    8940
aagttttcag gtgaccaatg gaatgatgta cttaaccttg ctaataatca cgagtttgaa    9000
attacaactc aaaatggtgt tgctttgaat gttgtcagta gcggctaag  aggtgcagtt    9060 ttgattttac aaactgctgt cgctaatgct gaaactccaa agtataagtt tattaaagca    9120
aattgtggtg atagttttac catagcttgc tcttatggtg gtacggtagt aggactttac    9180
cctgttacaa tgcgttctaa tggtactatt agagcctcat tcttgcagg  agcttgtggc    9240 tctgttggtt ttaatataga aagggtgta  gttaatttct tctatatgca ccatcttgag    9300
ttgcctaatg cattacacac aggaactgac ctaacgggag agttctatgg tggttatgtg    9360
gatgaagagg ttgcacaaag ggtgccacca gataatttag ttactaacaa tattgtagca    9420 tggcttatg  ccgcaattat tagtgttaaa gagagtagtt tctcattgcc taaatggttg    9480
gagagtacta cagttactgt tgatgattat aataagtggg ctggtgataa tggttttaca    9540
ccgtttgcta ctagtactgc cattactaaa ttaagtgcta ttacgggagt ggatgtttgt    9600
aaactccttc gcactattat ggcaaaaagt tgtcaatggg gtagtaaccc cattttaggc    9660
caatataatt ttgaagatga attgacacct gagtctgttt taaccagat  aggcggtgtt    9720 agattacagt cttcgtttgt aagaaaagct acatcttggt tttggagtag atgtattta    9780 gcttgtttct tatttgtgtt gtgtgctatt gtcttattta cggcagtgcc acttaggtat    9840
tatgtacatg cagctgttat tttgttagca gctgtattct tatttctttt tactgttaag    9900
```

```
catgttatgg cttatatgga cactttccta ttgccgacat tgcttacagt cattattgga      9960
gtttgtgctg aagtaccttt catctacaat actctaatta gtaggatagt tgtctttgtt     10020
agtcaatggt atgatcctgt agtctttgat actatggtac catggatgtt cttgccacta     10080
gtgttgtaca cagcatttaa gtgtgtgcag ggttgctata gtgtgaattc tttcaatact     10140
tctttgctag tactgtacca gttcttgaag ttaggctttg ttatttatgc ctcttctagc     10200
acgctggcag catacacaga aggtaattgg gatttatttt ttgaattagt tcacactact     10260
gtgttggcta atgttagtag taattcctta ataggtttgt ttgtgttcaa gttagctaag     10320
tggatgttgt attattgtaa tgctacatac tttaataatt atgtgctaat ggctgtcatt     10380
attaatggct ttggttggct cttcacttgt tactttggag tttattggtg gattaataag     10440
gtttttggtt taaccttagg taaatatgaa ttcaaagttt cagtagacca atataggtat     10500
atgtgtcttc ataagataaa tccgcctaaa actgtgtggg aagttttttc gacaaatata     10560
cttatacaag gaattggtgg tgatcgtgtg ttgcctattg ctacagttca atctaaattg     10620
agtgatataa agtgtacaac tgttgtttta atgcagcttt tgactaagct taatgttgaa     10680
gcaaattcaa aaatgcatgc ttatcttgtt gatttacaca ataaaattct tgcatctgat     10740
gatgttggag agtgcatgga taatttgttg ggtatgctta ttacactatt ttgtatagat     10800
tctactattg atttgagtga gtattgtgat gatatactta agaggtcaac tgttttacag     10860
tcagttactc aagagttctc acacataccc tcttatgctg aatatgaaag agctaagaat     10920
ctttatgaaa aggttttagc tgattctaaa aatggtggtg taacacagca agagcttgct     10980
gtatatcgta aagctgccaa tattgcaaag tcagttttttg atagagactt ggctgttcaa     11040
aagaagttag acagcatggc agaacgtgct atgacaacaa tgtataaaga ggcgcgtgta     11100
actgatagac gagcaaaatt agtttcatca ctacatgcgt tactgttttc aatgctcaag     11160
aaaatagatt ctgaaaagct taatgtatta tttgatcagg ctagtagtgg tgttgtacct     11220
ctagctactg ttccaattgt ttgtagtaat aagcttaccc ttgtaatacc agatccagaa     11280
acttgggtca agtgtgtgga aggtatgcat gttacttact caacagttgt ctggaatata     11340
gacactgtta ttgatgctga tggcacagaa ttacatccta cttctacagg tagtggattg     11400
acatactgtg taagtggtga caatatagcg tggccttttaa aggttagctt aactagaaat     11460
gggcataata gagttgacgt tgcgttgcag aacaacgagc ttatgcctca tggtgtaaag     11520
acaaaggctt gcgtggcggg tgtagatcaa gcacactgta gcgttgagtc taaatgttat     11580
tatacaaata ttagtggtaa ttcagttgta gctgctatta cttcttcaag tccaaatctg     11640
aaagttgcat ccttcttgaa cgaggcaggc aaccagattt atgtagactt agacccacct     11700
tgtaagtttg gtatgaaagt gggtgataag gttgaggttg tttacctgta tttttataaaa     11760 aatacaaggt ctattgttag gggtatggta cttggtgcta tatccaatgt tgttgtttta     11820
cagtctaaag ggcacgagac agaggaagta gatgctgttg gtattctttc actttgttca     11880
tttgcagtag atcctgcaga aacgtattgt aaatatgtgg ctgcaggtaa tcaacctta     11940 ggtaactgtg ttaaaatgtt gacagttcat aatggtagtg gttttgctat aacatcaaag     12000
ccaagtccaa ctcctgatca agattcttat ggaggagctt ctgtgtgtct cttttgtaga     12060
gcacatatag cacacccagg aggtgcagga aatttagatg acgttgtca atttaaaggt     12120 tcctttgtgc aaatacctac tacggagaaa gatcctgttg gttttgtct acgtaataag     12180 gtttgcactg tttgtcagtg ttggattggt tatggctgtc agtgtgattc acttagacaa     12240
ctaaaaccct tgtacaatc aactgctggt gcaattgatt tgataagaa ttatttaaac     12300
```

```
gggtacgggg tagcagtgag gctcggctga taccccttgc taatggatgt gatcctgatg   12360
ttgtaaagcg agcctttgat gtttgtaata aggaatcatg tggtatgttt caaaatttga   12420
agcgtaactg tgcaagattc caagaagtgc gtgatactga agacggaaat cttgagtatt   12480
gtgactctta ttttgtggtt aaacaaacca cccctagtaa ttatgaacat gagaaagctt   12540
gttacgaaga cttgaagtca gaagtaacag ctgctcatga ttttttttgtg ttcaataaga   12600 acatttataa tattagtagg caacggctta ctaagtatac tatgatggac ttttgctacg   12660
ccttgaggca ttttgaccca aaggactgcg aagttcttaa agaaatactt gtcacttatg   12720
gttgtataga agattatcac cctaagtggt ttgaagataa taaggattgg tacgacccaa   12780
tagaaaaccc aaaatattat gccatgttgg ctaaaatggg gcctattgta cgtcgtgctt   12840
tattgaatgc tattgagttc ggaaaccttta tggttgaaaa aggttatgtt ggtgttgtta   12900
cactagataa ccaagatctt aatggtaaat tttatgactt tggtgatttt cagaaaacgg   12960
cacctggtgc tggtgttcct gttttttgata catattattc ttacatgatg cccatcatag   13020
ccatgacgga tgctttggca cctgaaaggt attttgaata tgatgtgcat aagggttata   13080
agtcttatga tctcctcaag tatgattata ctgaggagaa acaagagttg tttcagaagt   13140
actttaagta ttgggatcag gagtaccatc ctaactgccg tgactgtagt gatgacaggt   13200
gtttgataca ttgtgcaaac ttcaacatct tgttttctac attgataccg cagacctctt   13260
ttggtaattt gtgtagaaaa gtgtttgttg atggtgtacc ttttatagct acttgtggct   13320
atcattctaa agaacttggt gttattatga atcaagataa caccatgtcg ttctcaaaaa   13380
tgggtttaag tcaactcatg cagtttgttg gagatcctgc cttgttagtg ggaacatcca   13440
ataaattagt tgatcttaga acgtcttgtt ttagtgtttg tgcattagcg tctggtatta   13500
ctcatcaaac agtaaaacca ggtcacttta acaaggattt ctatgatttt gcagagaagg   13560
ctggtatgtt taaagagggt tcttctatac cacttaaaca tttcttctac ccacaaactg   13620
gtaatgctgc tataaacgat tatgattact atcgttataa caggcctacc atgtttgata   13680
tacgtcaact tctatttgt ttagaagtga cttctaaata cttgaatgt tatgaaggcg   13740 gctgtatacc agcaagccaa gttgtagtta acaatttaga taagagcgca ggctatccgt   13800
tcaataagtt tggaaaagct cgtctctatt atgaaatgag tctagatgaa caggaccaac   13860
tctttgagat tacaaagaag aatgtcctac ccaccataac tcaaatgaat ttaaaatatg   13920
ccatatccgc gaaaaataga gcgcgtactg tggcaggtgt ttctatcctt tctactatga   13980
ctaataggca atttcatcag aaagttctta agtctatagt caatactaga aacgctcctg   14040
tagttattgg aacaaccaaa ttttatggtg gttgggacaa catgttgaga aatttgattc   14100
aaggtgttga agacccgatt ctcatggggtt gggattatcc aaagtgtgat agagcaatgc   14160
ctaatttgtt gcgtatagct gcatcttttgg ttcttgcccg taaacatact aattgttgta   14220
cttggtctga ccgcgtttat aggttgtata atgaatgcgc tcaggtttta tcggaaactg   14280
tcttagctac aggtggtatt tatgtgaaac ctggtggcac tagcagtggt gatgcaacta   14340
ctgcttatgc aaatagtgtt tttaacataa tacaagcgac atctgctaat gtcgcgcgtc   14400
ttttgagtgt cataacgcat gatattgtct atgatgacat taagagcctg cagtatgaat   14460
tgtatcagca ggtttatagg cgagtcaatt ttgacccatc ctttgttgag aagttttatt   14520
cttacttatg taagaacttt tcattgatga tcctgtctga tgatggtgtt gtttgttata   14580
acaacacact agccaggcaa ggtcttgttg cagatatttc tggttttaga gaaattctct   14640
```

| | |
|---|---|
| actaccaaaa taatgtttat atggctgatt ctaagtgttg ggttgagcct gacttagaaa | 14700 |
| aaggcccaca tgaattttgt tcacaacaca ccatgctagt ggaggttgat ggtgagctta | 14760 |
| aatacttgcc atacccagac ccttcacgca tcttaggtgc atgtgtattt gtagatgacg | 14820 |
| cggataagac agaacctgtg gctgttatgg agcgttatat cgctcttgcc atagatgctt | 14880 |
| acccgctagt acatcatgaa aatgaagagt acaaaaaggt gttctttgtg ctccttgcgt | 14940 |
| atatcagaaa actctatcaa gagctttctc aaaatatgct tatggactac tcttttgtaa | 15000 |
| tggatataga caagggtagt aaattttggg agcaggagtt ctatgaaaat atgtatagag | 15060 |
| cccctacaac tttacagtct tgtggcgttt gtgtagtgtg caatagtcaa actatactgc | 15120 |
| gctgtggtaa ttgtattcgc aaaccatttt tgtgttgtaa atgttgctat gaccacgtca | 15180 |
| tgcatacaga ccacaaaaat gttttgtcta taaacccata catttgctca cagcctggtt | 15240 |
| gcggcgaagc agatgttact aaattgtacc tcggaggcat gtcgtacttc tgtggtaatc | 15300 |
| ataaaccaaa gttatcaata ccgttagtat ctaatggtac agttttggaa atttacaggg | 15360 |
| ctaattgtgc tggtagcgaa aatgttgatg atttaatca actagctact accaattggt | 15420 |
| ctactgtgga accctatata ttagcaaatc gctgtagtga ttcattgaga cgctttgctg | 15480 |
| cagagacggt aaaagctaca gaggaattgc ataagcagca atttgctagt gcagaggtga | 15540 |
| gagaagttct ctcagaccgc gaattgattc tatcctggga gccaggtaaa actaggcctc | 15600 |
| cactgaatag aaactatgtc ttcacaggct accactttac aagaactagt aaagtgcagc | 15660 |
| ttggtgactt tattttgaa aaaggtgagg gtaaggatgt tgtctattac agggcaacgt | 15720 |
| ctactgctaa attgtctgtt ggggacattt ttgttttaac ttcacacaat gttgtttctc | 15780 |
| ttgtagcgcc aacattgtgt ccacaacaaa cttttctag gtttgtaaat ttaagaccta | 15840 |
| atgtaatggt accagaatgt tttgtgaata acattcctct ttaccattta gtaggtaagc | 15900 |
| acaagcgtac tacagtacaa ggcccacctg gcagtggtaa atcccacttt gctataggcc | 15960 |
| ttgcagctta ctttagtaat gctcgtgttg ttttactgc gtgctcccat gcagctgtag | 16020 |
| atgctttatg tgaaaagct tttaagtttc tcaaagttga tgattgcact cgtatagtac | 16080 |
| ctcaaaggac tactatcgat tgtttctcaa agtttaaagc taatgacaca ggcaaaagt | 16140 |
| acattttag tactataaat gccttgcctg aagttagttg tgacattctt ttggtcgatg | 16200 |
| aggtcagtat gttgaccaat tatgaattgt ctttcattaa tggtaagata aactaccaat | 16260 |
| atgttgtgta tgtaggtgat cctgctcaat taccagcacc tcgcactttg cttaatggtt | 16320 |
| cgctttcacc aaaggattat aatgttgtca caaaccttat ggtttgtgtt aaacccgaca | 16380 |
| ttttccttgc aaagtgttac cgctgtccta aagagattgt agacactgtg tctactcttg | 16440 |
| tctatgatgg aaagttttatt gcaaataacc cagaatcacg tcagtgcttc aaggttatag | 16500 |
| ttaataatgg taattctgat gtaggacacg aaagtggttc agcctacaac acaacccaat | 16560 |
| tagaatttgt gaaagatttt gttttgtcgca ataaagaatg gcgggaagca acattcattt | 16620 |
| caccttataa tgctatgaac cagagggcct accgtatgct tggacttaat gttcaaacag | 16680 |
| tagattcctc tcaaggttct gagtatgatt atgttatctt ttgtgttact gcggattcgc | 16740 |
| agcatgcgct gaatattaac aggtttaatg tggcgcttac aagagctaag cgtggtatat | 16800 |
| tggttgtcat gcgtcagcgt gatgaattgt attctgctct taagtttata gagttagata | 16860 |
| gtgaaacaag tctgcagggt acaggtttgt ttaaaatttg caacaaagaa tttagtggtg | 16920 |
| ttcaccctgc ttatgcggtc acaactaaag ctccttgctgc aacctacaaa gttaatgaag | 16980 |
| aacttgcagc ccttgttaat gtggaagctg gttcagaaat aacatataaa catctcattt | 17040 |

```
ctcttcttgg gtttaagatg agtgttagtg ttgaaggttg tcacaacatg tttattacac    17100
gtgatgaggc aattcgcaat gtaagaggtt gggtaggttt cgatgtggaa gctacacatg    17160
cctgtggtac taacattggt actaacctcc cttttcaagt gggcttctcg acaggtgcag    17220
attttgtagt cacacctgag ggacttgtag acacttcaat aggcaataat tttgagcctg    17280
tgaattctaa agcacctcca ggtgaacaat ttaatcactt gagagcttta tttaagagtg    17340
ctaaaccttg gcatgttata agaccaagga tagtgcaaat gttagcagat aacctatgca    17400
atgtttcaga ttgtgtagtg tttgtcacgt ggtgtcatgg tctagaacta actaccctgc    17460
gctattttgt taaaataggc aaggaacaaa tttgttcatg tggttctaga gctacgacct    17520
ttaattctcg cactcaaact tatgcttgtt ggaggcattg tttgggtttt gattttgtct    17580
ataacccact cttagtggat atccaacaat ggggttactc aggtaatctg cagtttaatc    17640
atgacttgca ctgtaatgtg catggacacg cgcatgtggc atctgcagat gctattatga    17700
cgcgttgtct tgcagttaac aatgcatttt gtcaagatgt taactgggat ttaacatacc    17760
ctcatattgc aaatgaggat gaagttaatt ctagttgtag atatttacag cgcatgtatc    17820
tcaatgcatg tgttgatgct cttaaagtta atgttgtcta tgacataggc aaccctaaag    17880
gcattaaatg tgttaggcgt ggggatgtca ctttcagatt ctatgataag aatccaatag    17940
tacccaacgt caagcagttt gagtatgact ataatcagca caagataag tttgctgatg     18000 gtctttgtat gttttggaat tgtaatgtgg ttgttatcc tgataattct ttggtttgta     18060
ggtatgacac acgaaatttg agtgtgttta acctaccagg ttgtaatggt ggtagccttt    18120
atgtcaacaa acatgcattc cacacaccta aatttgagcg caatagcttc cgtaatttga    18180
aagctatgcc attctttttc tatgactcgt caccgtgtga caccattcaa atagatggtg    18240
ttgcacagga tcttgtgtca ctagctacaa aagactgtat cacaaaatgc aacataggcg    18300
gcgccgtttg taaaaagcac gcgcaaatgt atgcagagtt cgtgacatct tataatgcag    18360
ctgttacggc tggctttact ttttgggtta ctaataattt taacccatac aatttgtgga    18420
aaagtttctc agctctccag tccattgaca acattgctta atatgtat aagggtggcc      18480 attatgatgc tattgcagga gaaatgccca ctatagtaac tggagataaa gtttttgtta    18540
ttgatcaagg tgtagaaaag gcagttttcg ttaatcaaac aactctgcct acatctgtgg    18600
catttgaatt gtatgcgaag agaaatattc gcacactgcc aaacaatcgt attttgaaag    18660
gccttggtgt agatgtgacc catggttttg taatttggga ttatgcaaac caagtaccat    18720
tgtatcgtaa tactgttaaa gtgtgtgtat acacagatat cgagccaaat ggcctaacgg    18780
ttctgtatga tgatagatat ggtgattacc agtctttct tgctgctgat aatgctgttc     18840
tagtttctac acagtgttat aagcggtact catatgtaga aataccatca gatcttcttg    18900
tccagaatgg tatgtcatta aaagatgggg cgaatctgta tgtttataag cgtgttaatg    18960
gtgcgtttgt tacgctacct aacacgctaa atacacaggg tcgcagttat gaaacttttg    19020
aaactcgtag tgacgttgag cgggattttc tcgccatgtc agaagaagac tttgtagaaa    19080
agtatggtaa agaccaggt ctacaacaca tactatatgg tgaagttgat aatcctcaat      19140
taggcggttt acacactgtt ataggtatgt atagactttt acgtgcgaat aaattgaacg    19200
caaagtctgt cactaattca gattctgatg tcatgcaaaa ttattttgta ttggcagaaa    19260
atggttccta taagcaggtc tgcaccgtag tggacttgtt gcttgatgac ttcttagaac    19320
ttcttagaaa catactcaag gagtatggtg ctaacaagtc taaagttgta acagtgtcaa    19380
```

```
ttgattacca tagcataaat tttatgacgt ggtttgataa tggcagtatt aaaacgtgtt    19440
atccgcagct tcaatctgca tggacgtgtg gttataatat gcctgagctc tataaagttc    19500
agaattgtgt tatggaacct tgcaatattc caaactatgg tgttggaata acgttgccaa    19560
gtggtattat gatgaatgtt gcaaagtaca cacaactttg ccaatatctt tctaaaacaa    19620
caatgtgtgt accgcataat atgcgagtta tgcattttgg agtaggtagt gacaaaggag    19680
tagcgccagg tagtactgtt cttaaacagt ggcttcctga aggaacactc ctcgttgaca    19740
atgatattgt agattatgtg tctgatgcac atgtttctgt gctttcagat tgcaataaat    19800
ataagacaga tcacaagttt gatcttgtga tatctgatat gtatacagat aatgattcta    19860
agagaaagca tgaaggcatg gtagccaata atggtaatga tgacgtcttc ataccctttc    19920
ccaacttcct tcgtaacaat ttggctctgg gtggcagttt tgctgtgaaa ttaacagaga    19980
caagttggca cgagaattta tatgacattg cacaggactg tgcatggtgg acaatgtttt    20040
gtacagcggt taatgcttct tcctcggagg catttctgat tggtgttaat tacttgggtg    20100
caagtaaaaa ggttaaagtt agtggaaaaa cactgcacgc aaattatata ttttggagga    20160
attgtaatta tttacaaacc tctgcttata gtgtatttga cgttgcaaag tttgaattaa    20220
aactaaaagc aacgccagtt gttaatttga aaactgaaca aaagacagac ttagtcttta    20280
atttaattaa gtgtggtaag ttactggtaa gagatgttgg gcaaaccgct tttactagtg    20340
actctttggt atgcactatg tagtgctttg ctttatgata aaaatactta cgttactac    20400 taccaaagtg cctttaggcc tggtcaaggt tggcatctac atgggggtgc ttatgcagta    20460
gataaggttt taatggaac caacaatgca gtcagtgtat ctgattgcac tgctggtact    20520
ttttatgaaa gctataatat ttctgctgct tctgtagcca tgacagtacc acctgctggt    20580
atgtcttggt cagttgcaca gttttgtaca gctcattgta acttctcaga ctttacagtg    20640
tttgttacgc attgtttaa aagtcaacaa ggtagttgtc cattgacagg tatgattcct    20700
cagaatcata ttcgtatttc tgctatgaga tctggatttt tgtttttataa tttaacagtt    20760 agcgtatcta aatacccctaa atttaaatcg cttcaatgtg ttggcaattc tacatctgtc    20820
tatttaaatg gtgatcttgt tttcactcct aatgaaacaa ctcacgttac gggtgcaggc    20880 gtttattta aaagtggtgg gcctgtaact tataaagtta tgaaagaagt taaagcccta    20940 gcctactta ttaatggtac cgcacaagag gttattttat gtgataactc acctagaggt    21000
ttgcttgcat gtcagtataa cactggtaat ttttcagatg gattctaccc ttttactaat    21060
tcttctttag ttaaggatag gtttattgta tatcgagaaa gtagcactaa cactactta    21120 gagttaacta atttcacttt tactaatgta agtaatgctt ctccctaattc aggtggcgtt    21180 gatacttttc caattatatca aacacatact gctcaggatg gttattataa ttttaattta    21240
tcatttctga gtagttttgt gtataaaaaca tctgatttta tgtatgggtc ataccaccca    21300
aattgtaatt ttagaccaga gaatattaat aatggcttat ggtttaattc attatctgtg    21360
tcacttactt acggacccat tcaaggtggt tgtaagcaat ctgttttag taataaagca    21420 acttgttgct atgcttattc ttaccgaggt cctactagat gtaagggtgt ttatagaggg    21480
gagctaacgc aatactttga atgtggactt ctagttatg taactaagag tgatggctct    21540
cgtatacaaa ctagaagtga accactggtg ttaactcaat ataattataa caacattact    21600
ttaaataagt gtgttgagta taatatata ggtagagttg gtcaaggttt tattactaat    21660
gtaactgaag caactgctaa ttatagttat ctagcagatg tggtttagc tatttttaagt    21720 acttcaggag ccatagacat atttgttgtt cgaggtgcat atggtcttaa ttattataag    21780
```

```
gttaatccct gtgaagatgt taaccaacag tttgtagtgt ctggtggcaa tttagttggc   21840
attcttacat ctcataatga aacagattct gaatttattg agaaccagtt ttacatcaaa   21900
ctcactaacg gaacacgtcg ctctagacgt tctgttactg ggaatgttac aaattgccct   21960
tatgttagtt atggcaagtt ttgtataaaa ccagatggtt ctttatttat aatagtacca   22020
caagagttag aacagtttgt ggcgccttta ctcaatgtta ctgagcatgt gctcatacct   22080 gatagttta  atttaactgt cacagatgag tacatacaaa ctcgtatgga taaggttcaa   22140
attaattgcc ttcagtatgt tgtggtaat  tctattgaat gcagaaagtt gtttcagcag   22200
tatgaccctg tttgtgataa tatattgtct gttgtaaatg gtgtaggtca agagaggat    22260 atggaacttt taagtttcta ttcgtctact aaacctagtg gttacaatac accaattttt   22320
aataatgtta gcactggtga ctttaatatt tctctcttac taacaccacc taatagtcct   22380
actgggcgct cttttattga agatcttctt tttacaagtg tagaatctgt tggattacca   22440
actgatgaag agtataaaaa gtgtacagca ggacctttag gttttgttaa ggaccttgtt   22500
tgtgctagag agtataatgg cttgcttgtg ttgcctccta ttattactgc agacatgcaa   22560
actatgtata ctagctcttt agtagcctct atggctttag gtggcattac tgcagctggt   22620
gctataccct ttgctacaca actgcaggcc agaattaacc atttgggtat tactaattct   22680
cttttgttga aaatcaaga  aaaaattgct gcttccttta taaggccat  cggtcatatg   22740 caggaagggt ttaaaagtac ttctctagca ttacaacaga ttcaagatgt tgttaataaa   22800
cagagttcta ttcttacaga gactatgcaa tcacttaata aaaattttgg tgctatttcc   22860
tccgtacttc aagacattta ccagcaactt gatgctattc aggcagatgc tcaggttgat   22920
cgtcttatta caggtagact ttcttcacta tctgttttag cttctgctaa acaggcagag   22980
tatcatagag tgtcacaaca gcgtgagttg gccactcaga aaattaatga gtgtgttaag   23040
tctcagtcta ataggtattc attttgtggt aatggaagac atgttttaac cataccacaa   23100
aatgcaccta atggtatagt gtttatacac tttacttata ctccagagag ttttgttaat   23160
gttactgcaa tagtgggttt ttgtgtaaat ccagctaatg ccagtcagta tgcaatagtg   23220
cccgttaata acagaggtat ttttattcaa gttaatggta gttactacat cactgcacgt   23280
gatatgtata tgccaagaga cattacagca ggagacatag ttatgcttac ttcttgtcaa   23340
gcaaattatg taagtgtaaa taagactgtc attactacat ttgtagataa tgatgacttt   23400
gattttgatg acgaattgtc aaaatggtgg aatgatacta agcatgagct accagatttc   23460
gacgaattca attatacagt accagtatta aatattgta  atgaaattga cagaattcaa   23520
gaagttattc agggattaaa tgactcccta atagatcttg aaacactctc aattcttaaa   23580
acttatatta agtggcttg  gtatgtgtgg cttgccatag cttttgccat tattatcttc   23640
atcctaatct aggatgggt  ttttcttcatg actggttgtt gtggttgttg ttgtgggtgc   23700
ttcggcatta ttcctttaat gagtaagtgt ggtaaaaaat cttcttacta cacgactttt   23760
gataatgatg tggtaactga acaatacaga cctaaaaagt ctgtttaatg attcaaagtc   23820
ccacatcttt tctaatagta ttaattcttc tttggtgtaa acttgcatta agctgtttta   23880
aagagtgtgt tataacactc cagcaactaa tacaagtttt actccaaatt attaatagta   23940
acttacagtc tagacttctg ctttggcaca gtctagacta atgttagatt ttgaagcaat   24000
tattgaaact ggtcagcaaa taattcaaca aatcagtttc aatttacagc acatttcaag   24060
tgtgttaagt tctgaattat ttgaccccct tgaagtttgt ttttacagag gaggtaatta   24120
```

```
ttgggaggta gattcagctg aagaattttc aggtgatgat gaacctactg aataagtcgt   24180
tagaggaaaa tggaagtttt ctaacagcgg tttacgtgtt ttgtgcattt gtagcacttt   24240
acctattagg tagagcgctc caagctttcg tacaagctgc tgatgcttgt tgtctttttt   24300
ggtacacatg ggtagttgtt cctggagcca agggtacatc ctttgtgtac aaacacacat   24360
atgggaaaaa acttaacaat ccggaattag aaagcgttat tgttaacgag tttcctaaga   24420
acggttggaa taataaaaac ccagcaaatt tccaaaatgg aaaattgcac acttgacgct   24480
gaacaggcag ttcagctatt taaagattat aatctattta taactgcatt cctgttgttt   24540
ctaaccatac tacttcagta cggctatgca actaggagtc ggattattta catactgaaa   24600
atgatagtgt tatggtgctt ctggccccctt aacattgcag taggtgtaat ttcatgtata   24660
tacccaccaa acacaggagg tcttgtcgca gcgataatac ttactgtgtt tgcgtgtctt   24720
tctttttag gttattggat ccagagcatt aggctcttta agcggtgcag atcatggtgg   24780
tcatttaacc cagaatctaa cgccgtaggt tcaatactcc taactaatgg tcaacaatgt   24840
aattttgcta tagagagtgt gccgatggtg ctttctccta ttataaagaa tggtgctctt   24900
tattgtgagg gtcagtggct tgctaagtgt gaaccagacc acttgcctaa agacattttt   24960
gtttgcacac cagatagacg taatatctat cgtatggtgc agaaatacac tggtgaccaa   25020
agcggaaata agaaaaggtt tgctacattt gtctatgcga agcagtcagt agatactggc   25080
gagctagaaa gtgtagcaac agtaggaagt agtctttaca cataaatgtg tgtgtgtaaa   25140
gaatatttaa aattattctt tgacagtgcc tctatcttaa gagcgtggaa gagtattatt   25200
tttgaggata ttaatataaa ccctctttgc ttcatactct cttttcagga gttattattt   25260
aaaaaacagt ttttccactc ttttgtgcca aaaacagttt gtgttaatgg ggtgtccttc   25320
caagtagaca atgaaaagt ctattacgaa ggaaaaccaa ttttccaaaa aggttgttgt   25380
aggttgtggt ctagttataa gaaagattag aataattaaa ccaccaacaa cacttacttt   25440
taaaagggc gttttatgtt ataagcgctt aacaaacacg gacgatgaaa tggcttacta   25500
gttttggaag agcattcatc tcctgttata aatccctatt actaactcaa cttagagtat   25560
tagataggtt aaatttagag cacggaccaa accgcgtttt aacgtgtagt aggcgagtgc   25620
ttttagttca attagattta gtttataggt tggcttgtac gcccacccaa tcgctggtat   25680
gaataatagt aaagataatc cttttcgcgg agcaatagca agaaaagcgc gaatttatct   25740
gagagaagga ttagattgtg tttactttct taacaaagca ggacaagcag agccttgtcc   25800
cgcgtgcacc tctctagtat tccacgggaa aacttgtgag gcgcacataa ataataataa   25860
tctttatca tggcaagcgg taaggcagct ggaaaaacag acgccccagc gccagtcatc   25920
aaactaggcg gaccaaaacc accaaaagtt ggttcttcag gaaatgcatc ttggttccag   25980
gcaataaagg ccaagaaact taattcaccc cagcctaagt ttgaaggtag tggtgttcct   26040
gaaaatgaaa acttaaaatc aagccagcag cacggatact ggagacgcca acaccggtat   26100
aaaccaggta aaggcggaag aaaaccagtt ccagatgctt ggtacttta ttacactgga   26160
acaggaccag ccgctgacct gaattggggt gataaccaag atggtatagt gtgggttgct   26220
gctaaaggtg ctgatactaa atctagatct aaccagggta caagagatcc tgataagttt   26280
gaccaatacc cactgcgatt ctcagacggg gaccggatg gtaacttccg ttgggatttc   26340
attcctataa atcgtggtag gagtggaaga tcaacagcag cttcatctgc tgcttctagt   26400
agagcaccat ctcgtgaagg gtcacgtgga cgtagaagtg gagctgaaga tgatcttata   26460
gctcgtgcag caaagattat tcaggaccaa caaaagaagg gttctcgcat taccaaggca   26520
```

-continued

```
aaggctgatg aaatggctca tcgccggtat tgcaagcgca ctgttccacc cggttataag   26580
gttgatcaag tatttggtcc ccgtactaaa ggtaaggagg gaaattttgg tgatgacaag   26640
atgaatgagg aagtattaa ggatgggcgt gttacagcaa tgctcaacct agtccctagc    26700
agccatgctt gtcttttgg aagtagagtg acgcctaaac ttcaaccaga tgggctccac    26760
ttgagatttg agtttactac tgtggttcca cgtgatgacc cgcagtttga taattatgtg   26820
aaaatttgtg atcagtgtgt cgatggtgta ggaacgcgtc caaaagacga tgaaccgaga   26880
ccaaagtcac gcccaaattc aagacctgca acaagaggaa attctcctgc gccaagacaa   26940
cagcgccaaa agaaggagaa aaagccaaag aagcaggaag atgatgtaga taaggcattg   27000
acctcagatg aagagaggaa caatgcacag ctcgagtttg atgatgaacc caaagtgatt   27060
aattggggag attcagctct tggggaaaat gaattgtaag taacataatg gacttgctgc   27120
atttgctgtc acattttgtt aaatactatt ttgttgcttt cctatcaatt attacaggca   27180
ttgattgtga ttatgtgcaa tatttaagct acttttggtt gcttttgct tgttgtattg     27240 ttgctgtgct ttttattatt gtgattctca ttagtttgct ttatcgtaga agtgcaatag   27300
taagagttaa ggaagatagg catgtagctt gattacctac atgtctatcg ccagggaaat   27360
gtctaatctg tctacttagt agcctggaaa cgaacggtag acccttagat tttaatttag   27420 tttaatttt agtttagttt aagttagttt agagtaggta taaagaagcc agtgccgggg    27480
ccacgcggag tacgatcgag ggtacagcac taggacgccc actagggaa gagctaaatt     27540 ttagtttaag ttaagtttaa ttggctaagt atagttaaaa tttataggct agtatagagt   27600
tagagcaaaa aaaaaaaa                                                  27618
```

<210> SEQ ID NO 54
<211> LENGTH: 1164
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 54

```
Met Leu Gly Lys Pro Leu Leu Val Thr Leu Trp Tyr Ala Leu Cys
1               5                   10                  15

Ser Ala Leu Leu Tyr Asp Lys Asn Thr Tyr Val Tyr Tyr Gln Ser
            20                  25                  30

Ala Phe Arg Pro Gly Gln Gly Trp His Leu His Gly Ala Tyr Ala
            35                  40                  45

Val Asp Lys Val Phe Asn Gly Thr Asn Asn Ala Val Ser Val Ser Asp
        50                  55                  60

Cys Thr Ala Gly Thr Phe Tyr Glu Ser Tyr Asn Ile Ser Ala Ala Ser
65                  70                  75                  80

Val Ala Met Thr Val Pro Pro Ala Gly Met Ser Trp Ser Val Ala Gln
                    85                  90                  95

Phe Cys Thr Ala His Cys Asn Phe Ser Asp Phe Thr Val Phe Val Thr
                    100                 105                 110

His Cys Phe Lys Ser Gln Gln Gly Ser Cys Pro Leu Thr Gly Met Ile
            115                 120                 125

Pro Gln Asn His Ile Arg Ile Ser Ala Met Arg Ser Gly Phe Leu Phe
        130                 135                 140

Tyr Asn Leu Thr Val Ser Val Ser Lys Tyr Pro Lys Phe Lys Ser Leu
145                 150                 155                 160
```

```
Gln Cys Val Gly Asn Ser Thr Ser Val Tyr Leu Asn Gly Asp Leu Val
                165                 170                 175
Phe Thr Pro Asn Glu Thr Thr His Val Thr Gly Ala Gly Val Tyr Phe
                180                 185                 190
Lys Ser Gly Gly Pro Val Thr Tyr Lys Val Met Lys Glu Val Lys Ala
                195                 200                 205
Leu Ala Tyr Phe Ile Asn Gly Thr Ala Gln Glu Val Ile Leu Cys Asp
                210                 215                 220
Asn Ser Pro Arg Gly Leu Leu Ala Cys Gln Tyr Asn Thr Gly Asn Phe
225                 230                 235                 240
Ser Asp Gly Phe Tyr Pro Phe Thr Asn Ser Ser Leu Val Lys Asp Arg
                245                 250                 255
Phe Ile Val Tyr Arg Glu Ser Ser Thr Asn Thr Thr Leu Glu Leu Thr
                260                 265                 270
Asn Phe Thr Phe Thr Asn Val Ser Asn Ala Ser Pro Asn Ser Gly Gly
                275                 280                 285
Val Asp Thr Phe Gln Leu Tyr Gln Thr His Thr Ala Gln Asp Gly Tyr
                290                 295                 300
Tyr Asn Phe Asn Leu Ser Phe Leu Ser Ser Phe Val Tyr Lys Pro Ser
305                 310                 315                 320
Asp Phe Met Tyr Gly Ser Tyr His Pro Asn Cys Asn Phe Arg Pro Glu
                325                 330                 335
Asn Ile Asn Asn Gly Leu Trp Phe Asn Ser Leu Ser Val Ser Leu Thr
                340                 345                 350
Tyr Gly Pro Ile Gln Gly Gly Cys Lys Gln Ser Val Phe Ser Asn Lys
                355                 360                 365
Ala Thr Cys Cys Tyr Ala Tyr Ser Tyr Arg Gly Pro Thr Arg Cys Lys
                370                 375                 380
Gly Val Tyr Arg Gly Glu Leu Thr Gln Tyr Phe Glu Cys Gly Leu Leu
385                 390                 395                 400
Val Tyr Val Thr Lys Ser Asp Gly Ser Arg Ile Gln Thr Arg Ser Glu
                405                 410                 415
Pro Leu Val Leu Thr Gln Tyr Asn Tyr Asn Asn Ile Thr Leu Asn Lys
                420                 425                 430
Cys Val Glu Tyr Asn Ile Tyr Gly Arg Val Gly Gln Gly Phe Ile Thr
                435                 440                 445
Asn Val Thr Glu Ala Thr Ala Asn Tyr Ser Tyr Leu Ala Asp Gly Gly
                450                 455                 460
Leu Ala Ile Leu Asp Thr Ser Gly Ala Ile Asp Ile Phe Val Val Arg
465                 470                 475                 480
Gly Ala Tyr Gly Leu Asn Tyr Tyr Lys Val Asn Pro Cys Glu Asp Val
                485                 490                 495
Asn Gln Gln Phe Val Val Ser Gly Gly Asn Leu Val Gly Ile Leu Thr
                500                 505                 510
Ser His Asn Glu Thr Asp Ser Glu Phe Ile Glu Asn Gln Phe Tyr Ile
                515                 520                 525
Lys Leu Thr Asn Gly Thr Arg Arg Ser Arg Arg Ser Val Thr Gly Asn
                530                 535                 540
Val Thr Asn Cys Pro Tyr Val Ser Tyr Gly Lys Phe Cys Ile Lys Pro
545                 550                 555                 560
Asp Gly Ser Leu Phe Ile Ile Val Pro Gln Glu Leu Glu Gln Phe Val
                565                 570                 575
```

```
Ala Pro Leu Leu Asn Val Thr Glu His Val Leu Ile Pro Asp Ser Phe
            580                 585                 590

Asn Leu Thr Val Thr Asp Glu Tyr Ile Gln Thr Arg Met Asp Lys Val
        595                 600                 605

Gln Ile Asn Cys Leu Gln Tyr Val Cys Gly Asn Ser Ile Glu Cys Arg
        610                 615                 620

Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
                645                 650                 655

Ser Ser Thr Lys Pro Ser Gly Tyr Asn Thr Pro Ile Phe Asn Asn Val
            660                 665                 670

Ser Thr Gly Asp Phe Asn Ile Ser Leu Leu Leu Thr Pro Pro Asn Ser
        675                 680                 685

Pro Thr Gly Arg Ser Phe Ile Glu Asp Leu Leu Phe Thr Ser Val Glu
        690                 695                 700

Ser Val Gly Leu Pro Thr Asp Glu Glu Tyr Lys Lys Cys Thr Ala Gly
705                 710                 715                 720

Pro Leu Gly Phe Val Lys Asp Leu Val Cys Ala Arg Glu Tyr Asn Gly
                725                 730                 735

Leu Leu Val Leu Pro Pro Ile Ile Thr Ala Asp Met Gln Thr Met Tyr
            740                 745                 750

Thr Ser Ser Leu Val Ala Ser Met Ala Leu Gly Gly Ile Thr Ala Ala
        755                 760                 765

Gly Ala Ile Pro Phe Ala Thr Gln Leu Gln Ala Arg Ile Asn His Leu
        770                 775                 780

Gly Ile Thr Asn Ser Leu Leu Leu Lys Asn Gln Glu Lys Ile Ala Ala
785                 790                 795                 800

Ser Phe Asn Lys Ala Ile Gly His Met Gln Glu Gly Phe Lys Ser Thr
                805                 810                 815

Ser Leu Ala Leu Gln Gln Ile Gln Asp Val Val Asn Lys Gln Ser Ser
            820                 825                 830

Ile Leu Thr Glu Thr Met Gln Ser Leu Asn Lys Asn Phe Gly Ala Ile
        835                 840                 845

Ser Ser Val Leu Gln Asp Ile Tyr Gln Gln Leu Asp Ala Ile Gln Ala
        850                 855                 860

Asp Ala Gln Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
                885                 890                 895

Arg Glu Leu Ala Thr Gln Lys Ile Asn Glu Cys Val Lys Ser Gln Ser
            900                 905                 910

Asn Arg Tyr Ser Phe Cys Gly Asn Gly Arg His Val Leu Thr Ile Pro
        915                 920                 925

Gln Asn Ala Pro Asn Gly Ile Val Phe Ile His Phe Thr Tyr Thr Pro
        930                 935                 940

Glu Ser Phe Val Asn Val Thr Ala Ile Val Gly Phe Cys Val Asn Pro
945                 950                 955                 960

Ala Asn Ala Ser Gln Tyr Ala Ile Val Pro Val Asn Asn Arg Gly Ile
                965                 970                 975

Phe Ile Gln Val Asn Gly Ser Tyr Tyr Ile Thr Ala Arg Asp Met Tyr
            980                 985                 990

Met Pro Arg Asp Ile Thr Ala Gly  Asp Ile Val Met Leu  Thr Ser Cys
```

```
                995              1000              1005

Gln  Ala  Asn  Tyr  Val  Ser  Val  Asn  Lys  Thr  Val  Ile  Thr  Thr  Phe
         1010                1015                1020

Val  Asp  Asn  Asp  Asp  Phe  Asp  Phe  Asp  Asp  Glu  Leu  Ser  Lys  Trp
         1025                1030                1035

Trp  Asn  Asp  Thr  Lys  His  Glu  Leu  Pro  Asp  Phe  Asp  Glu  Phe  Asn
         1040                1045                1050

Tyr  Thr  Val  Pro  Val  Leu  Asn  Ile  Ser  Asn  Glu  Ile  Asp  Arg  Ile
         1055                1060                1065

Gln  Glu  Val  Ile  Gln  Gly  Leu  Asn  Asp  Ser  Leu  Ile  Asp  Leu  Glu
         1070                1075                1080

Thr  Leu  Ser  Ile  Leu  Lys  Thr  Tyr  Ile  Lys  Trp  Pro  Trp  Tyr  Val
         1085                1090                1095

Trp  Leu  Ala  Ile  Ala  Phe  Ala  Ile  Ile  Ile  Phe  Ile  Leu  Ile  Leu
         1100                1105                1110

Gly  Trp  Val  Phe  Phe  Met  Thr  Gly  Cys  Cys  Gly  Cys  Cys  Cys  Gly
         1115                1120                1125

Cys  Phe  Gly  Ile  Ile  Pro  Leu  Met  Ser  Lys  Cys  Gly  Lys  Lys  Ser
         1130                1135                1140

Ser  Tyr  Tyr  Thr  Thr  Phe  Asp  Asn  Asp  Val  Val  Thr  Glu  Gln  Tyr
         1145                1150                1155

Arg  Pro  Lys  Lys  Ser  Val
         1160

<210> SEQ ID NO 55
<211> LENGTH: 588
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 55

Met  Leu  Val  Lys  Pro  Leu  Leu  Leu  Val  Thr  Leu  Leu  Phe  Ala  Leu  Cys
1                 5                   10                  15

Ser  Ala  Leu  Leu  Tyr  Asp  Glu  Gly  His  Asn  Tyr  Val  Tyr  Tyr  Tyr  Gln
            20                  25                  30

Ser  Ala  Phe  Arg  Pro  Gly  Val  Gly  Trp  His  Leu  His  Gly  Gly  Ala  Tyr
            35                  40                  45

Ala  Val  Asp  Ser  Val  Phe  Asn  Val  Thr  Asn  Ala  Gly  Ser  Ala  His  Cys
    50                      55                  60

Thr  Ala  Gly  Thr  Phe  Tyr  Glu  Ser  Leu  Asn  Ile  Ser  Ala  Ala  Ser  Val
65                      70                  75                      80

Ala  Met  Thr  Ala  Pro  Asp  Thr  Gly  Met  Ser  Trp  Ser  Val  Val  Gln  Phe
                85                  90                  95

Cys  Thr  Ala  His  Cys  Asn  Phe  Ser  Asp  Val  Thr  Val  Phe  Val  Thr  His
                100                 105                 110

Cys  Tyr  Ile  Asn  Gln  Gln  Gly  Ser  Cys  Ser  Leu  Thr  Gly  Met  Ile  Pro
            115                 120                 125

Lys  Asn  His  Ile  Arg  Ile  Ala  Ala  Met  Lys  Asn  Arg  Gln  Leu  Phe  Phe
    130                 135                 140

Asn  Ser  Thr  Val  Ser  Val  Ser  Lys  Tyr  Pro  Arg  Phe  Lys  Ser  Leu  Gln
145                     150                 155                 160

Cys  Val  Ser  Asn  Phe  Thr  Ser  Val  Tyr  Leu  Asn  Gly  Asp  Leu  Val  Phe
                165                 170                 175
```

```
Ser Ser Asn Glu Thr Ser Pro Val Thr Gly Ala Gly Val Tyr Phe Gly
            180                 185                 190

Arg Gly Gly Pro Val Thr Tyr Lys Val Met Lys Glu Val Lys Ala Leu
        195                 200                 205

Ala Tyr Phe Val Asn Gly Thr Ala Gln Glu Val Ile Leu Cys Asp Asn
    210                 215                 220

Ser Pro Arg Gly Leu Leu Ala Cys Gln Tyr Asn Thr Gly Asn Phe Ser
225                 230                 235                 240

Asp Gly Phe Tyr Pro Phe Thr Asn Ser Ser Leu Val Lys Asp Arg Phe
                245                 250                 255

Ile Val Tyr Arg Glu Ser Ser Thr Asn Thr Thr Leu Glu Leu Thr Asn
            260                 265                 270

Phe Thr Phe Thr Asn Val Ser Asn Ala Ser Pro Asn Ser Gly Gly Val
        275                 280                 285

Asp Thr Phe Gln Leu Tyr Gln Thr His Thr Ala Gln Asp Gly Tyr Tyr
    290                 295                 300

Asn Phe Asn Leu Ser Phe Leu Ser Ser Phe Val Tyr Ile Pro Ser Asp
305                 310                 315                 320

Phe Met Tyr Gly Ser Tyr His Pro Glu Cys Thr Phe Arg Pro Glu Thr
                325                 330                 335

Ile Asn Asn Gly Leu Trp Phe Asn Ser Leu Ser Val Ser Leu Thr Tyr
            340                 345                 350

Gly Pro Ile Gln Gly Gly Cys Lys Gln Ser Val Phe Asn Lys Arg Ala
        355                 360                 365

Thr Cys Cys Tyr Ala Tyr Ser Tyr Gln Gly Pro Asn Arg Cys Lys Gly
    370                 375                 380

Val Tyr Arg Gly Glu Leu Lys Gln Glu Phe Glu Cys Gly Leu Leu Val
385                 390                 395                 400

Tyr Val Thr Lys Ser Gly Gly Ser Arg Ile Gln Thr Arg Ser Glu Pro
                405                 410                 415

Leu Val Leu Thr Gln Tyr Asn Tyr Asn Asn Ile Thr Leu Asn Lys Cys
            420                 425                 430

Val Asp Tyr Asn Ile Tyr Gly Arg Val Gly Gln Gly Phe Ile Thr Asn
        435                 440                 445

Val Thr Glu Ala Thr Ala Asn Tyr Ser Tyr Leu Ala Asp Gly Gly Leu
    450                 455                 460

Ala Ile Leu Asp Thr Ser Gly Ala Ile Asp Ile Phe Val Val Gln Gly
465                 470                 475                 480

Ala Tyr Gly Leu Asn Tyr Tyr Lys Val Asn Pro Cys Glu Asp Val Asn
                485                 490                 495

Gln Gln Phe Val Val Ser Gly Gly Asn Leu Val Gly Ile Leu Thr Ser
            500                 505                 510

Tyr Asn Glu Thr Gly Ser Glu Ser Ile Glu Asn Gln Phe Tyr Ile Lys
        515                 520                 525

Leu Thr Ile Gly Thr Arg Arg Ser Arg Arg Ser Ile Thr Gly Asn Val
    530                 535                 540

Thr Asn Cys Pro Tyr Val Ser Tyr Gly Lys Phe Cys Ile Lys Pro Asp
545                 550                 555                 560

Gly Ser Leu Ser Thr Ile Val Pro Gln Glu Leu Glu His Phe Val Ala
                565                 570                 575

Pro Leu Leu Asn Val Thr Glu His Val Leu Ile Pro
            580                 585
```

```
<210> SEQ ID NO 56
<211> LENGTH: 539
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 56
```

| Met | Leu | Asp | Lys | Pro | Le

-continued

```
Ala Thr Cys Cys Tyr Ala Tyr Ser Tyr Gln Gly Pro Ser Arg Cys Lys
    370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
    450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
            500                 505                 510

Ser His Asn Glu Thr Gly Ser Glu Ser Ile Glu Asn Gln Phe Tyr Ile
        515                 520                 525

Lys Leu Thr Asn Gly Thr Arg Arg Ser Arg Arg
    530                 535

<210> SEQ ID NO 57
<211> LENGTH: 409
<212> TYPE: PRT
<213> ORGANISM: Unknown
<220> FEATURE:
<223> OTHER INFORMATION: Description of Unknown:
      Avian infectious bronchitis virus sequence <400> SEQUENCE: 57

Met Ala Ser Gly Lys Ala Ala Gly Lys Thr Asp Ala Pro Ala Pro Val
1               5                   10                  15

Ile Lys Leu Gly Gly Pro Lys Pro Pro Lys Val Gly Ser Ser Gly Asn
            20                  25                  30

Ala Ser Trp Phe Gln Ala Ile Lys Ala Lys Lys Leu Asn Ser Pro Gln
        35                  40                  45

Pro Lys Phe Glu Gly Ser Gly Val Pro Glu Asn Glu Asn Leu Lys Ser
    50                  55                  60

Ser Gln Gln His Gly Tyr Trp Arg Arg Gln His Arg Tyr Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asp Leu Asn Trp Gly Asp Asn Gln Asp Gly
            100                 105                 110

Ile Val Trp Val Ala Ala Lys Gly Ala Asp Thr Lys Ser Arg Ser Asn
        115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Ile
145                 150                 155                 160

Asn Arg Gly Arg Ser Gly Arg Ser Thr Ala Ala Ser Ser Ala Ala Ser
                165                 170                 175

Ser Arg Ala Pro Ser Arg Glu Gly Ser Arg Gly Arg Arg Ser Gly Ala
            180                 185                 190
```

```
Glu Asp Asp Leu Ile Ala Arg Ala Lys Ile Ile Gln Asp Gln Gln
            195                 200                 205

Lys Lys Gly Ser Arg Ile Thr Lys Ala Lys Ala Asp Glu Met Ala His
210                 215                 220

Arg Arg Tyr Cys Lys Arg Thr Val Pro Pro Gly Tyr Lys Val Asp Gln
225                 230                 235                 240

Val Phe Gly Pro Arg Thr Lys Gly Lys Glu Gly Asn Phe Gly Asp Asp
                245                 250                 255

Lys Met Asn Glu Glu Gly Ile Lys Asp Gly Arg Val Thr Ala Met Leu
            260                 265                 270

Asn Leu Val Pro Ser Ser His Ala Cys Leu Phe Gly Ser Arg Val Thr
        275                 280                 285

Pro Lys Leu Gln Pro Asp Gly Leu His Leu Arg Phe Glu Phe Thr Thr
    290                 295                 300

Val Val Pro Arg Asp Asp Pro Gln Phe Asp Asn Tyr Val Lys Ile Cys
305                 310                 315                 320

Asp Gln Cys Val Asp Gly Val Gly Thr Arg Pro Lys Asp Asp Glu Pro
                325                 330                 335

Arg Pro Lys Ser Arg Pro Asn Ser Arg Pro Ala Thr Arg Gly Asn Ser
            340                 345                 350

Pro Ala Pro Arg Gln Gln Arg Gln Lys Lys Glu Lys Lys Pro Lys Lys
        355                 360                 365

Gln Glu Asp Asp Val Asp Lys Ala Leu Thr Ser Asp Glu Glu Arg Asn
    370                 375                 380

Asn Ala Gln Leu Glu Phe Asp Asp Glu Pro Lys Val Ile Asn Trp Gly
385                 390                 395                 400

Asp Ser Ala Leu Gly Glu Asn Glu Leu
                405

<210> SEQ ID NO 58
<211> LENGTH: 106
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 58

Met Met Asn Leu Leu Asn Lys Ser Leu Glu Glu Asn Gly Ser Phe Leu
1               5                   10                  15

Thr Ala Val Tyr Val Phe Cys Ala Phe Val Ala Leu Tyr Leu Leu Gly
            20                  25                  30

Arg Ala Leu Gln Ala Phe Val Gln Ala Ala Asp Ala Cys Cys Leu Phe
        35                  40                  45

Trp Tyr Thr Trp Val Val Pro Gly Ala Lys Gly Thr Ser Phe Val
50                  55                  60

Tyr Lys His Thr Tyr Gly Lys Lys Leu Asn Asn Pro Glu Leu Glu Ser
65                  70                  75                  80

Val Ile Val Asn Glu Phe Pro Lys Asn Gly Trp Asn Lys Asn Pro
                85                  90                  95

Ala Asn Phe Gln Asn Gly Lys Leu His Thr
                100                 105

<210> SEQ ID NO 59
<211> LENGTH: 222
<212> TYPE: PRT
<213> ORGANISM: Unknown
```

<220> FEATURE:
<223> OTHER INFORMATION: Description of Unknown:
      Avian infectious bronchitis virus sequence

<400> SEQUENCE: 59

```
Met Glu Asn Cys Thr Leu Asp Ala Glu Gln Ala Val Gln Leu Phe Lys
1               5                   10                  15

Asp Tyr Asn Leu Phe Ile Thr Ala Phe Leu Leu Phe Leu Thr Ile Leu
            20                  25                  30

Leu Gln Tyr Gly Tyr Ala Thr Arg Ser Arg Ile Ile Tyr Ile Leu Lys
        35                  40                  45

Met Ile Val Leu Trp Cys Phe Trp Pro Leu Asn Ile Ala Val Gly Val
50                  55                  60

Ile Ser Cys Ile Tyr Pro Pro Asn Thr Gly Gly Leu Val Ala Ala Ile
65                  70                  75                  80

Ile Leu Thr Val Phe Ala Cys Leu Ser Phe Leu Gly Tyr Trp Ile Gln
                85                  90                  95

Ser Ile Arg Leu Phe Lys Arg Cys Arg Ser Trp Trp Ser Phe Asn Pro
            100                 105                 110

Glu Ser Asn Ala Val Gly Ser Ile Leu Leu Thr Asn Gly Gln Gln Cys
        115                 120                 125

Asn Phe Ala Ile Glu Ser Val Pro Met Val Leu Ser Pro Ile Ile Lys
130                 135                 140

Asn Gly Ala Leu Tyr Cys Glu Gly Gln Trp Leu Ala Lys Cys Glu Pro
145                 150                 155                 160

Asp His Leu Pro Lys Asp Ile Phe Val Cys Thr Pro Asp Arg Arg Asn
                165                 170                 175

Ile Tyr Arg Met Val Gln Lys Tyr Thr Gly Asp Gln Ser Gly Asn Lys
            180                 185                 190

Lys Arg Phe Ala Thr Phe Val Tyr Ala Lys Gln Ser Val Asp Thr Gly
        195                 200                 205

Glu Leu Glu Ser Val Ala Thr Val Gly Ser Ser Leu Tyr Thr
    210                 215                 220
```

<210> SEQ ID NO 60
<211> LENGTH: 539
<212> TYPE: PRT
<213> ORGANISM: Unknown
<220> FEATURE:
<223> OTHER INFORMATION: Description of Unknown:
      Avian infectious bronchitis virus sequence

<400> SEQUENCE: 60

```
Met Leu Gly Lys Pro Leu Leu Val Thr Leu Trp Tyr Ala Leu Cys
1               5                   10                  15

Ser Ala Leu Leu Tyr Asp Lys Asn Thr Tyr Val Tyr Tyr Gln Ser
            20                  25                  30

Ala Phe Arg Pro Gly Gln Gly Trp His Leu His Gly Gly Ala Tyr Ala
        35                  40                  45

Val Asp Lys Val Phe Asn Gly Thr Asn Asn Ala Val Ser Val Ser Asp
50                  55                  60

Cys Thr Ala Gly Thr Phe Tyr Glu Ser Tyr Asn Ile Ser Ala Ala Ser
65                  70                  75                  80

Val Ala Met Thr Val Pro Pro Ala Gly Met Ser Trp Ser Val Ala Gln
                85                  90                  95

Phe Cys Thr Ala His Cys Asn Phe Ser Asp Phe Thr Val Phe Val Thr
            100                 105                 110
```

```
His Cys Phe Lys Ser Gln Gln Gly Ser Cys Pro Leu Thr Gly Met Ile
            115                 120                 125

Pro Gln Asn His Ile Arg Ile Ser Ala Met Arg Ser Gly Phe Leu Phe
130                 135                 140

Tyr Asn Leu Thr Val Ser Val Ser Lys Tyr Pro Lys Phe Lys Ser Leu
145                 150                 155                 160

Gln Cys Val Gly Asn Ser Thr Ser Val Tyr Leu Asn Gly Asp Leu Val
                165                 170                 175

Phe Thr Ser Asn Glu Thr Thr His Val Thr Gly Ala Gly Val Tyr Phe
                180                 185                 190

Lys Ser Gly Gly Pro Val Thr Tyr Lys Val Met Lys Glu Val Lys Ala
                195                 200                 205

Leu Ala Tyr Phe Ile Asn Gly Thr Ala Gln Glu Val Ile Leu Cys Asp
210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn Ser Ser Leu Val Lys Asp Arg
                245                 250                 255

Phe Ile Val Tyr Arg Glu Ser Ser Thr Asn Thr Thr Leu Glu Leu Thr
                260                 265                 270

Asn Phe Thr Phe Thr Asn Val Ser Asn Ala Ser Pro Asn Ser Gly Gly
                275                 280                 285

Val Asp Thr Phe Gln Leu Tyr Gln Thr His Thr Ala Gln Asp Gly Tyr
                290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro Asn Cys Asn Phe Arg Pro Glu
                325                 330                 335

Asn Ile Asn Asn Gly Leu Trp Phe Asn Ser Leu Ser Val Ser Leu Thr
                340                 345                 350

Tyr Gly Pro Ile Gln Gly Gly Cys Lys Gln Ser Val Phe Ser Asn Lys
                355                 360                 365

Ala Thr Cys Cys Tyr Ala Tyr Ser Tyr Arg Gly Pro Thr Arg Cys Lys
            370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
                420                 425                 430

Cys Val Glu Tyr Asn Ile Tyr Gly Arg Val Gly Gln Gly Phe Ile Thr
            435                 440                 445

Asn Val Thr Glu Ala Thr Ala Asn Tyr Ser Tyr Leu Ala Asp Gly Gly
            450                 455                 460

Leu Ala Ile Leu Asp Thr Ser Gly Ala Ile Asp Ile Phe Val Val Arg
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Ile Gly Ile Leu Thr
            500                 505                 510

Ser His Asn Glu Thr Asp Ser Glu Phe Ile Glu Asn Gln Phe Tyr Ile
515                 520                 525
```

```
Lys Pro Thr Asn Gly Thr Arg Arg Ser Arg Arg
    530                 535

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ggtaacttaa caatacagac ctaaaaagtc tg                                      32
```